(12) United States Patent
Walter et al.

(10) Patent No.: US 9,708,247 B2
(45) Date of Patent: Jul. 18, 2017

(54) MODULATORS OF THE EIF2ALPHA PATHWAY

(71) Applicant: The Regents of the University of California, Oakland, CA (US)

(72) Inventors: Peter Walter, San Francisco, CA (US); Carmela Sidrauski, Saratoga, CA (US); Diego Acosta Alvear, San Francisco, CA (US); Michelle R. Arkin, San Francisco, CA (US); Christopher G. Wilson, Berkeley, CA (US); Kean Hooi Ang, San Francisco, CA (US); Brian R. Hearn, Lafayette, CA (US); Punitha Vedantham, Burlingame, CA (US); Adam R. Renslo, Oakland, CA (US); Mervyn Maze, San Francisco, CA (US); Susana Vacas, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/849,428

(22) Filed: Sep. 9, 2015

(65) Prior Publication Data
US 2016/0096800 A1    Apr. 7, 2016

Related U.S. Application Data

(63) Continuation of application No. PCT/US2014/029568, filed on Mar. 14, 2014.

(60) Provisional application No. 61/787,633, filed on Mar. 15, 2013.

(51) Int. Cl.
| | | |
|---|---|---|
| *C07C 235/14* | (2006.01) |
| *A61K 31/165* | (2006.01) |
| *A61K 31/4192* | (2006.01) |
| *C07D 403/12* | (2006.01) |
| *C07D 495/04* | (2006.01) |
| *C07C 255/54* | (2006.01) |
| *C07C 257/14* | (2006.01) |
| *C07C 271/24* | (2006.01) |
| *C07C 271/52* | (2006.01) |
| *C07C 211/29* | (2006.01) |
| *C07C 317/22* | (2006.01) |
| *C07C 317/44* | (2006.01) |
| *C07C 323/60* | (2006.01) |
| *C07C 235/20* | (2006.01) |
| *C07C 235/22* | (2006.01) |
| *C07C 235/24* | (2006.01) |
| *C07F 7/08* | (2006.01) |

(52) U.S. Cl.
CPC .......... *C07C 235/14* (2013.01); *A61K 31/165* (2013.01); *A61K 31/4192* (2013.01); *C07C 211/29* (2013.01); *C07C 235/20* (2013.01); *C07C 235/22* (2013.01); *C07C 235/24* (2013.01); *C07C 255/54* (2013.01); *C07C 257/14* (2013.01); *C07C 271/24* (2013.01); *C07C 271/52* (2013.01); *C07C 317/22* (2013.01); *C07C 317/44* (2013.01); *C07C 323/60* (2013.01); *C07D 403/12* (2013.01); *C07D 495/04* (2013.01); *C07F 7/0818* (2013.01); *C07C 2101/04* (2013.01); *C07C 2101/14* (2013.01)

(58) Field of Classification Search
CPC  A61K 31/165; A61K 31/4192; C07C 211/29; C07C 235/14; C07C 235/20; C07C 235/22; C07C 235/24; C07C 255/54; C07C 257/14; C07C 271/24; C07C 271/52; C07C 317/22; C07C 317/44; C07C 323/60; C07C 2101/04; C07C 2101/14; C07D 403/12; C07D 495/04; C07F 7/0818
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 7,097,996 B2 | 8/2006 | Ron et al. |
| 2004/0138286 A1 | 7/2004 | Imazaki et al. |
| 2008/0300205 A1 | 12/2008 | Tsai et al. |

FOREIGN PATENT DOCUMENTS

| | | | |
|---|---|---|---|
| EP | 2 439 194 A1 | 4/2012 | |
| WO | WO 0244126 A2 * | 6/2002 | ........... C07C 233/65 |
| WO | WO-2004/020599 A2 | 3/2004 | |
| WO | WO-2004/020599 A3 | 3/2004 | |
| WO | WO-2010/043631 A1 | 4/2010 | |

(Continued)

OTHER PUBLICATIONS

Chabner et. al., Nature Reviews Cancer, 2005, Nature Publishing Group, vol. 5, pp. 65-72.*
Leaf, Fortune, 2004, Time Inc., pp. 1-26.*
Freedman et. al., Canadian Journal of Neurological Sciences, 2004, vol. 3, pp. 157-168.*
Van Laar et. al., PLoS Medicine, 2005, www.plosmedicine.org, PLoS One, vol. 2(2), pp. 1230-1231.*
Ross et. al., The Lancet: Neurology, 2011, vol. 9, pp. 83-98.*
Lu et. al., Journal of Medicinal Chemistry, 2009, American Chemical Society, vol. 52, pp. 1701-1711.*
CAS STN search results excerpt: RN 852678-56-9; RN 548481-19-2; RN 548478-33-7; RN 548470-11-7, publ. 2003 & 2005.*

(Continued)

*Primary Examiner* — Sarah Pihonak
(74) *Attorney, Agent, or Firm* — Mintz Levin Cohn Ferris Glovsky and Popeo, P.C.

(57) ABSTRACT

Provided herein, inter alia, are compounds and methods useful for modulating the translational effects of eIF2α phosphorylation, the Integrated Stress Response (ISR), and the unfolded protein response (UPR); for treating diseases; for increasing protein production, and for improving long-term memory.

6 Claims, 41 Drawing Sheets

(56) References Cited

FOREIGN PATENT DOCUMENTS

| WO | WO-2014/144952 A2 | 9/2014 |
|---|---|---|
| WO | WO-2014/144952 A3 | 9/2014 |

OTHER PUBLICATIONS

Al-Muhammed, J. et al. (May-Jun. 1996). "In-vivo studies on dexamethasone sodium phosphate liposomes," *J Microencapsul* 13(3):293-306.
Avivar-Valderas A. et al. (Sep. 2011, e-published Jun. 27, 2011). "PERK integrates autophagy and oxidative stress responses to promote survival during extracellular matrix detachment," *Mol Cel Biol* 31(17):3616-3629.
Berge, S.M. et al. (Jan. 1977). "Pharmaceutical salts," *J Pharm Sci* 66(1):1-19.
Bi M. et al. (Oct. 5, 2005, e-published Sep. 8, 2005). "ER stress-regulated translation increases tolerance to extreme hypoxia and promotes tumor growth," *EMBO J.* 24(19):3470-3481.
Borck G. et al. (Nov. 30, 2012, e-published Oct. 11, 2012). "eIF2γ Mutation that Disrupts eIF2 Complex Integrity Links Intellectual Disability to Impaired Translation Initiation," *Mol Cell.* 48:1-6.
Chen A. et al. (Aug. 14, 2003). "Inducible enhancement of memory storage and synaptic plasticity in transgenic mice expressing an inhibitor of ATF4 (CREB-2) and C/EBP proteins," *Neuron* 39(4):655-669.
Chen T. et al. (Jul. 17, 2011). "Chemical genetics identify eIF2α kinase heme-regulated inhibitor as an anticancer target," *Nature Chemical Biology* 7(9):610-616.
Chonn, A. et al. (Dec. 1995). "Recent advances in liposomal drug-delivery systems," *Curr Opin Biotechnol* 6(6):698-708.
Costa-Mattioli M. et al. (Aug. 25, 20050. "Translational control of hippocampal synaptic plasticity and memory by the eIF2alpha kinase GCN2," *Nature* 36(7054):1166-1173.
Costa-Mattioli M, Gobert D, Stern E, Gamache K, Colina R, Cuello C, et al. eIF2alpha phosphorylation bidirectionally regulates the switch from short- to long-term synaptic plasticity and memory. Cell. Apr. 6, 2007;129(1):195-206.
Eyles, J.E. et al. (Jul. 1997). "Oral delivery and fate of poly(lactic acid) microsphere-encapsulated interferon in rats," *J Pharm Pharmacol* 49(7):669-674.
Fogli, A. et al. (Feb. 2006). "The large spectrum of eIF2B-related diseases," *Biochem Soc Trans* 34(Part 1):22-29.
Gao, Z.H. et al. (Jun. 1995). "Controlled release of a contraceptive steroid from biodegradable and injectable gel formulations: in vitro evaluation," *Pharm Res* 12(6):857-863.
Gardner BM. et al. (Sep. 30, 2011, e-published Aug. 18, 2011). "Unfolded proteins are Ire1-activating ligands that directly induce the unfolded protein response," *Science* 333(6051):1891-1894.
Hinnebusch AG et al. (Oct. 1, 2012). "The mechanism of eukaryotic translation initiation: new insights and challenges," *Cold Spring Harb Perspect Biol.* 4(10), 25 pages.
International Search Report mailed on Aug. 29, 2014, for PCT Application No. PCT/US2014/029568, filed Mar. 14, 2014, 4 pages.
Jackson RJ. et al. (Feb. 2010). "The mechanism of eukaryotic translation initiation and principles of its regulation," *Nat Rev Mol Cell Biol.* 11(2):113-127.
Jiang Z et al. (Feb. 17, 2010). "eIF2alpha Phosphorylation-dependent translation in CA1 pyramidal cells impairs hippocampal memory consolidation without affecting general translation," *Journal of Neuroscience* 30(7):2582-2594.
Krishnamoorthy T. et al. (Aug. 2001). "Tight binding of the phosphorylated alpha subunit of initiation factor 2 (eIF2alpha) to the regulatory subunits of guanine nucleotide exchange factor eIF2B is required for inhibition of translation initiation," *Mol Cell Biol.* 21(15):5018-5030.
Li, H. et al. (Sep. 14, 2010, e-published Aug. 26, 2010). "Mammalian endoplasmic reticulum stress sensor IRE1 signals by dynamic clustering," *Proceedings of the National Academy of Sciences USA* 107(37):16113-16118.

Li X. et al. (Dec. 25, 1998). "Generation of destabilized green fluorescent protein as a transcription reporter," *J Biol Chem.* 273(52):34970-34875.
Li W et al. (Apr. 2004). "Mutations Linked to Leukoencephalopathy with Vanishing White Matter Impair the Function of the Eukaryotic Initiation Factor 2B Complex in Diverse Ways," *Mol Cell Biol.* 24(8):3295-306.
Lu, PD. et al. (Jan. 14, 2004, e-published Jan. 8, 2004). "Cytoprotection by preemptive conditional phosphorylation of translation initiation factor 2," *EMBO J.* 23(1):169-79.
Moreno JA. et al. (May 6, 2012). "Sustained translational repression by eIF2α-P mediates prion neurodegeneration," *Nature* 485(7399):507-511.
Ostro, M.J. et al. (Aug. 1989). "Use of liposomes as injectable-drug delivery systems," *Am J Hosp Pharm* 46(8):1576-1587.
Palam LR. et al. (Apr. 1, 2011, e-published Feb. 1, 2011). "Phosphorylation of eIF2 facilitates ribosomal bypass of an inhibitory upstream ORF to enhance CHOP translation," *Journal of Biological Chemistry* 286(13):10939-10949.
Pavitt GD. et al. (Mar. 1997). "Homologous segments in three subunits of the guanine nucleotide exchange factor eIF2B mediate translational regulation by phosphorylation of eIF2," *Mol Cell Biol.* 17(3):1298-1313.
Pavitt GD. et al. (Feb. 15, 1998). "eIF2 independently binds two distinct eIF2B subcomplexes that catalyze and regulate guanine-nucleotide exchange," *Genes Dev.* 12(4):514-526.
Pavitt GD. et al. (Jun. 1, 2012). "New insights into translational regulation in the endoplasmic reticulum unfolded protein response," *Cold Spring Harb Perspect Biol.*4(6), 13 pages.
Rikitake, Y. et al. (Oct. 2005, e-published Sep. 1, 2005). "Inhibition of Rho kinase (ROCK) leads to increased cerebral blood flow and stroke protection," *Stroke* 36(10):2251-2257.
Shore, GC. et al. (Apr. 2011). "Signaling cell death from the endoplasmic reticulum stress response," *Current Opinion in Cell Biology* 23(2):143-149.
Teske, B.F. et al. (Nov. 2011, e-published Sep. 14, 2011). "The eIF2 kinase PERK and the integrated stress response facilitate activation of ATF6 during endoplasmic reticulum stress," *Mol Biol Cell* 22(22):4390-4405.
Thoreen CC. et al. (May 2, 2012). "A unifying model for mTORC1-mediated regulation of mRNA translation," *Nature* 485(7396):109-113.
Trinh, MA. et al. (Jun. 28, 2012, e-published May 24, 2012). "Brain-specific disruption of the eIF2α kinase PERK decreases ATF4 expression and impairs behavioral flexibility," *Cell Rep.* 1(6):676-688.
Van Harten, A.E. et al. (Mar. 2012). "A review of postoperative cognitive dysfunction and neuroinflammation associated with cardiac surgery and anaesthesia," *Anaesthesia* 67(3):280-293.
Vazquez de Aldana CR. et al. (May 1994). "Mutations in the GCD7 subunit of yeast guanine nucleotide exchange factor eIF-2B overcome the inhibitory effects of phosphorylated eIF-2 on translation initiation," *Mol Cell Biol.* 14(5):3208-3222.
Vattem KM. et al. (Aug. 3, 2004, e-published Jul. 26, 2004). "Reinitiation involving upstream ORFs regulates ATF4 mRNA translation in mammalian cells," *Proc Natl Acad Sci USA* 101(31):11269-11274.
Wek RC. et al. (Feb. 2006). "Coping with stress: eIF2 kinases and translational control," *Biochem. Soc. Trans.* 34(Pt 1):7-11.
Woo, CW. et al. (Dec. 2009, e-published Oct. 25, 2009). "Adaptive suppression of the ATF4-CHOP branch of the unfolded protein response by toll-like receptor signaling," *Nat Cell Biol.* 11(12):1473-1480.
Woo, CW. et al. (Jan. 8, 2012). "Toll-like receptor activation suppresses ER stress factor CHOP and translation inhibition through activation of eIF2B," *Nat Cell Biol.* 14(2):192-200.
Written Opinion mailed on Aug. 29, 2014, for PCT Application No. PCT/US2014/029568, filed Mar. 14, 2014, 23 pages.
Ye J. et al. (Jun. 16, 2010, e-published May 14, 2010). "The GCN2-ATF4 pathway is critical for tumour cell survival and proliferation in response to nutrient deprivation," *EMBO J.* 29(12):2082-2096.

(56) References Cited

OTHER PUBLICATIONS

Zeenko V. V. et al. (Mar. 2008, e-published Jan. 29, 2008). "An efficient in vitro translation system from mammalian cell lacking translational inhibition caused by eIF2 phosphorylation," *RNA* 14(3):593-602.

Zhu PJ. et al. (Dec. 9, 2011). "Suppression of PKR Promotes Network Excitability and Enhanced Cognition by Interferon-γ-Mediated Disinhibition," *Cell* 147(6):1384-1396.

Font, M. et al. (Mar. 15, 2006, e-published Nov. 10, 2005). "Structural characteristics of novel symmetrical diaryl derivatives with nitrogenated functions. Requirements for cytotoxic activity," *Bioorg Med Chem* 14(6):1942-1948.

Tumiatti, V. et al. (Nov. 27, 2008). "Structure-activity relationships of acetylcholinesterase noncovalent inhibitors based on a polyamine backbone. 4. Further investigation on the inner spacer," *J Med Chem* 51(22):7308-7312.

Vital-Reyes, V. et al. (Aug. 2006). "Celecoxib inhibits cellular growth, decreases Ki-67 expression and modifies apoptosis in ovarian cancer cell lines," *Arch Med Res* 37(6):689-695.

\* cited by examiner

Cell dilution

SMDC 750213: SAR Overview

SMDC 750213

- ~110 analogs synthesized to date
  - 7 with $IC_{50}$ < 5 nM
  - 9 with $IC_{50}$ < 15 nM
  - 17 with 15 nM < $IC_{50}$ ≤ 150 nM

- Several sites may be altered without significantly impacting potency
  - Analogs with improved solubility (major limitation of series)
  - Probes with bioorthogonal handles for target ID

MODULATORS OF THE EIF2ALPHA PATHWAY

CROSS-REFERENCES TO RELATED APPLICATIONS

This application is a continuation of International Patent Application No. PCT/US2014/029568, filed Mar. 14, 2014, which claims the benefit of U.S. Provisional Patent Application No. 61/787,633, filed Mar. 15, 2013, all of which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 84850-903323_ST25.TXT, created Mar. 14, 2014, 3,576 bytes, machine format IBM-PC, MS-Windows operating system, is hereby incorporated by reference.

BACKGROUND OF THE INVENTION

In metazoa, diverse stress signals converge at a single phosphorylation event at serine 51 of a common effector, the translation initiation factor eIF2α. This step is carried out by four eIF2α kinases in mammalian cells: PERK, which responds to an accumulation of unfolded proteins in the endoplasmic reticulum (ER), GCN2 to amino acid starvation and UV light, PKR to viral infection, and HRI to heme deficiency. This collection of signaling pathways has been termed the "integrated stress response" (ISR), as they converge on the same molecular event. eIF2α phosphorylation results in an attenuation of translation with consequences that allow cells to cope with the varied stresses (1).

eIF2 (which is comprised of three subunits, α, β and γ) binds GTP and the initiator Met-tRNA to form the ternary complex (eIF2-GTP-Met-tRNA$_i$), which, in turn, associates with the 40S ribosomal subunit scanning the 5'UTR of mRNAs to select the initiating AUG codon. Upon phosphorylation of its α-subunit, eIF2 becomes a competitive inhibitor of its GTP-exchange factor (GEF), eIF2B (2). The tight and nonproductive binding of phosphorylated eIF2 to eIF2B prevents loading of the eIF2 complex with GTP thus blocking ternary complex formation and reducing translation initiation (3). Because eIF2B is less abundant than eIF2, phosphorylation of only a small fraction of the total eIF2 has a dramatic impact on eIF2B activity in cells.

Paradoxically, under conditions of reduced protein synthesis, a small group of mRNAs that contain upstream open reading frames (uORFs) in their 5'UTR are translationally upregulated (4,5). These include mammalian ATF4 (a cAMP element binding (CREB) transcription factor) and CHOP (a pro-apoptotic transcription factor) (6-8). ATF4 regulates the expression of many genes involved in metabolism and nutrient uptake and additional transcription factors, such as CHOP, which is under both translational and transcriptional control (9). Phosphorylation of eIF2α thus leads to preferential translation of key regulatory molecules and directs diverse changes in the transcriptome of cells upon cellular stress.

One of the eIF2α kinases, PERK, lies at the intersection of the ISR and the unfolded protein response (UPR) that maintains homeostasis of protein folding in the ER (10). The UPR is activated by unfolded or misfolded proteins that accumulate in the ER lumen because of an imbalance between protein folding load and protein folding capacity, a condition known as "ER stress". In mammals, the UPR is comprised of three signaling branches mediated by ER-localized transmembrane sensors, PERK, IRE1, and ATF6. These sensor proteins detect the accumulation of unfolded protein in the ER and transmit the information across the ER membrane, initiating unique signaling pathways that converge in the activation of an extensive transcriptional response, which ultimately results in ER expansion (11). The lumenal stress-sensing domains of PERK and IRE1 are homologous and likely activated in analogous ways by direct binding to unfolded peptides (12). This binding event leads to oligomerization and trans-autophosphorylation of their cytosolic kinase domains, and, for PERK, phosphorylation of its only known substrate, eIF2α. In this way, PERK activation results in a quick reduction in the load of newly synthesized proteins that are translocated into the ER-lumen (13).

Upon ER stress, both the transcription factor XBP1s, produced as the consequence of a non-conventional mRNA splicing reaction initiated by IRE1, and the transcription factor ATF6, produced by proteolysis and release from the ER membrane, collaborate with ATF4 to induce the vast UPR transcriptional response. Transcriptional targets of the UPR include the ER protein folding machinery, the ER-associated degradation machinery, and many other components functioning in the secretory pathway (14). Although the UPR initially mitigates ER stress and as such confers cytoprotection, persistent and severe ER stress leads to activation of apoptosis that eliminates damaged cells (15, 16).

Small-molecule therapeutics that inhibit the UPR and/or the Integrated Stress Response could be used in cancer as a single agent or in combination with other chemotherapeutics [1] [2] [3], for enhancement of long-term memory [5] [6], in neurodegenerative and prion associated diseases [4], in white matter disease (VWM) [7] and in biotechnology applications that would benefit from increased protein translation.

Disclosed herein, inter alia, are solutions to these and other problems in the art.

BRIEF SUMMARY OF THE INVENTION

In a first aspect is provided a method of treating an integrated stress response-associated disease in a patient in need of such treatment, the method including administering a therapeutically effective amount of a compound, or a pharmaceutically acceptable salt thereof, to the patient, wherein the compound has the formula:

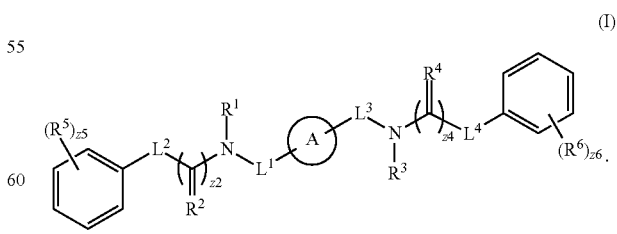

(I)

Ring A is substituted or unsubstituted cycloalkylene or substituted or unsubstituted arylene. $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently =NR$^7$, =O, or =S; z2 and z4 are independently 0 or 1; and z5 and z6 are independently an integer from 0 to 5.

In another aspect is provided a method of treating a disease associated with phosphorylation of eIF2α in a patient in need of such treatment, the method including administering a therapeutically effective amount of a compound, or a pharmaceutically acceptable salt thereof, to the patient, wherein the compound has the formula:

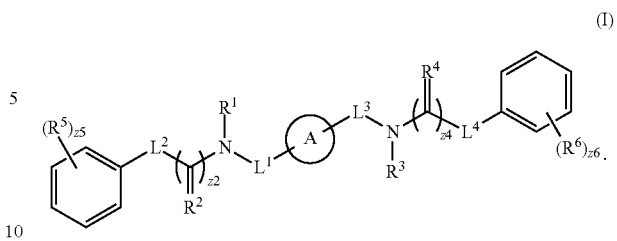

(I)

Ring A is substituted or unsubstituted cycloalkylene or substituted or unsubstituted arylene. $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently =NR$^7$, =O, or =S; z2 and z4 are independently 0 or 1; and z5 and z6 are independently an integer from 0 to 5.

In another aspect is provided a method of treating an inflammatory disease in a patient in need of such treatment, the method including administering a therapeutically effective amount of a compound, or a pharmaceutically acceptable salt thereof, to the patient, wherein the compound has the formula:

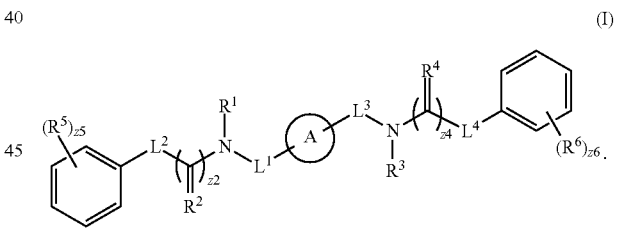

(I)

Ring A is substituted or unsubstituted cycloalkylene or substituted or unsubstituted arylene. $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently =NR$^7$, =O, In another aspect is provided a method of treating a disease in a patient in need of such treatment, the method including administering a therapeutically effective amount of a compound to the patient, wherein the disease is selected from the group consisting of cancer, a neurodegenerative disease, vanishing white matter disease, childhood ataxia with CNS hypo-myelination, and an intellectual disability syndrome; and wherein the compound has the formula:

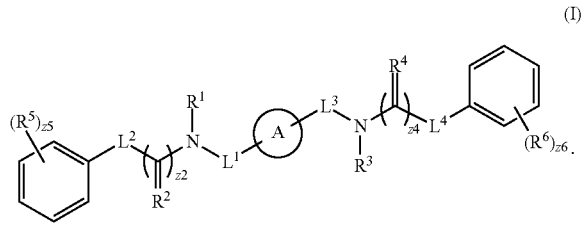

(I)

or =S; z2 and z4 are independently 0 or 1; and z5 and z6 are independently an integer from 0 to 5.

In another aspect is provided a method of improving long-term memory in a patient, the method including administering a therapeutically effective amount of a compound to the patient, wherein the compound is a compound described herein.

In another aspect is provided a method of increasing protein expression of a cell or in vitro expression system, the method including administering an effective amount of a compound to the cell or expression system, wherein the compound is a compound described herein.

In another aspect is provided a compound, or a pharmaceutically acceptable salt thereof, having the formula:

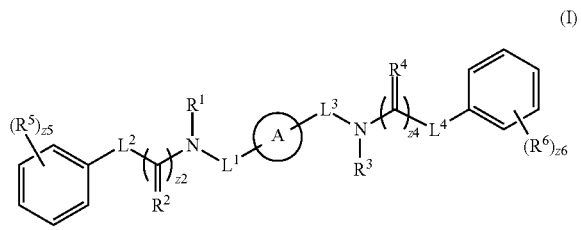

(I)

wherein. ring A, $L^1$, $L^2$, $L^3$, $L^4$, $R^1$, $R^2$, $R^3$, $R^4$, $R^5$, $R^6$, $R^7$, z2, z4, z5 and z6, are as described herein, including embodiments and in the method of treatment section herein above. In embodiments, Ring A is substituted or unsubstituted cycloalkylene or substituted or unsubstituted arylene. In embodiments, $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene. In embodiments, $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ and $R^4$ are independently =NR$^7$, =O, or =S. The symbols z2 and z4 are each independently 0 or 1. The symbols z5 and z6 are each independently an integer from 0 to 5.

In another aspect is provided a pharmaceutical composition including a pharmaceutically acceptable excipient and a compound, or pharmaceutically acceptable salt thereof, as described herein.

BRIEF DESCRIPTION OF THE DRAWINGS

(FIG. 1A) schematic representation of the ATF4 luciferase reporter used in the primary screen; the 5' UTR of human ATF4 containing the uORFs 1 and 2 was fused to firefly luciferase and inserted into a retroviral expression system; (FIG. 1B) primary screen optimization; HEK293T stably expressing the ATF4 luciferase reporter were plated in 384 well plates and treated for 6 h with 100 nM thapsigargin (Tg) or DMSO as a no ER stress control; luciferase production was measured at the end point after 6 h; the Z' was calculated as 1–(3(σ Tg+σ DMSO)/(μ Tg–μ DMSO)); (FIG. 1C) primary screen results; the ATF4 luciferase reporter cell line was treated for 6 h with 100 nM thapsigargin and library compounds (10 μM); inhibition of the luciferase activity reporter was calculated as the percent reduction in relative luminescence normalized to thapsigargin treatment (0% inhibition) and the no-ER stress control (100% inhibition); compounds were considered hits if they lied beyond 3 standard deviations (SD) from the thapsigargin treatment mean (line).

(FIG. 2A) structures of ISRIB isosteromers; (FIG. 2B) inhibition of the ATF4 luciferase reporter in HEK293T cells by ISRIB stereoisomers; inhibition is plotted in relation to the concentration of either the cis or trans isomer of ISRIB; cells were treated with 2 μg/ml of tunicamycin to induce ER stress and different concentrations of the inhibitors for 7 h (N=2); (FIG. 2C) effect of ISRIB on production of endogenous ATF4, PERK phosphorylation, and XBP1s production; an immunoblot analysis of PERK, ATF4 and XBP1s in HEK293T cells treated with different ER stress inducers (2.5 μg/ml tunicamycin (Tm) or 100 nM thapsigargin (Tg)) with or without 200 nM ISRIB for 3 h is shown; the arrowhead marks the XBP1s specific band; (FIG. 2D) effect of ISRIB on XBP1 mRNA splicing; TAQMAN® assays for XBP1 unspliced (XBP1u) and XBP1 spliced (XBP1s) on cDNA synthesized from total RNA extracted from U2OS cells treated with 2 μg/ml of tunicamycin in the presence or absence of 200 nM ISRIB for the indicated times are shown; percent splicing was calculated as the ratio of XBP1s over total XBP1 mRNA (XBP1u+XBP1s).

(FIG. 3A) ISRIB does not block eIF2α phosphorylation upon ER stress; eIF2α phosphorylation was measured using an Alpha-Screen Surefire eIF2α p-S51 assay; U2OS cells were plated in 96 well plates and treated with 2 μg/ml tunicamycin or 100 nM thapsigargin in the presence or absence of 100 nM ISRIB for the indicated times or with ISRIB alone for 120 m (N=4, SD); see FIG. 7A for supporting Western blot analysis of eIF2α phosphorylation; (FIG. 3B) ISRIB blocks global translational attenuation observed after eIF2α phosphorylation during ER stress; HEK293T cells were treated with 100 nM thapsigargin and 200 nM ISRIB for either 1 or 3 h prior to a 20 min pulse with $^{35}$S methionine before lysis; equal amounts of lysate were loaded on an SDS-PAGE gel and quantification of radiolabeled methionine incorporation of lysates was done by gel densitometry (N=2, SD) using Image J; (see FIG. 7B for SDS-PAGE); (FIG. 3C) polysome gradient analysis showing the block in global translational attenuation upon addition of ISRIB on ER-stressed cells; MEFs were grown in the presence or absence of 2 μg/ml of tunicamycin with or without 200 nM ISRIB for 1 h; cell lysates were loaded on a 10-50% sucrose gradient, centrifuged at 150,000×g for 2.4 h and absorbance at 254 nm was measured across the gradient (see FIG. 7C for quantitation of polysome profile); a representative experiment is shown (N=3); (FIG. 3D) cells treated with ISRIB are resistant to the global translational attenuation exerted by forced expression of eIF2α (S51D); HEK293Trex cells were transduced with a tetracycline inducible phospho-mimetic (S51D) allele of eIF2α; transgene expression was induced by addition of 25 nM doxycycline for 14 h in the presence or absence of 200 nM ISRIB; lysates were collected and analyzed as described in (FIG. 3C above (see FIG. 7D for quantitation of polysome profile); a representative experiment is shown (N=2); (FIG. 3E) ISRIB does not reverse global translational attenuation exerted through inhibition of CAP-dependent initiation; wild-type MEFs were treated with 750 nM torin-1 in the presence or absence of 200 nM ISRIB for 2 h; lysates were collected and analyzed as described in FIG. 3C above; a representative experiment is shown (N=2); (FIG. 3F) ISRIB blocks production of ATF4 upon GCN2 or HRI activation; an immunoblot analysis of PERK, ATF4 and total eIF2α in HEK293T cells starved for cysteine and methionine or treated with an HRI activator (6 μM) for 5 h in the presence or absence of 200 nM ISRIB is shown; tunicamycin was used as a positive control for induction of ATF4 and the shift in PERK mobility; under amino acid starvation we consistently observe a partial reduction of ATF4 production by ISRIB by Western blot analysis but observe a complete block in induction of the ATF4 luciferase reporter (see FIG. 7E).

(FIG. 4A) ER-stress dependent induction of CHOP and GADD34 mRNA is impaired in cells treated with ISRIB; qPCR analysis of total RNA extracted from U2OS cells treated with 2 μg/ml of tunicamycin in the presence or absence of 200 nM ISRIB for the indicated times; mRNA levels for each sample were normalized to GAPDH (N=4); P values are derived from a one tail Student's t-test for unpaired samples; statistical significance: CHOP, P=0.0006 (*); GADD34, P=0.0008 (*); (FIG. 4B) ISRIB blocks CHOP production during ER stress; an immunofluorescence analysis of U2OS cells treated with 100 nM thapsigargin for 2 h in the presence or absence of 200 nM ISRIB is shown; a secondary Alexa Dye 488 anti-mouse antibody and rhodamine-phalloidin were used to visualize CHOP and actin, respectively.

(FIG. 5A) ISRIB sensitizes cells to acute ER stress; HEK293T cells were subjected with an acute dose of tunicamycin (2 μg/mL), ISRIB (200 nM) or a combination of both for 24 h; the treated cells were equally diluted to a concentration that would allow single cell clonal expansion and re-seeded onto 6-well plates in a 3-fold dilution series; clonal colonies were visualized by Crystal Violet stain; (FIG. 5B) ISRIB synergizes with ER stress to activate caspase 3/7; Hela cells were plated in 96 well plates and treated with 5 μg/ml of tunicamycin or 500 nM thapsigargin with or without 25 nM ISRIB for the indicated times; caspase3/7 activation was measured using CELLPLAYER™ kinetic caspase 3/7 reagent and cells were imaged in an INCUCYTE™ system; green object count/mm² representing caspase-3/7 activation was measured at 2 h intervals (See FIG. 8A for endpoint quantitation of % cells with activated caspase 3/7); (FIG. 5C) IRE1 oligomers are sustained on ER-stressed cells treated with ISRIB; confocal microscopy micrographs of HEK293Trex cells carrying an inducible GFP-tagged IRE1 allele were treated with 10 nM doxycycline for 24 h to induce the transgene, followed by treatment with 5 μg/ml of tunicamycin in the presence or absence of 200 nM ISRIB for the indicated times; (See FIG. 8B for corresponding XBP1 mRNA splicing data); (FIG. 5D) ATF6 cleavage is sustained in ER-stressed cells treated with ISRIB; immunoblot analysis of ATF6 processing in HEK293Trex cells carrying an inducible FLAG epitope-tagged ATF6; cells were treated with 50 nM doxycycline for 18 h to induce the transgene followed by treatment with 100 nM thapsigargin in the presence or absence of 200 nM ISRIB for the indicated times; total eIF2α is used as a loading control.

(FIG. 6A) escape latencies are significantly shorter in mice treated with ISRIB. Data (means+/−SEM) were obtained in a weak 5 days-long training session in the hidden platform version of the Morris water maze (1 trial per day); mean escape latencies were plotted as a function of training days in mice treated with ISRIB (closed squares, N=8) or vehicle (open circles N=8) (P<0.05, (*)); mice were injected daily with ISRIB immediately after training; (FIG. 6B) after completion of training in the study shown in FIG. 6A above, mice treated with ISRIB (black column) showed a significant preference for the target quadrant (P<0.05, (*)); the probe test was performed 24 h after the last training session; P values are derived from a two-tailed Student's t test for unpaired samples; (FIG. 6C) after completion of training in the study shown in FIG. 6A above, mice treated with ISRIB (black column) increased the number of times they crossed the platform location as compared to the vehicle-treated mice (grey column) (P<0.05, (*)); P values are derived from a two-tailed Student's t test for unpaired samples; (FIG. 6D) chronic systemic administration of ISRIB (intraperitoneally for 4 consecutive days) enhances long-term contextual fear memory (right bars, 24 h), while it does not affect short-term memory (left bars, 1 h) (n=8 per group, p<0.05, (*)); data are presented as mean±SEM; (FIG. 6E) auditory fear conditioning is enhanced in rats treated with ISRIB; freezing in response to a tone was assessed 3 h (short-term memory, STM, left panel) and 24 h (long-term memory, LTM, right panel) after training (vehicle-treated N=8, and ISRIB-treated N=7) after tone presentation (CS) and before tone presentation (pre-CS); for these experiments vehicle or ISRIB was infused directly by cannula into the amygdala after training; ISRIB-infused rats show increase freezing at 24 h (P<0.05, (*)).

(FIG. 7A) ISRIB does not inhibit eIF2α phosphorylation; immunoblot analysis of PERK, ATF4, phospho-eIF2α and total eIF2α in HEK293T cells treated with or without 2 μg/ml of tunicamycin or 100 nM thapsigargin in the presence or absence of 200 nM ISRIB for 3 h; (FIG. 7B) ISRIB blocks translational attenuation upon ER stress; autoradiogram (top) and total protein (bottom) obtained from HEK293T cells that were treated with 100 nM thapsigargin with or without 200 nM ISRIB for either 1 or 3 h prior to a 20 min pulse with $^{35}$S methionine before lysis; equal amounts of lysate were loaded on an SDS-PAGE gel; (FIG. 7C) ISRIB blocks translational attenuation upon ER stress; the polysome profile in FIG. 3C was quantitated by calculating the area under the curve corresponding to the monosome peak (80S), or the area under the curve corresponding to the trace covering the polysome region and then plotted as a ratio over the area under the curve corresponding to the peak of the 60S subunit; (FIG. 7D) ISRIB sustains translation upon expression of eIF2α (S51D); the polysome profile in FIG. 3D was quantitated as described in FIG. 7C; (FIG. 7E) ISRIB blocks induction of the ATF4 luciferase translational reporter upon HRI and GCN2 activation; HEK293T carrying the ATF4 luciferase reporter were treated with 2 μg/ml of tunicamycin to induce ER stress, 6 μM of the HRI activator or grown in media lacking cysteine and methionine for 7 h in the presence or absence of 200 nM ISRIB (N=4); the relative luciferase units are normalized to the no treatment control; using this reporter we observe a smaller fold change in production of luciferase by amino acid starvation that is fully blocked by addition of ISRIB.

(FIG. 8A) ISRIB synergizes with ER-stress to induce caspase 3/7; green object count/mm$^2$ representing caspace-3/7 activation depicted in FIG. 5A was normalized to the total number of cells at two different endpoints; in order to quantify the total number of cells, VYBRANT® DYECYCLE™ Green staining solution (1 µM) was added directly to the well immediately after the Caspase-3/7 scan and incubated for 1 h prior to acquiring final images at both 46 and 72 h; data is presented as % cells with activated caspase 3/7 at these two endpoints; note that by 72 h the ER-stress inducing conditions used in this experiment are so detrimental that they diminish the synergistic effects observed by addition of ISRIB; the synergy was clearly seen at the 46 h time-point; (FIG. 8B) XBP1 splicing is sustained in ER-stressed cells upon addition of ISRIB; HEK293T cells were treated with tunicamycin (2 µg/ml) for the indicated times in the presence or absence of 200 nM ISRIB; (FIG. 8C) RNA was isolated from the cells and reverse transcribed followed by PCR with oligos that amplify both the unspliced and spliced versions of XBP1 mRNA or GAPDH; the DNA was electrophoresed in a 2.5% agarose gel; the asterix (*) denotes a hybrid PCR product.

DETAILED DESCRIPTION OF THE INVENTION

Definitions

Figure 1A:
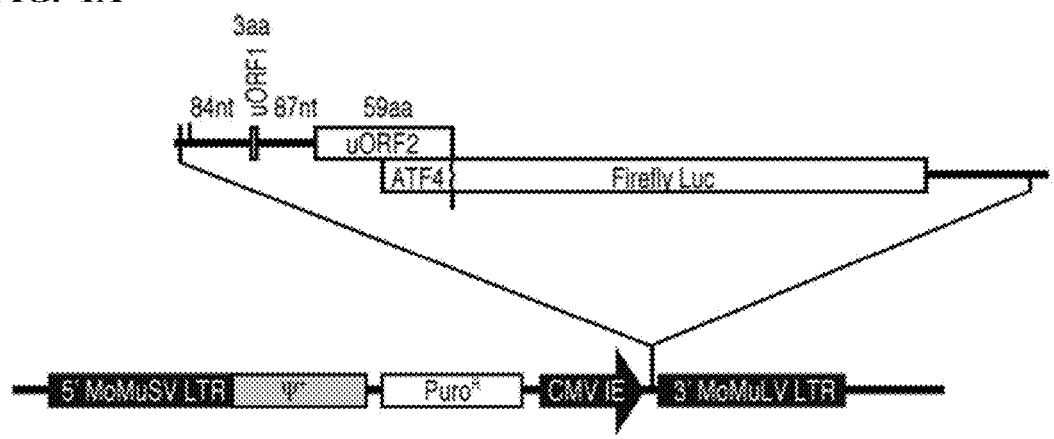
FIGS. 1A-1C. High-throughput cell-based screen for inhibitors of PERK signaling.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a non-cyclic straight (i.e., unbranched) or branched carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —R', —N$_3$, —CH(Ph)$_2$, fluoro($C_1$-$C_4$)alkoxy, and fluoro ($C_1$-$C_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer (e.g. pancreatic cancer, breast cancer, multiple myeloma, cancers of secretory cells), neurodegenerative diseases, vanishing white matter disease, childhood ataxia with CNS hypo-myelination, inflammatory diseases (e.g. postsurgical cognitive dysfunction or traumatic brain injury), and/or intellectual disability syndromes (e.g. associated with impaired function of eIF2 or components in a signal transduction or signaling pathway including eIF2). For example certain methods herein treat cancer by decreasing or reducing or preventing the occurrence, growth, metastasis, or progression of cancer; treat neurodegeneration by improving mental wellbeing, increasing mental function, slowing the decrease of mental function, decreasing dementia, delaying the onset of dementia, improving cognitive skills, decreasing the loss of cognitive skills, improving memory, decreasing the degradation of memory, or extending survival; treat vanishing white matter disease by reducing a symptom of vanishing white matter disease or reducing the loss of white matter or reducing the loss of myelin or increasing the amount of myelin or increasing the amount of white matter; treat childhood ataxia with CNS hypo-myelination by decreasing a symptom of childhood ataxia with CNS hypo-myelination or increasing the level of myelin or decreasing the loss of myelin; treat an intellectual disability syndrome by decreasing a symptom of an intellectual disability syndrome, treat cancer by decreasing a symptom of cancer, treat neurodegeneration by treating a symptom of neurodegeneration; treat an inflammatory disease (e.g. postsurgical cognitive dysfunction or traumatic brain injury) by treating a symptom of the inflammatory disease (e.g. postsurgical cognitive dysfunction or traumatic brain injury). Symptoms of cancer (e.g. pancreatic cancer, breast cancer, multiple myeloma, cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2), or inflammatory diseases (e.g. postsurgical cognitive dysfunction or traumatic brain injury), would be known or may be determined by a person of ordinary skill in the art. The term "treating" and conjugations thereof, include prevention of an injury, pathology, condition, or disease (e.g. preventing the development of one or more symptoms of cancer (e.g. pancreatic cancer, breast cancer, multiple myeloma, cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2), or inflammatory diseases (e.g. postsurgical cognitive dysfunction or traumatic brain injury),).

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein relative to the absence of the antagonist. An "activity increasing amount," as used herein, refers to an amount of agonist (activator) required to increase the activity of an enzyme or protein relative to the absence of the agonist. A "function disrupting amount," as used herein, refers to the amount of antagonist (inhibitor) required to disrupt the function of an enzyme or protein relative to the absence of the antagonist. A "function increasing amount," as used herein, refers to the amount of agonist (activator) required to increase the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Reming-* ton: *The Science and Practice of Pharmacy,* 20th Edition, 2003, Gennaro, Ed., Lippincott, Williams & Wilkins).

The term "associated" or "associated with" in the context of a substance or substance activity or function associated with a disease (e.g cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2)) means that the disease (e.g. cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2)) is caused by (in whole or in part), or a symptom of the disease is caused by (in whole or in part) the substance or substance activity or function. For example, a symptom of a disease or condition associated with an increase in eIF2α activity may be a symptom that results (entirely or partially) from an increase in eIF2α activity (e.g increase in eIF2α phosphorylation or activity of phosphorylated eIF2α or activity of eIF2α or increase in activity of an eIF2α signal transduction or signalling pathway). As used herein, what is described as being associated with a disease, if a causative agent, could be a target for treatment of the disease. For example, a disease associated with increased eIF2α activity or eIF2α pathway activity (e.g. phosphorylated eIF2α activity or pathway), may be treated with an agent (e.g. compound as described herein) effective for decreasing the level of activity of eIF2α activity or eIF2α pathway or phosphorylated eIF2α activity or pathway. For example, a disease associated with phosphorylated eIF2α, may be treated with an agent (e.g. compound as described herein) effective for decreasing the level of activity of phosphorylated eIF2α or a downstream component or effector of phosphorylated eIF2α. For example, a disease associated with eIF2α, may be treated with an agent (e.g. compound as described herein) effective for decreasing the level of activity of eIF2α or a downstream component or effector of eIF2α.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. eIF2α or phosphorylated eIF2α or component of eIF2α pathway or component of phosphorylated eIF2α pathway). In some embodiments contacting includes allowing a compound described herein to interact with a protein or enzyme that is involved in a signaling pathway (e.g. phosphorylated eIF2α pathway or eIF2α pathway).

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a signal transduction pathway or signaling pathway (e.g. eIF2α or phosphorylated eIF2α or eIF2α pathway or phosphorylated eIF2α pathway or pathway activated by eIF2α phosphorylation). Thus, inhibition may include, at least in part, partially or totally decreasing stimulation, decreasing or reducing activation, or inactivating, desensitizing, or down-regulating signal transduction or enzymatic activity or the amount of a protein increased in a disease (e.g. level of eIF2α activity or protein or level or activity of a component of an eIF2α pathway or level of phosphorylated eIF2α activity or protein or level or activity of a component of a phosphorylated eIF2α pathway, wherein each is associated with cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2)) Inhibition may include, at least in part, partially or totally decreasing stimulation, decreasing or reducing activation, or deactivating, desensitizing, or down-regulating signal transduction or enzymatic activity or the amount of a protein (e.g. eIF2α, phosphorylated eIF2α, protein downstream in a pathway from eIF2α, protein downstream in a pathway activated by phosphorylated eIF2α) that may modulate the level of another protein or increase cell survival (e.g. decrease in phosphorylated eIF2α pathway activity may increase cell survival in cells that may or may not have a increase in phosphorylated eIF2α pathway activity relative to a non-disease control or decrease in eIF2α pathway activity may increase cell survival in cells that may or may not have a increase in eIF2α pathway activity relative to a non-disease control).

As defined herein, the term "activation", "activate", "activating" and the like in reference to a protein-activator (e.g. agonist) interaction means positively affecting (e.g. increasing) the activity or function of the protein (e.g. eIF2α, phosphorylated eIF2α, component of pathway including eIF2α, or component of pathway including phosphorylated eIF2α) relative to the activity or function of the protein in the absence of the activator (e.g. compound described herein). In some embodiments, activation refers to an increase in the activity of a signal transduction pathway or signaling pathway (e.g. eIF2α or phosphorylated eIF2α pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. level of eIF2α activity or level of protein or activity decreased by phosphorylation of eIF2α or protein associated with cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2)). Activation may include, at least in part, partially or totally increasing stimulation, increasing or enabling activation, or activating, sensitizing, or up-regulating signal transduction or enzymatic activity or the amount of a protein (e.g. eIF2α, protein downstream of eIF2α, protein activated or upregulated by eIF2α, protein activated or upregulated by phosphorylation of eIF2α) that may modulate the level of another protein or increase cell survival (e.g. increase in eIF2α activity may increase cell survival in cells that may or may not have a reduction in eIF2α activity relative to a non-disease control).

The term "modulator" refers to a composition that increases or decreases the level of a target molecule or the function of a target molecule. In some embodiments, a modulator of eIF2α or eIF2α pathway or phosphorylation of eIF2α or pathway activated by phosphorylation of eIF2α is a compound that reduces the severity of one or more symptoms of a disease associated with eIF2α or eIF2α pathway (e.g. disease associated with an increase in the level of eIF2α activity or protein or eIF2α pathway activity or protein or eIF2α phosphorylation or pathway activated by eIF2α phosphorylation, for example cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2)) or a disease that is not caused by eIF2α or eIF2α pathway but may benefit from modulation of eIF2α or eIF2α pathway activity (e.g. decreasing in level or level of activity of eIF2α or eIF2α pathway). In embodiments, a modulator of eIF2α or eIF2α pathway (e.g. phosphorylated eIF2α or phosphorylated eIF2α pathway) is an anti-cancer agent. In embodiments, a modulator of eIF2α or eIF2α pathway (e.g. phosphorylated eIF2α or phosphorylated eIF2α pathway) is a neuroprotectant. In embodiments, a modulator of eIF2α or eIF2α pathway (e.g. phosphorylated eIF2α or phosphorylated eIF2α pathway) is a memory enhancing agent. In embodiments, a modulator of eIF2α or eIF2α pathway is a long-term memory enhancing agent. In embodiments, a modulator of eIF2α or eIF2α pathway (e.g. phosphorylated eIF2α or phosphorylated eIF2α pathway) is a neuroprotective agent. In embodiments, a modulator of eIF2α or eIF2α pathway (e.g. phosphorylated eIF2α or phosphorylated eIF2α pathway) is an anti-inflammatory agent.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a domesticated animal. In some embodiments, a patient is a dog. In some embodiments, a patient is a parrot. In some embodiments, a patient is livestock animal. In some embodiments, a patient is a mammal. In some embodiments, a patient is a cat. In some embodiments, a patient is a horse. In some embodiments, a patient is bovine. In some embodiments, a patient is a canine. In some embodiments, a patient is a feline. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a hamster. In some embodiments, a patient is a test animal. In some embodiments, a patient is a newborn animal. In some embodiments, a patient is a newborn human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

"Disease" or "condition" refer to a state of being or health status of a patient or subject capable of being treated with a compound, pharmaceutical composition, or method provided herein. In some embodiments, the disease is a disease related to (e.g. caused by) an increase in the level of eIF2α, eIF2α phosphorylation, or eIF2α pathway activity, or pathway activated by phosphorylation of eIF2α. In some embodiments, the disease is a disease related to (e.g. caused by) neurodegeneration. In some embodiments, the disease is a disease related to (e.g. caused by) neural cell death. In some embodiments, the disease is a disease related to (e.g. caused by) a increase in the level of eIF2α activity, eIF2α phosphorylation, eIF2α pathway activity, or phosphorylated eIF2α pathway activity. In some embodiments, the disease is cancer (e.g. pancreatic cancer, breast cancer, multiple myeloma, or cancers of secretory cells). In some embodiments, the disease is a neurodegenerative disease. In some embodiments, the disease is vanishing white matter disease. In some embodiments, the disease is childhood ataxia with CNS hypo-myelination. In some embodiments, the disease is an intellectual disability syndrome (e.g. associated with impaired function of eIF2 or components in a signal transduction pathway including eIF2)). In some embodiments, the disease is an inflammatory disease (e.g. postoperative cognitive dysfunction or traumatic brain injury).

Examples of diseases, disorders, or conditions include, but are not limited to, cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2). In some instances, "disease" or "condition" refers to cancer. In some further instances, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma. In embodiments, a disease is unsatisfactory long-term memory.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the term "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

As used herein, the term "inflammatory disease" refers to a disease or condition characterized by aberrant inflammation (e.g. an increased level of inflammation compared to a control such as a healthy person not suffering from a disease). Examples of inflammatory diseases include postoperative cognitive dysfunction, traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis. Proteins associated with inflammation and inflammatory diseases (e.g. aberrant expression being a symptom or cause or marker of the disease) include interleukin-6 (IL-6), interleukin-8 (IL-8), interleukin-18 (IL-18), TNF-α (tumor necrosis factor-alpha), and C-reactive protein (CRP).

The term "postoperative cognitive dysfunction" refers to a decline in cognitive function (e.g. memory or executive function (e.g. working memory, reasoning, task flexibility, speed of processing, or problem solving)) following surgery.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. eIF2α or component of eIF2α signal transduction pathway or component of phosphorylated eIF2α pathway), and/or reducing, eliminating, or slowing the progression of disease symptoms (e.g. symptoms of cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2)). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2)), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2), or inflammatory diseases (e.g. POCD or TBI), such as surgery.

The term "eIF2alpha" or "eIF2α" refers to the protein "Eukaryotic translation initiation factor 2A". In embodiments, "eIF2alpha" or "eIF2α" refers to the human protein. Included in the term "eIF2alpha" or "eIF2α" are the wild-type and mutant forms of the protein. In embodiments, "eIF2alpha" or "eIF2α" refers to the protein associated with Entrez Gene 83939, OMIM 609234, UniProt Q9BY44, and/or RefSeq (protein) NP_114414. In embodiments, the reference numbers immediately above refer to the protein, and associated nucleic acids, known as of the date of filing of this application.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (GLEEVEC®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. TAXOL™ (i.e. paclitaxel), TAXOTERE™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Methods of Treatment

In a first aspect is provided a method of treating an integrated stress response-associated disease in a patient in need of such treatment, the method including administering a therapeutically effective amount of a compound, or a pharmaceutically acceptable salt thereof, to the patient, wherein the compound has the formula:

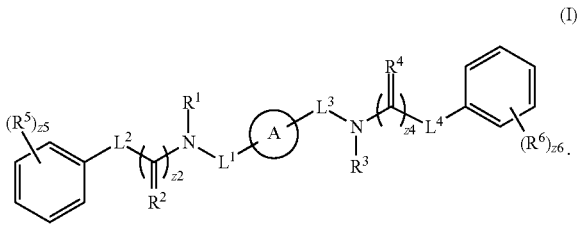

(I)

Ring A is substituted or unsubstituted cycloalkylene or substituted or unsubstituted arylene. $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently ═NR$^7$, ═O, or ═S; z2 and z4 are independently 0 or 1; and z5 and z6 are independently an integer from 0 to 5.

In embodiments, the integrated stress response-associated disease is cancer. In embodiments, the integrated stress response-associated disease is a neurodegenerative disease. In embodiments, the integrated stress response-associated disease is vanishing white matter disease. In embodiments, the integrated stress response-associated disease is childhood ataxia with CNS hypo-myelination. In embodiments, the integrated stress response-associated disease is an intellectual disability syndrome.

In another aspect is provided a method of treating a disease associated with phosphorylation of eIF2α in a patient in need of such treatment, the method including administering a therapeutically effective amount of a compound, or a pharmaceutically acceptable salt thereof, to the patient, wherein the compound has the formula:

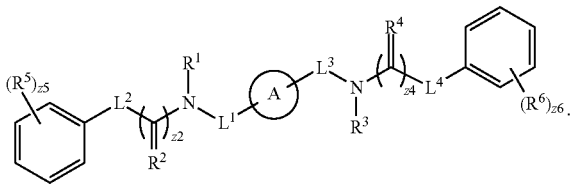

(I)

Ring A is substituted or unsubstituted cycloalkylene or substituted or unsubstituted arylene. $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently ═NR$^7$, ═O, or ═S; z2 and z4 are independently 0 or 1; and z5 and z6 are independently an integer from 0 to 5.

In embodiments, the disease associated with phosphorylation of eIF2α is cancer. In embodiments, the disease associated with phosphorylation of eIF2α is a neurodegenerative disease. In embodiments, the disease associated with phosphorylation of eIF2α is vanishing white matter disease. In embodiments, the disease associated with phosphorylation of eIF2α is childhood ataxia with CNS hypo-myelination. In embodiments, the disease associated with phosphorylation of eIF2α is an intellectual disability syndrome In another aspect is provided a method of treating a disease in a patient in need of such treatment, the method including administering a therapeutically effective amount of a compound to the patient, wherein the disease is selected from the group consisting of cancer, a neurodegenerative disease, vanishing white matter disease, childhood ataxia with CNS hypo-myelination, and an intellectual disability syndrome; and wherein the compound has the formula:

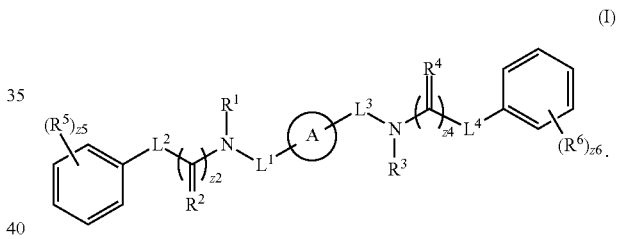

(I)

Ring A is substituted or unsubstituted cycloalkylene or substituted or unsubstituted arylene. $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently ═NR$^7$, ═O, or ═S; z2 and z4 are independently 0 or 1; and z5 and z6 are independently an integer from 0 to 5.

In embodiments, the disease is cancer. In embodiments, the disease is a neurodegenerative disease. In embodiments, the disease is vanishing white matter disease. In embodiments, the disease is childhood ataxia with CNS hypo-myelination. In embodiments, the disease is an intellectual disability syndrome In another aspect is provided a method of treating an inflammatory disease in a patient in need of such treatment, the method including administering a therapeutically effective amount of a compound, or a pharmaceutically acceptable salt thereof, to the patient, wherein the compound has the formula:

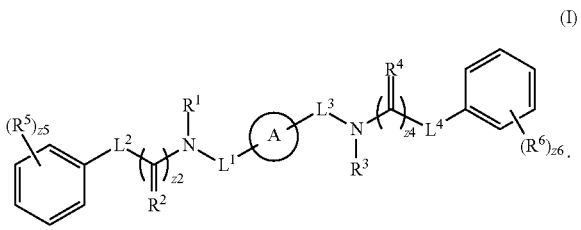

(I)

Ring A is substituted or unsubstituted cycloalkylene or substituted or unsubstituted arylene. $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently =NR$^7$, =O, or =S; z2 and z4 are independently 0 or 1; and z5 and z6 are independently an integer from 0 to 5.

In embodiments, the inflammatory disease is associated with neurological inflammation. In embodiments, the inflammatory disease is postoperative cognitive dysfunction. In embodiments, the inflammatory disease is traumatic brain injury.

The embodiments described herein below may be applied to any of the methods of treatment described herein.

In embodiments, ring A is substituted or unsubstituted cycloalkylene. In embodiments, ring A is substituted or unsubstituted C$_3$-C$_8$ cycloalkylene. In embodiments, ring A is substituted or unsubstituted C$_3$-C$_6$ cycloalkylene. In embodiments, ring A is substituted or unsubstituted C$_3$-C$_4$ cycloalkylene. In embodiments, ring A is substituted or unsubstituted C$_4$-C$_8$ cycloalkylene. In embodiments, ring A is substituted or unsubstituted C$_4$-C$_6$ cycloalkylene. In embodiments, ring A is substituted or unsubstituted cyclohexylene. In embodiments, ring A is substituted or unsubstituted cyclobutylene. In embodiments, ring A is substituted or unsubstituted cyclopentylene. In embodiments, ring A is substituted or unsubstituted C$_4$-C$_6$ cycloalkenylene. In embodiments, ring A is unsubstituted cycloalkylene. In embodiments, ring A is unsubstituted C$_3$-C$_8$ cycloalkylene. In embodiments, ring A is unsubstituted C$_3$-C$_6$ cycloalkylene. In embodiments, ring A is unsubstituted C$_3$-C$_4$ cycloalkylene. In embodiments, ring A is unsubstituted C$_4$-C$_8$ cycloalkylene. In embodiments, ring A is unsubstituted C$_4$-C$_6$ cycloalkylene. In embodiments, ring A is unsubstituted cyclohexylene. In embodiments, ring A is unsubstituted cyclobutylene. In embodiments, ring A is unsubstituted cyclopentylene. In embodiments, ring A is unsubstituted C$_4$-C$_6$ cycloalkenylene. In embodiments, ring A is substituted or unsubstituted arylene. In embodiments, ring A is substituted or unsubstituted C$_6$-C$_{10}$ arylene. In embodiments, ring A is substituted or unsubstituted phenylene. In embodiments, ring A is substituted or unsubstituted naphthylene. In embodiments, ring A is unsubstituted C$_6$-C$_{10}$ arylene. In embodiments, ring A is unsubstituted phenylene. In embodiments, ring A is unsubstituted naphthylene. It is understood that when ring A is unsubstituted, it does not include additional substituents in addition to the bonds explicitly shown in the formula of interest (e.g. formula I, Ia, etc.).

$L^1$ may be a bond or substituted or unsubstituted alkylene. $L^1$ may be substituted or unsubstituted C$_1$-C$_5$ alkylene. $L^1$ may be substituted or unsubstituted C$_1$-C$_3$ alkylene. $L^1$ may be substituted or unsubstituted methylene. $L^1$ may be a bond. $L^1$ may be an unsubstituted alkylene. $L^1$ may be an unsubstituted methylene. $L^1$ may be an unsubstituted ethylene. $L^1$ may be a methylene substituted with an unsubstituted alkyl $L^1$ may be a methylene substituted with an unsubstituted C$_1$-C$_4$ alkyl $L^1$ may be a methylene substituted with an unsubstituted C$_1$-C$_3$ alkyl.

$L^3$ may be a bond or substituted or unsubstituted alkylene. $L^3$ may be substituted or unsubstituted C$_1$-C$_5$ alkylene. $L^3$ may be substituted or unsubstituted C$_1$-C$_3$ alkylene. $L^3$ may be substituted or unsubstituted methylene. $L^3$ may be a bond. $L^3$ may be an unsubstituted alkylene. $L^3$ may be an unsubstituted methylene. $L^3$ may be an unsubstituted ethylene. $L^3$ may be a methylene substituted with an unsubstituted alkyl $L^3$ may be a methylene substituted with an unsubstituted C$_1$-C$_4$ alkyl $L^3$ may be a methylene substituted with an unsubstituted C$_1$-C$_3$ alkyl. In embodiments, $L^1$ and $L^3$ may be a bond. In embodiments, $L^1$ and $L^3$ may independently be an unsubstituted alkylene. In embodiments, $L^1$ and $L^3$ may be an unsubstituted methylene.

In embodiments, $R^1$ is hydrogen. In embodiments, $R^1$ is —CH$_2$CCH. In embodiments, $R^1$ is

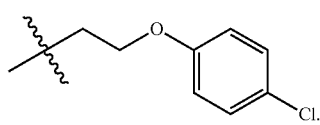 [SMILES: *CCOc1ccc(Cl)cc1]

In embodiments, $R^1$ is

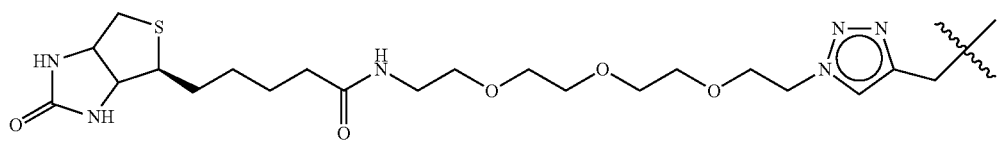

.

In embodiments, R¹ is

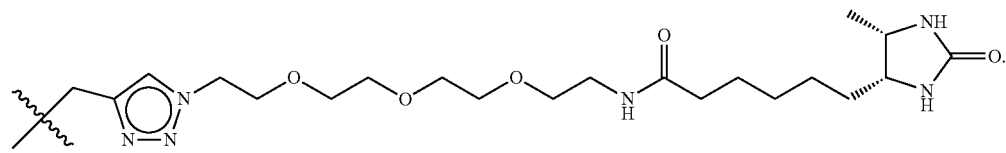

In embodiments, R¹ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R¹ is substituted or unsubstituted alkyl. In embodiments, R¹ is substituted or unsubstituted $C_1$-$C_8$ alkyl. In embodiments, R¹ is substituted or unsubstituted $C_1$-$C_6$ alkyl. In embodiments, R¹ is substituted or unsubstituted $C_1$-$C_4$ alkyl. In embodiments, R¹ is unsubstituted alkyl. In embodiments, R¹ is unsubstituted $C_1$-$C_8$ alkyl. In embodiments, R¹ is unsubstituted $C_1$-$C_6$ alkyl. In embodiments, R¹ is unsubstituted $C_1$-$C_4$ alkyl. In embodiments, R¹ is substituted or unsubstituted heteroalkyl. In embodiments, R¹ is substituted or unsubstituted 2 to 8 membered heteroalkyl. In embodiments, R¹ is unsubstituted 2 to 8 membered heteroalkyl.

In embodiments, R³ is hydrogen. In embodiments, R³ is —CH₂CCH. In embodiments, R³ is

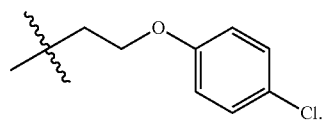

In embodiments, R³ is

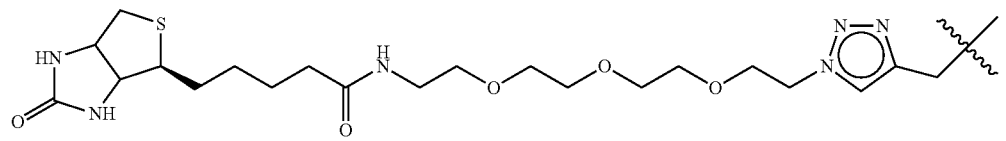

In embodiments, R³ is

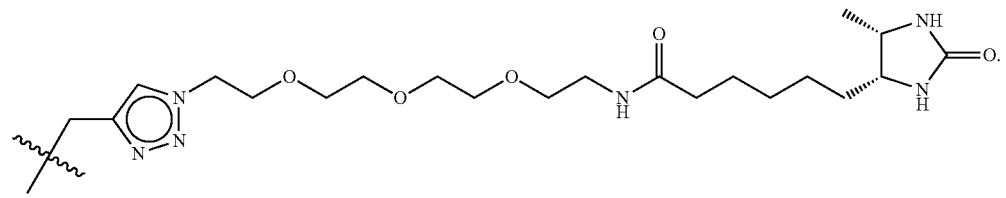

In embodiments, R³ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R³ is substituted or unsubstituted alkyl. In embodiments, R³ is substituted or unsubstituted $C_1$-$C_8$ alkyl. In embodiments, R³ is substituted or unsubstituted $C_1$-$C_6$ alkyl. In embodiments, R³ is substituted or unsubstituted $C_1$-$C_4$ alkyl. In embodiments, R³ is unsubstituted alkyl. In embodiments, R³ is unsubstituted $C_1$-$C_8$ alkyl. In embodiments, R³ is unsubstituted $C_1$-$C_6$ alkyl. In embodiments, R³ is unsubstituted $C_1$-$C_4$ alkyl. In embodiments, R³ is substituted or unsubstituted heteroalkyl. In embodiments, R³ is substituted or unsubstituted 2 to 8 membered heteroalkyl. In embodiments, R³ is unsubstituted 2 to 8 membered heteroalkyl.

In embodiments, R⁵ is independently halogen, —OCH₃, —OCH₂Ph, —C(O)Ph, —CH₃, —CF₃, —CCl₃, —CN, —S(O)CH₃, —OH, —NH₂, —COOH, —CONH₂, —NO₂, —C(O)CH₃, —CH(CH₃)₂, —CCSi(CH₃)₃, —CCH, —CH₂CCH, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)OH, —NHOH, —OCH₃, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R⁵ is independently halogen, —OCH₃, —OCH₂Ph, —CH₃, —OH, —CF₃, —CCl₃, —CN, —S(O)CH₃, —NO₂, —C(O)CH₃, —C(O)Ph, —CH(CH₃)₂, —CCSi(CH₃)₃, or —CCH. In embodiments, R⁵ is —F. In embodiments, R⁵ is —Cl. In embodiments, R⁵ is —Br. In embodiments, R⁵ is —I. In embodiments, R⁵ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R⁵ is unsubstituted alkyl, unsubstituted heteroalkyl, unsubstituted cycloalkyl, unsubstituted heterocycloalkyl, unsubstituted aryl, or unsubstituted heteroaryl. In embodiments, R⁵ is —OCH₃. In embodiments, R⁵ is —OCH₂Ph. In embodiments, R⁵ is —CH₃. In embodiments, R⁵ is —OH. In embodiments, R⁵ is —CF₃. In embodiments, R⁵ is —CCl₃. In embodiments, R⁵ is —CN. In embodiments, $R^5$ is —S(O)CH$_3$. In embodiments, $R^5$ is —NO$_2$. In embodiments, $R^5$ is —C(O)CH$_3$. In embodiments, $R^5$ is —C(O)Ph. In embodiments, $R^5$ is —CH(CH$_3$)$_2$. In embodiments, $R^5$ is —CCSi(CH$_3$)$_3$. In embodiments, $R^5$ is —C(NN)CF$_3$. In embodiments, $R^5$ is —C(NH—NH)CF$_3$. In embodiments, $R^5$ is —CCH. In embodiments, $R^5$ is —CH$_2$CCH. In embodiments, $R^5$ is —SH. In embodiments, $R^5$ is —SO$_2$Cl. In embodiments, $R^5$ is —SO$_3$H. In embodiments, $R^5$ is —SO$_4$H. In embodiments, $R^5$ is —SO$_2$NH$_2$. In embodiments, $R^5$ is —NHNH$_2$. In embodiments, $R^5$ is —ONH$_2$. In embodiments, $R^5$ is —NHC═(O)NHNH$_2$. In embodiments, $R^5$ is —NHC═(O)NH$_2$. In embodiments, $R^5$ is —NHSO$_2$H. In embodiments, $R^5$ is —NHC═(O)H. In embodiments, $R^5$ is —NHC(O)OH. In embodiments, $R^5$ is —NHOH. In embodiments, $R^5$ is —OCH$_3$. In embodiments, $R^5$ is —OCF$_3$. In embodiments, $R^5$ is —OCHF$_2$. In embodiments, $R^5$ is —N$_3$. In embodiments, $R^5$ is eroalkyl, substituted or unsubstituted cycloalkyl, substituted or unsubstituted heterocycloalkyl, substituted or unsubstituted aryl, or substituted or unsubstituted heteroaryl. In embodiments, $R^6$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^6$ is —OCH$_3$. In embodiments, $R^6$ is —OCH$_2$Ph. In embodiments, $R^6$ is —CH$_3$. In embodiments, $R^6$ is —OH. In embodiments, $R^6$ is —CF$_3$. In embodiments, $R^6$ is —CCl$_3$. In embodiments, $R^6$ is —CN. In embodiments, $R^6$ is —S(O)CH$_3$. In embodiments, $R^6$ is —NO$_2$. In embodiments, $R^6$ is —C(O)CH$_3$. In embodiments, $R^6$ is —C(O)Ph. In embodiments, $R^6$ is —CH(CH$_3$)$_2$. In embodiments, $R^6$ is —CCSi(CH$_3$)$_3$. In embodiments, $R^6$ is —C(NN)CF$_3$. In embodiments, $R^6$ is —C(NH—NH)CF$_3$. In embodiments, $R^6$ is —CCH. In embodiments, $R^6$ is —CH$_2$CCH. In

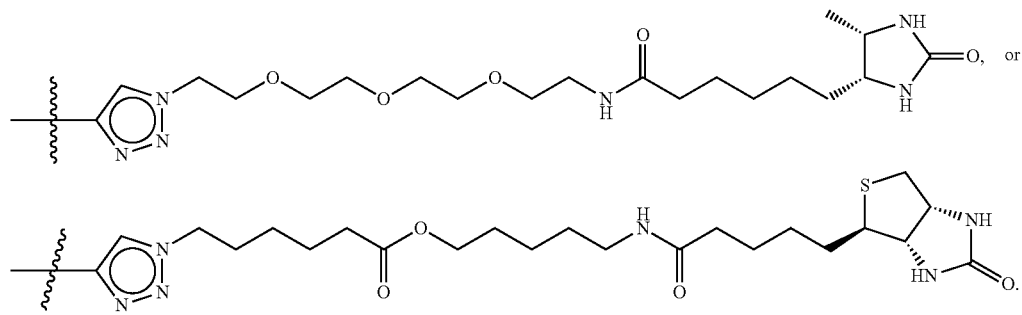

In embodiments, $R^6$ is independently halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is independently halogen, —OCH$_3$, embodiments, $R^6$ is —SH. In embodiments, $R^6$ is —SO$_2$Cl. In embodiments, $R^6$ is —SO$_3$H. In embodiments, $R^6$ is —SO$_4$H. In embodiments, $R^6$ is —SO$_2$NH$_2$. In embodiments, $R^6$ is —NHNH$_2$. In embodiments, $R^6$ is —ONH$_2$. In embodiments, $R^6$ is —NHC═(O)NHNH$_2$. In embodiments, $R^6$ is —NHC═(O)NH$_2$. In embodiments, $R^6$ is —NHSO$_2$H. In embodiments, $R^6$ is —NHC═(O)H. In embodiments, $R^6$ is —NHC(O)OH. In embodiments, $R^6$ is —NHOH. In embodiments, $R^6$ is —OCH$_3$. In embodiments, $R^6$ is —OCF$_3$. In embodiments, $R^6$ is —OCHF$_2$. In embodiments, $R^6$ is —N$_3$. In embodiments, $R^6$ is

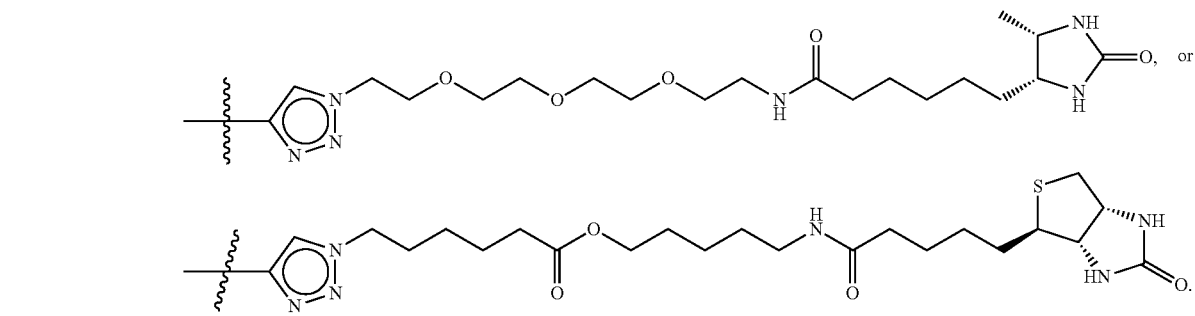

—OCH$_2$Ph, —CH$_3$, —OH, —CF$_3$, —CCl$_3$, —CN, —S(O)CH$_3$, —NO$_2$, —C(O)CH$_3$, —C(O)Ph, —CH(CH$_3$)$_2$, —CCSi(CH$_3$)$_3$, or —CCH. In embodiments, $R^6$ is —F. In embodiments, $R^6$ is —Cl. In embodiments, $R^6$ is —Br. In embodiments, $R^6$ is —I. In embodiments, $R^6$ is substituted or unsubstituted alkyl, substituted or unsubstituted het- In embodiments, $R^7$ is independently hydrogen. In embodiments, $R^7$ is independently halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^7$ is independently unsubstituted alkyl, unsubstituted heteroalkyl, unsubstituted cycloalkyl, unsubstituted heterocycloalkyl, unsubstituted aryl, or unsubstituted heteroaryl. In embodiments, R$^7$ is independently substituted or unsubstituted C$_1$-C$_8$ alkyl. In embodiments, R$^7$ is independently substituted or unsubstituted C$_1$-C$_6$ alkyl. In embodiments, R$^7$ is independently substituted or unsubstituted C$_1$-C$_4$ alkyl. In embodiments, R$^7$ is independently unsubstituted C$_1$-C$_8$ alkyl. In embodiments, R$^7$ is independently unsubstituted C$_1$-C$_6$ alkyl. In embodiments, R$^7$ is independently unsubstituted C$_1$-C$_4$ alkyl. In embodiments, R$^7$ is independently unsubstituted methyl.

In embodiments, R$^2$ is =NR$^7$. In embodiments, R$^2$ is =NH. In embodiments, R$^2$ is =O. In embodiments, R$^2$ is =S. In embodiments, R$^4$ is =NR$^7$. In embodiments, R$^4$ is =NH. In embodiments, R$^4$ is =O. In embodiments, R$^4$ is =S. In embodiments, R$^2$ and R$^4$ are =NH. In embodiments, R$^2$ and R$^4$ are =O. In embodiments, R$^2$ and R$^4$ are =S. In embodiments, R$^2$ and R$^4$ are =NR$^7$.

In embodiments, L$^2$ is a bond. In embodiments, L$^2$ is a substituted or unsubstituted alkylene. In embodiments, L$^2$ is a substituted or unsubstituted heteroalkylene. In embodiments, L$^2$ is L$^{2A}$-L$^{2B}$-L$^{2C}$ and L$^{2A}$ is bonded to the substituted or unsubstituted phenyl, which may be substituted with R$^5$. L$^{2A}$ is a bond, —O—, —S—, —NH—, —S(O)—, or —S(O)$_2$—. L$^{2B}$ is a bond or substituted or unsubstituted alkylene. L$^{2C}$ is a bond, —O—, or —NH—. In embodiments, L$^{2A}$ is a bond. In embodiments, L$^{2A}$ is —O—. In embodiments, L$^{2A}$ is —S—. In embodiments, L$^{2A}$ is —NH—. In embodiments, L$^{2A}$ is —S(O)—. In embodiments, L$^{2A}$ is —S(O)$_2$—. In embodiments, L$^{2B}$ is a bond. In embodiments, L$^{2B}$ is a substituted or unsubstituted alkylene. In embodiments, L$^{2B}$ is an unsubstituted alkylene. In embodiments, L$^{2B}$ is a substituted or unsubstituted C$_1$-C$_8$ alkylene. In embodiments, L$^{2B}$ is an unsubstituted C$_1$-C$_8$ alkylene. In embodiments, L$^{2B}$ is a substituted or unsubstituted C$_1$-C$_6$ alkylene. In embodiments, L$^{2B}$ is an unsubstituted C$_1$-C$_6$ alkylene. In embodiments, L$^{2B}$ is a substituted or unsubstituted C$_1$-C$_4$ alkylene. In embodiments, L$^{2B}$ is an unsubstituted alkylene. In embodiments, L$^{2B}$ is a substituted alkylene. In embodiments, L$^{2B}$ is a substituted C$_1$-C$_8$ alkylene. In embodiments, L$^{2B}$ is a substituted C$_1$-C$_6$ alkylene. In embodiments, L$^{2B}$ is a substituted C$_1$-C$_4$ alkylene. In embodiments, L$^{2B}$ is an alkylene substituted with —CF$_3$. In embodiments, L$^{2C}$ is a bond. In embodiments, L$^{2C}$ is —O—. In embodiments, L$^{2C}$ is —NH—. In embodiments, L$^{2A}$ is a bond; L$^{2B}$ is unsubstituted methylene; and L$^{2C}$ is —O—.

In embodiments, L$^4$ is a bond. In embodiments, L$^4$ is a substituted or unsubstituted alkylene. In embodiments, L$^4$ is a substituted or unsubstituted heteroalkylene. In embodiments, L$^4$ is L$^{4A}$-L$^{4B}$-L$^{4C}$ and L$^{4A}$ is bonded to the substituted or unsubstituted phenyl, which may be substituted with R$^6$. L$^{4A}$ is a bond, —O—, —S—, —NH—, —S(O)—, or —S(O)$_2$—. L$^{4B}$ is a bond or substituted or unsubstituted alkylene. L$^{4C}$ is a bond, —O—, or —NH—. In embodiments, L$^{4A}$ is a bond. In embodiments, L$^{4A}$ is —O—. In embodiments, L$^{4A}$ is —S—. In embodiments, L$^{4A}$ is —NH—. In embodiments, L$^{4A}$ is —S(O)—. In embodiments, L$^{4A}$ is —S(O)$_2$—. In embodiments, L$^{4B}$ is a bond. In embodiments, L$^{4B}$ is a substituted or unsubstituted alkylene. In embodiments, L$^{4B}$ is an unsubstituted alkylene. In embodiments, L$^{4B}$ is a substituted or unsubstituted C$_1$-C$_8$ alkylene. In embodiments, L$^{4B}$ is an unsubstituted C$_1$-C$_8$ alkylene. In embodiments, L$^{4B}$ is a substituted or unsubstituted C$_1$-C$_6$ alkylene. In embodiments, L$^{4B}$ is an unsubstituted C$_1$-C$_6$ alkylene. In embodiments, L$^{4B}$ is a substituted or unsubstituted C$_1$-C$_4$ alkylene. In embodiments, L$^{4B}$ is an unsubstituted alkylene. In embodiments, L$^{4B}$ is a substituted alkylene. In embodiments, L$^{4B}$ is a substituted C$_1$-C$_8$ alkylene. In embodiments, L$^{4B}$ is a substituted C$_1$-C$_6$ alkylene. In embodiments, L$^{4B}$ is a substituted C$_1$-C$_4$ alkylene. In embodiments, L$^{4B}$ is an alkylene substituted with —CF$_3$. In embodiments, L$^{4C}$ is a bond. In embodiments, L$^{4C}$ is —O—. In embodiments, L$^{4C}$ is —NH—. In embodiments, L$^{4A}$ is a bond; L$^{4B}$ is unsubstituted methylene; and L$^{4C}$ is —O—.

In embodiments, the symbol z2 is 0. In embodiments, the symbol z2 is 1. In embodiments, the symbol z4 is 0. In embodiments, the symbol z4 is 1. In embodiments, the symbols z2 and z4 are 0. In embodiments, the symbols z2 and z4 are 1. In embodiments, the symbol z5 is 0. In embodiments, the symbol z5 is 1. In embodiments, the symbol z5 is 2. In embodiments, the symbol z5 is 3. In embodiments, the symbol z5 is 4. In embodiments, the symbol z5 is 5. In embodiments, the symbol z6 is 0. In embodiments, the symbol z6 is 1. In embodiments, the symbol z6 is 2. In embodiments, the symbol z6 is 3. In embodiments, the symbol z6 is 4. In embodiments, the symbol z6 is 5.

In embodiment, L$^1$ is a bond. In embodiment, L$^1$ is —CH$_2$—. In embodiment, L$^1$ is —O—. In embodiment, L$^1$ is —S—. In embodiment, L$^1$ is —NH—. In embodiment, L$^2$ is a bond. In embodiment, L$^2$ is —CH$_2$—. In embodiment, L$^2$ is —O—. In embodiment, L$^2$ is —S—. In embodiment, L$^2$ is —NH—. In embodiment, L$^3$ is —CH$_2$O—. In embodiment, L$^3$ is —OCH$_2$—. In embodiment, L$^3$ is —CH$_2$—. In embodiment, L$^3$ is a bond. In embodiment, L$^3$ is —CH$_2$CH$_2$—. In embodiment, L$^3$ is —CH$_2$CH$_2$O—. In embodiment, L$^3$ is —OCH2CH2-. In embodiment, L$^3$ is —CH$_2$S—. In embodiment, L$^3$ is —SCH$_2$—. In embodiment, L$^3$ is —CH$_2$S(O)—. In embodiment, L$^3$ is —S(O)CH$_2$—. In embodiment, L$^3$ is —CH$_2$S(O)$_2$—. In embodiment, L$^3$ is —S(O)$_2$CH$_2$—. In embodiment, L$^3$ is —CH$_2$NH—. In embodiment, L$^3$ is —NHCH$_2$—. In embodiment, L$^3$ is —CH(CH$_3$)O—. In embodiment, L$^3$ is —OCH(CH$_3$)—. In embodiment, L$^3$ is —O—. In embodiment, L$^3$ is —S—. In embodiment, L$^3$ is —NH—. In embodiment, L$^4$ is —CH2O—. In embodiment, L$^4$ is —OCH$_2$—. In embodiment, L$^4$ is —CH$_2$—. In embodiment, L$^4$ is a bond. In embodiment, L$^4$ is —CH$_2$CH$_2$—. In embodiment, L$^4$ is —CH$_2$CH$_2$O—. In embodiment, L$^4$ is —OCH$_2$CH$_2$—. In embodiment, L$^4$ is —CH$_2$S—. In embodiment, L$^4$ is —SCH$_2$—. In embodiment, L$^4$ is —CH$_2$S(O)—. In embodiment, L$^4$ is —S(O)CH$_2$—. In embodiment, L$^4$ is —CH$_2$S(O)$_2$—. In embodiment, L$^4$ is —S(O)$_2$CH$_2$—. In embodiment, L$^4$ is —CH$_2$NH—. In embodiment, L$^4$ is —NHCH$_2$—. In embodiment, L$^4$ is —CH(CH$_3$)O—. In embodiment, L$^4$ is —OCH(CH$_3$)—. In embodiment, L$^4$ is —O—. In embodiment, L$^4$ is —S—. In embodiment, L$^4$ is —NH—.

In embodiments, the compound has the formula:

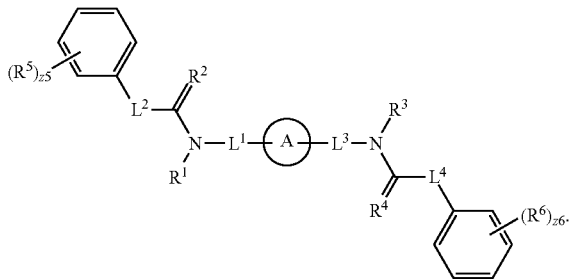
(Ia)

Ring A, $L^1$, $L^2$, $L^3$, $L^4$, $R^1$, $R^2$, $R^3$, $R^4$, $R^5$, $R^6$, $R^7$, z5, and z6 are as described for compounds of formula (I) above, including embodiments.

In embodiments, the compound has the formula:

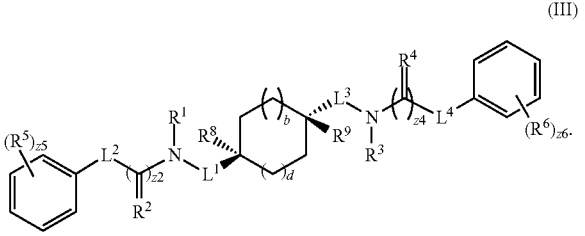
(III)

$L^1$, $L^2$, $L^3$, $L^4$, $R^1$, $R^2$, $R^3$, $R^4$, $R^5$, $R^6$, $R^7$, z2, z4, z5, and z6 are as described for compounds of formula (I) above, including embodiments. $R^8$ and $R^9$ are independently hydrogen, halogen, —$OCH_3$, —$OCH_2Ph$, —C(O)Ph, —$CH_3$, —$CF_3$, —$CCl_3$, —CN, —S(O)$CH_3$, —OH, —$NH_2$, —COOH, —$CONH_2$, —$NO_2$, —C(O)$CH_3$, —CH($CH_3$)$_2$, —CCSi($CH_3$)$_3$, —CCH, —$CH_2$CCH, —SH, —$SO_2$Cl, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)—OH, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols b and d are independently 0 or 1.

In embodiments, $R^8$ is hydrogen. In embodiments, $R^8$ is substituted or unsubstituted alkyl. In embodiments, $R^8$ is substituted or unsubstituted $C_1$-$C_8$ alkyl. In embodiments, $R^8$ is substituted or unsubstituted $C_1$-$C_6$ alkyl. In embodiments, $R^8$ is substituted or unsubstituted $C_1$-$C_4$ alkyl. In embodiments, $R^8$ is substituted or unsubstituted $C_1$-$C_3$ alkyl. In embodiments, $R^8$ is substituted or unsubstituted $C_1$-$C_8$ alkenyl. In embodiments, $R^8$ is substituted or unsubstituted $C_1$-$C_8$ alkynyl. In embodiments, $R^8$ is substituted or unsubstituted alkenyl. In embodiments, $R^8$ is substituted or unsubstituted alkynyl. In embodiments, $R^8$ is unsubstituted alkyl. In embodiments, $R^8$ is unsubstituted $C_1$-$C_8$ alkyl. In embodiments, $R^8$ is unsubstituted $C_1$-$C_6$ alkyl. In embodiments, $R^8$ is unsubstituted $C_1$-$C_4$ alkyl. In embodiments, $R^8$ is unsubstituted $C_1$-$C_3$ alkyl. In embodiments, $R^8$ is unsubstituted $C_1$-$C_8$ alkenyl. In embodiments, $R^8$ is unsubstituted $C_1$-$C_8$ alkynyl. In embodiments, $R^8$ is unsubstituted $C_1$-$C_4$ alkenyl. In embodiments, $R^8$ is unsubstituted alkynyl. In embodiments, $R^8$ is —CCH. In embodiments, $R^8$ is

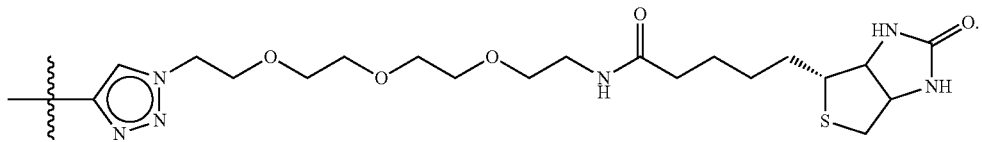

In embodiments, $R^8$ is

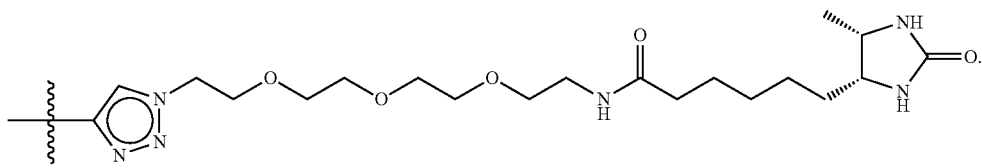

In embodiments, $R^9$ is hydrogen. In embodiments, $R^9$ is substituted or unsubstituted alkyl. In embodiments, $R^9$ is substituted or unsubstituted $C_1$-$C_8$ alkyl. In embodiments, $R^9$ is substituted or unsubstituted $C_1$-$C_6$ alkyl. In embodiments, $R^9$ is substituted or unsubstituted $C_1$-$C_4$ alkyl. In embodiments, $R^9$ is substituted or unsubstituted $C_1$-$C_3$ alkyl. In embodiments, $R^9$ is substituted or unsubstituted $C_1$-$C_8$ alkenyl. In embodiments, $R^9$ is substituted or unsubstituted $C_1$-$C_8$ alkynyl. In embodiments, $R^9$ is substituted or unsubstituted $C_1$-$C_4$ alkenyl. In embodiments, $R^9$ is substituted or unsubstituted alkynyl. In embodiments, $R^9$ is unsubstituted alkyl. In embodiments, $R^9$ is unsubstituted $C_1$-$C_8$ alkyl. In embodiments, $R^9$ is unsubstituted $C_1$-$C_6$ alkyl. In embodiments, $R^9$ is unsubstituted $C_1$-$C_4$ alkyl. In embodiments, $R^9$ is unsubstituted $C_1$-$C_3$ alkyl. In embodiments, $R^9$ is unsubstituted $C_1$-$C_8$ alkenyl. In embodiments, $R^9$ is unsubstituted $C_1$-$C_8$ alkynyl. In embodiments, $R^9$ is unsubstituted $C_1$-$C_4$ alkenyl. In embodiments, $R^9$ is unsubstituted alkynyl. In embodiments, $R^9$ is —CCH. In embodiments, $R^9$ is

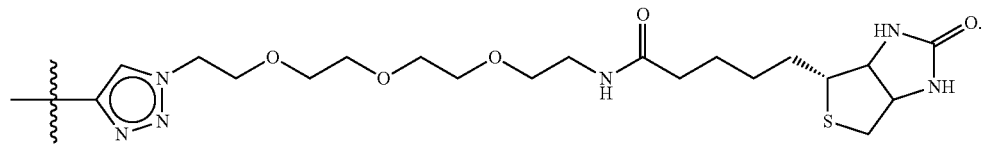

In embodiments, $R^9$ is

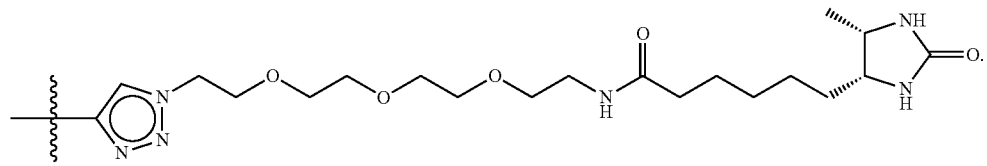

In embodiments, $R^8$ and $R^9$ are hydrogen.

In embodiments, the symbol b is 0. In embodiments, the symbol b is 1. In embodiments, the symbol d is 0. In embodiments, the symbol d is 1. In embodiments, the symbols b and d are 0. In embodiments, the symbols b and d are 1. In embodiments, the symbol b is 0 and d is 1. In embodiments, the symbol b is 1 and d is 0.

In embodiments, the compound has the formula:

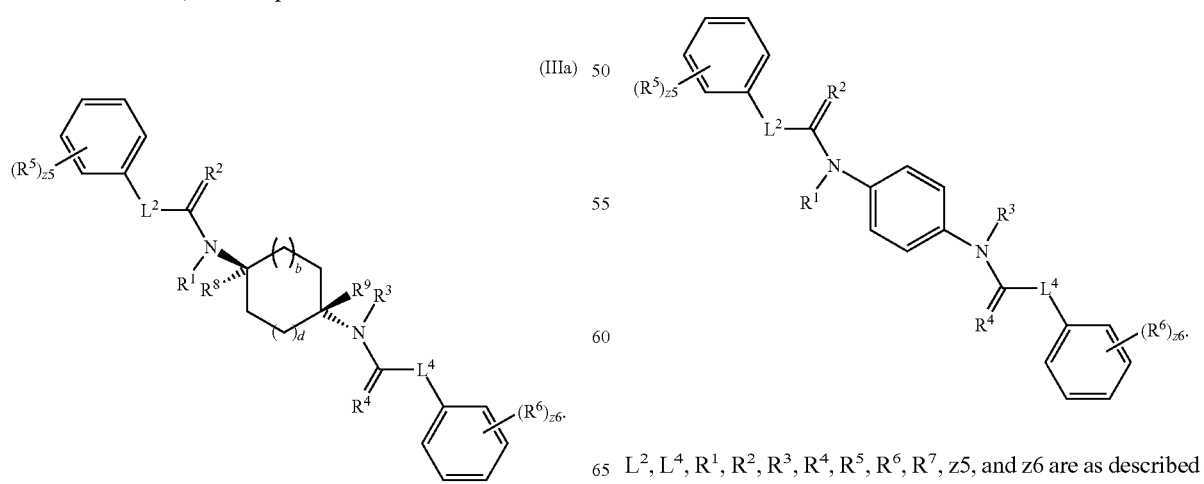

$L^2$, $L^4$, $R^1$, $R^2$, $R^3$, $R^4$, $R^5$, $R^6$, $R^7$, $R^8$, $R^9$, b, d, z5, and z6 are as described for compounds of formula (I), (Ia), and (III) above, including embodiments.

In embodiments, the compound has the formula:

$L^2$, $L^4$, $R^1$, $R^2$, $R^3$, $R^4$, $R^5$, $R^6$, $R^7$, z5, and z6 are as described for compounds of formula (I), (Ia), (III), and (IIIa) above, including embodiments.

In embodiments, the compound has the formula:

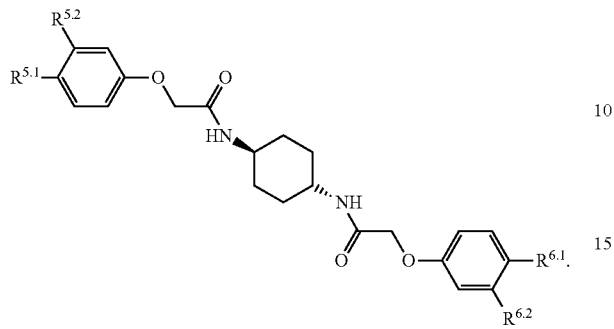

(IIIb)

$R^{5.1}$ and $R^{5.2}$ are as independently described for $R^5$, including embodiments. $R^{6.1}$ and $R^{6.2}$ are as independently described for $R^6$, including embodiments. In embodiments, $R^{5.1}$ is independently hydrogen, halogen, —CF$_3$, —CN, —N$_3$, substituted or unsubstituted C$_1$-C$_4$ alkyl, substituted or unsubstituted 2 to 4 membered heteroalkyl, substituted or unsubstituted 5 to 6 membered heteroaryl,

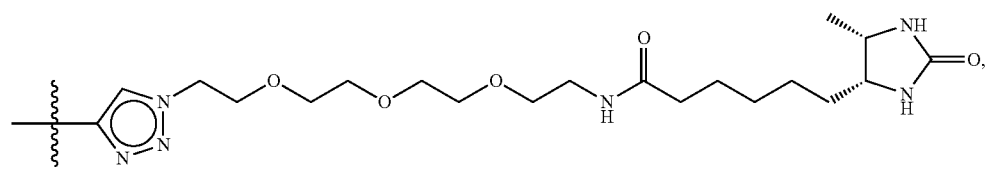

or

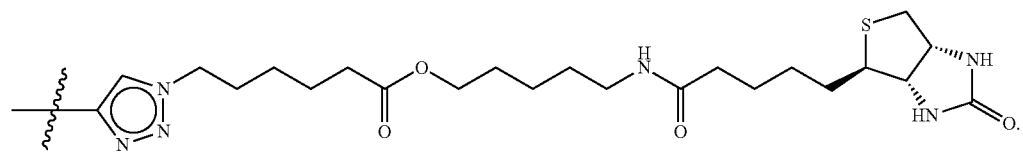

In embodiments, $R^{6.1}$ is independently hydrogen, halogen, —CF$_3$, —CN, —N$_3$, substituted or unsubstituted C$_1$-C$_4$ alkyl, substituted or unsubstituted 2 to 4 membered heteroalkyl, substituted or unsubstituted 5 to 6 membered heteroaryl,

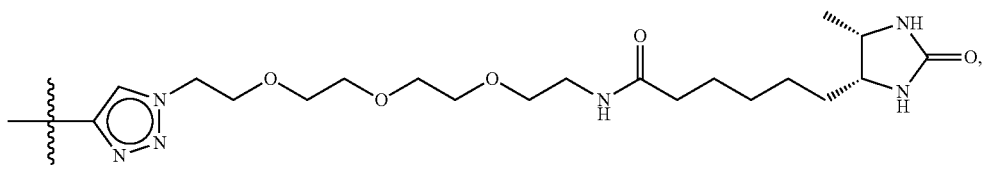

or

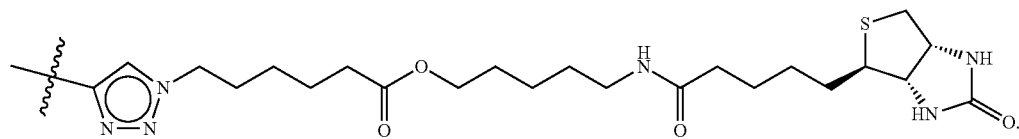

In embodiments, $R^{5.2}$ is independently hydrogen, halogen, —CCSi(CH$_3$)$_3$, —CF$_3$, —NO$_2$, —CN, —N$_3$, substituted or unsubstituted C$_1$-C$_4$ alkyl, substituted or unsubstituted 2 to 4 membered heteroalkyl, substituted or unsubstituted 5 to 6 membered heteroaryl,

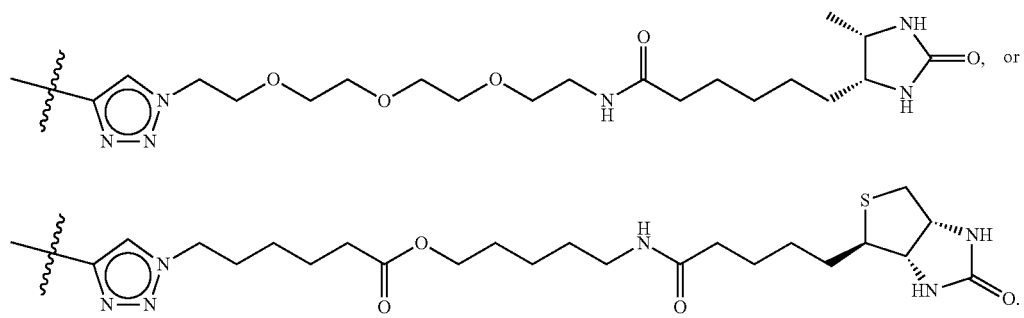

In embodiments, $R^{6.2}$ is independently hydrogen, halogen, —CCSi(CH$_3$)$_3$, —CF$_3$, —NO$_2$, —CN, —N$_3$, substituted or unsubstituted C$_1$-C$_4$ alkyl, substituted or unsubstituted 2 to 4 membered heteroalkyl, substituted or unsubstituted 5 to 6 membered heteroaryl,

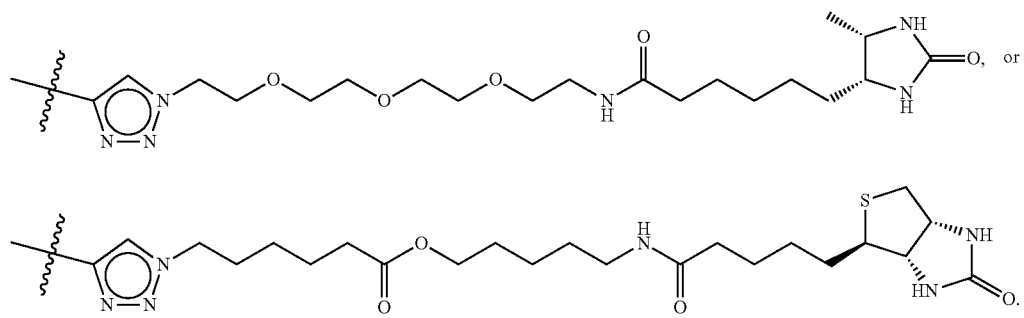

In embodiments, $R^{5.1}$ is independently halogen, unsubstituted C$_1$-C$_3$ alkyl, or unsubstituted C$_1$-C$_3$ haloalkyl. In embodiments, $R^{6.1}$ is independently halogen, unsubstituted C$_1$-C$_3$ alkyl, or unsubstituted C$_1$-C$_3$ haloalkyl. In embodiments, $R^{5.2}$ is independently hydrogen, halogen, —CCSi(CH$_3$)$_3$, —NO$_2$, unsubstituted C$_1$-C$_3$ alkyl, or unsubstituted C$_1$-C$_3$ haloalkyl. In embodiments, $R^{6.2}$ is independently hydrogen, halogen, —CCSi(CH$_3$)$_3$, —NO$_2$, unsubstituted C$_1$-C$_3$ alkyl, or unsubstituted C$_1$-C$_3$ haloalkyl. In embodiments, $R^5$ is independently —Cl, —I, —CF$_3$, —CH$_3$, or —CCH. In embodiments, $R^{6.1}$ is independently —Cl, —I, —CF$_3$, —CH$_3$, or —CCH. In embodiments, $R^{5.2}$ is independently hydrogen, —Cl, —F, —I, —CCSi(CH$_3$)$_3$, —CF$_3$, —NO$_2$, —CH$_3$, or —CCH. In embodiments, $R^{6.2}$ is independently hydrogen, —Cl, —F, —I, —CCSi(CH$_3$)$_3$, —CF$_3$, —NO$_2$, —CH$_3$, or —CCH.

In embodiments, the compound is

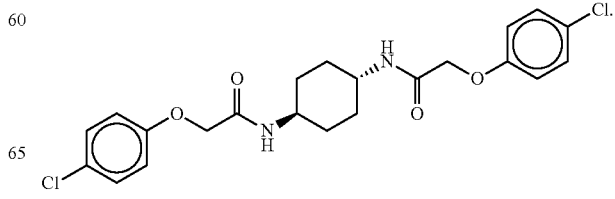

In embodiments, the compound is

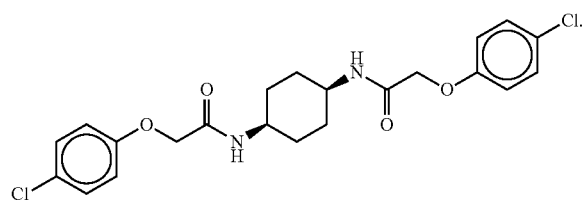

In embodiments, the compound is

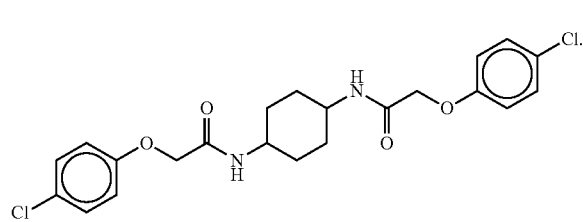

In embodiments, the compound is ISRIB. In embodiments, the compound is trans-ISRIB. In embodiments, the compound is cis-ISRIB. In embodiments, the compound is a mixture of trans- and cis-ISRIB. In embodiments, the compound is

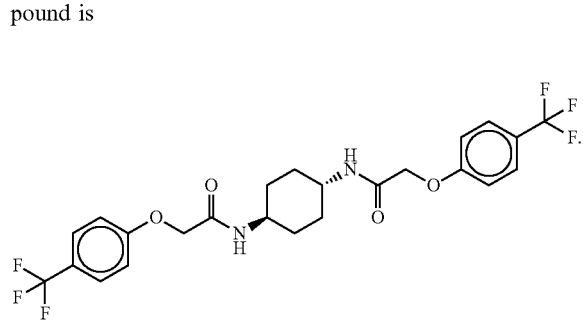

In embodiments, the compound is

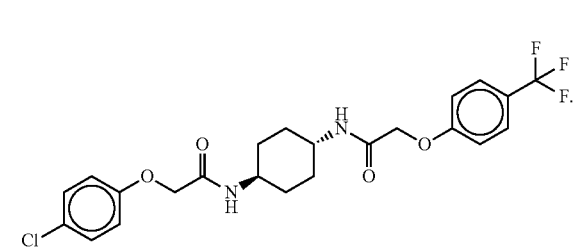

In embodiments, the compound is

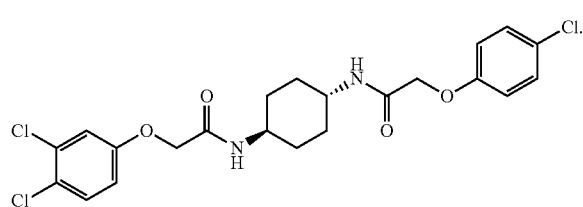 [SMILES: O=C(COc1ccc(Cl)cc1)N[C@H]1CC[C@H](NC(=O)COc2ccc(Cl)c(I)c2)CC1]

In embodiments, the compound is

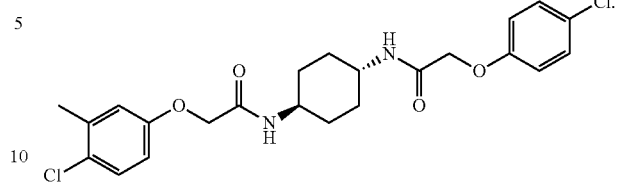

In embodiments, the compound is

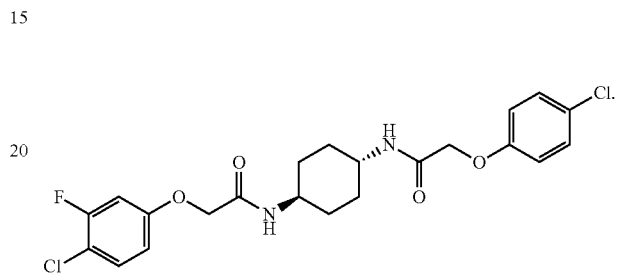

In embodiments, the compound is

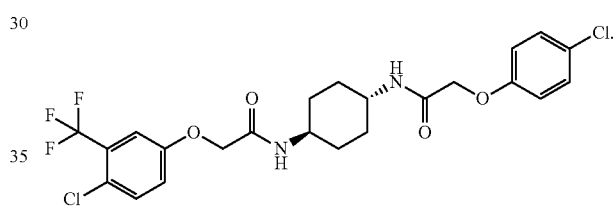

In embodiments, the compound is

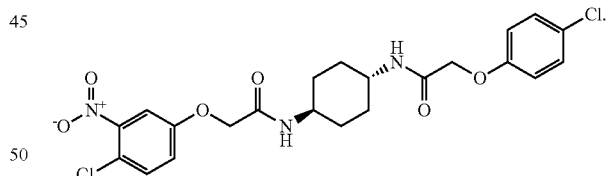

In embodiments, the compound is

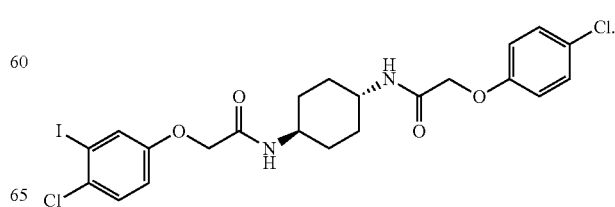

In embodiments, the compound is
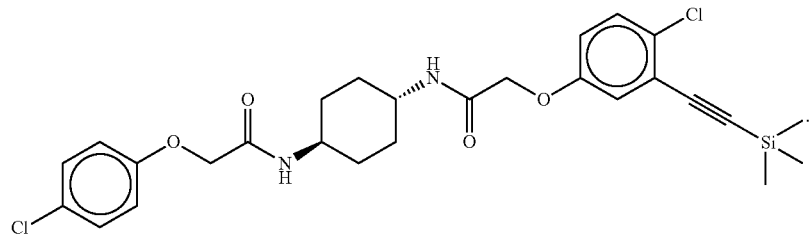
In embodiments, the compound is
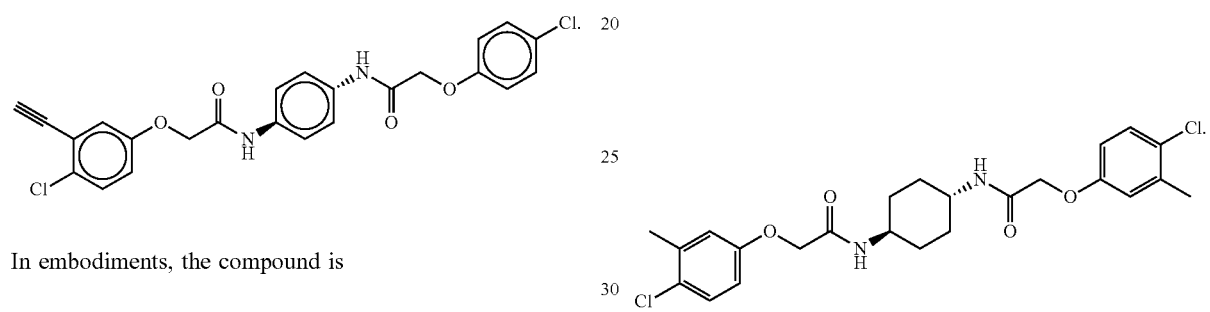
In embodiments, the compound is
In embodiments, the compound is
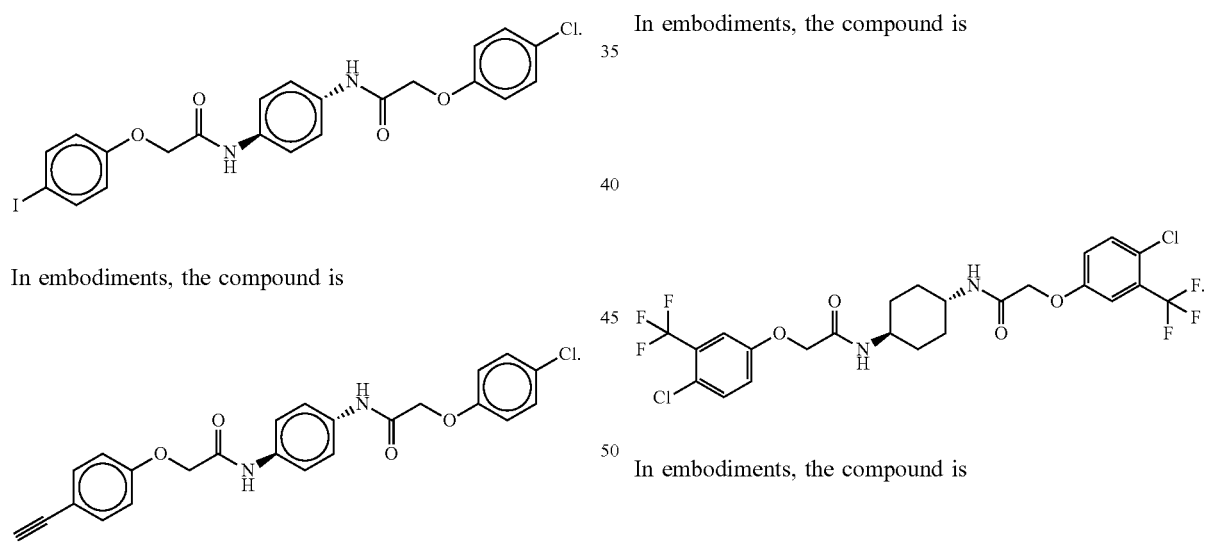
In embodiments, the compound is
In embodiments, the compound is
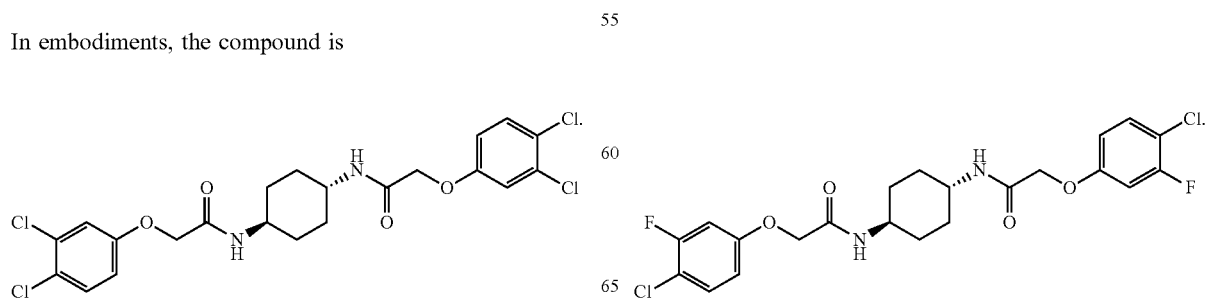

In embodiments, the compound is

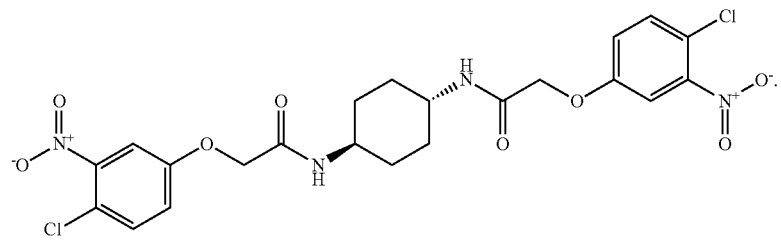

In embodiments, the compound is a mixture of cis-ISRIB and trans-ISRIB.

In embodiments of the method of treating a disease, the disease is selected from the group consisting of cancer, a neurodegenerative disease, vanishing white matter disease, childhood ataxia with CNS hypo-myelination, and an intellectual disability syndrome. In embodiments of the method of treating a disease, the disease is cancer. In embodiments of the method of treating a disease, the disease is a neurodegenerative disease. In embodiments of the method of treating a disease, the disease is vanishing white matter disease. In embodiments of the method of treating a disease, the disease is childhood ataxia with CNS hypo-myelination. In embodiments of the method of treating a disease, the disease is an intellectual disability syndrome. In embodiments of the method of treating a disease, the disease is associated with phosphorylation of eIF2α. In embodiments of the method of treating a disease, the disease is associated with an eIF2α signaling pathway. In embodiments of the method of treating a disease, the disease is a cancer of a secretory cell type. In embodiments of the method of treating a disease, the disease is pancreatic cancer. In embodiments of the method of treating a disease, the disease is breast cancer. In embodiments of the method of treating a disease, the disease is multiple myeloma. In embodiments of the method of treating a disease, the disease is lymphoma. In embodiments of the method of treating a disease, the disease is leukemia. In embodiments of the method of treating a disease, the disease is a hematopoietic cell cancer.

In embodiments of the method of treating a disease, the disease is Alzheimer's disease. In embodiments of the method of treating a disease, the disease is Amyotrophic lateral sclerosis. In embodiments of the method of treating a disease, the disease is Creutzfeldt-Jakob disease. In embodiments of the method of treating a disease, the disease is frontotemporal dementia. In embodiments of the method of treating a disease, the disease is Gerstmann-Sträussler-Scheinker syndrome. In embodiments of the method of treating a disease, the disease is Huntington's disease. In embodiments of the method of treating a disease, the disease is HIV-associated dementia. In embodiments of the method of treating a disease, the disease is kuru. In embodiments of the method of treating a disease, the disease is Lewy body dementia. In embodiments of the method of treating a disease, the disease is Multiple sclerosis. In embodiments of the method of treating a disease, the disease is Parkinson's disease. In embodiments of the method of treating a disease, the disease is a Prion disease.

In embodiments of the method of treating a disease, the disease is an inflammatory disease. In embodiments, the inflammatory disease is postoperative cognitive dysfunction. In embodiments, the inflammatory disease is traumatic brain injury. In embodiments, the inflammatory disease is arthritis. In embodiments, the inflammatory disease is rheumatoid arthritis. In embodiments, the inflammatory disease is psoriatic arthritis. In embodiments, the inflammatory disease is juvenile idiopathic arthritis. In embodiments, the inflammatory disease is multiple sclerosis. In embodiments, the inflammatory disease is systemic lupus erythematosus (SLE). In embodiments, the inflammatory disease is myasthenia gravis. In embodiments, the inflammatory disease is juvenile onset diabetes. In embodiments, the inflammatory disease is diabetes mellitus type 1. In embodiments, the inflammatory disease is Guillain-Barre syndrome. In embodiments, the inflammatory disease is Hashimoto's encephalitis. In embodiments, the inflammatory disease is Hashimoto's thyroiditis. In embodiments, the inflammatory disease is ankylosing spondylitis. In embodiments, the inflammatory disease is psoriasis. In embodiments, the inflammatory disease is Sjogren's syndrome. In embodiments, the inflammatory disease is vasculitis. In embodiments, the inflammatory disease is glomerulonephritis. In embodiments, the inflammatory disease is auto-immune thyroiditis. In embodiments, the inflammatory disease is Behcet's disease. In embodiments, the inflammatory disease is Crohn's disease. In embodiments, the inflammatory disease is ulcerative colitis. In embodiments, the inflammatory disease is bullous pemphigoid. In embodiments, the inflammatory disease is sarcoidosis. In embodiments, the inflammatory disease is ichthyosis. In embodiments, the inflammatory disease is Graves ophthalmopathy. In embodiments, the inflammatory disease is inflammatory bowel disease. In embodiments, the inflammatory disease is Addison's disease. In embodiments, the inflammatory disease is Vitiligo. In embodiments, the inflammatory disease is asthma. In embodiments, the inflammatory disease is allergic asthma. In embodiments, the inflammatory disease is acne vulgaris. In embodiments, the inflammatory disease is celiac disease. In embodiments, the inflammatory disease is chronic prostatitis. In embodiments, the inflammatory disease is inflammatory bowel disease. In embodiments, the inflammatory disease is pelvic inflammatory disease. In embodiments, the inflammatory disease is reperfusion injury. In embodiments, the inflammatory disease is sarcoidosis. In embodiments, the inflammatory disease is transplant rejection. In embodiments, the inflammatory disease is interstitial cystitis. In embodiments, the inflammatory disease is atherosclerosis. In embodiments, the inflammatory disease is atopic dermatitis.

In embodiments, the method of treatment is a method of prevention. For example, a method of treating postsurgical cognitive dysfunction may include preventing postsurgical cognitive dysfunction or a symptom of postsurgical cognitive dysfunction or reducing the severity of a symptom of postsurgical cognitive dysfunction by administering a compound described herein prior to surgery.

In embodiments, the compounds set forth herein are provided as pharmaceutical compositions including the compound and a pharmaceutically acceptable excipient. In embodiments of the method, the compound, or a pharmaceutically acceptable salt thereof, is co-adminstered with a second agent (e.g. therapeutic agent). In embodiments of the method, the compound, or a pharmaceutically acceptable salt thereof, is co-adminstered with a second agent (e.g. therapeutic agent), which is administered in a therapeutically effective amount. In embodiments of the method, the second agent is an agent for treating cancer (e.g. pancreatic cancer, breast cancer, multiple myeloma, or cancers of secretory cells), neurodegenerative diseases, vanishing white matter disease, childhood ataxia with CNS hypomyelination, and/or intellectual disability syndromes (e.g. associated with impaired function of eIF2 or components in a signal transduction pathway including eIF2), or an inflammatory disease (e.g. POCD or TBI). In embodiments, the second agent is an anti-cancer agent. In embodiments, the second agent is a chemotherapeutic. In embodiments, the second agent is an agent for improving memory. In embodiments, the second agent is an agent for treating a neurodegenerative disease. In embodiments, the second agent is an agent for treating vanishing white matter disease. In embodiments, the second agent is an agent for treating childhood ataxia with CNS hypo-myelination. In embodiments, the second agent is an agent for treating an intellectual disability syndrome. In embodiments, the second agent is an agent for treating pancreatic cancer. In embodiments, the second agent is an agent for treating breast cancer. In embodiments, the second agent is an agent for treating multiple myeloma. In embodiments, the second agent is an agent for treating myeloma. In embodiments, the second agent is an agent for treating a cancer of a secretory cell. In embodiments, the second agent is an agent for reducing eIF2α phosphorylation. In embodiments, the second agent is an agent for inhibiting a pathway activated by eIF2α phosphorylation. In embodiments, the second agent is an agent for inhibiting the integrated stress response. In embodiments, the second agent is an anti-inflammatory agent.

In some embodiments, the compound is a compound described herein. In some embodiments, the compound is a compound described in the Examples, an example, a table, the figures, or a figure. In some embodiments, the compound is a compound described in Table 2. In some embodiments, the compound is a compound described in the Compounds section below.

The Integrated Stress Response (ISR) is a collection of cellular stress response pathways that converge in phosphorylation of the translation initiation factor eIF2α resulting in a reduction in overall translation in cells. Mammalian cells have four eIF2α kinases that phosphorylate this initiation factor in the same residue (serine 51); PERK is activated by the accumulation of unfolded proteins in the endoplasmic reticulum (ER), GCN2 is activated by amino acid starvation, PKR by viral infection and HRI by heme deficiency. Activation of these kinases decreases bulk protein synthesis but it also culminates in increased expression of specific mRNAs that contain uORFs. Two examples of these mRNAs are the transcription factor ATF4 and the pro-apoptotic gene CHOP. Phosphorylation of eIF2α upon stress and the concomitant reduction in protein translation has been shown to both have cytoprotective and cytotoxic effects depending on the cellular context and duration and severity of the stress. An integrated stress response-associated disease is a disease characterized by increased activity in the integrated stress response (e.g. increased phosphorylation of eIF2α by an eIF2α kinase compared to a control such as a subject without the disease). A disease associated with phosphorylation of eIF2α is disease characterized by an increase in phosphorylation of eIF2α relative to a control, such as a subject without the disease.

Activation of PERK occurs upon ER stress and hypoxic conditions and its activation and effect on translation has been shown to be cytoprotective for tumor cells [47]. Adaptation to hypoxia in the tumor microenvironment is critical for survival and metastatic potential. PERK has also been shown to promote cancer proliferation by limiting oxidative DNA damage and death [48, 49]. Moreover, a newly identified PERK inhibitor has been shown to have antitumor activity in a human pancreatic tumor xenograft mode [50]. Compounds disclosed herein (e.g. ISRIB) decrease the viability of cells that are subjected to ER-stress. Thus, pharmacological and acute inhibition of the PERK branch with the compounds disclosed herein results in reduced cellular fitness. During tumor growth, compounds disclosed herein (e.g. ISRIB), that block the cytoprotective effects of eIF2α phosphorylation upon stress may prove potent anti-proliferative agents.

It is known that under certain stress conditions several eIF2α kinases can be simultaneously activated. For example, during tumor growth, the lack of nutrients and hypoxic conditions are known to both activate GCN2 and PERK. Like PERK, GCN2 and their common target, ATF4, have been proposed to play a cytoprotective role [51]. By blocking signaling by both kinases, compounds disclosed herein (e.g. ISRIB) may bypass the ability of the ISR to protect cancer cells against the effects of low nutrients and oxygen levels encountered during the growth of the tumor.

Prolonged ER stress leads to the accumulation of CHOP, a pro-apoptotic molecule. In a prion mouse model, overexpression of the phosphatase of eIF2α increased survival of prion-infected mice whereas sustained eIF2α phosphorylation decreased survival [52]. The restoration of protein translation rates during prion disease was shown to rescue synaptic deficits and neuronal loss. Compounds disclosed herein (e.g. ISRIB) make cells insensitive to eIF2α phosphorylation and thus sustains protein translation. Compounds disclosed herein (e.g. ISRIB) could prove potent inhibitors of neuronal cell death in prion disease by blocking the deleterious effects of prolonged eIF2α phosphorylation. Given the prevalence of protein misfolding and activation on the UPR in several neurodegenerative diseases (e g Alzheimer's (AD) and Parkinson's (PD)), manipulation of the PERK-eIF2α branch could prevent synaptic failure and neuronal death across the spectrum of these disorders.

Another example of tissue-specific pathology that is linked to heightened eIF2α phosphorylation is the fatal brain disorder, vanishing white matter disease (VWM) or childhood ataxia with CNS hypo-myelination (CACH). This disease has been linked to mutation in eIF2B, the GTP exchange factor that is necessary for eIF2 function in translation [53]. eIF2α phosphorylation inhibits the activity of eIF2B and mutations in this exchange factor that reduce its exchange activity exacerbate the effects of eIF2α phosphorylation. The severe consequences of the CACH mutations point to the dangers of UPR hyper-activation, especially as it pertains to the myelin-producing oligodendrocyte. Small molecules, such compounds disclosed herein (e.g. ISRIB), that block signaling through eIF2α phosphorylation may reduce the deleterious effects of its hyper-activation in VWM.

Methods of Improving Memory

In another aspect is provided a method of improving long-term memory in a patient, the method including administering a therapeutically effective amount of a compound to the patient, wherein the compound is a compound described herein, including embodiments (e.g. compound of formula I, Ia, Ib, Ic, Id, Ie, If, Ig, Ih, II, III, IIIa, IIIb, IIIc, or IV, or any embodiment thereof, including compounds described for use in a different method herein or in the Compounds section below or in an example, table, figure, or claim). In embodiments, the patient is human. In embodiments, the patient is a non-human mammal. In embodiments, the patient is a domesticated animal. In embodiments, the patient is a dog. In embodiments, the patient is a bird. In embodiments, the patient is a horse. In embodiments, the patient is a bovine. In embodiments, the patient is a primate.

In embodiments, the compounds set forth herein are provided as pharmaceutical compositions including the compound and a pharmaceutically acceptable excipient. In embodiments of the method, the compound, or a pharmaceutically acceptable salt thereof, is co-adminstered with a second agent (e.g. therapeutic agent). In embodiments of the method, the compound, or a pharmaceutically acceptable salt thereof, is co-adminstered with a second agent (e.g. therapeutic agent), which is administered in a therapeutically effective amount. In embodiments, the second agent is an agent for improving memory.

In some embodiments, the compound is a compound described herein. In some embodiments, the compound is a compound described in the Examples, an example, a table, the figures, or a figure. In some embodiments, the compound is a compound described in Table 2.

Induction of long-term memory (LTM) has been shown to be facilitated by decreased and impaired by increased eIF2α phosphorylation. The data strongly support the notion that under physiological conditions, a decrease in eIF2α phosphorylation constitutes a critical step for the long term synaptic changes required for memory formation and ATF4 has been shown to be an important regulator of these processes [54] [55] [56]. It is not known what the contributions of the different eIF2α kinases to learning is or whether each play a differential role in the different parts of the brain. Regardless of the eIF2α kinase/s responsible for phosphorylation of eIF2α in the brain, compounds disclosed herein (e.g. ISRIB), block translation attenuation and ATF4 production making them ideal molecules to block the effects of this phosphorylation event on memory. We have shown that pharmacological treatment with compounds disclosed herein (e.g. ISRIB) increases spatial memory and enhances both auditory and contextual fear conditioning.

Regulators of translation, such as compounds disclosed herein (e.g. ISRIB), could serve as therapeutic agents that improve memory in human disorders associated with memory loss such as Alzheimer's disease and in other neurological disorders that activate the UPR in neurons and thus could have negative effects on memory consolidation such as Parkinson's disease, Amyotrophic lateral sclerosis and prion diseases. In addition, a mutation in eIF2γ, that disrupts complex integrity linked intellectual disability (intellectual disability syndrome or ID) to impaired translation initiation in humans [57]. Hence, two diseases with impaired eIF2 function, ID and VWM, display distinct phenotypes but both affect mainly the brain and impair learning.

Methods of Increasing Protein Production

We have also shown that compounds disclosed herein (e.g. ISRIB) increase translation in an in vitro rabbit reticulocyte translation system. Compounds disclosed herein (e.g. ISRIB) could prove useful in applications where increasing protein production output is desirable, such as in vitro cell free systems for protein production. In vitro systems have basal levels of eIF2a phosphorylation that reduce translational output [58, 59]. Similarly production of antibodies by hybridomas may also be improved by addition of compounds disclosed herein (e.g. ISRIB).

In another aspect is provided a method of increasing protein expression of a cell or in vitro expression system, the method including administering an effective amount of a compound to the cell or expression system, wherein the compound is a compound described herein, including embodiments (e.g. compound of formula I, Ia, Ib, Ic, Id, Ie, If, Ig, Ih, II, III, IIIc, IIIb, IIIc, or IV, or any embodiment thereof, including compounds described for use in a different method herein or in the Compounds section below or in an example, table, figure, or claim). In embodiments, the method is a method of increasing protein expression by a cell and includes administering an effective amount of a compound described herein (e.g. compound of formula I, Ia, Ib, Ic, Id, Ie, If, Ig, Ih, II, III, IIIa, IIIb, IIIc, or IV, or any embodiment thereof, including compounds described for use in a different method herein or in the Compounds section below or in an example, table, figure, or claim) to the cell. In embodiments, the method is a method of increasing protein expression by an in vitro protein expression system and includes administering an effective amount of a compound described herein (e.g. compound of formula I, Ia, Ib, Ic, Id, Ie, If, Ig, Ih, II, III, IIIa, IIIb, IIIc, or IV, or any embodiment thereof, including compounds described for use in a different method herein or in the Compounds section below or in an example, table, figure, or claim) to the in vitro (e.g. cell free) protein expression system.

In embodiments, the compounds set forth herein are provided as pharmaceutical compositions including the compound and a pharmaceutically acceptable excipient. In embodiments of the method, the compound, or a pharmaceutically acceptable salt thereof, is co-adminstered with a second agent. In embodiments of the method, the compound, or a pharmaceutically acceptable salt thereof, is co-adminstered with a second agent, which is administered in a therapeutically effective amount. In embodiments, the second agent is an agent for improving protein expression.

In some embodiments, the compound is a compound described herein. In some embodiments, the compound is a compound described in the Examples, an example, a table, the figures, or a figure. In some embodiments, the compound is a compound described in Table 2.

Compounds

The compounds described in this Compounds section may be included in any of the methods described herein. Thus, we have identified a series of small molecule inhibitors (e.g. ISRIB) of the PERK-mediated signal that leads to translational attenuation in cell-based assays. In addition, the compounds inhibit the action of the other three eIF2α kinases: GCN2, PKR and HRI, which lead to eIF2α phosphorylation on the same residue (serine 51) and thus are ISR inhibitors. The disclosed compounds (e.g. ISRIB), make cells resistant to the effects of eIF2α phosphorylation. No small molecules have been identified that can make cells insensitive to the effects of eIF2α phosphorylation on translation initiation. To date, these compounds have not shown toxicity and have good Pharmacokinetic properties. These compounds can be used to block translational regulation by the four eIF2α kinases PERK (activated by ER stress), PKR (activated by viral infection), HRI (activated by heme deficiency) and GCN2 (activated by amino acid starvation).

Compounds useful in the methods disclosed herein are described above and below. Thus, the compounds described herein, including those set forth below in this Compounds section, are useful in the methods provided here, including all embodiments thereof. In addition to the compounds disclosed above, in another aspect is provided a compound, or a pharmaceutically acceptable salt thereof, having the formula:

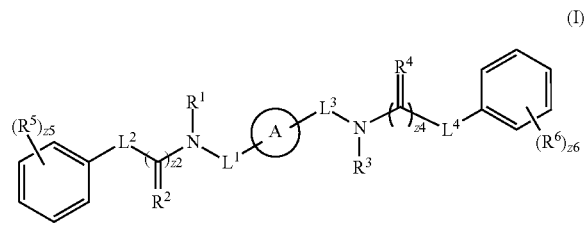

(I)

wherein. ring A, $L^1$, $L^2$, $L^3$, $L^4$, $R^1$, $R^2$, $R^3$, $R^4$, $R^5$, $R^6$, $R^7$, z2, z4, z5 and z6, are as described herein, including embodiments and in the method of treatment section herein above. In embodiments, Ring A is substituted or unsubstituted cycloalkylene or substituted or unsubstituted arylene. In embodiments, $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene. In embodiments, $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ and $R^4$ are independently =NR$^7$, =O, or =S. The symbols z2 and z4 are each independently 0 or 1. The symbols z5 and z6 are each independently an integer from 0 to 5. In embodiments, the compound is not

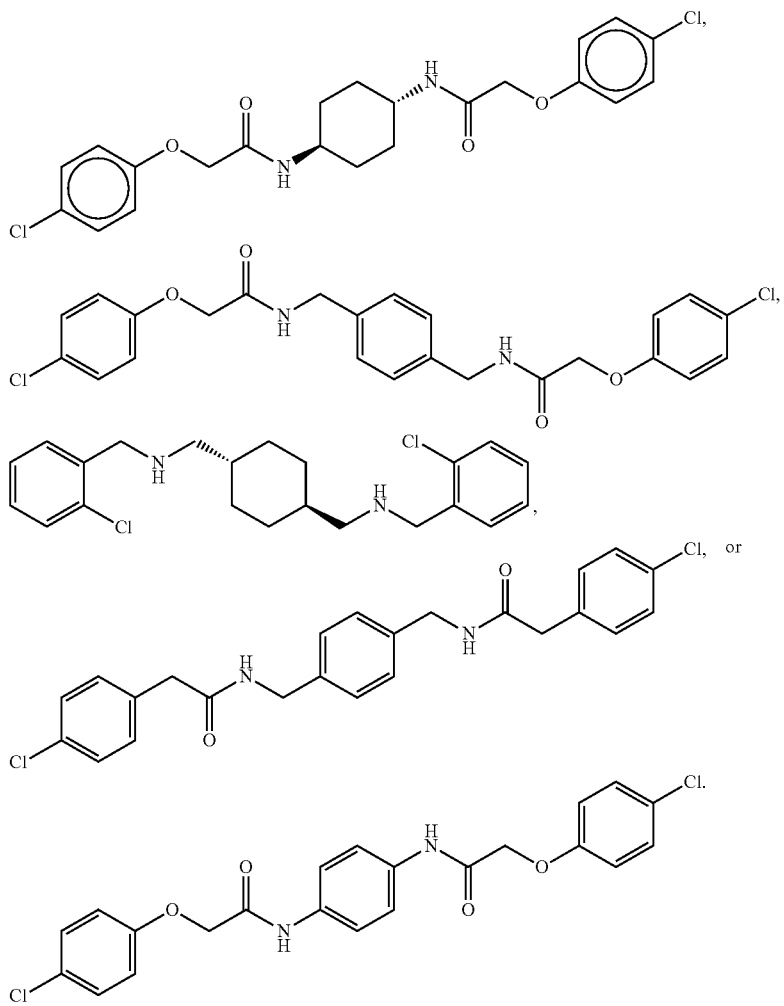

In embodiments, ring A is substituted or unsubstituted cycloalkylene. In embodiments, ring A is substituted or unsubstituted $C_3$-$C_8$ cycloalkylene. In embodiments, ring A is substituted or unsubstituted $C_3$-$C_6$ cycloalkylene. In embodiments, ring A is substituted or unsubstituted $C_3$-$C_4$ cycloalkylene. In embodiments, ring A is substituted or unsubstituted $C_4$-$C_8$ cycloalkylene. In embodiments, ring A is substituted or unsubstituted $C_4$-$C_6$ cycloalkylene. In embodiments, ring A is substituted or unsubstituted cyclohexylene. In embodiments, ring A is substituted or unsubstituted cyclobutylene. In embodiments, ring A is substituted or unsubstituted cyclopentylene. In embodiments, ring A is substituted or unsubstituted $C_4$-$C_6$ cycloalkenylene. In embodiments, ring A is unsubstituted cycloalkylene. In embodiments, ring A is unsubstituted $C_3$-$C_8$ cycloalkylene. In embodiments, ring A is unsubstituted $C_3$-$C_6$ cycloalkylene. In embodiments, ring A is unsubstituted $C_3$-$C_4$ cycloalkylene. In embodiments, ring A is unsubstituted $C_4$-$C_8$ cycloalkylene. In embodiments, ring A is unsubstituted $C_4$-$C_6$ cycloalkylene. In embodiments, ring A is unsubstituted cyclohexylene. In embodiments, ring A is unsubstituted cyclobutylene. In embodiments, ring A is unsubstituted cyclopentylene. In embodiments, ring A is unsubstituted $C_4$-$C_6$ cycloalkenylene. In embodiments, ring A is substituted or unsubstituted arylene. In embodiments, ring A is substituted or unsubstituted $C_6$-$C_{10}$ arylene. In embodiments, ring A is substituted or unsubstituted phenylene. In embodiments, ring A is substituted or unsubstituted naphthylene. In embodiments, ring A is unsubstituted $C_6$-$C_{10}$ arylene. In embodiments, ring A is unsubstituted phenylene. In embodiments, ring A is unsubstituted naphthylene.

$L^1$ may be a bond or substituted or unsubstituted alkylene. $L^1$ may be substituted or unsubstituted $C_1$-$C_5$ alkylene. $L^1$ may be substituted or unsubstituted $C_1$-$C_3$ alkylene. $L^1$ may be substituted or unsubstituted methylene. $L^1$ may be a bond. $L^1$ may be an unsubstituted alkylene. $L^1$ may be an unsubstituted methylene. $L^1$ may be an unsubstituted ethylene. $L^1$ may be a methylene substituted with an unsubstituted alkyl $L^1$ may be a methylene substituted with an unsubstituted $C_1$-$C_4$ alkyl $L^1$ may be a methylene substituted with an unsubstituted $C_1$-$C_3$ alkyl.

$L^3$ may be a bond or substituted or unsubstituted alkylene. $L^3$ may be substituted or unsubstituted $C_1$-$C_5$ alkylene. $L^3$ may be substituted or unsubstituted $C_1$-$C_3$ alkylene. $L^3$ may be substituted or unsubstituted methylene. $L^3$ may be a bond. $L^3$ may be an unsubstituted alkylene. $L^3$ may be an unsubstituted methylene. $L^3$ may be an unsubstituted ethylene. $L^3$ may be a methylene substituted with an unsubstituted alkyl $L^3$ may be a methylene substituted with an unsubstituted $C_1$-$C_4$ alkyl $L^3$ may be a methylene substituted with an unsubstituted $C_1$-$C_3$ alkyl. $L^1$ and $L^3$ may be a bond. In embodiments, $L^1$ and $L^3$ may independently be an unsubstituted alkylene. In embodiments, $L^1$ and $L^3$ may be an unsubstituted methylene.

In embodiments, $R^1$ is hydrogen. In embodiments, $R^1$ is —CH$_2$CCH. In embodiments, $R^1$ is

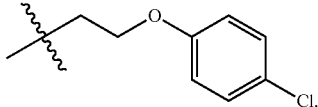 [SMILES: *CCOc1ccc(Cl)cc1]

In embodiments, $R^1$ is

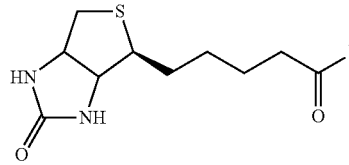

In embodiments, $R^1$ is

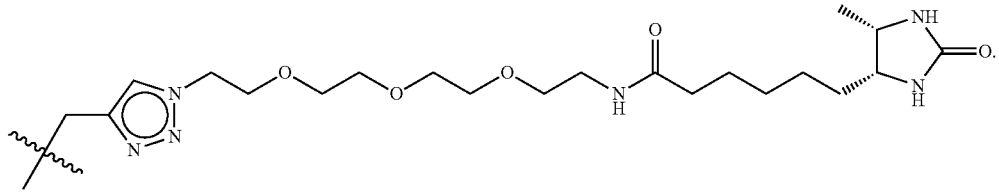

In embodiments, $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is substituted or unsubstituted alkyl. In embodiments, $R^1$ is substituted or unsubstituted $C_1$-$C_8$ alkyl. In embodiments, $R^1$ is substituted or unsubstituted $C_1$-$C_6$ alkyl. In embodiments, $R^1$ is substituted or unsubstituted $C_1$-$C_4$ alkyl. In embodiments, $R^1$ is unsubstituted alkyl. In embodiments, $R^1$ is unsubstituted $C_1$-$C_8$ alkyl. In embodiments, $R^1$ is unsubstituted $C_1$-$C_6$ alkyl. In embodiments, $R^1$ is unsubstituted $C_1$-$C_4$ alkyl. In embodiments, $R^1$ is substituted or unsubstituted heteroalkyl. In embodiments, $R^1$ is substituted or unsubstituted 2 to 8 membered heteroalkyl. In embodiments, $R^1$ is unsubstituted 2 to 8 membered heteroalkyl.

In embodiments, $R^3$ is hydrogen. In embodiments, $R^3$ is —CH$_2$CCH. In embodiments, $R^3$ is

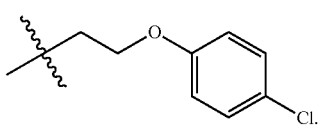 [SMILES: *CCOc1ccc(Cl)cc1]

In embodiments, R³ is

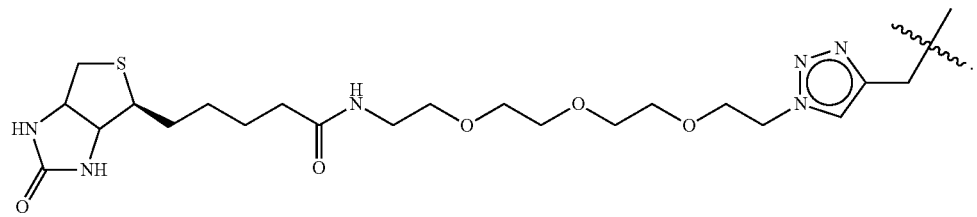

In embodiments, R³ is

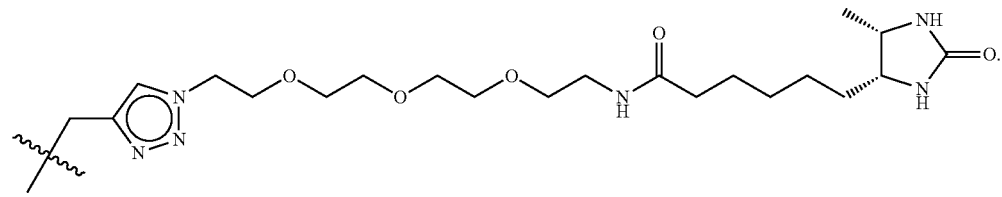

In embodiments, R³ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R³ is substituted or unsubstituted alkyl. In embodiments, R³ is substituted or unsubstituted $C_1$-$C_8$ alkyl. In embodiments, R³ is substituted or unsubstituted $C_1$-$C_6$ alkyl. In embodiments, R³ is substituted or unsubstituted $C_1$-$C_4$ alkyl. In embodiments, R³ is unsubstituted alkyl. In embodiments, R³ is unsubstituted $C_1$-$C_8$ alkyl. In embodiments, R³ is unsubstituted $C_1$-$C_6$ alkyl. In embodiments, R³ is unsubstituted $C_1$-$C_4$ alkyl. In embodiments, R³ is substituted or unsubstituted heteroalkyl. In embodiments, R³ is substituted or unsubstituted 2 to 8 membered heteroalkyl. In embodiments, R³ is unsubstituted 2 to 8 membered heteroalkyl.

In embodiments, R⁵ is independently halogen, —OCH₃, —OCH₂Ph, —C(O)Ph, —CH₃, —CF₃, —CCl₃, —CN, —S(O)CH₃, —OH, —NH₂, —COOH, —CONH₂, —NO₂, —C(O)CH₃, —CH(CH₃)₂, —CCSi(CH₃)₃, —CCH, —CH₂CCH, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)OH, —NHOH, —OCH₃, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R⁵ is independently halogen, —OCH₃, —OCH₂Ph, —CH₃, —OH, —CF₃, —CCl₃, —CN, —S(O)CH₃, —NO₂, —C(O)CH₃, —C(O)Ph, —CH(CH₃)₂, —CCSi(CH₃)₃, or —CCH. In embodiments, R⁵ is independently halogen. In embodiments, R⁵ is independently —OCH₃. In embodiments, R⁵ is independently —OCH₂Ph. In embodiments, R⁵ is independently —CH₃. In embodiments, R⁵ is independently —OH. In embodiments, R⁵ is independently —CF₃. In embodiments, R⁵ is independently —CCl₃. In embodiments, R⁵ is independently —CN. In embodiments, R⁵ is independently —S(O)CH₃. In embodiments, R⁵ is independently —NO₂. In embodiments, R⁵ is independently —C(O)CH₃. In embodiments, R⁵ is independently —C(O)Ph. In embodiments, R⁵ is independently —CH(CH₃)₂. In embodiments, R⁵ is independently —CCSi(CH₃)₃. In embodiments, R⁵ is independently —CCH. In embodiments, R⁵ is —F. In embodiments, R⁵ is —Cl. In embodiments, R⁵ is —Br. In embodiments, R⁵ is —I. In embodiments, R⁵ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R⁵ is unsubstituted alkyl, unsubstituted heteroalkyl, unsubstituted cycloalkyl, unsubstituted heterocycloalkyl, unsubstituted aryl, or unsubstituted heteroaryl. In embodiments, R⁵ is substituted or unsubstituted alkyl. In embodiments, R⁵ is substituted or unsubstituted $C_1$-$C_8$ alkyl. In embodiments, R⁵ is substituted or unsubstituted $C_1$-$C_6$ alkyl. In embodiments, R⁵ is substituted or unsubstituted $C_1$-$C_4$ alkyl. In embodiments, R⁵ is unsubstituted alkyl. In embodiments, R⁵ is unsubstituted $C_1$-$C_8$ alkyl. In embodiments, R⁵ is unsubstituted $C_1$-$C_6$ alkyl. In embodiments, R⁵ is unsubstituted $C_1$-$C_4$ alkyl. In embodiments, R⁵ is substituted alkyl. In embodiments, R⁵ is substituted $C_1$-$C_8$ alkyl. In embodiments, R⁵ is substituted $C_1$-$C_6$ alkyl. In embodiments, R⁵ is substituted $C_1$-$C_4$ alkyl. In embodiments, R⁵ is substituted $C_1$-$C_3$ alkyl. In embodiments, R⁵ is substituted or unsubstituted heteroalkyl. In embodiments, R⁵ is substituted or unsubstituted 2 to 8 membered heteroalkyl. In embodiments, R⁵ is unsubstituted 2 to 6 membered heteroalkyl. In embodiments, R⁵ is unsubstituted 2 to 4 membered heteroalkyl. In embodiments, R⁵ is substituted 2 to 8 membered heteroalkyl. In embodiments, R⁵ is substituted 2 to 6 membered heteroalkyl. In embodiments, R⁵ is substituted 2 to 4 membered heteroalkyl. In embodiments, R⁵ is independently —N₃. In embodiments, R⁵ is independently —C(NN)CF₃. In embodiments, R⁵ is independently —C(NH—NH)CF₃. In embodiments, R⁵ is

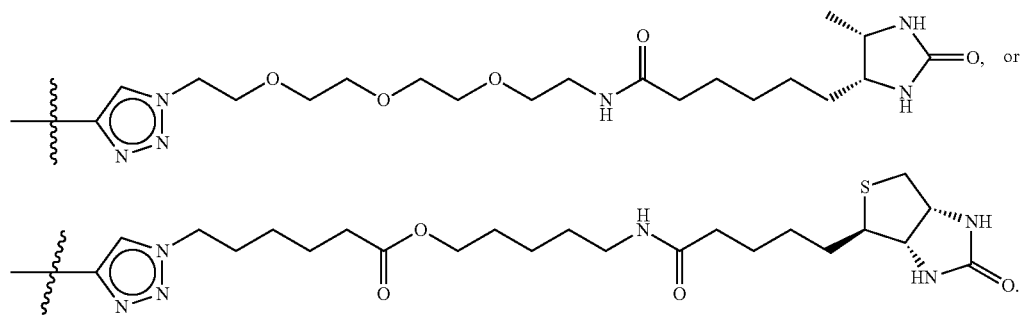

In embodiments, $R^6$ is independently halogen, —$OCH_3$, —$OCH_2Ph$, —C(O)Ph, —$CH_3$, —$CF_3$, —$CCl_3$, —CN, —S(O)$CH_3$, —OH, —$NH_2$, —COOH, —$CONH_2$, —$NO_2$, —C(O)$CH_3$, —CH($CH_3$)$_2$, —CCSi($CH_3$)$_3$, —CCH, —$CH_2$CCH, —SH, —$SO_2$Cl, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)OH, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is independently halogen, —$OCH_3$, —$OCH_2Ph$, —$CH_3$, —OH, —$CF_3$, —$CCl_3$, —CN, —S(O)$CH_3$, —$NO_2$, —C(O)$CH_3$, —C(O)Ph, —CH($CH_3$)$_2$, —CCSi($CH_3$)$_3$, or —CCH. In embodiments, $R^6$ is independently halogen. In embodiments, $R^6$ is independently —$OCH_3$. In embodiments, $R^6$ is independently —$OCH_2Ph$. In embodiments, $R^6$ is independently —$CH_3$. In embodiments, $R^6$ is independently —OH. In embodiments, $R^6$ is independently —$CF_3$. In embodiments, $R^6$ is independently —$CCl_3$. In embodiments, $R^6$ is independently —CN. In embodiments, $R^6$ is independently —S(O)$CH_3$. In embodiments, $R^6$ is independently —$NO_2$. In embodiments, $R^6$ is independently —C(O)$CH_3$. In embodiments, $R^6$ is independently —C(O)Ph. In embodiments, $R^6$ is independently cycloalkyl, unsubstituted heterocycloalkyl, unsubstituted aryl, or unsubstituted heteroaryl. In embodiments, $R^6$ is substituted or unsubstituted alkyl. In embodiments, $R^6$ is substituted or unsubstituted $C_1$-$C_8$ alkyl. In embodiments, $R^6$ is substituted or unsubstituted $C_1$-$C_6$ alkyl. In embodiments, $R^6$ is substituted or unsubstituted $C_1$-$C_4$ alkyl. In embodiments, $R^6$ is unsubstituted alkyl. In embodiments, $R^6$ is unsubstituted $C_1$-$C_8$ alkyl. In embodiments, $R^6$ is unsubstituted $C_1$-$C_6$ alkyl. In embodiments, $R^6$ is unsubstituted $C_1$-$C_4$ alkyl. In embodiments, $R^6$ is substituted alkyl. In embodiments, $R^6$ is substituted $C_1$-$C_8$ alkyl. In embodiments, $R^6$ is substituted $C_1$-$C_6$ alkyl. In embodiments, $R^6$ is substituted $C_1$-$C_4$ alkyl. In embodiments, $R^6$ is substituted $C_1$-$C_3$ alkyl. In embodiments, $R^6$ is substituted or unsubstituted heteroalkyl. In embodiments, $R^6$ is substituted or unsubstituted 2 to 8 membered heteroalkyl. In embodiments, $R^6$ is unsubstituted 2 to 6 membered heteroalkyl. In embodiments, $R^6$ is unsubstituted 2 to 4 membered heteroalkyl. In embodiments, $R^6$ is substituted 2 to 8 membered heteroalkyl. In embodiments, $R^6$ is substituted 2 to 6 membered heteroalkyl. In embodiments, $R^6$ is substituted 2 to 4 membered heteroalkyl. In embodiments, $R^6$ is independently —$N_3$. In embodiments, $R^6$ is independently —C(NN)$CF_3$. In embodiments, $R^6$ is independently —C(NH—NH)$CF_3$. In embodiments, $R^6$ is —CH($CH_3$)$_2$. In embodiments, $R^6$ is independently —CCSi($CH_3$)$_3$. In embodiments, $R^6$ is independently —CCH. In embodiments, $R^6$ is —F. In embodiments, $R^6$ is —Cl. In embodiments, $R^6$ is —Br. In embodiments, $R^6$ is —I. In embodiments, $R^6$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is unsubstituted alkyl, unsubstituted heteroalkyl, unsubstituted

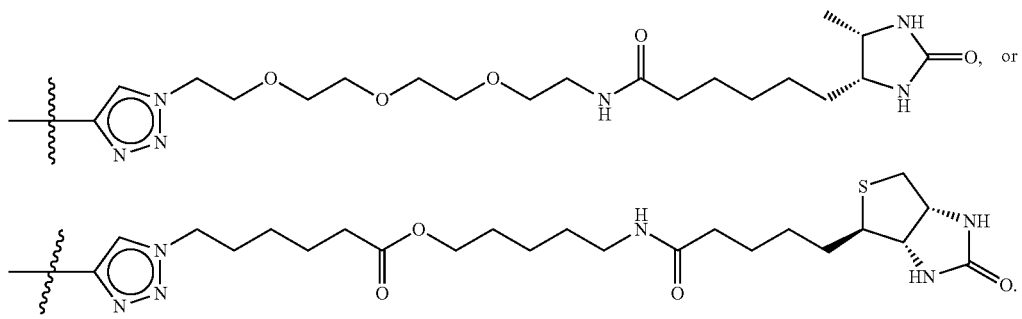

In embodiments, $R^7$ is independently hydrogen. In embodiments, $R^7$ is independently halogen, —$OCH_3$, —$OCH_2Ph$, —C(O)Ph, —$CH_3$, —$CF_3$, —$CCl_3$, —CN, —S(O)$CH_3$, —OH, —$NH_2$, —COOH, —$CONH_2$, —$NO_2$, —C(O)$CH_3$, —CH($CH_3$)$_2$, —CCSi($CH_3$)$_3$, —CCH, —$CH_2$CCH, —SH, —$SO_2$Cl, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)OH, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^7$ is independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^7$ is independently substituted or unsubstituted $C_1$-$C_8$ alkyl. In embodiments, $R^7$ is independently substituted or unsubstituted $C_1$-$C_6$ alkyl. In embodiments, $R^7$ is independently substituted or unsubstituted $C_1$-$C_4$ alkyl. In embodiments, $R^7$ is independently unsubstituted $C_1$-$C_8$ alkyl. In embodiments, $R^7$ is independently unsubstituted $C_1$-$C_6$ alkyl. In embodiments, $R^7$ is independently unsubstituted $C_1$-$C_4$ alkyl. In embodiments, $R^7$ is independently unsubstituted methyl.

In embodiments, $R^2$ is $=NR^7$. In embodiments, $R^2$ is $=NH$. In embodiments, $R^2$ is $=O$. In embodiments, $R^2$ is $=S$. In embodiments, $R^4$ is $=NR^7$. In embodiments, $R^4$ is $=NH$. In embodiments, $R^4$ is $=O$. In embodiments, $R^4$ is $=S$. In embodiments, $R^2$ and $R^4$ are $=NH$. In embodiments, $R^2$ and $R^4$ are $=O$. In embodiments, $R^2$ and $R^4$ are $=S$. In embodiments, $R^2$ and $R^4$ are $=NR^7$.

In embodiments, $L^2$ is a bond. In embodiments, $L^2$ is a substituted or unsubstituted alkylene. In embodiments, $L^2$ is a substituted or unsubstituted heteroalkylene. In embodiments, $L^2$ is $L^{2A}$-$L^{2B}$-$L^{2C}$ and $L^{2A}$ is bonded to the substituted or unsubstituted phenyl, which may be substituted with $R^5$. $L^{2A}$ is a bond, —O—, —S—, —NH—, —S(O)—, or —S(O)$_2$—. $L^{2B}$ is a bond or substituted or unsubstituted alkylene. $L^{2C}$ is a bond, —O—, or —NH—. In embodiments, $L^{2A}$ is a bond. In embodiments, $L^{2A}$ is —O—. In embodiments, $L^{2A}$ is —S—. In embodiments, $L^{2A}$ is —NH—. In embodiments, $L^{2A}$ is —S(O)—. In embodiments, $L^{2A}$ is —S(O)$_2$—. In embodiments, $L^{2B}$ is a bond. In embodiments, $L^{2B}$ is a substituted or unsubstituted alkylene. In embodiments, $L^{2B}$ is an unsubstituted alkylene. In embodiments, $L^{2B}$ is a substituted or unsubstituted $C_1$-$C_8$ alkylene. In embodiments, $L^{2B}$ is an unsubstituted $C_1$-$C_8$ alkylene. In embodiments, $L^{2B}$ is a substituted or unsubstituted $C_1$-$C_6$ alkylene. In embodiments, $L^{2B}$ is an unsubstituted $C_1$-$C_6$ alkylene. In embodiments, $L^{2B}$ is a substituted or unsubstituted alkylene. In embodiments, $L^{2B}$ is an unsubstituted alkylene. In embodiments, $L^{2B}$ is a substituted alkylene. In embodiments, $L^{2B}$ is a substituted $C_1$-$C_8$ alkylene. In embodiments, $L^{2B}$ is a substituted $C_1$-$C_6$ alkylene. In embodiments, $L^{2B}$ is a substituted $C_1$-$C_4$ alkylene. In embodiments, $L^{2B}$ is an alkylene substituted with —CF$_3$. In embodiments, $L^{2C}$ is a bond. In embodiments, $L^{2C}$ is —O—. In embodiments, $L^{2C}$ is —NH—. In embodiments, $L^{2A}$ is a bond; $L^{2B}$ is unsubstituted methylene; and $L^{2C}$ is —O—.

In embodiments, $L^4$ is a bond. In embodiments, $L^4$ is a substituted or unsubstituted alkylene. In embodiments, $L^4$ is a substituted or unsubstituted heteroalkylene. In embodiments, $L^4$ is $L^{4A}$-$L^{4B}$-$L^{4C}$ and $L^{4A}$ is bonded to the substituted or unsubstituted phenyl, which may be substituted with $R^6$. $L^{4A}$ is a bond, —O—, —S—, —NH—, —S(O)—, or —S(O)$_2$—. $L^{4B}$ is a bond or substituted or unsubstituted alkylene. $L^{4C}$ is a bond, —O—, or —NH—. In embodiments, $L^{4A}$ is a bond. In embodiments, $L^{4A}$ is —O—. In embodiments, $L^{4A}$ is —S—. In embodiments, $L^{4A}$ is —NH—. In embodiments, $L^{4A}$ is —S(O)—. In embodiments, $L^{4A}$ is —S(O)$_2$—. In embodiments, $L^{4B}$ is a bond. In embodiments, $L^{4B}$ is a substituted or unsubstituted alkylene. In embodiments, $L^{4B}$ is an unsubstituted alkylene. In embodiments, $L^{4B}$ is a substituted or unsubstituted $C_1$-$C_8$ alkylene. In embodiments, $L^{4B}$ is an unsubstituted $C_1$-$C_8$ alkylene. In embodiments, $L^{4B}$ is a substituted or unsubstituted $C_1$-$C_6$ alkylene. In embodiments, $L^{4B}$ is an unsubstituted $C_1$-$C_6$ alkylene. In embodiments, $L^{4B}$ is a substituted or unsubstituted alkylene. In embodiments, $L^{4B}$ is an unsubstituted alkylene. In embodiments, $L^{4B}$ is a substituted alkylene. In embodiments, $L^{4B}$ is a substituted $C_1$-$C_8$ alkylene. In embodiments, $L^{4B}$ is a substituted $C_1$-$C_6$ alkylene. In embodiments, $L^{4B}$ is a substituted $C_1$-$C_4$ alkylene. In embodiments, $L^{4B}$ is an alkylene substituted with —CF$_3$. In embodiments, $L^{4C}$ is a bond. In embodiments, $L^{4C}$ is —O—. In embodiments, $L^{4C}$ is —NH—. In embodiments, $L^{4A}$ is a bond; $L^{4B}$ is unsubstituted methylene; and $L^{4C}$ is —O—.

In embodiments, the symbol z2 is 0. In embodiments, the symbol z2 is 1. In embodiments, the symbol z4 is 0. In embodiments, the symbol z4 is 1. In embodiments, the symbols z2 and z4 are 0. In embodiments, the symbols z2 and z4 are 1. In embodiments, the symbol z5 is 0. In embodiments, the symbol z5 is 1. In embodiments, the symbol z5 is 2. In embodiments, the symbol z5 is 3. In embodiments, the symbol z5 is 4. In embodiments, the symbol z5 is 5. In embodiments, the symbol z6 is 0. In embodiments, the symbol z6 is 1. In embodiments, the symbol z6 is 2. In embodiments, the symbol z6 is 3. In embodiments, the symbol z6 is 4. In embodiments, the symbol z6 is 5.

In embodiment, $L^1$ is a bond. In embodiment, $L^1$ is —CH$_2$—. In embodiment, $L^1$ is —O—. In embodiment, $L^1$ is —S—. In embodiment, $L^1$ is —NH—. In embodiment, $L^2$ is a bond. In embodiment, $L^2$ is —CH$_2$—. In embodiment, $L^2$ is —O—. In embodiment, $L^2$ is —S—. In embodiment, $L^2$ is —NH—. In embodiment, $L^3$ is —CH$_2$O—. In embodiment, $L^3$ is —OCH$_2$—. In embodiment, $L^3$ is —CH$_2$—. In embodiment, $L^3$ is a bond. In embodiment, $L^3$ is —CH$_2$CH$_2$—. In embodiment, $L^3$ is —CH$_2$CH$_2$O—. In embodiment, $L^3$ is —OCH2CH2-. In embodiment, $L^3$ is —CH$_2$S—. In embodiment, $L^3$ is —SCH$_2$—. In embodiment, $L^3$ is —CH$_2$S(O)—. In embodiment, $L^3$ is —S(O)CH$_2$—. In embodiment, $L^3$ is —CH$_2$S(O)$_2$—. In embodiment, $L^3$ is —S(O)$_2$CH$_2$—. In embodiment, $L^3$ is —CH$_2$NH—. In embodiment, $L^3$ is —NHCH$_2$—. In embodiment, $L^3$ is —CH(CH$_3$)O—. In embodiment, $L^3$ is —OCH(CH$_3$)—. In embodiment, $L^3$ is —O—. In embodiment, $L^3$ is —S—. In embodiment, $L^3$ is —NH—. In embodiment, $L^4$ is —CH2O—. In embodiment, $L^4$ is —OCH$_2$—. In embodiment, $L^4$ is —CH$_2$—. In embodiment, $L^4$ is a bond. In embodiment, $L^4$ is —CH$_2$CH$_2$—. In embodiment, $L^4$ is —CH$_2$CH$_2$O—. In embodiment, $L^4$ is —OCH$_2$CH$_2$—. In embodiment, $L^4$ is —CH$_2$S—. In embodiment, $L^4$ is —SCH$_2$—. In embodiment, $L^4$ is —CH$_2$S(O)—. In embodiment, $L^4$ is —S(O)CH$_2$—. In embodiment, $L^4$ is —$CH_2S(O)_2$—. In embodiment, $L^4$ is —$S(O)_2CH_2$—. In embodiment, $L^4$ is —$CH_2NH$—. In embodiment, $L^4$ is —$NHCH_2$—. In embodiment, $L^4$ is —$CH(CH_3)O$—. In embodiment, $L^4$ is —$OCH(CH_3)$—. In embodiment, $L^4$ is —O—. In embodiment, $L^4$ is —S—. In embodiment, $L^4$ is —NH—.

In embodiments, the compound has the formula:

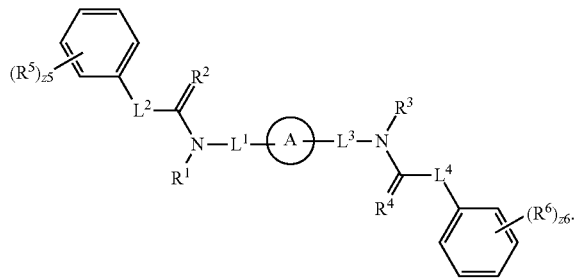

Ring A, $L^1$, $L^2$, $L^3$, $L^4$, $R^1$, $R^2$, $R^3$, $R^4$, $R^5$, $R^6$, $R^7$, z5, and z6 are as described for compounds of formula (I) above, including embodiments.

including embodiments. $R^8$ and $R^9$ are independently hydrogen, halogen, —$OCH_3$, —$OCH_2Ph$, —C(O)Ph, —$CH_3$, —$CF_3$, —$CCl_3$, —CN, —$S(O)CH_3$, —OH, —$NH_2$, —COOH, —$CONH_2$, —$NO_2$, —$C(O)CH_3$, —$CH(CH_3)_2$, —$CCSi(CH_3)_3$, —CCH, —$CH_2CCH$, —SH, —$SO_2Cl$, —$SO_3H$, —$SO_4H$, —$SO_2NH_2$, —$NHNH_2$, —$ONH_2$, —NHC=(O)NHNH_2, —NHC=(O)NH_2, —$NHSO_2H$, —NHC=(O)H, —NHC(O)—OH, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols b and d are independently 0 or 1.

In embodiments, $R^8$ is hydrogen. In embodiments, $R^8$ is substituted or unsubstituted alkyl. In embodiments, $R^8$ is substituted or unsubstituted $C_1$-$C_8$ alkyl. In embodiments, $R^8$ is substituted or unsubstituted $C_1$-$C_6$ alkyl. In embodiments, $R^8$ is substituted or unsubstituted $C_1$-$C_4$ alkyl. In embodiments, $R^8$ is substituted or unsubstituted $C_1$-$C_3$ alkyl. In embodiments, $R^8$ is substituted or unsubstituted $C_1$-$C_8$ alkenyl. In embodiments, $R^8$ is substituted or unsubstituted $C_1$-$C_8$ alkynyl. In embodiments, $R^8$ is substituted or unsubstituted $C_1$-$C_4$ alkenyl. In embodiments, $R^8$ is substituted or unsubstituted alkynyl. In embodiments, $R^8$ is unsubstituted alkyl. In embodiments, $R^8$ is unsubstituted $C_1$-$C_8$ alkyl. In embodiments, $R^8$ is unsubstituted $C_1$-$C_6$ alkyl. In embodiments, $R^8$ is unsubstituted $C_1$-$C_4$ alkyl. In embodiments, $R^8$ is unsubstituted $C_1$-$C_3$ alkyl. In embodiments, $R^8$ is unsubstituted $C_1$-$C_8$ alkenyl. In embodiments, $R^8$ is unsubstituted $C_1$-$C_8$ alkynyl. In embodiments, $R^8$ is unsubstituted $C_1$-$C_4$ alkenyl. In embodiments, $R^8$ is unsubstituted alkynyl. In embodiments, $R^8$ is —CCH. In embodiments, $R^8$ is

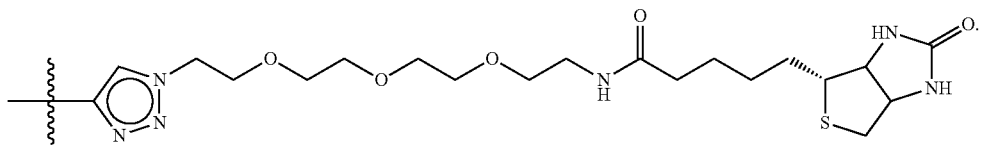

In embodiments, $R^8$ is

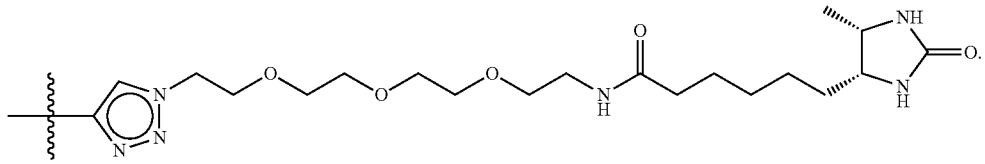

In embodiments, the compound has the formula:

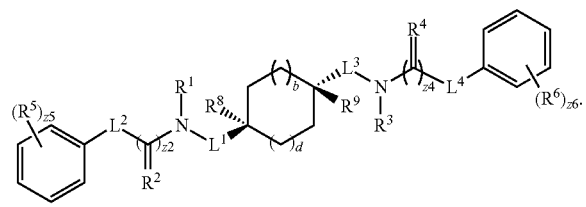

$L^1$, $L^2$, $L^3$, $L^4$, $R^1$, $R^2$, $R^3$, $R^4$, $R^5$, $R^6$, $R^7$, z2, z4, z5, and z6 are as described for compounds of formula (I) above, In embodiments, $R^9$ is hydrogen. In embodiments, $R^9$ is substituted or unsubstituted alkyl. In embodiments, $R^9$ is substituted or unsubstituted $C_1$-$C_8$ alkyl. In embodiments, $R^9$ is substituted or unsubstituted $C_1$-$C_6$ alkyl. In embodiments, $R^9$ is substituted or unsubstituted $C_1$-$C_4$ alkyl. In embodiments, $R^9$ is substituted or unsubstituted $C_1$-$C_3$ alkyl. In embodiments, $R^9$ is substituted or unsubstituted $C_1$-$C_8$ alkenyl. In embodiments, $R^9$ is substituted or unsubstituted $C_1$-$C_8$ alkynyl. In embodiments, $R^9$ is substituted or unsubstituted $C_1$-$C_4$ alkenyl. In embodiments, $R^9$ is substituted or unsubstituted alkynyl. In embodiments, $R^9$ is unsubstituted alkyl. In embodiments, $R^9$ is unsubstituted $C_1$-$C_8$ alkyl. In embodiments, $R^9$ is unsubstituted $C_1$-$C_6$ alkyl. In embodiments, $R^9$ is unsubstituted $C_1$-$C_4$ alkyl. In embodiments, $R^9$ is unsubstituted $C_1$-$C_3$ alkyl. In embodiments, $R^9$ is unsubstituted $C_1$-$C_8$ alkenyl. In embodiments, $R^9$ is unsubstituted $C_1$-$C_8$ alkynyl. In embodiments, $R^9$ is unsubstituted $C_1$-$C_4$ alkenyl. In embodiments, $R^9$ is unsubstituted $C_1$-$C_4$ alkynyl. In embodiments, $R^9$ is —CCH. In embodiments, $R^9$ is

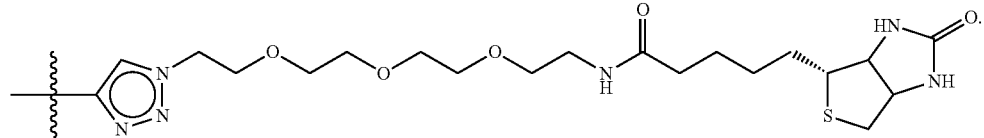

In embodiments, $R^9$ is

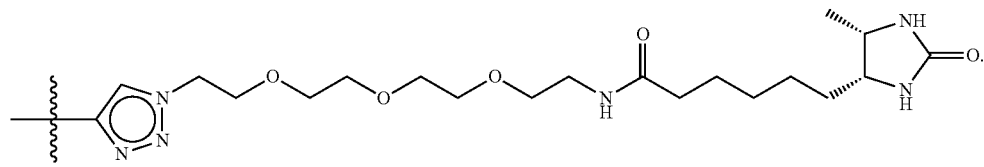

In embodiments, $R^8$ and $R^9$ are hydrogen.

In embodiments, the symbol b is 0. In embodiments, the symbol b is 1. In embodiments, the symbol d is 0. In embodiments, the symbol d is 1. In embodiments, the symbols b and d are 0. In embodiments, the symbols b and d are 1. In embodiments, the symbol b is 0 and d is 1. In embodiments, the symbol b is 1 and d is 0.

In embodiments, the compound has the formula:

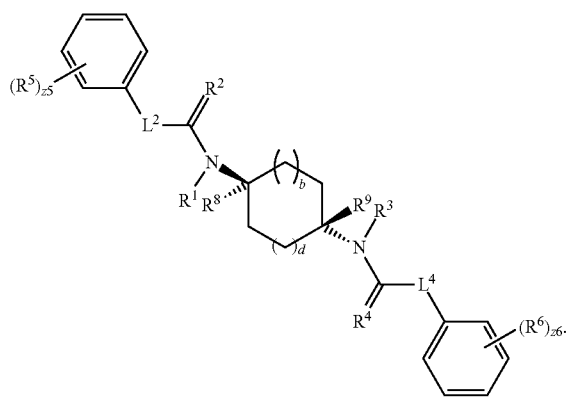

(IIIa)

$L^2$, $L^4$, $R^1$, $R^2$, $R^3$, $R^4$, $R^5$, $R^6$, $R^7$, $R^8$, $R^9$, b, d, z5, and z6 are as described for compounds of formula (I), (Ia), and (III) above, including embodiments.

In embodiments, the compound has the formula:

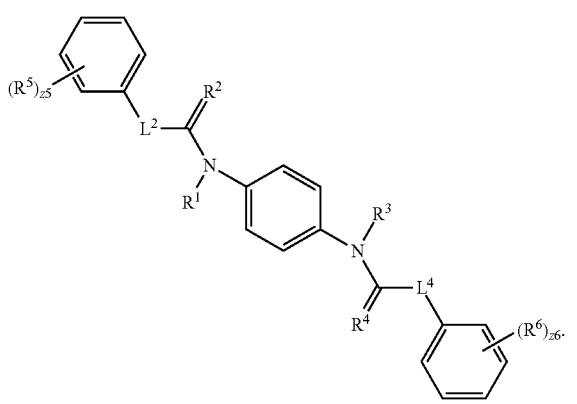

(IV)

$L^2$, $L^4$, $R^1$, $R^2$, $R^3$, $R^4$, $R^5$, $R^6$, $R^7$, z5, and z6 are as described for compounds of formula (I), (Ia), (III), and (IIIa) above, including embodiments.

In embodiments, the compound has the formula:

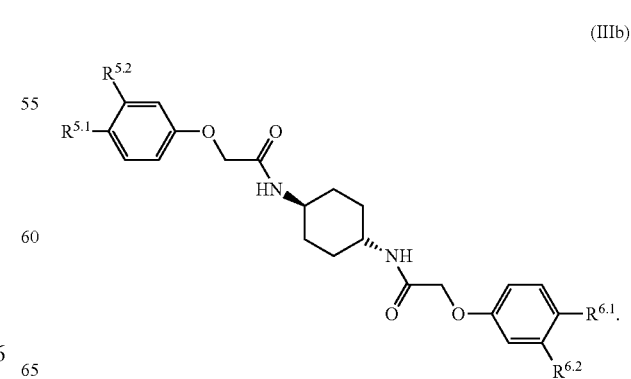

(IIIb)

$R^{5.1}$ and $R^{5.2}$ are independently as described for $R^5$, including embodiments. $R^{6.1}$ and $R^{6.2}$ are independently as described for $R^6$, including embodiments. In embodiments, $R^{5.1}$ is independently hydrogen, halogen, —$CF_3$, —CN, —$N_3$, substituted or unsubstituted $C_1$-$C_4$ alkyl, substituted or unsubstituted 2 to 4 membered heteroalkyl, substituted or unsubstituted 5 to 6 membered heteroaryl,

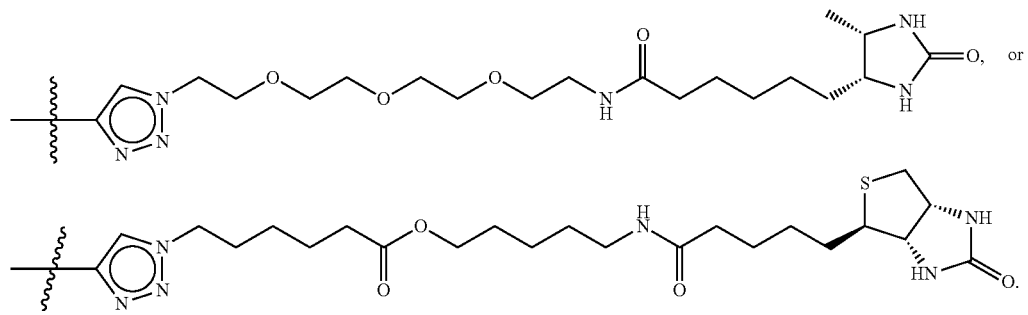

In embodiments, $R^{6.1}$ is independently hydrogen, halogen, —$CF_3$, —CN, —$N_3$, substituted or unsubstituted $C_1$-$C_4$ alkyl, substituted or unsubstituted 2 to 4 membered heteroalkyl, substituted or unsubstituted 5 to 6 membered heteroaryl,

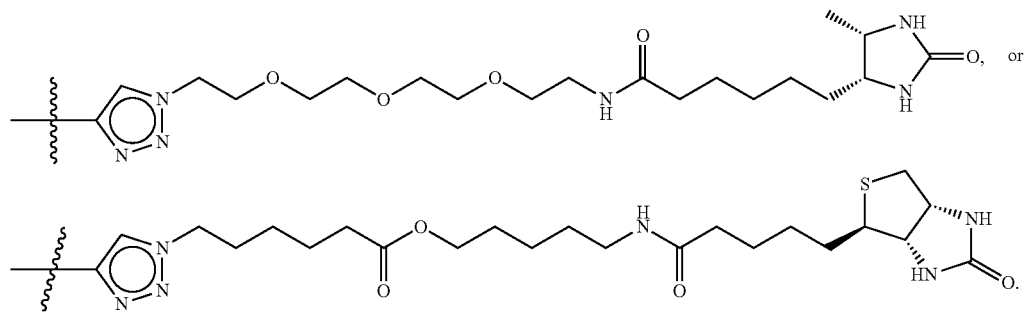

In embodiments, $R^{5.2}$ is independently hydrogen, halogen, —CCSi($CH_3$)$_3$, —$CF_3$, —$NO_2$, —CN, —$N_3$, substituted or unsubstituted $C_1$-$C_4$ alkyl, substituted or unsubstituted 2 to 4 membered heteroalkyl, substituted or unsubstituted 5 to 6 membered heteroaryl,

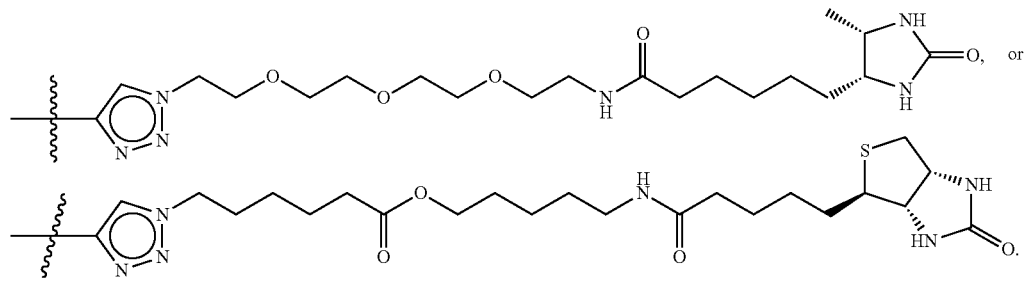

In embodiments, $R^{6.2}$ is independently hydrogen, halogen, —CCSi($CH_3$)$_3$, —$CF_3$, —$NO_2$, —CN, —$N_3$, substituted or unsubstituted $C_1$-$C_4$ alkyl, substituted or unsubstituted 2 to 4 membered heteroalkyl, substituted or unsubstituted 5 to 6 membered heteroaryl,

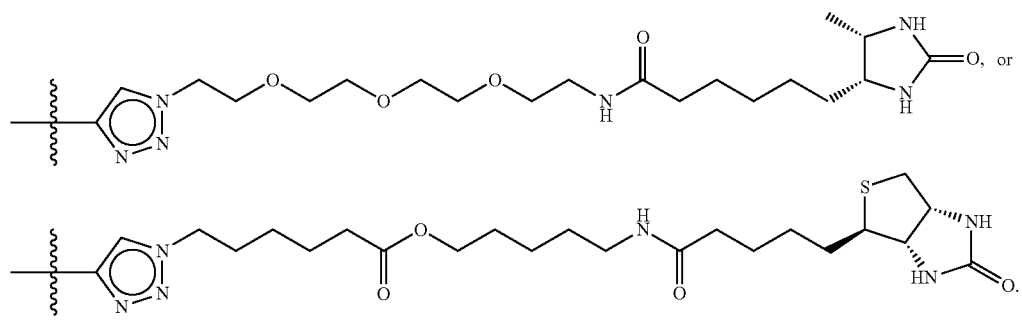

In embodiments, $R^{5.1}$ is independently halogen, unsubstituted $C_1$-$C_3$ alkyl, or unsubstituted $C_1$-$C_3$ haloalkyl. In embodiments, $R^{6.1}$ is independently halogen, unsubstituted $C_1$-$C_3$ alkyl, or unsubstituted $C_1$-$C_3$ haloalkyl. In embodiments, $R^{5.2}$ is independently hydrogen, halogen, —CCSi$(CH_3)_3$, —$NO_2$, unsubstituted $C_1$-$C_3$ alkyl, or unsubstituted $C_1$-$C_3$ haloalkyl. In embodiments, $R^{6.2}$ is independently hydrogen, halogen, —CCSi$(CH_3)_3$, —$NO_2$, unsubstituted $C_1$-$C_3$ alkyl, or unsubstituted $C_1$-$C_3$ haloalkyl. In embodiments, $R^{5.1}$ is independently —Cl, —I, —$CF_3$, —$CH_3$, or —CCH. In embodiments, $R^{6.1}$ is independently —Cl, —I, —$CF_3$, —$CH_3$, or —CCH. In embodiments, $R^{5.2}$ is independently hydrogen, —Cl, —F, —I, —CCSi$(CH_3)_3$, —$CF_3$, —$NO_2$, —$CH_3$, or —CCH. In embodiments, $R^{6.2}$ is independently hydrogen, —Cl, —F, —I, —CCSi$(CH_3)_3$, —$CF_3$, —$NO_2$, —$CH_3$, or —CCH. In embodiments, $R^{5.1}$ is independently hydrogen. In embodiments, $R^{5.1}$ is independently halogen. In embodiments, $R^{5.1}$ is independently —$CF_3$. In embodiments, $R^{5.1}$ is independently —CN. In embodiments, $R^{5.1}$ is independently —$N_3$. In embodiments, $R^{5.1}$ is independently unsubstituted $C_1$-$C_4$ alkyl. In embodiments, $R^{5.1}$ is independently unsubstituted 2 to 4 membered heteroalkyl. In embodiments, $R^{5.1}$ is independently unsubstituted 5 to 6 membered heteroaryl. In embodiments, $R^{5.1}$ is independently substituted $C_1$-$C_4$ alkyl. In embodiments, $R^{5.1}$ is independently substituted 2 to 4 membered heteroalkyl. In embodiments, $R^{5.1}$ is independently substituted 5 to 6 membered heteroaryl. In embodiments, $R^{6.1}$ is independently hydrogen. In embodiments, $R^{6.1}$ is independently halogen. In embodiments, $R^{6.1}$ is independently —$CF_3$. In embodiments, $R^{6.1}$ is independently —CN. In embodiments, $R^{6.1}$ is independently —$N_3$. In embodiments, $R^{6.1}$ is independently unsubstituted $C_1$-$C_4$ alkyl. In embodiments, $R^{6.1}$ is independently unsubstituted 2 to 4 membered heteroalkyl. In embodiments, $R^{6.1}$ is independently unsubstituted 5 to 6 membered heteroaryl. In embodiments, $R^{6.1}$ is independently substituted $C_1$-$C_4$ alkyl. In embodiments, $R^{6.1}$ is independently substituted 2 to 4 membered heteroalkyl. In embodiments, $R^{6.1}$ is independently substituted 5 to 6 membered heteroaryl. In embodiments, $R^{5.2}$ is independently hydrogen. In embodiments, $R^{5.2}$ is independently halogen. In embodiments, $R^{5.2}$ is independently —CCSi$(CH_3)_3$. In embodiments, $R^{5.2}$ is independently —$CF_3$. In embodiments, $R^{5.2}$ is independently —$NO_2$. In embodiments, $R^{5.2}$ is independently —CN. In embodiments, $R^{5.2}$ is independently —$N_3$. In embodiments, $R^{5.2}$ is independently unsubstituted $C_1$-$C_4$ alkyl. In embodiments, $R^{5.2}$ is independently unsubstituted 2 to 4 membered heteroalkyl. In embodiments, $R^{5.2}$ is independently unsubstituted 5 to 6 membered heteroaryl. In embodiments, $R^{5.2}$ is independently substituted $C_1$-$C_4$ alkyl. In embodiments, $R^{5.2}$ is substituted 2 to 4 membered heteroalkyl. In embodiments, $R^{5.2}$ is independently substituted 5 to 6 membered heteroaryl. In embodiments, $R^{6.2}$ is independently hydrogen. In embodiments, $R^{6.2}$ is independently halogen. In embodiments, $R^{6.2}$ is independently —CCSi$(CH_3)_3$. In embodiments, $R^{6.2}$ is independently —$CF_3$. In embodiments, $R^{6.2}$ is independently —$NO_2$. In embodiments, $R^{6.2}$ is independently —CN. In embodiments, $R^{6.2}$ is independently —$N_3$. In embodiments, $R^{6.2}$ is independently unsubstituted $C_1$-$C_4$ alkyl. In embodiments, $R^{6.2}$ is independently unsubstituted 2 to 4 membered heteroalkyl. In embodiments, $R^{6.2}$ is independently unsubstituted 5 to 6 membered heteroaryl. In embodiments, $R^{6.2}$ is independently substituted $C_1$-$C_4$ alkyl. In embodiments, $R^{6.2}$ is independently substituted 2 to 4 membered heteroalkyl. In embodiments, $R^{6.2}$ is independently substituted 5 to 6 membered heteroaryl.

In embodiments, the compound has the formula:

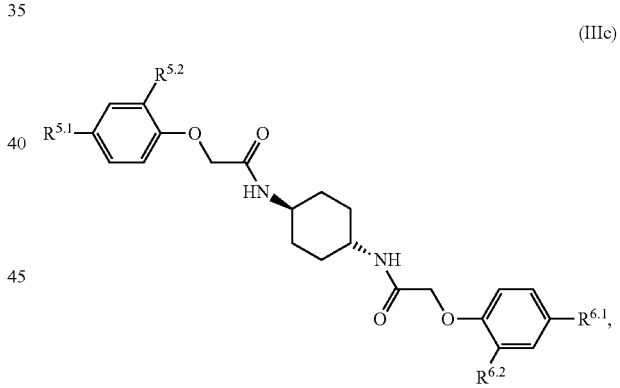

(IIIc)

wherein $R^{5.1}$ and $R^{5.2}$ are independently as described for $R^5$, including embodiments. $R^{6.1}$ and $R^{6.2}$ are independently as described for $R^6$, including embodiments.

In embodiments, the compound has the formula:

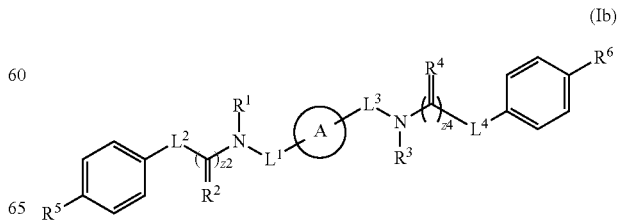

(Ib)

wherein, ring A, $L^1$, $L^2$, $L^3$, $L^4$, $R^1$, $R^2$, $R^3$, $R^4$, $R^5$, $R^6$, $R^7$, z2, and z4, are as described herein. In embodiments, the compound has the formula:

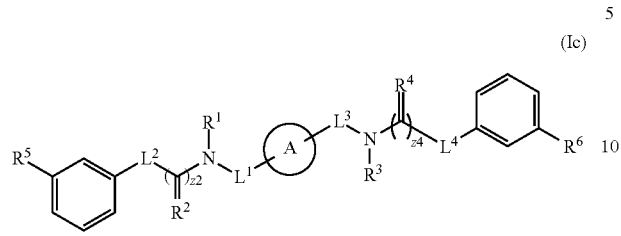
(Ic)

wherein, ring A, $L^1$, $L^2$, $L^3$, $L^4$, $R^1$, $R^2$, $R^3$, $R^4$, $R^5$, $R^6$, $R^7$, z2, and z4, are as described herein. In embodiments, the compound has the formula:

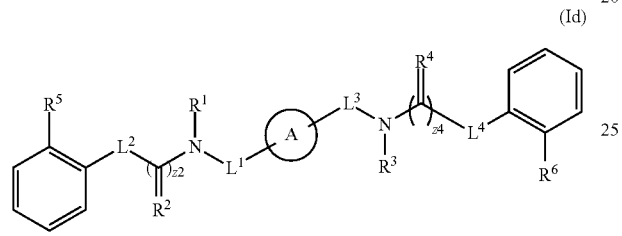
(Id)

wherein, ring A, $L^1$, $L^2$, $L^3$, $L^4$, $R^1$, $R^2$, $R^3$, $R^4$, $R^5$, $R^6$, $R^7$, z2, and z4, are as described herein. In embodiments, the compound has the formula:

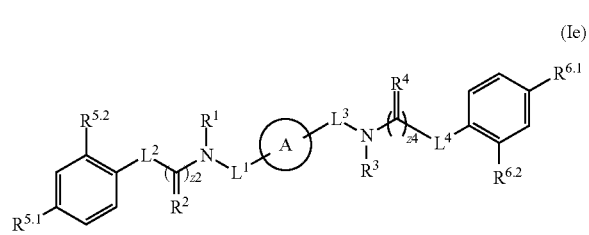
(Ie)

wherein, ring A, $L^1$, $L^2$, $L^3$, $L^4$, $R^1$, $R^2$, $R^3$, $R^4$, $R^5$, z2, and z4, are as described herein. $R^{5.1}$ and $R^{5.2}$ are independently as described for $R^5$, including embodiments. $R^{6.1}$ and $R^{6.2}$ are independently as described for $R^6$, including embodiments. In embodiments, the compound has the formula:

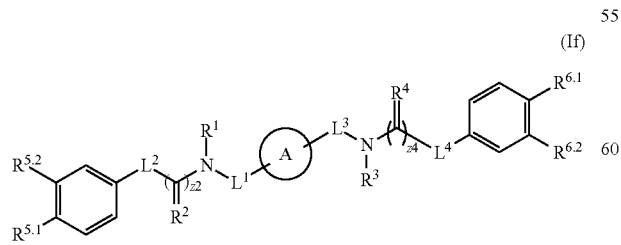
(If)

wherein, ring A, $L^1$, $L^2$, $L^3$, $L^4$, $R^1$, $R^2$, $R^3$, $R^4$, $R^7$, z2, and z4, are as described herein. $R^{5.1}$ and $R^{5.2}$ are independently as described for $R^5$, including embodiments. $R^{6.1}$ and $R^{6.2}$ are independently as described for $R^6$, including embodiments. In embodiments, the compound has the formula:

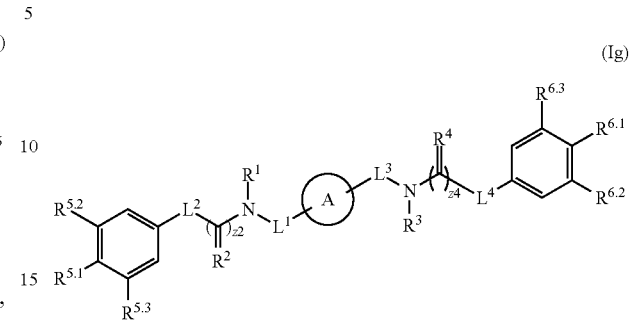
(Ig)

wherein, ring A, $L^1$, $L^2$, $L^3$, $L^4$, $R^1$, $R^2$, $R^3$, $R^4$, $R^7$, z2, and z4, are as described herein. $R^{5.1}$, $R^{5.2}$, and $R^{5.3}$ are independently as described for $R^5$, including embodiments. $R^{6.1}$, $R^{6.2}$, and $R^{6.3}$ are independently as described for $R^6$, including embodiments. In embodiments, the compound has the formula:

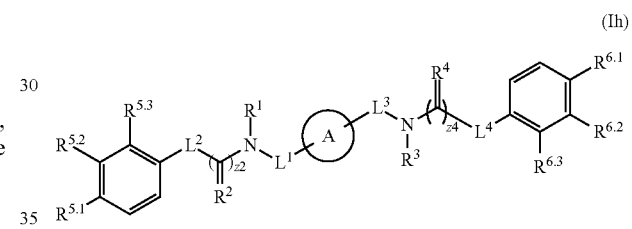
(Ih)

wherein, ring A, $L^1$, $L^2$, $L^3$, $L^4$, $R^1$, $R^2$, $R^3$, $R^4$, $R^7$, z2, and z4, are as described herein. $R^{5.1}$, $R^{5.2}$, and $R^{5.3}$ are independently as described for $R^5$, including embodiments. $R^{6.1}$, $R^{6.2}$, and $R^{6.3}$ are independently as described for $R^6$, including embodiments.

In embodiments, the compound is

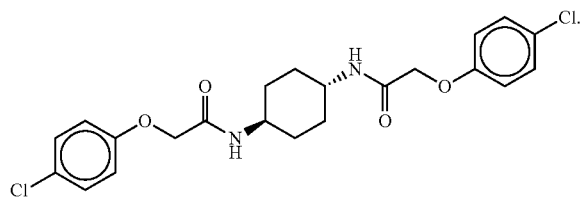

In embodiments, the compound is

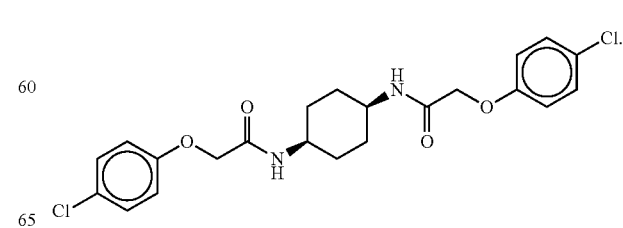

In embodiments, the compound is

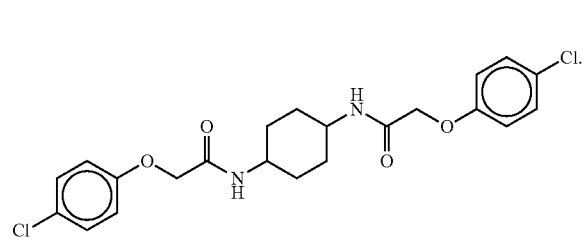

In embodiments, the compound is ISRIB. In embodiments, the compound is trans-ISRIB. In embodiments, the compound is cis-ISRIB. In embodiments, the compound is a mixture of trans- and cis-ISRIB. In embodiments, the compound is

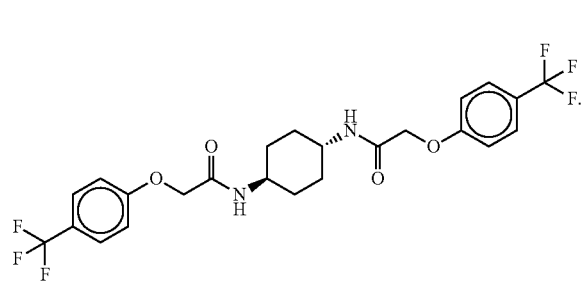

In embodiments, the compound is

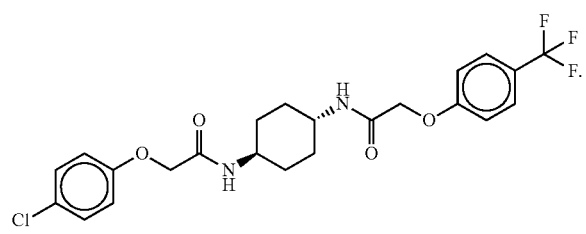

In embodiments, the compound is

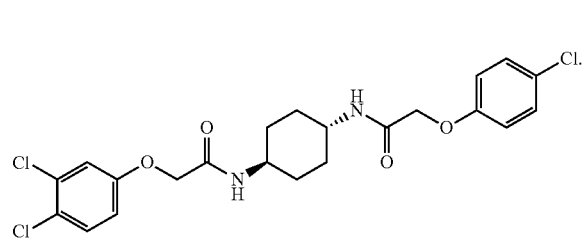

In embodiments, the compound is

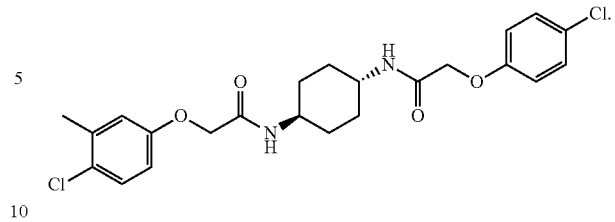

In embodiments, the compound is

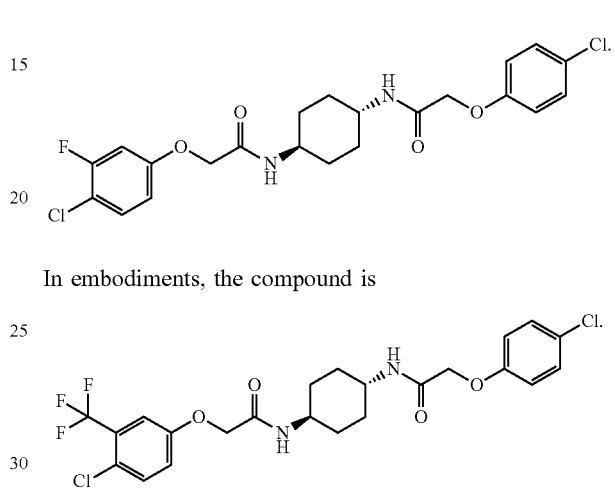

In embodiments, the compound is

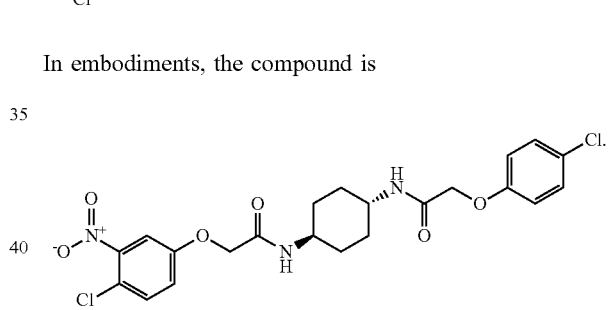

In embodiments, the compound is

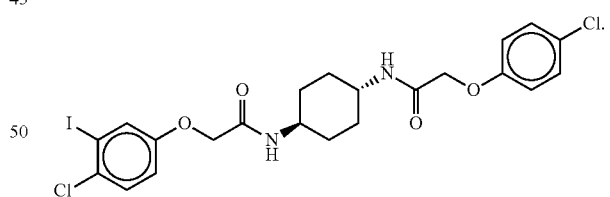

In embodiments, the compound is

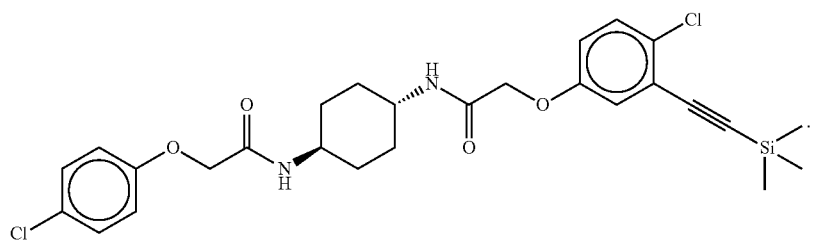

In embodiments, the compound is
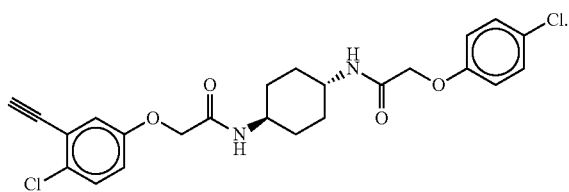
In embodiments, the compound is
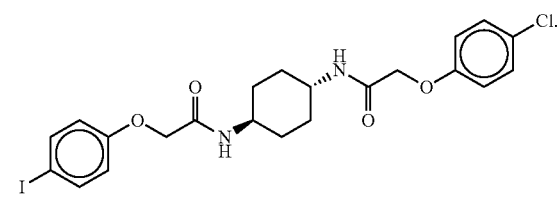
In embodiments, the compound is
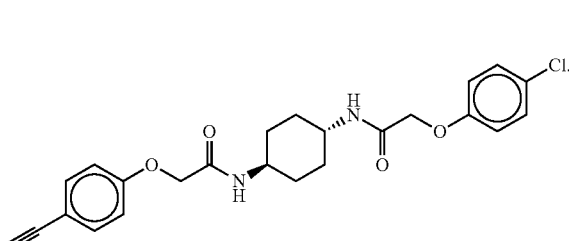
In embodiments, the compound is
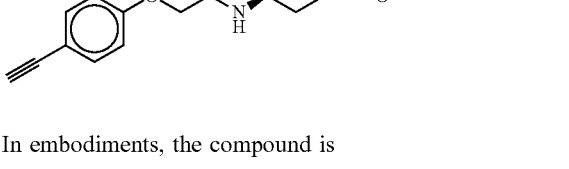
In embodiments, the compound is
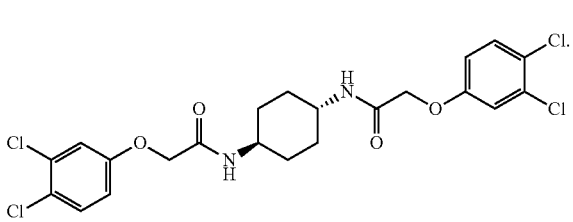 [SMILES: O=C(COc1ccc(Cl)c(Cl)c1)N[C@H]1CC[C@H](NC(=O)COc2ccc(Cl)c(Cl)c2)CC1]
In embodiments, the compound is
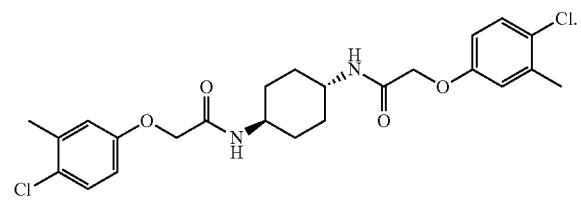
In embodiments, the compound is
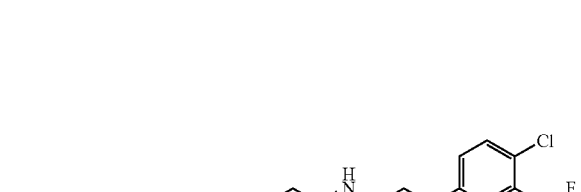
In embodiments, the compound is
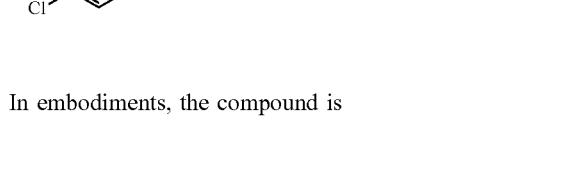
In embodiments, the compound is
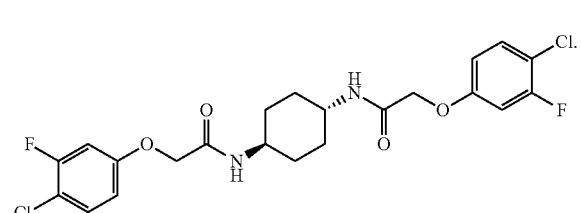
In embodiments, the compound is
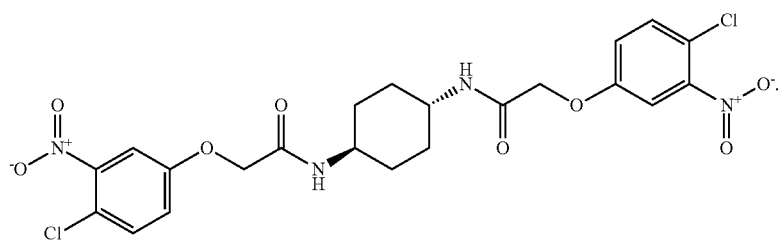

In embodiments, the compound is a mixture of cis-ISRIB and trans-ISRIB.

In embodiments, the compound is not

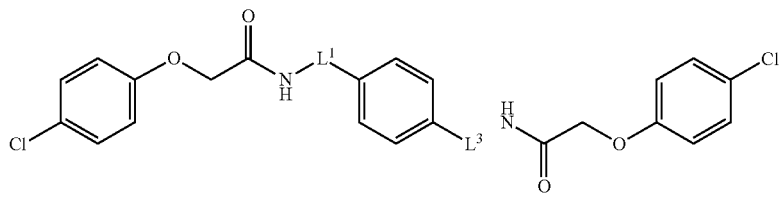

wherein $L^1$ and $L^2$ are both a bond or an unsubstituted $C_1$-$C_2$ alkylene. In embodiments, the compound is not a compound of formula Va wherein $L^1$ and $L^2$ are both a bond or an unsubstituted $C_1$-$C_3$ alkylene. In embodiments, the compound is not a compound of formula Va wherein $L^1$ and $L^2$ are both a bond or an unsubstituted $C_1$-$C_4$ alkylene.

In embodiments, the compound is not (Vb)

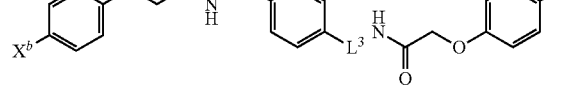

wherein $L^3$ and $L^4$ are both unsubstituted $C_1$-$C_2$ alkylene or unsubstituted 2 to 3 membered heteroalkylene. In embodiments, the compound is not a compound of formula Vb wherein $L^3$ and $L^4$ are both unsubstituted $C_1$-$C_3$ alkylene or unsubstituted 2 to 3 membered heteroalkylene. In embodiments, the compound is not a compound of formula Vb wherein $L^3$ and $L^4$ are both unsubstituted $C_1$-$C_3$ alkylene or unsubstituted 2 to 4 membered heteroalkylene.

In embodiments, the compound is not (Vc)

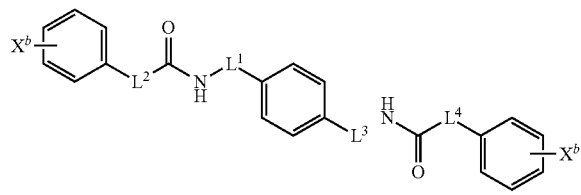

wherein $L^1$ and $L^2$ are both a bond or an unsubstituted $C_1$-$C_2$ alkylene and $L^3$ and $L^4$ are both unsubstituted $C_1$-$C_2$ alkylene or unsubstituted 2 to 3 membered heteroalkylene, and $X^b$ is —Cl. In embodiments, the compound is not a compound of formula (Vc) wherein $L^1$ and $L^2$ are both a bond or an unsubstituted $C_1$-$C_2$ alkylene and $L^3$ and $L^4$ are both unsubstituted $C_1$-$C_2$ alkylene or unsubstituted 2 to 3 membered heteroalkylene, and $X^b$ is a halide. In embodiments, the compound is not a compound of formula (Vc) wherein $L^1$ and $L^2$ are both a bond or an unsubstituted $C_1$-$C_3$ alkylene and $L^3$ and $L^4$ are both unsubstituted $C_1$-$C_3$ alkylene or unsubstituted 2 to 3 membered heteroalkylene, and $X^b$ is a halide. In embodiments, the compound is not a compound of formula (Vc) wherein $L^1$ and $L^2$ are both a bond or an unsubstituted $C_1$-$C_3$ alkylene and $L^3$ and $L^4$ are both unsubstituted $C_1$-$C_3$ alkylene or unsubstituted 2 to 4 membered heteroalkylene, and $X^b$ is a halide.

In embodiments, the compound is not (Vd)

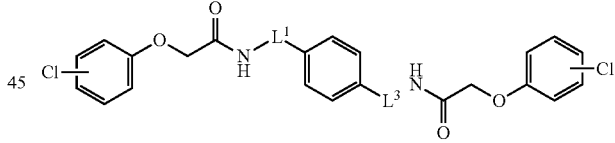

wherein $L^1$ and $L^2$ are both a bond or an unsubstituted methylene and $X^b$ is a halide. In embodiments, the compound is not a compound of formula (Vd) wherein $L^1$ and $L^2$ are independently a bond or an unsubstituted methylene and $X^b$ is a halide.

In embodiments, the compound is not (Ve)

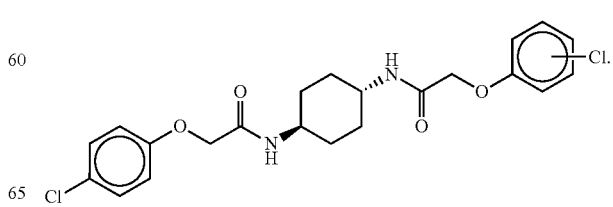

wherein $L^1$ and $L^2$ are both a bond or an unsubstituted methylene. In embodiments, the compound is not a compound of formula (Ve) wherein $L^1$ and $L^2$ are independently a bond or an unsubstituted methylene.

In embodiments, the compound is not (VIa)

In embodiments, the compound is not

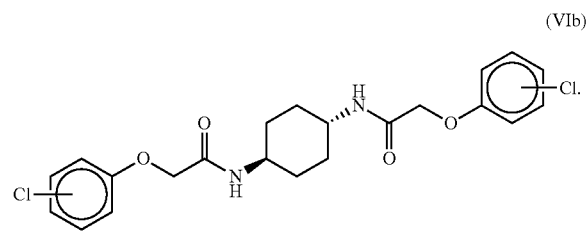
(VIb)

In embodiments, the compound is not

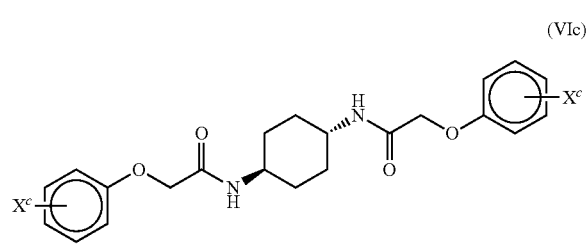
(VIc)

wherein $X^c$ is a halide. In embodiments, the compound is not a compound of formula (VIc) wherein $X^c$ is halide or —CH₃. In embodiments, the compound is not a compound of formula (VIc) wherein $X^c$ is halide, —CH₃, or —CF₃. In embodiments, the compound is not a compound of formula (VIc) wherein $X^c$ is halide, —CH₃, —CCl₃, or —CF₃. In embodiments, the compound is not a compound of formula (VIc) wherein is halide, —CH₃, —CCl₃, —CN, or —CF₃. In embodiments, the compound is not a compound of formula (VIc) wherein $X^c$ is halide, —CH₃, —CCl₃, —OH, —CN, or —CF₃. In embodiments, the compound is not a compound of formula (VIc) wherein $X^c$ is halide, —CH₃, —CCl₃, —OH, —SH, —CN, —OCH₃, or —CF₃. In embodiments, the compound is not a compound of formula (VIc) wherein $X^c$ is unsubstituted C₁-C₂ alkyl, halide, CCl₃, —OH, —SH, —CN, —OCH₃, or —CF₃. In embodiments, the compound is not a compound of formula (VIc) wherein $X^c$ is unsubstituted C₁-C₃ alkyl, halide, CCl₃, —OH, —SH, —CN, —OCH₃, or —CF₃. In embodiments, the compound is not a compound of formula (VIc) wherein $X^c$ is unsubstituted C₁-C₄ alkyl, halide, CCl₃, —OH, —SH, —CN, —OCH₃, or —CF₃. In embodiments, the compound is not a compound of formula (VIc) wherein $X^c$ is $R^5$. In embodiments, the compound is not

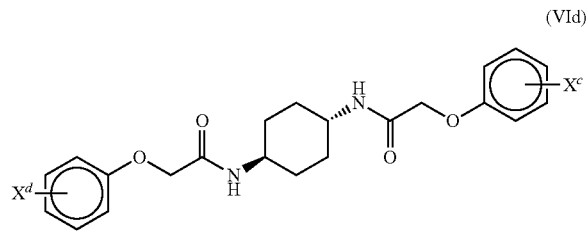
(VId)

wherein $X^c$ and $X^d$ are independently a halide. In embodiments, the compound is not a compound of formula (VId) wherein $X^c$ and $X^d$ are independently a halide or —CH₃. In embodiments, the compound is not a compound of formula (VId) wherein $X^c$ and $X^d$ are independently a halide, —CH₃, or —CF₃. In embodiments, the compound is not a compound of formula (VId) wherein $X^c$ and $X^d$ are independently a halide, —CH₃, —CCl₃, or —CF₃. In embodiments, the compound is not a compound of formula (VId) wherein $X^c$ and $X^d$ are independently a halide, —CH₃, —CCl₃, —CN, or —CF₃. In embodiments, the compound is not a compound of formula (VId) wherein $X^c$ and $X^d$ are independently a halide, —CH₃, —CCl₃, —OH, —CN, or —CF₃. In embodiments, the compound is not a compound of formula (VId) wherein $X^c$ and $X^d$ are independently a halide, —CH₃, —CCl₃, —OH, —SH, —CN, —OCH₃, or —CF₃. In embodiments, the compound is not a compound of formula (VId) wherein $X^c$ and $X^d$ are independently a unsubstituted C₁-C₂ alkyl, halide, —CCl₃, —OH, —SH, —CN, —OCH₃, or —CF₃. In embodiments, the compound is not a compound of formula (VId) wherein $X^c$ and $X^d$ are independently a unsubstituted C₁-C₃ alkyl, halide, —CCl₃, —OH, —SH, —CN, —OCH₃, or —CF₃. In embodiments, the compound is not a compound of formula (VId) wherein $X^c$ and $X^d$ are independently a unsubstituted C₁-C₄ alkyl, halide, —CCl₃, —OH, —SH, —CN, —OCH₃, or —CF₃. In embodiments, the compound is not a compound of formula (VId) wherein $X^c$ and $X^d$ are independently an $R^5$.

In embodiments, the compound is not

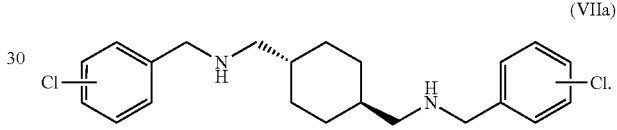
(VIIa)

In embodiments, the compound is not

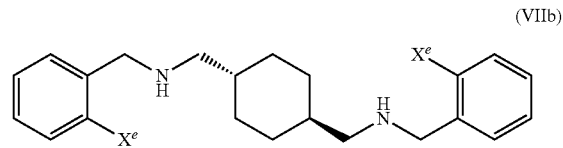
(VIIb)

wherein $X^e$ is a halide. In embodiments, the compound is not

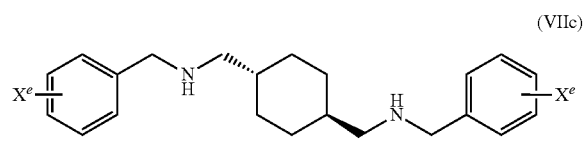
(VIIc)

wherein $X^e$ is a halide.

In embodiments, the compound is not

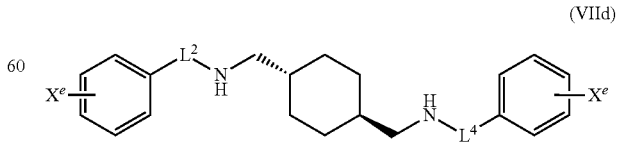
(VIId)

wherein $X^e$ is a halide and $L^2$ and $L^4$ are a bond or unsubstituted C₁-C₂ alkylene. In embodiments, the compound is not a compound of formula (VIId) wherein $X^e$ is a halide and $L^2$ and $L^4$ are a bond or unsubstituted $C_1$-$C_3$ alkylene. In embodiments, the compound is not a compound of formula (VIId) wherein $X^e$ is a halide and $L^2$ and $L^4$ are a bond or unsubstituted alkylene.

In embodiments, the compound is not

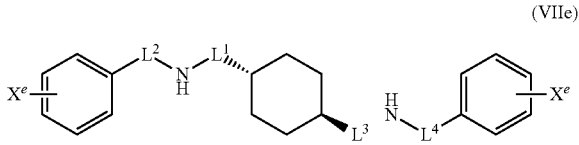

(VIIe)

wherein $X^e$ is a halide and $L^2$ and $L^4$ are a bond or unsubstituted $C_1$-$C_2$ alkylene and $L^1$ and $L^3$ are a bond or unsubstituted $C_1$-$C_2$ alkylene. In embodiments, the compound is not a compound of formula (VIIe) wherein $X^e$ is a halide and $L^2$ and $L^4$ are a bond or unsubstituted $C_1$-$C_2$ alkylene and $L^1$ and $L^3$ are a bond or unsubstituted $C_1$-$C_3$ alkylene. In embodiments, the compound is not a compound of formula (VIIe) wherein $X^e$ is a halide and $L^2$ and $L^4$ are a bond or unsubstituted $C_1$-$C_2$ alkylene and $L^1$ and $L^3$ are a bond or unsubstituted $C_1$-$C_4$ alkylene. In embodiments, the compound is not a compound of formula (VIIe) wherein $X^e$ is a halide and $L^2$ and $L^4$ are a bond or unsubstituted $C_1$-$C_3$ alkylene and $L^1$ and $L^3$ are a bond or unsubstituted $C_1$-$C_3$ alkylene. In embodiments, the compound is not a compound of formula (VIIe) wherein $X^e$ is a halide and $L^2$ and $L^4$ are a bond or unsubstituted alkylene and $L^1$ and $L^3$ are a bond or unsubstituted alkylene. In embodiments, the compound is not a compound of formula VIIa, VIIb, VIIc, VIId, or VIIe wherein $X^e$ is an unsubstituted methyl or halide. In embodiments, the compound is not a compound of formula VIIa, VIIb, VIIc, VIId, or VIIe wherein $X^e$ is a unsubstituted $C_1$-$C_2$ alkyl, halide, or —$CF_3$. In embodiments, the compound is not a compound of formula VIIa, VIIb, VIIc, VIId, or VIIe wherein $X^e$ is a unsubstituted $C_1$-$C_4$ alkyl, halide, —$CCl_3$, or —$CF_3$. In embodiments, the compound is not a compound of formula VIIa, VIIb, VIIc, VIId, or VIIe wherein $X^e$ is a unsubstituted $C_1$-$C_4$ alkyl, halide, —$CCl_3$, —CN, or —$CF_3$. In embodiments, the compound is not a compound of formula VIIa, VIIb, VIIc, VIId, or VIIe wherein $X^e$ is a unsubstituted $C_1$-$C_4$ alkyl, halide, $CCl_3$, —OH, —SH, —CN, —$OCH_3$, or —$CF_3$. In embodiments, the compound is not a compound of formula VIIa, VIIb, VIIc, VIId, or VIIe wherein $X^e$ is an $R^5$.

In embodiments, the compound is not

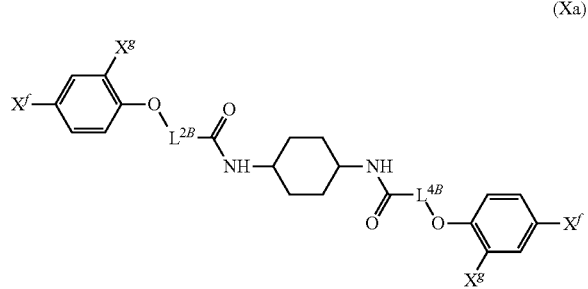

(Xa)

wherein $L^{2B}$ is substituted or unsubstituted alkylene; $L^{4B}$ is substituted or unsubstituted alkylene; $X^f$ is halide, $C_1$-$C_4$ substituted or unsubstituted alkyl, $C_1$-$C_4$ or substituted or unsubstituted alkoxy; $X^g$ is hydrogen, substituted or unsubstituted $C_1$-$C_4$ alkyl, $C_1$-$C_4$ or substituted or unsubstituted alkoxy. In embodiments, $L^{2B}$ is substituted or unsubstituted $C_1$-$C_3$ alkylene. In embodiments, $L^{2B}$ is substituted or unsubstituted $C_1$-$C_2$ alkylene. In embodiments, $L^{2B}$ is substituted or unsubstituted methylene. In embodiments, $L^{2B}$ is unsubstituted methylene. In embodiments, $L^{2B}$ is methylene substituted with unsubstituted $C_1$-$C_4$ alkyl. In embodiments, $L^{2B}$ is methylene substituted with unsubstituted $C_1$-$C_3$ alkyl. In embodiments, $L^{2B}$ is methylene substituted with unsubstituted $C_1$-$C_2$ alkyl. In embodiments, $L^{2B}$ is methylene substituted with unsubstituted methyl. In embodiments, $L^{2B}$ is methylene substituted with one unsubstituted methyl. In embodiments, $L^{4B}$ is substituted or unsubstituted $C_1$-$C_3$ alkylene. In embodiments, $L^{4B}$ is substituted or unsubstituted $C_1$-$C_2$ alkylene. In embodiments, $L^{4B}$ is substituted or unsubstituted methylene. In embodiments, $L^{4B}$ is unsubstituted methylene. In embodiments, $L^{4B}$ is methylene substituted with unsubstituted $C_1$-$C_4$ alkyl. In embodiments, $L^{4B}$ is methylene substituted with unsubstituted $C_1$-$C_3$ alkyl. In embodiments, $L^{4B}$ is methylene substituted with unsubstituted $C_1$-$C_2$ alkyl. In embodiments, $L^{4B}$ is methylene substituted with unsubstituted methyl. In embodiments, $L^{4B}$ is methylene substituted with one unsubstituted methyl. In embodiments, $X^f$ is halide. In embodiments, $X^f$ is —Cl. In embodiments, $X^f$ is —F. In embodiments, $X^f$ is —Br. In embodiments, $X^f$ is —I. In embodiments, $X^f$ is substituted or unsubstituted $C_1$-$C_4$ alkyl. In embodiments, $X^f$ is substituted or unsubstituted $C_1$-$C_3$ alkyl. In embodiments, $X^f$ is substituted or unsubstituted $C_1$-$C_2$ alkyl. In embodiments, $X^f$ is substituted or unsubstituted methyl. In embodiments, $X^f$ is unsubstituted methyl. In embodiments, $X^f$ is unsubstituted $C_1$-$C_4$ alkyl. In embodiments, $X^f$ is unsubstituted $C_1$-$C_3$ alkyl. In embodiments, $X^f$ is unsubstituted $C_1$-$C_2$ alkyl. In embodiments, $X^f$ is substituted or unsubstituted alkoxy. In embodiments, $X^f$ is substituted or unsubstituted $C_1$-$C_3$ alkoxy. In embodiments, $X^f$ is substituted or unsubstituted $C_1$-$C_2$ alkoxy. In embodiments, $X^f$ is substituted or unsubstituted methoxy. In embodiments, $X^f$ is unsubstituted methoxy. In embodiments, $X^f$ is unsubstituted alkoxy. In embodiments, $X^f$ is unsubstituted $C_1$-$C_3$ alkoxy. In embodiments, $X^f$ is unsubstituted $C_1$-$C_2$ alkoxy. In embodiments, $X^g$ is halide. In embodiments, $X^g$ is —Cl. In embodiments, $X^g$ is —F. In embodiments, $X^g$ is —Br. In embodiments, $X^g$ is —I. In embodiments, $X^g$ is substituted or unsubstituted $C_1$-$C_4$ alkyl. In embodiments, $X^g$ is substituted or unsubstituted $C_1$-$C_3$ alkyl. In embodiments, $X^g$ is substituted or unsubstituted $C_1$-$C_2$ alkyl. In embodiments, $X^g$ is substituted or unsubstituted methyl. In embodiments, $X^g$ is unsubstituted methyl. In embodiments, $X^g$ is unsubstituted $C_1$-$C_4$ alkyl. In embodiments, $X^g$ is unsubstituted $C_1$-$C_3$ alkyl. In embodiments, $X^g$ is unsubstituted $C_1$-$C_2$ alkyl. In embodiments, $X^g$ is substituted or unsubstituted $C_1$-$C_4$ alkoxy. In embodiments, $X^g$ is substituted or unsubstituted $C_1$-$C_3$ alkoxy. In embodiments, $X^g$ is substituted or unsubstituted $C_1$-$C_2$ alkoxy. In embodiments, $X^g$ is substituted or unsubstituted methoxy. In embodiments, $X^g$ is unsubstituted methoxy. In embodiments, $X^g$ is unsubstituted $C_1$-$C_4$ alkoxy. In embodiments, $X^g$ is unsubstituted $C_1$-$C_3$ alkoxy. In embodiments, $X^g$ is unsubstituted $C_1$-$C_2$ alkoxy. In embodiments, $X^g$ is hydrogen. In embodiments, the compound is not 95
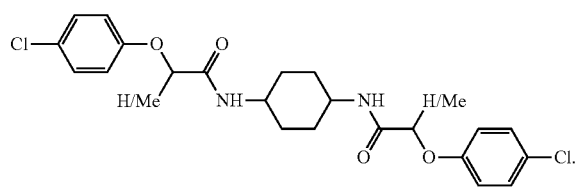
In embodiments, the compound is not
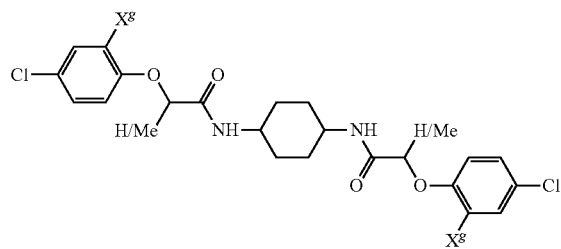
96
wherein $X^g$ is H, —Cl, —CH$_3$, or —OCH$_3$. In embodiments, the compound is not
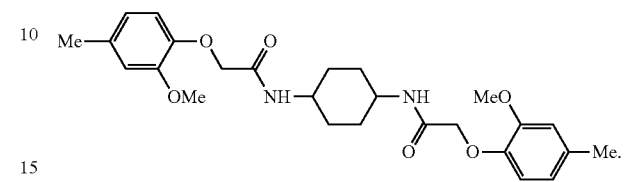
In embodiments, the compound is not a compound selected from the group consisting of:
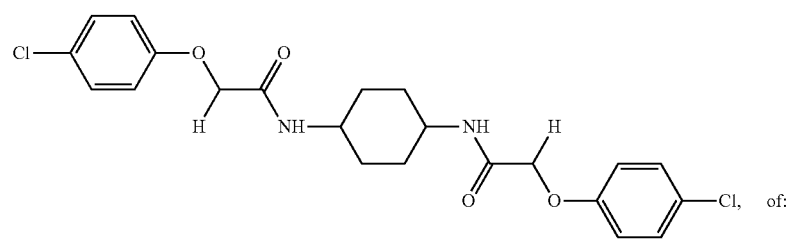
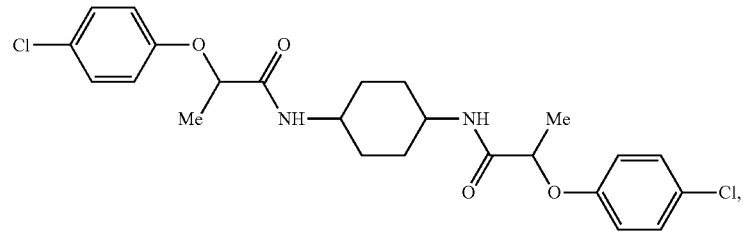
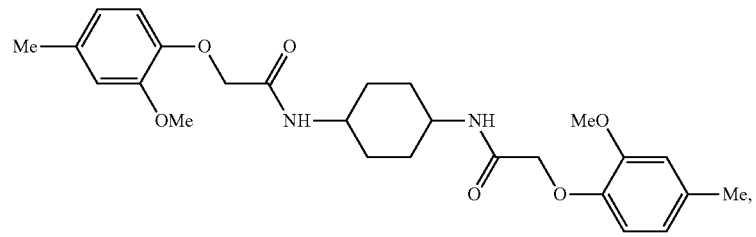
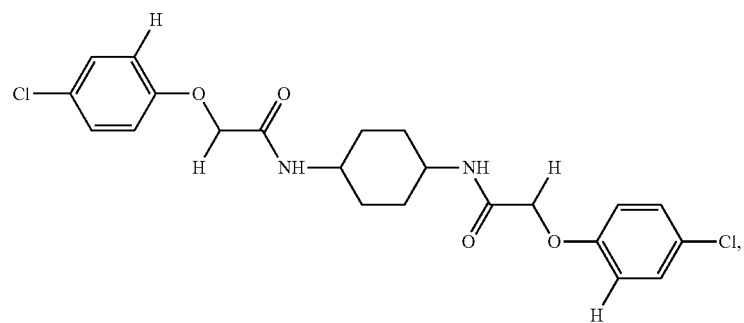

-continued
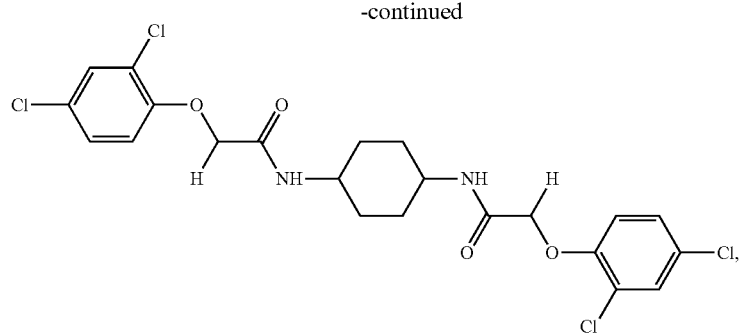
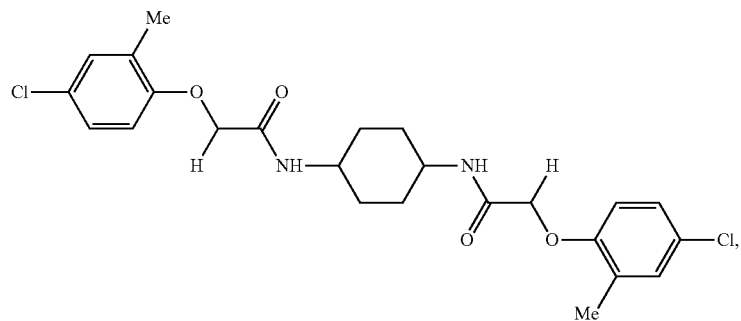
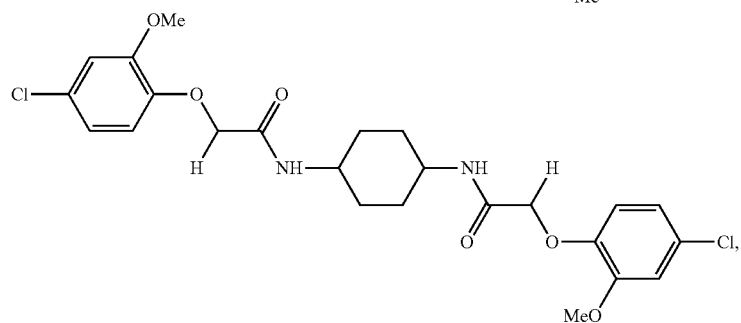
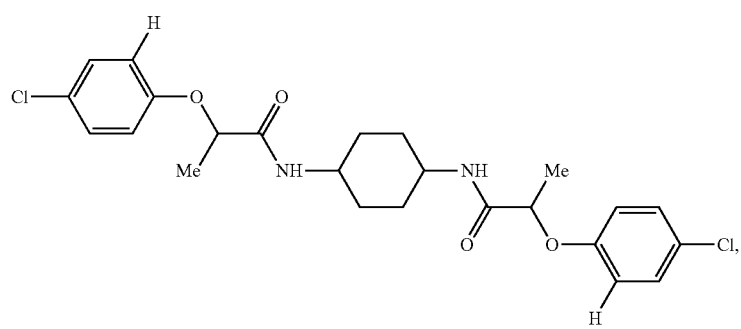
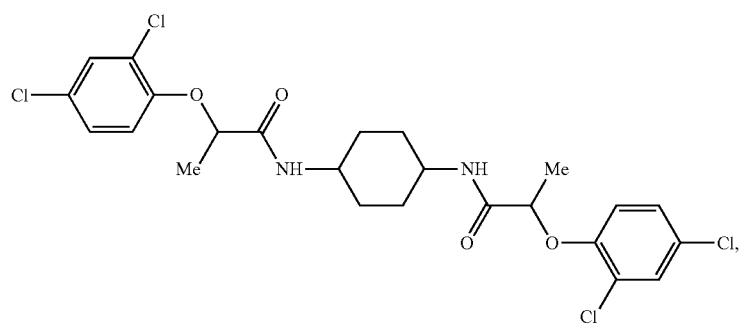 [SMILES: COc1cc(Cl)ccc1OC(C)C(=O)NC1CCC(NC(=O)C(C)Oc2ccc(Cl)cc2OC)CC1]

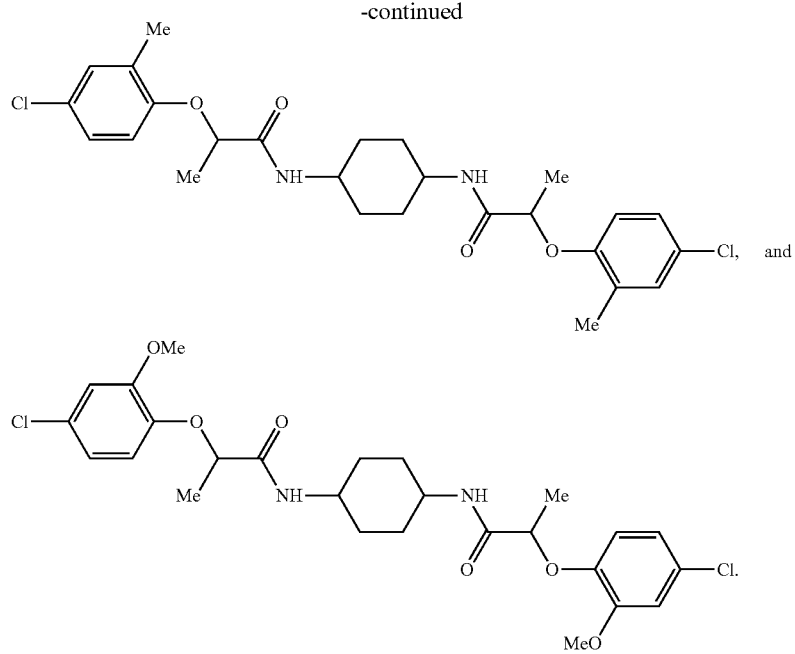

In embodiments, the compound is not a compound selected from the group consisting of the compounds of Table 2.

In embodiments, the compound is an inhibitor of the integrated stress response. In embodiments, the compound is an inhibitor of a pathway activated by eIF2α phosphorylation. In embodiments, the compound is an inhibitor of a pathway activated by PERK activity. In embodiments, the compound is an inhibitor of a pathway activated by accumulation of unfolded proteins in the endoplasmic reticulum. In embodiments, the compound is an inhibitor of a pathway activated by GCN2 activity. In embodiments, the compound is an inhibitor of a pathway activated by amino acid starvation. In embodiments, the compound is an inhibitor of a pathway activated by PKR activity. In embodiments, the compound is an inhibitor of a pathway activated by viral infection. In embodiments, the compound is an inhibitor of a pathway activated by HRI activity. In embodiments, the compound is an inhibitor of a pathway activated by heme deficiency. In embodiments, the compound is an inhibitor of a pathway that decreases bulk protein synthesis and includes eIF2α. In embodiments, the compound is an inhibitor of a pathway activated by ATF4. In embodiments, the compound is an inhibitor of a pathway activated by CHOP activity. In embodiments, the compound is an activator of apoptosis. In embodiments, the compound increases the level of apoptosis relative to the level of apoptosis in the absence of the compound. In embodiments, the compound is an inhibitor of a pathway activated by hypoxic conditions that includes eIF2α. In embodiments, the compound is an inhibitor of a pathway downstream of eIF2α phosphorylation. In embodiments, the compound is an inhibitor of a pathway downstream of eIF2α phosphorylation of serine 51 (in the human protein or the corresponding residue in a non-human protein). In embodiments, the compound is an inhibitor of a pathway downstream of eIF2α phosphorylation by PERK, GCN2, PKR, or HRI. In embodiments, the compound is an inhibitor of neuronal cell death. In embodiments, the compound is a cytotoxic agent. In embodiments, the compound is an anti-cancer agent. In embodiments, the compound is an inhibitor of a protein activated by eIF2α phosphorylation (directly or indirectly). In embodiments, the compound is an inhibitor of a protein, wherein the level of protein (e.g. amount or activity level) is increased by eIF2α phosphorylation (directly or indirectly). In embodiments, the compound increases caspase 3 activity. In embodiments, the compound increases caspase 7 activity. In embodiments, the compound increases apoptosis in cells under ER stress. In embodiments, the compound increases apoptosis in cells under ER stress but not cells under the same conditions except that they are not under ER stress. In embodiments, the compound increases apoptosis in cells under ER stress more than in cells under the same conditions except that they are not under ER stress. In embodiments, the compound inhibits the formation of the eIF2 complex.

In embodiments, $R^1$ is independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCH$_3$, —OCF$_3$, —OCHF$_2$, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl.

In embodiments, $R^3$ is independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCH$_3$, —OCF$_3$, —OCHF$_2$, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl.

In embodiments, $R^5$ is independently hydrogen, halogen, —$OCH_3$, —$OCH_2Ph$, —$C(O)Ph$, —$CH_3$, —$CF_3$, —$CCl_3$, —$CN$, —$S(O)CH_3$, —$OH$, —$NH_2$, —$COOH$, —$CONH_2$, —$NO_2$, —$C(O)CH_3$, —$CH(CH_3)_2$, —$CCSi(CH_3)_3$, —$CCH$, —$CH_2CCH$, —$SH$, —$SO_2Cl$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)OH$, —$NHOH$, —$OCH_3$, —$OCF_3$, —$OCHF_2$, $R^{15}$-substituted or unsubstituted alkyl, le-substituted or unsubstituted heteroalkyl, le-substituted or unsubstituted cycloalkyl, le-substituted or unsubstituted heterocycloalkyl, le-substituted or unsubstituted aryl, or $R^{15}$-substituted or unsubstituted heteroaryl.

In embodiments, $R^6$ is independently hydrogen, halogen, —$OCH_3$, —$OCH_2Ph$, —$C(O)Ph$, —$CH_3$, —$CF_3$, —$CCl_3$, —$CN$, —$S(O)CH_3$, —$OH$, —$NH_2$, —$COOH$, —$CONH_2$, —$NO_2$, —$C(O)CH_3$, —$CH(CH_3)_2$, —$CCSi(CH_3)_3$, —$CCH$, —$CH_2CCH$, —$SH$, —$SO_2Cl$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)OH$, —$NHOH$, —$OCH_3$, —$OCF_3$, —$OCHF_2$, $R^{16}$-substituted or unsubstituted alkyl, le-substituted or unsubstituted heteroalkyl, $R^{16}$-substituted or unsubstituted cycloalkyl, le-substituted or unsubstituted heterocycloalkyl, $R^{16}$-substituted or unsubstituted aryl, or $R^{15}$-substituted or unsubstituted heteroaryl.

In embodiments, $R^7$ is independently hydrogen, halogen, —$OCH_3$, —$OCH_2Ph$, —$C(O)Ph$, —$CH_3$, —$CF_3$, —$CCl_3$, —$CN$, —$S(O)CH_3$, —$OH$, —$NH_2$, —$COOH$, —$CONH_2$, —$NO_2$, —$C(O)CH_3$, —$CH(CH_3)_2$, —$CCSi(CH_3)_3$, —$CCH$, —$CH_2CCH$, —$SH$, —$SO_2Cl$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)OH$, —$NHOH$, —$OCH_3$, —$OCF_3$, —$OCHF_2$, $R^r$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl.

In embodiments, $R^8$ is independently hydrogen, halogen, —$OCH_3$, —$OCH_2Ph$, —$C(O)Ph$, —$CH_3$, —$CF_3$, —$CCl_3$, —$CN$, —$S(O)CH_3$, —$OH$, —$NH_2$, —$COOH$, —$CONH_2$, —$NO_2$, —$C(O)CH_3$, —$CH(CH_3)_2$, —$CCSi(CH_3)_3$, —$CCH$, —$CH_2CCH$, —$SH$, —$SO_2Cl$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)OH$, —$NHOH$, —$OCH_3$, —$OCF_3$, —$OCHF_2$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl.

In embodiments, $R^9$ is independently hydrogen, halogen, —$OCH_3$, —$OCH_2Ph$, —$C(O)Ph$, —$CH_3$, —$CF_3$, —$CCl_3$, —$CN$, —$S(O)CH_3$, —$OH$, —$NH_2$, —$COOH$, —$CONH_2$, —$NO_2$, —$C(O)CH_3$, —$CH(CH_3)_2$, —$CCSi(CH_3)_3$, —$CCH$, —$CH_2CCH$, —$SH$, —$SO_2Cl$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)OH$, —$NHOH$, —$OCH_3$, —$OCF_3$, —$OCHF_2$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In embodiments, $L^1$ is independently a bond, $R^{21}$-substituted or unsubstituted alkylene, or $R^{21}$-substituted or unsubstituted heteroalkylene.

In embodiments, $L^2$ is independently a bond, $R^{22}$-substituted or unsubstituted alkylene, or $R^{22}$-substituted or unsubstituted heteroalkylene.

In embodiments, $L^{2B}$ is independently a bond or $R^{22B}$-substituted or unsubstituted alkylene.

In embodiments, $L^3$ is independently a bond, $R^{23}$-substituted or unsubstituted alkylene, or $R^{23}$-substituted or unsubstituted heteroalkylene.

In embodiments, $L^4$ is independently a bond, $R^{24}$-substituted or unsubstituted alkylene, or $R^{24}$-substituted or unsubstituted heteroalkylene.

In embodiments, $L^{4B}$ is independently a bond or $R^{24B}$-substituted or unsubstituted alkylene.

In embodiments, ring A is independently an $R^{25}$-substituted or unsubstituted cycloalkylene, or $R^{25}$-substituted or unsubstituted arylene.

Each $R^{11}$, $R^{13}$, $R^{15}$, $R^{16}$, $R^{17}$, $R^{18}$, $R^{19}$, $R^{21}$, $R^{22}$, $R^{22B}$, $R^{23}$, $R^{24}$, $R^{24B}$, and $R^{25}$ is independently hydrogen, oxo, halogen, —$OCH_3$, —$OCH_2Ph$, —$C(O)Ph$, —$CH_3$, —$CF_3$, —$CCl_3$, —$CN$, —$S(O)CH_3$, —$OH$, —$NH_2$, —$COOH$, —$CONH_2$, —$NO_2$, —$C(O)CH_3$, —$CH(CH_3)_2$, —$CCSi(CH_3)_3$, —$CCH$, —$CH_2CCH$, —$SH$, —$SO_2Cl$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)OH$, —$NHOH$, —$OCH_3$, —$OCF_3$, —$OCHF_2$, —$N_3$, —$OCH_2CCH$, —$NHC(O)CH_3$, —$NHCH_3$, —$NHC(S)CH_3$, —$N(CH_3)_2$, —$C(O)NHNH_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{22}$ is —$CF_3$. In embodiments, $R^{22B}$ is —$CF_3$. In embodiments, $R^{24}$ is —$CF_3$. In embodiments, $R^{24B}$ is —$CF_3$.

In some embodiments, a compound as described herein may include multiple instances of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{22B}$, $R^{24B}$ and/or other variables. In such embodiments, each variable may optional be different and be appropriately labeled to distinguish each group for greater clarity. For example, where each $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{22B}$, and/or $R^{24B}$, is different, they may be referred to for example, as $R^{5.1}$, $R^{5.2}$, $R^{5.3}$, $R^{5.4}$, $R^{5.5}$, $R^{6.1}$, $R^{6.2}$, $R^{6.3}$, $R^{6.4}$, $R^{6.5}$, $R^{7.1}$, $R^{7.2}$, $R^{7.3}$, $R^{7.4}$, $R^{7.5}$, $R^{8.1}$, $R^{8.2}$, $R^{8.3}$, $R^{8.4}$, $R^{8.5}$, $R^{9.1}$, $R^{9.2}$, $R^{9.3}$, $R^{9.4}$, $R^{9.5}$, $R^{10.1}$, $R^{10.2}$, $R^{10.3}$, $R^{10.4}$, $R^{10.5}$, $R^{11.1}$, $R^{11.2}$, $R^{11.3}$, $R^{11.4}$, $R^{11.5}$, $R^{12.1}$, $R^{12.2}$, $R^{12.3}$, $R^{12.4}$, $R^{12.5}$, $R^{13.1}$, $R^{13.2}$, $R^{13.3}$, $R^{13.4}$, $R^{13.5}$, $R^{14.1}$, $R^{14.2}$, $R^{14.3}$, $R^{14.4}$, $R^{14.5}$, $R^{15.1}$, $R^{15.2}$, $R^{15.3}$, $R^{15.4}$, $R^{15.5}$, $R^{16.1}$, $R^{16.2}$, $R^{16.3}$, $R^{16.4}$, $R^{16.5}$, $R^{17.1}$, $R^{17.2}$, $R^{17.3}$, $R^{17.4}$, $R^{17.5}$, $R^{18.1}$, $R^{18.2}$, $R^{18.3}$, $R^{18.4}$, $R^{18.5}$, $R^{19.1}$, $R^{19.2}$, $R^{19.3}$, $R^{19.4}$, $R^{19.5}$, $R^{20.1}$, $R^{20.2}$, $R^{20.3}$, $R^{20.4}$, $R^{20.5}$, $R^{21.1}$, $R^{21.2}$, $R^{21.3}$, $R^{21.4}$, $R^{21.5}$, $R^{22.1}$, $R^{22.2}$, $R^{22.3}$, $R^{22.4}$, $R^{22.5}$, $R^{23.1}$, $R^{23.2}$, $R^{23.3}$, $R^{23.4}$, $R^{23.5}$, $R^{24.1}$, $R^{24.2}$, $R^{24.3}$, $R^{24.4}$, $R^{24.5}$, $R^{25.1}$, $R^{25.2}$, $R^{25.3}$, $R^{25.4}$, $R^{25.5}$, $R^{22B.1}$, $R^{22B.2}$, $R^{22B.3}$, $R^{22B.4}$, $R^{22B.5}$, $R^{24B1}$, $R^{24B.2}$, $R^{24B.3}$, $R^{24B.4}$, and/or $R^{24B.5}$, respectively, wherein the definition of $R^5$ is assumed by $R^{5.1}$, $R^{5.2}$, $R^{5.3}$, $R^{5.4}$, and/or $R^{5.5}$, the definition of $R^6$ is assumed by $R^{6.1}$, $R^{6.2}$, $R^{6.3}$, $R^{6.4}$, and/or $R^{6.5}$, the definition of $R^7$ is assumed by $R^{7.1}$, $R^{7.2}$, $R^{7.3}$, $R^{7.4}$, and/or $R^{7.5}$, the definition of $R^8$ is assumed by $R^{8.1}$, $R^{8.2}$, $R^{8.3}$, $R^{8.4}$, and/or $R^{8.5}$, the definition of $R^9$ is assumed by $R^{9.1}$, $R^{9.2}$, $R^{9.3}$, $R^{9.4}$, and/or $R^{9.5}$, the definition of $R^{10}$ is assumed by $R^{10.1}$, $R^{10.2}$, $R^{10.3}$, $R^{10.4}$, and/or $R^{10.5}$, the definition of $R^{11}$ is assumed by $R^{11.1}$, $R^{11.2}$, $R^{11.3}$, $R^{11.4}$, and/or $R^{11.5}$, the definition of $R^{12}$ is assumed by $R^{12.1}$, $R^{12.2}$, $R^{12.3}$, $R^{12.4}$, and/or $R^{12.5}$, the definition of $R^{13}$ is assumed by $R^{13.1}$, $R^{13.2}$, $R^{13.3}$, $R^{13.4}$, and/or $R^{13.5}$, the definition of $R^{14}$ is assumed by $R^{14.1}$, $R^{14.2}$, $R^{14.3}$, $R^{14.4}$, and/or $R^{14.5}$, the definition of $R^{15}$ is assumed by $R^{15.1}$, $R^{15.2}$, $R^{15.3}$, $R^{15.4}$, and/or $R^{15.5}$, the definition of $R^{16}$ is assumed by $R^{16.1}$, $R^{16.2}$, $R^{16.3}$, $R^{16.4}$, and/or $R^{16.5}$, the definition of $R^{17}$ is assumed by $R^{17.1}$, $R^{17.2}$, $R^{17.3}$, $R^{17.4}$, and/or $R^{17.5}$, the definition of $R^{18}$ is assumed by $R^{18.1}$, $R^{18.2}$, $R^{18.3}$, $R^{18.4}$, and/or $R^{18.5}$, the definition of $R^{19}$ is assumed by $R^{19.1}$, $R^{19.2}$, $R^{19.3}$, $R^{19.4}$, and/or $R^{19.5}$, the definition of $R^{20}$ is assumed by $R^{20.1}$, $R^{20.2}$, $R^{20.3}$, $R^{20.4}$ and/or $R^{20.5}$, the definition of $R^{21}$ is assumed by $R^{21.1}$, $R^{21.2}$, $R^{21.3}$, $R^{21.4}$, and/or $R^{21.5}$, the definition of $R^{22}$ is assumed by $R^{22.1}$, $R^{22.2}$, $R^{22.3}$, $R^{22.4}$, and/or $R^{22.5}$, the definition of $R^{23}$ is assumed by $R^{23.1}$, $R^{23.2}$, $R^{23.3}$, $R^{23.4}$, and/or $R^{23.5}$, the definition of $R^{24}$ is assumed by $R^{24.1}$, $R^{24.2}$, $R^{24.3}$, $R^{24.4}$, and/or $R^{24.5}$, the definition of $R^{25}$ is assumed by $R^{25.1}$, $R^{25.2}$, $R^{25.3}$, $R^{25.4}$, and/or $R^{25.5}$, the definition of $R^{22B}$ is assumed by $R^{22B.1}$, $R^{22B.2}$, $R^{22B.3}$, $R^{22B.4}$, and/or $R^{22B.5}$, and the definition of $R^{24B}$ is assumed by $R^{24B.1}$, $R^{24B.2}$, $R^{24B.3}$, $R^{24B.4}$, and/or $R^{24B.5}$. The variables used within a definition of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{22B}$, $R^{24B}$, and/or other variables that appear at multiple instances and are different may similarly be appropriately labeled to distinguish each group for greater clarity.

In embodiments, the compounds set forth herein are provided as pharmaceutical compositions including the compound and a pharmaceutically acceptable excipient.

In some embodiments, the compound is a compound described herein (e.g. compound of formula I, Ia, II, III, IIIa, IIIb, or IV, or any embodiment thereof, including compounds described for use in a method). In some embodiments, the compound is a compound described in the Examples, an example, a table, the figures, or a figure. In some embodiments, the compound is a compound described in Table 2.

Pharmaceutical Compositions

In another aspect is provided a pharmaceutical composition including a pharmaceutically acceptable excipient and a compound, or pharmaceutically acceptable salt thereof, as described herein, including embodiments (e.g. compound of formula I, Ia, Ib, Ic, Id, Ie, If, Ig, Ih, II, III, IIIa, IIIb, IIIc, or IV, or any embodiment thereof, including compounds described for use in a method herein or in the Compounds section above or in an example, table, figure, or claim). In some embodiments, the compound is a compound described in Table 2. In embodiments of the pharmaceutical compositions, the compound, or pharmaceutically acceptable salt thereof, as described herein, including embodiments (e.g. compound of formula I, Ia, Ib, Ic, Id, Ie, If, Ig, Ih, II, III, IIIa, IIIb, IIIc, or IV, or any embodiment thereof, including compounds described for use in a method herein or in the Compounds section above or in an example, table, figure, or claim) is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2). In embodiments, the second agent is an anti-cancer agent. In embodiments, the second agent is a chemotherapeutic. In embodiments, the second agent is an agent for improving memory. In embodiments, the second agent is an agent for treating a neurodegenerative disease. In embodiments, the second agent is an agent for treating vanishing white matter disease. In embodiments, the second agent is an agent for treating childhood ataxia with CNS hypo-myelination. In embodiments, the second agent is an agent for treating an intellectual disability syndrome. In embodiments, the second agent is an agent for treating pancreatic cancer. In embodiments, the second agent is an agent for treating breast cancer. In embodiments, the second agent is an agent for treating multiple myeloma. In embodiments, the second agent is an agent for treating myeloma. In embodiments, the second agent is an agent for treating a cancer of a secretory cell. In embodiments, the second agent is an agent for reducing eIF2α phosphorylation. In embodiments, the second agent is an agent for inhibiting a pathway activated by eIF2α phosphorylation. In embodiments, the second agent is an agent for inhibiting a pathway activated by eIF2α. In embodiments, the second agent is an agent for inhibiting the integrated stress response. In embodiments, the second agent is an anti-inflammatory agent. In embodiments, the second agent is an agent for treating postsurgical cognitive dysfunction (POCD). In embodiments, the second agent is an agent for treating traumatic brain injury (TBI).

Additional Embodiments

1p. A method of treating a disease in a patient in need of such treatment, said method comprising administering a therapeutically effective amount of a compound, or a pharmaceutically acceptable salt thereof, to said patient, wherein said disease is selected from the group consisting of cancer, a neurodegenerative disease, vanishing white matter disease, childhood ataxia with CNS hypo-myelination, and an intellectual disability syndrome; and wherein said compound has the formula:

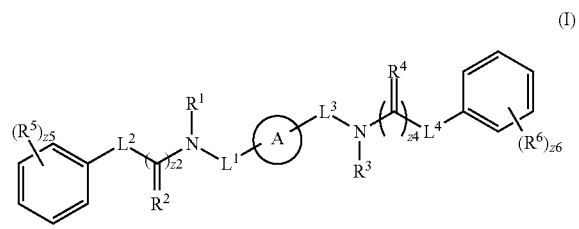

(I)

wherein, ring A is substituted or unsubstituted cycloalkylene or substituted or unsubstituted arylene; $L^1$, $L^2$, $L^3$, and $L^4$ are independently a bond, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^4$ are independently =$NR^7$, =O, or =S; z2 and z4 are independently 0 or 1; and z5 and z6 are independently an integer from 0 to 5.

2p. The method of embodiment 1p, wherein the compound has the formula:

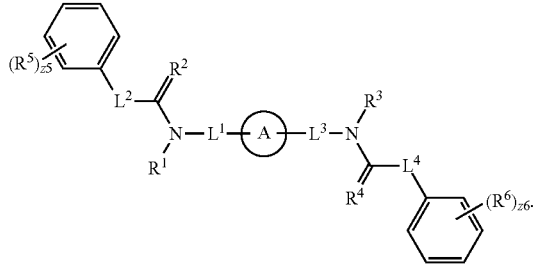

(Ia)

3p. The method of any one of embodiments 1p to 2p, wherein $L^1$ and $L^3$ are independently a bond or substituted or unsubstituted alkylene.

4p. The method of any one of embodiments 1p to 3p, wherein $L^1$ and $L^3$ are independently substituted or unsubstituted $C_1$-$C_5$ alkylene.

5p. The method of any one of embodiments 1p to 4p, wherein $L^1$ and $L^3$ are independently substituted or unsubstituted $C_1$-$C_3$ alkylene.

6p. The method of any one of embodiments 1p to 5p, wherein $L^1$ and $L^3$ are independently substituted or unsubstituted methylene.

7p. The method of any one of embodiments 1p to 3p, wherein $L^1$ and $L^3$ are independently a bond.

8p. The method of any one of embodiments 1p to 3p, wherein $L^1$ and $L^3$ are independently an unsubstituted alkylene.

9p. The method of embodiment 1p, wherein the compound has the formula:

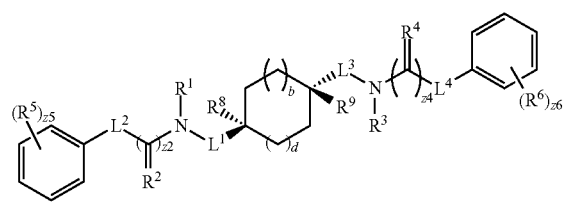

(III)

wherein, $R^8$ and $R^9$ are independently hydrogen, halogen, —$OCH_3$, —$OCH_2Ph$, —C(O)Ph, —$CH_3$, —$CF_3$, —$CCl_3$, —CN, —S(O)$CH_3$, —OH, —$NH_2$, —COOH, —$CONH_2$, —$NO_2$, —C(O)$CH_3$, —CH($CH_3$)$_2$, —CCSi($CH_3$)$_3$, —CCH, —$CH_2$CCH, —SH, —$SO_2$Cl, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and b and d are independently 0 or 1.

10p. The method of embodiment 9p, wherein the compound has the formula:

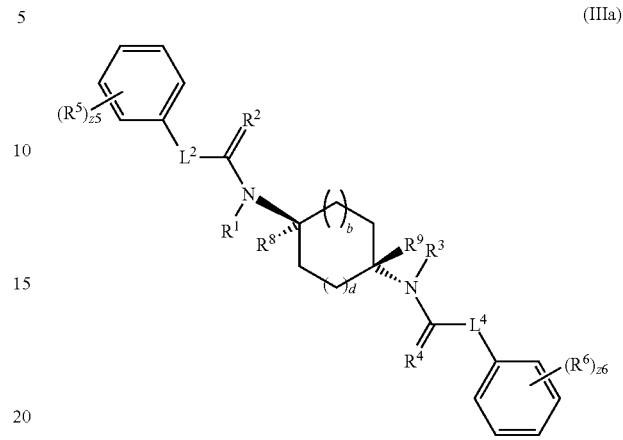

(IIIa)

11p. The method of any one of embodiments 9p to 10p, wherein b and d are 1.

12p. The method of any one of embodiments 9p to 11p, wherein $R^8$ and $R^9$ are hydrogen.

13p. The method of embodiment 1p, wherein the compound has the formula:

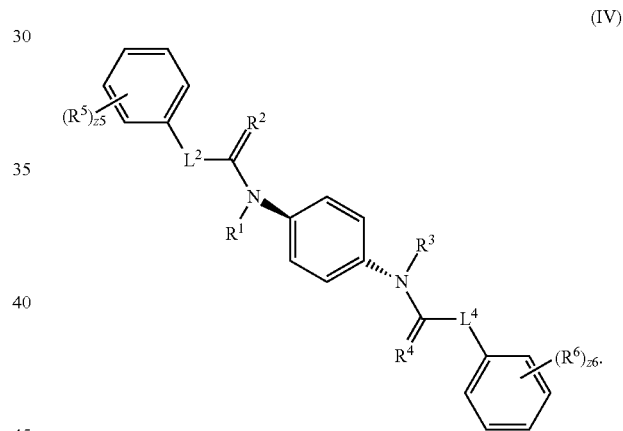

(IV)

14p. The method of any one of embodiments 1p to 13p, wherein $R^1$ and $R^3$ are hydrogen.

15p. The method of any one of embodiments 1p to 14p, wherein $R^2$ and $R^4$ are =O.

16p. The method of any one of embodiments 1p to 15p, wherein $L^2$ is $L^{2A}$-$L^{2B}$-$L^{2C}$, wherein $L^{2A}$ is bonded to the substituted or unsubstituted phenyl; $L^{2A}$ is a bond, —O—, —S—, —NH—, —S(O)—, or —S(O)$_2$—; $L^{2B}$ is a bond or substituted or unsubstituted alkylene; and $L^{2C}$ is a bond, —O—, or —NH—.

17p. The method of embodiment 16p, wherein $L^{2A}$ is bonded to the substituted or unsubstituted phenyl; $L^{2A}$ is a bond; $L^{2B}$ is unsubstituted methylene; and $L^{2C}$ is —O—.

18p. The method of any one of embodiments 1p to 17p, wherein $L^4$ is $L^{4A}$-$L^{4B}$-$L^{4C}$, wherein $L^{4A}$ is bonded to the substituted or unsubstituted phenyl; $L^{4A}$ is a bond, —O—, —S—, —NH—, —S(O)—, or —S(O)$_2$—; $L^{4B}$ is a bond or substituted or unsubstituted alkylene; and $L^{4C}$ is a bond, —O—, or —NH—.

19p. The method of embodiment 18p, wherein $L^{4A}$ is bonded to the substituted or unsubstituted phenyl; $L^{4A}$ is a bond; $L^{4B}$ is unsubstituted methylene; and $L^{4C}$ is —O—.

20p. The method of any one of embodiments 1p to 19p, wherein $R^5$ and $R^6$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

21p. The method of any one of embodiments 1p to 20p, wherein z5 and z6 are independently 0 to 2.

22p. The method of any one of embodiments 1p to 21p, wherein the compound is

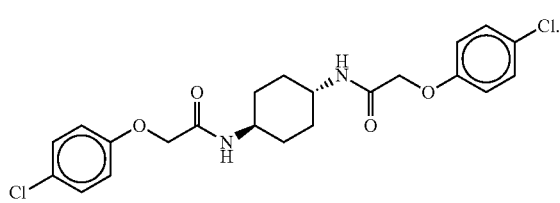

23p. The method of any one of embodiments 1p to 22p, wherein the disease is cancer.

24p. The method of any one of embodiments 1p to 22p, wherein the disease is a neurodegenerative disease.

25p. The method of any one of embodiments 1p to 22p, wherein the disease is vanishing white matter disease.

26p. The method of any one of embodiments 1p to 22p, wherein the disease is childhood ataxia with CNS hypomyelination.

27p. The method of any one of embodiments 1p to 22p, wherein the disease is associated with eIF2α phosphorylation.

28p. A method of increasing protein expression by a cell or in vitro expression system, said method comprising administering an effective amount of a compound, or a pharmaceutically acceptable salt thereof, to said cell or expression system, wherein said compound has the formula:

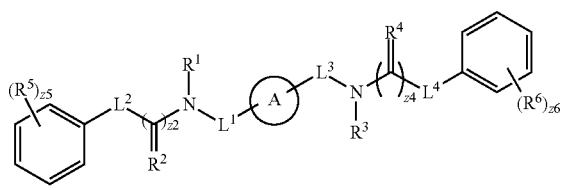

wherein, ring A is substituted or unsubstituted cycloalkylene or substituted or unsubstituted arylene; $L^1$, $L^2$, $L^3$, and $L^4$ are independently a bond, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently =NR$^7$, =O, or =S; z2 and z4 are independently 0 or 1; and z5 and z6 are independently an integer from 0 to 5.

29p. The method of embodiment 28p, wherein the compound has the formula:

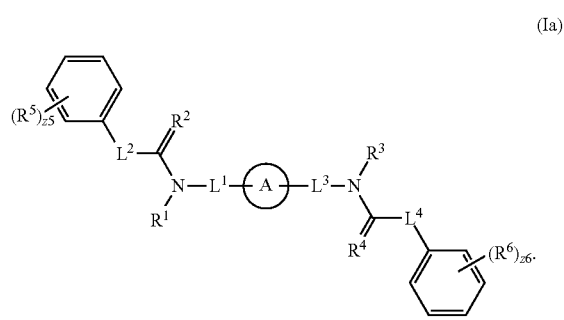

30p. A method of improving long-term memory in a patient, said method comprising administering a therapeutically effective amount of a compound, or a pharmaceutically acceptable salt thereof, to said patient, wherein said compound has the formula:

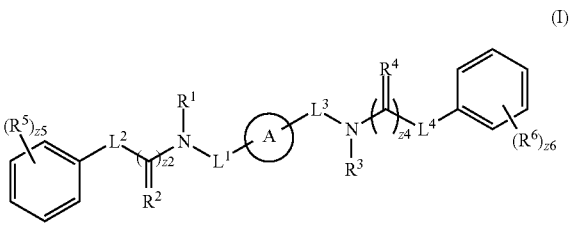

wherein, ring A is substituted or unsubstituted cycloalkylene or substituted or unsubstituted arylene; $L^1$, $L^2$, $L^3$, and $L^4$ are independently a bond, substituted or unsubstituted alkylene or substituted or unsubstituted heteroalkylene; $R^1$, $R^3$, $R^5$, $R^6$ and $R^7$ are independently hydrogen; halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently =NR$^7$, =O, or =S; z2 and z4 are independently 0 or 1; and z5 and z6 are independently an integer from 0 to 5.

31p. The method of embodiment 30p, wherein said compound has the formula:

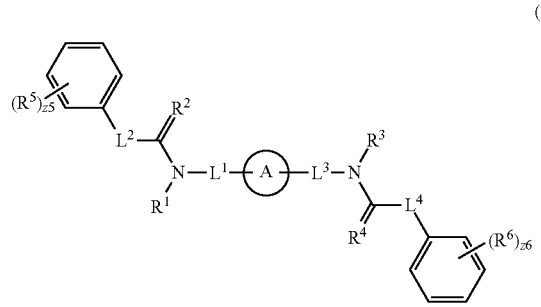

(Ia)

wherein, ring A is substituted or unsubstituted cycloalkylene or substituted or unsubstituted arylene; $L^1$, $L^2$, $L^3$, and $L^4$ are independently a bond, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently ═NR$^7$, ═O, or ═S; and z5 and z6 are independently an integer from 0 to 5.

32p. A compound, or a pharmaceutically acceptable salt thereof, having the formula:

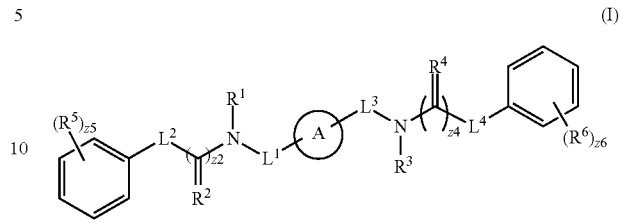

(I)

wherein, ring A is substituted or unsubstituted cycloalkylene or substituted or unsubstituted arylene; $L^1$, $L^2$, $L^3$, and $L^4$ are independently a bond, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently ═NR$^7$, ═O, or ═S; z2 and z4 are independently 0 or 1; and z5 and z6 are independently an integer from 0 to 5; with the proviso that the compound is not

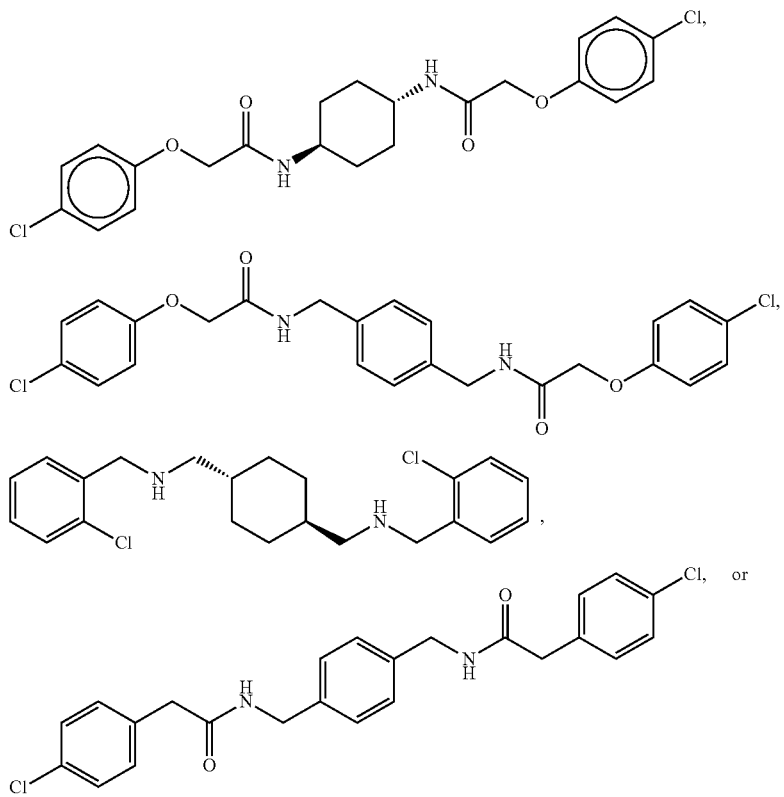

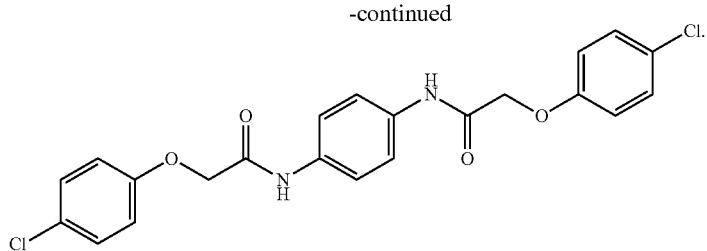

33p. The compound, or a pharmaceutically acceptable salt thereof, of embodiment 32p, wherein said compound has the formula:

(Ia)

34p. The compound, or a pharmaceutically acceptable salt thereof, of any one of embodiments 32p to 33p, wherein $L^1$ and $L^3$ are independently a bond or substituted or unsubstituted alkylene.

35p. The compound, or a pharmaceutically acceptable salt thereof, of any one of embodiments 32p to 34p, wherein $L^1$ and $L^3$ are independently substituted or unsubstituted $C_1$-$C_5$ alkylene.

36p. The compound, or a pharmaceutically acceptable salt thereof, of any one of embodiments 32p to 35p, wherein $L^1$ and $L^3$ are independently substituted or unsubstituted $C_1$-$C_3$ alkylene.

37p. The compound, or a pharmaceutically acceptable salt thereof, of any one of embodiments 32p to 36p, wherein $L^1$ and $L^3$ are independently substituted or unsubstituted methylene.

38p. The compound, or a pharmaceutically acceptable salt thereof, of any one of embodiments 32p to 34p, wherein $L^1$ and $L^3$ are independently a bond.

39p. The compound, or a pharmaceutically acceptable salt thereof, of any one of embodiments 32p to 34p, wherein $L^1$ and $L^3$ are independently an unsubstituted alkylene.

40p. The compound, or a pharmaceutically acceptable salt thereof, of embodiment 32p, wherein the compound has the formula:

(III)

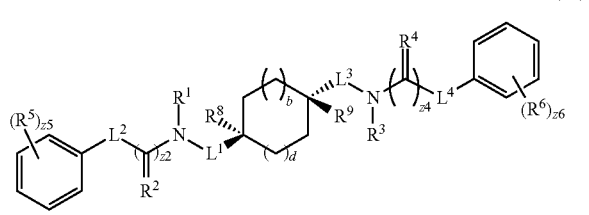

wherein, $R^8$ and $R^9$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and b and d are independently 0 or 1.

41p. The compound, or a pharmaceutically acceptable salt thereof, of embodiment 40p, wherein the compound has the formula:

(IIIa)

42p. The compound, or a pharmaceutically acceptable salt thereof, of any one of embodiments 40p to 41p, wherein b and d are 1.

43p. The compound, or a pharmaceutically acceptable salt thereof, of any one of embodiments 40p to 42p, wherein $R^8$ and $R^9$ are hydrogen.

44p. The compound, or a pharmaceutically acceptable salt thereof, of embodiment 32p, wherein the compound has the formula:

(IV)

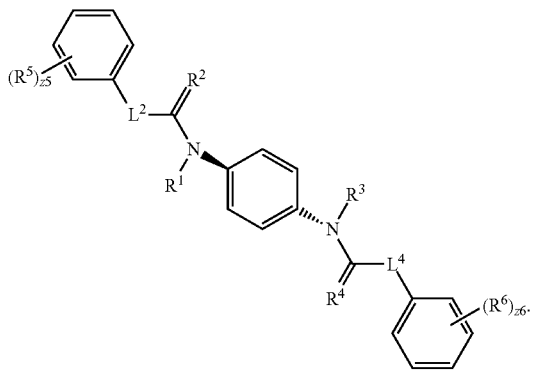

45p. The compound, or a pharmaceutically acceptable salt thereof, of any one of embodiments 32p to 44p, wherein $R^1$ and $R^3$ are hydrogen.

46p. The compound, or a pharmaceutically acceptable salt thereof, of any one of embodiments 32p to 45p, wherein $R^2$ and $R^4$ are =O.

47p. The compound, or a pharmaceutically acceptable salt thereof, of any one of embodiments 32p to 46p, wherein $L^2$ is $L^{2A}$-$L^{2B}$-$L^{2C}$, wherein $L^{2A}$ is bonded to the substituted or unsubstituted phenyl; $L^{2A}$ is a bond, —O—, —S—, —NH—, —S(O)—, or —S(O)$_2$—; $L^{2B}$ is a bond or substituted or unsubstituted alkylene; and $L^{2C}$ is a bond, —O—, or —NH—.

48p. The compound, or a pharmaceutically acceptable salt thereof, of embodiment 47p, wherein $L^{2A}$ is bonded to the substituted or unsubstituted phenyl; $L^{2A}$ is a bond; $L^{2B}$ is unsubstituted methylene; and $L^{2C}$ is —O—.

49p. The compound, or a pharmaceutically acceptable salt thereof, of any one of embodiments 32p to 48p, wherein $L^4$ is $L^{4A}$-$L^{4B}$-$L^{4C}$, wherein $L^{4A}$ is bonded to the substituted or unsubstituted phenyl; $L^{4A}$ is a bond, —O—, —S—, —NH—, —S(O)—, or —S(O)$_2$—; $L^{4B}$ is a bond or substituted or unsubstituted alkylene; and $L^{4C}$ is a bond, —O—, or —NH—.

50p. The compound, or a pharmaceutically acceptable salt thereof, of embodiment 49p, wherein $L^{4A}$ is bonded to the substituted or unsubstituted phenyl; $L^{4A}$ is a bond; $L^{4B}$ is unsubstituted methylene; and $L^{4C}$ is —O—.

51p. The compound, or a pharmaceutically acceptable salt thereof, of any one of embodiments 32p to 48p, wherein $R^5$ and $R^6$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

52p. The compound, or a pharmaceutically acceptable salt thereof, of any one of embodiments 32p to 51p, wherein z5 and z6 are independently 0 to 2.

53p. A pharmaceutical composition comprising a pharmaceutically acceptable excipient and a compound, or pharmaceutically acceptable salt thereof, of any one of embodiments 32p to 52p.

1. A compound, or a pharmaceutically acceptable salt thereof, having the formula:

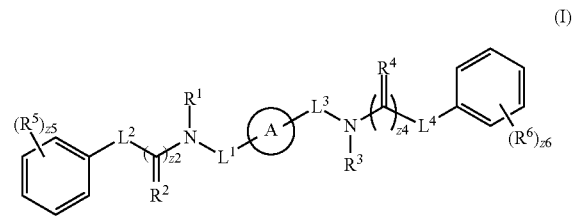

(I)

wherein, ring A is substituted or unsubstituted cycloalkylene or substituted or unsubstituted arylene; $L^1$, $L^2$, $L^3$, and $L^4$ are independently a bond, —NH—, —O—, —S—, —S(O)—, —S(O)$_2$—, substituted or unsubstituted alkylene or substituted or unsubstituted heteroalkylene; $R^1$, $R^3$, $R^5$, $R^6$ and $R^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^4$ are independently =NR$^7$, =O, or =S; z2 and z4 are independently 0 or 1; and z5 and z6 are independently an integer from 0 to 5; with the proviso that the compound is not

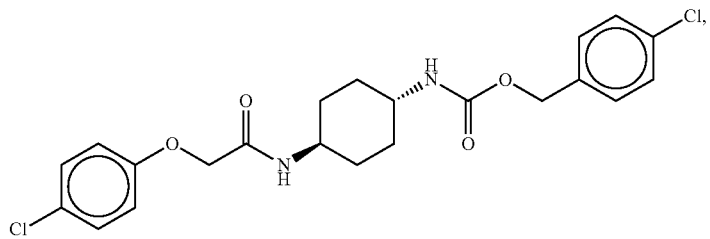

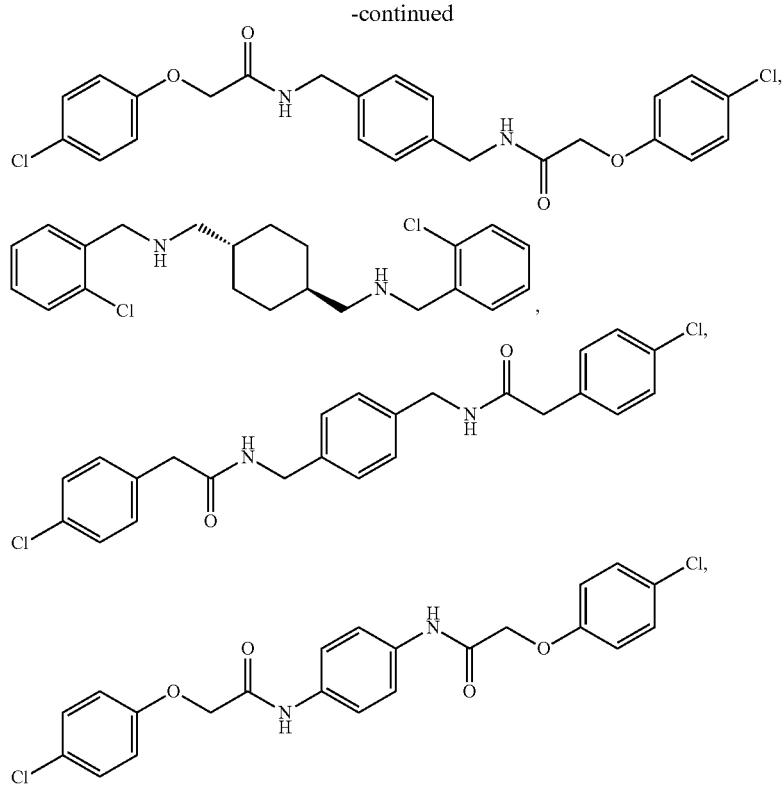

2. The compound of embodiment 1, wherein said compound has the formula:

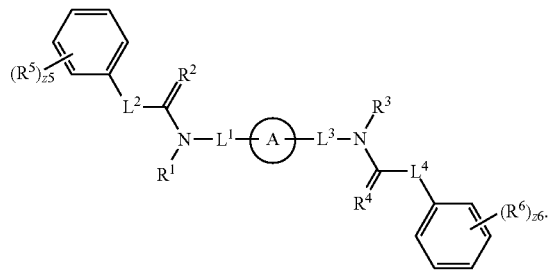

3. The compound of any one of embodiments 1 to 2, wherein $L^1$ and $L^3$ are independently a bond or substituted or unsubstituted alkylene.

4. The compound of any one of embodiments 1 to 3, wherein $L^1$ and $L^3$ are independently substituted or unsubstituted $C_1$-$C_5$ alkylene.

5. The compound of any one of embodiments 1 to 4, wherein $L^1$ and $L^3$ are independently substituted or unsubstituted $C_1$-$C_3$ alkylene.

6. The compound of any one of embodiments 1 to 5, wherein $L^1$ and $L^3$ are independently substituted or unsubstituted methylene.

7. The compound of any one of embodiments 1 to 3, wherein $L^1$ and $L^3$ are independently a bond.

8. The compound of any one of embodiments 1 to 3, wherein $L^1$ and $L^3$ are independently an unsubstituted alkylene.

9. The compound of embodiment 1, wherein the compound has the formula:

(III)

wherein, $R^8$ and $R^9$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and b and d are independently 0 or 1.

10. The compound of embodiment 9, wherein the compound has the formula:

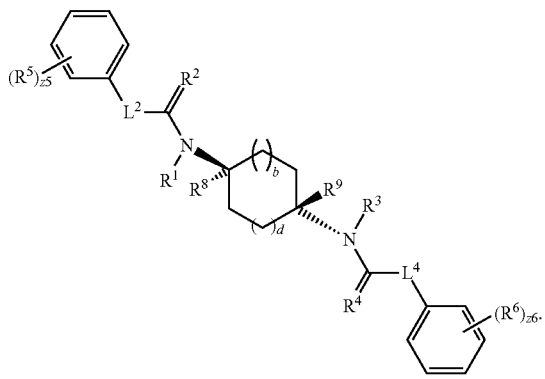

(IIIa)

11. The compound of any one of embodiments 9 to 10, wherein b and d are 1.

12. The compound of any one of embodiments 9 to 11, wherein $R^8$ and $R^9$ are hydrogen.

13. The compound of one of embodiments 1 to 8, wherein the compound has the formula:

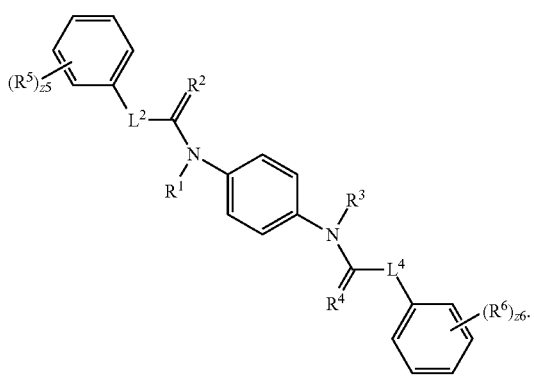

(IV)

14. The compound of any one of embodiments 1 to 13, wherein $R^1$ and $R^3$ are hydrogen.

15. The compound of any one of embodiments 1 to 14, wherein $R^2$ and $R^4$ are =O.

16. The compound of any one of embodiments 1 to 15, wherein $L^2$ is $L^{2A}$-$L^{2B}$-$L^{2C}$, wherein $L^{2A}$ is bonded to the substituted or unsubstituted phenyl; $L^{2A}$ is a bond, —O—, —S—, —NH—, —S(O)—, or —S(O)$_2$—; $L^{2B}$ is a bond or substituted or unsubstituted alkylene; and $L^{2C}$ is a bond, —O—, or —NH—.

17. The compound, or a pharmaceutically acceptable salt thereof, of embodiment 16, wherein $L^{2A}$ is bonded to the substituted or unsubstituted phenyl; $L^{2A}$ is a bond; $L^{2B}$ is unsubstituted methylene; and $L^{2C}$ is —O—.

18. The compound, or a pharmaceutically acceptable salt thereof, of any one of embodiments 1 to 17, wherein $L^4$ is $L^{4A}$-$L^{4B}$-$L^{4C}$, wherein $L^{4A}$ is bonded to the substituted or unsubstituted phenyl; $L^{4A}$ is a bond, —O—, —S—, —NH—, —S(O)—, or —S(O)$_2$—; $L^{4B}$ is a bond or substituted or unsubstituted alkylene; and $L^{4C}$ is a bond, —O—, or —NH—.

19. The compound, or a pharmaceutically acceptable salt thereof, of embodiment 18, wherein $L^{4A}$ is bonded to the substituted or unsubstituted phenyl; $L^{4A}$ is a bond; $L^{4B}$ is unsubstituted methylene; and $L^{4C}$ is —O—.

20. The compound, or a pharmaceutically acceptable salt thereof, of any one of embodiments 1 to 19, wherein $R^5$ and $R^6$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

21. The compound of any one of embodiments 1 to 20, wherein z5 and z6 are independently 0 to 2.

22. The compound of embodiment 21, wherein the compound has the formula:

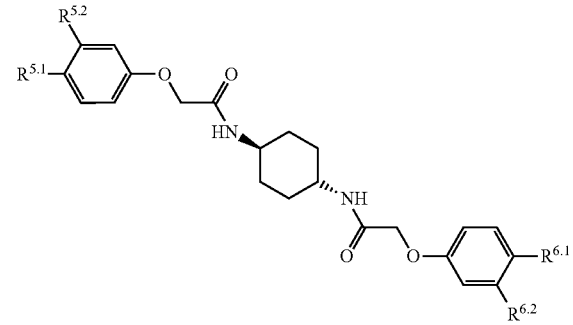

(IIIb)

$R^{5.1}$ and $R^{6.1}$ are independently hydrogen, halogen, —CF$_3$, —CN, —N$_3$, substituted or unsubstituted C$_1$-C$_4$ alkyl, substituted or unsubstituted 2 to 4 membered heteroalkyl, substituted or unsubstituted 5 to 6 membered heteroaryl,

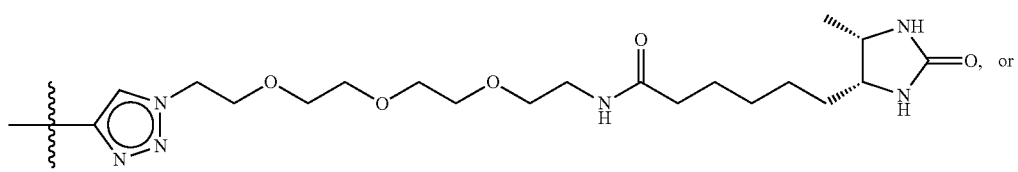

-continued

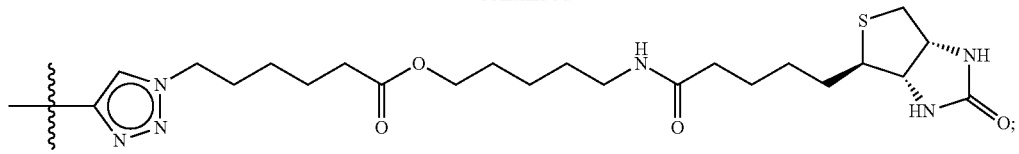

$R^{5.2}$ and $R^{6.2}$ are independently hydrogen, halogen, —CCSi(CH$_3$)$_3$, —CF$_3$, —NO$_2$, —CN, —N$_3$, substituted or unsubstituted C$_1$-C$_4$ alkyl, substituted or unsubstituted 2 to 4 membered heteroalkyl, substituted or unsubstituted 5 to 6 membered heteroaryl, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC═(O)

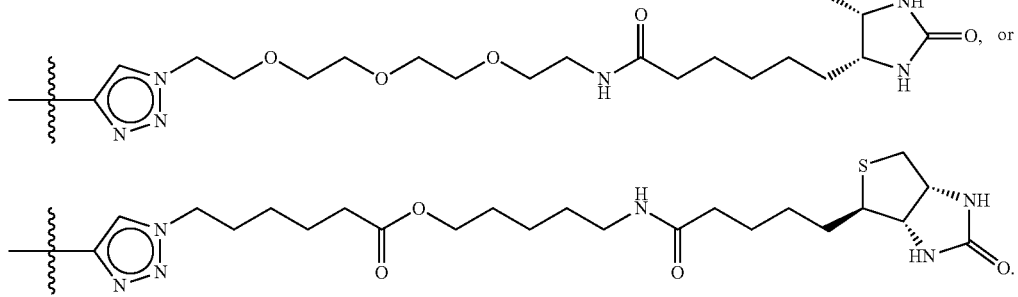

23. The compound of embodiment 22, wherein, $R^{5.1}$ and $R^{6.1}$ are independently halogen, unsubstituted C$_1$-C$_3$ alkyl, or unsubstituted C$_1$-C$_3$ haloalkyl; $R^{5.2}$ and $R^{6.2}$ are independently hydrogen, halogen, —CCSi(CH$_3$)$_3$, —NO$_2$, unsubstituted C$_1$-C$_3$ alkyl, or unsubstituted C$_1$-C$_3$ haloalkyl.

24. The compound of embodiment 23, wherein, $R^{5.1}$ and $R^{6.1}$ are independently —Cl, —I, —CF$_3$, —CH$_3$, or —CCH; $R^{5.2}$ and $R^{6.2}$ are independently hydrogen, —Cl, —F, —I, —CCSi(CH$_3$)$_3$, —CF$_3$, —NO$_2$, —CH$_3$, or —CCH.

25. A pharmaceutical composition comprising a pharmaceutically acceptable excipient and a compound, or pharmaceutically acceptable salt thereof, of any one of embodiments 1 to 24.

26. A method of treating an integrated stress response-associated disease in a patient in need of such treatment, said method comprising administering a therapeutically effective amount of a compound, or a pharmaceutically acceptable salt thereof, to said patient, wherein said compound has the formula:

(I)

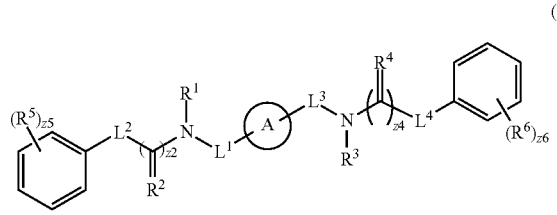

wherein, ring A is substituted or unsubstituted cycloalkylene or substituted or unsubstituted arylene; L$^1$, L$^2$, L$^3$, and L$^4$ are independently a bond, —NH—, —O—, —S—, —S(O)—, —S(O)$_2$—, substituted or unsubstituted alkylene or substituted or unsubstituted heteroalkylene; R$^1$, R$^3$, R$^5$, R$^6$ and R$^7$ are independently hydrogen, halogen, —OCH$_3$, —OCH$_2$Ph, NHNH$_2$, —NHC═(O)NH$_2$, —NHSO$_2$H, —NHC═(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^2$ and R$^4$ are independently ═NR$^7$, ═O, or ═S; z2 and z4 are independently 0 or 1; and z5 and z6 are independently an integer from 0 to 5.

27. A method of treating a disease associated with phosphorylation of eIF2α in a patient in need of such treatment, said method comprising administering a therapeutically effective amount of a compound, or a pharmaceutically acceptable salt thereof, to said patient, wherein said compound has the formula:

(I)

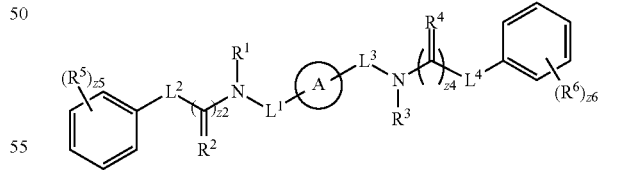

wherein, ring A is substituted or unsubstituted cycloalkylene or substituted or unsubstituted arylene; L$^1$, L$^2$, L$^3$, and L$^4$ are independently a bond, —NH—, —O—, —S—, —S(O)—, —S(O)$_2$—, substituted or unsubstituted alkylene or substituted or unsubstituted heteroalkylene; R$^1$, R$^3$, R$^5$, R$^6$ and R$^7$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —C(NN)CF$_3$, —C(NH—NH)CF$_3$, —CCH, —CH$_2$CCH, —SH, —SO$_2$Cl, —SO$_3$H, —SO₄H, —SO₂NH₂, —NHNH₂, —ONH₂, —NHC═(O)NHNH₂, —NHC═(O)NH₂, —NHSO₂H, —NHC═(O)H, —NHC(O)OH, —NHOH, —OCH₃, —OCF₃, —OCHF₂, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R² and R⁴ are independently ═NR⁷, ═O, or ═S; z2 and z4 are independently 0 or 1; and z5 and z6 are independently an integer from 0 to 5.

28. The method of one of embodiments 26 to 27, wherein said disease is cancer, a neurodegenerative disease, vanishing white matter disease, childhood ataxia with CNS hypo-myelination, or an intellectual disability syndrome.

29. The method of embodiment 28, wherein the disease is cancer.

30. The method of embodiment 28, wherein the disease is a neurodegenerative disease.

31. The method of embodiment 28, wherein the disease is vanishing white matter disease.

32. The method of embodiment 28, wherein the disease is childhood ataxia with CNS hypo-myelination.

33. The method of embodiment 28, wherein the disease is an intellectual disability syndrome.

34. A method of treating an inflammatory disease in a patient in need of such treatment, said method comprising administering a therapeutically effective amount of a compound, or a pharmaceutically acceptable salt thereof, to said patient, wherein said compound has the formula:

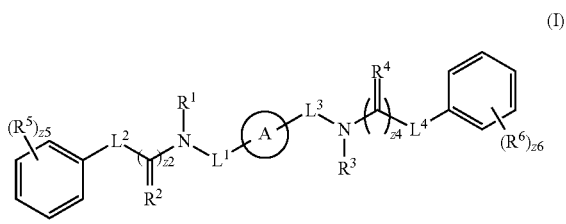

(I)

wherein, ring A is substituted or unsubstituted cycloalkylene or substituted or unsubstituted arylene; L¹, L², L³, and L⁴ are independently a bond, —NH—, —O—, —S—, —S(O)—, —S(O)₂—, substituted or unsubstituted alkylene or substituted or unsubstituted heteroalkylene; R¹, R³, R⁵, R⁶ and R⁷ are independently hydrogen, halogen, —OCH₃, —OCH₂Ph, —C(O)Ph, —CH₃, —CF₃, —CCl₃, —CN, —S(O)CH₃, —OH, —NH₂, —COOH, —CONH₂, —NO₂, —C(O)CH₃, —CH(CH₃)₂, —CCSi(CH₃)₃, —C(NN)CF₃, —C(NH—NH)CF₃, —CCH, —CH₂CCH, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)OH, —NHOH, —OCH₃, —OCF₃, —OCHF₂, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R² and R⁴ are independently ═NR⁷, ═O, or ═S; z2 and z4 are independently 0 or 1; and z5 and z6 are independently an integer from 0 to 5.

35. The method of embodiment 34, wherein said inflammatory disease is associated with neurological inflammation.

36. The method of one of embodiments 34 to 35, wherein said inflammatory disease is postoperative cognitive dysfunction.

37. The method of one of embodiments 34 to 35, wherein said inflammatory disease is traumatic brain injury.

38. A method of improving long-term memory in a patient, said method comprising administering a therapeutically effective amount of a compound, or a pharmaceutically acceptable salt thereof, to said patient, wherein said compound has the formula:

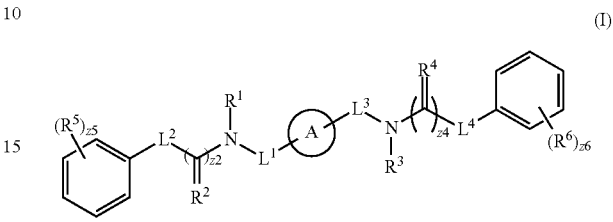

(I)

wherein, ring A is substituted or unsubstituted cycloalkylene or substituted or unsubstituted arylene; L¹, L², L³, and L⁴ are independently a bond, —NH—, —O—, —S—, —S(O)—, —S(O)₂—, substituted or unsubstituted alkylene or substituted or unsubstituted heteroalkylene; R¹, R³, R⁵, R⁶ and R⁷ are independently hydrogen, halogen, —OCH₃, —OCH₂Ph, —C(O)Ph, —CH₃, —CF₃, —CCl₃, —CN, —S(O)CH₃, —OH, —NH₂, —COOH, —CONH₂, —NO₂, —C(O)CH₃, —CH(CH₃)₂, —CCSi(CH₃)₃, —C(NN)CF₃, —C(NH—NH)CF₃, —CCH, —CH₂CCH, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)OH, —NHOH, —OCH₃, —OCF₃, —OCHF₂, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R² and R⁴ are independently ═NR⁷, ═O, or ═S; z2 and z4 are independently 0 or 1; and z5 and z6 are independently an integer from 0 to 5.

39. A method of increasing protein expression by a cell or in vitro expression system, said method comprising administering an effective amount of a compound, or a pharmaceutically acceptable salt thereof, to said cell or expression system, wherein said compound has the formula:

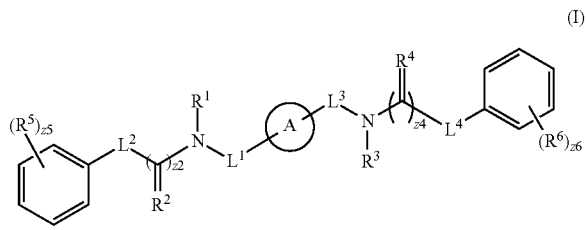

(I)

wherein, ring A is substituted or unsubstituted cycloalkylene or substituted or unsubstituted arylene; L¹, L², L³, and L⁴ are independently a bond, —NH—, —O—, —S—, —S(O)—, —S(O)₂—, substituted or unsubstituted alkylene or substituted or unsubstituted heteroalkylene; R¹, R³, R⁵, R⁶ and R⁷ are independently hydrogen, halogen, —OCH₃, —OCH₂Ph, —C(O)Ph, —CH₃, —CF₃, —CCl₃, —CN, —S(O)CH₃, —OH, —NH₂, —COOH, —CONH₂, —NO₂, —C(O)CH₃, —CH(CH₃)₂, —CCSi(CH₃)₃, —C(NN)CF₃, —C(NH—NH)CF₃, —CCH, —CH₂CCH, —SH, —SO₂Cl, —SO₃H, —SO₄H, —SO₂NH₂, —NHNH₂, —ONH₂, —NHC═(O)

NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^2$ and R$^4$ are independently =NR$^7$, =O, or =S; z2 and z4 are independently 0 or 1; and z5 and z6 are independently an integer from 0 to 5.

40. The method of one of embodiments 26 to 39, wherein the compound has the formula:

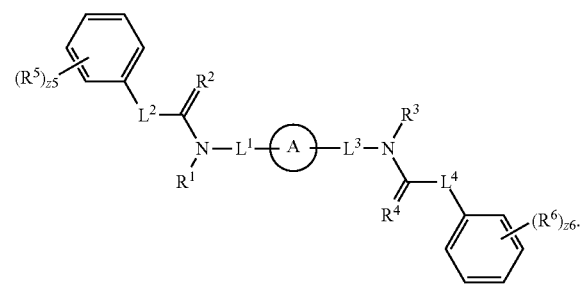

(Ia)

41. The method of any one of embodiments 26 to 40, wherein L$^1$ and L$^3$ are independently a bond or substituted or unsubstituted alkylene.

42. The method of any one of embodiments 26 to 41, wherein L$^1$ and L$^3$ are independently substituted or unsubstituted C$_1$-C$_5$ alkylene.

43. The method of any one of embodiments 26 to 42, wherein L$^1$ and L$^3$ are independently substituted or unsubstituted C$_1$-C$_3$ alkylene.

44. The method of any one of embodiments 26 to 43, wherein L$^1$ and L$^3$ are independently substituted or unsubstituted methylene.

45. The method of any one of embodiments 26 to 41, wherein L$^1$ and L$^3$ are independently a bond.

46. The method of any one of embodiments 26 to 41, wherein L$^1$ and L$^3$ are independently an unsubstituted alkylene.

47. The method of any one of embodiments 26 to 46, wherein the compound has the formula:

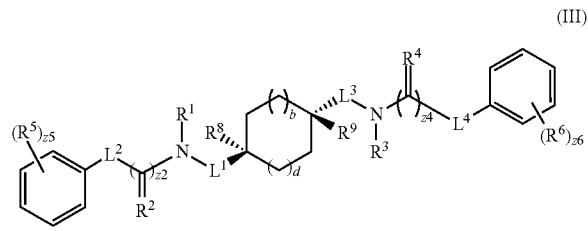

(III)

wherein, R$^8$ and R$^9$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and b and d are independently 0 or 1.

48. The method of embodiment 47, wherein the compound has the formula:

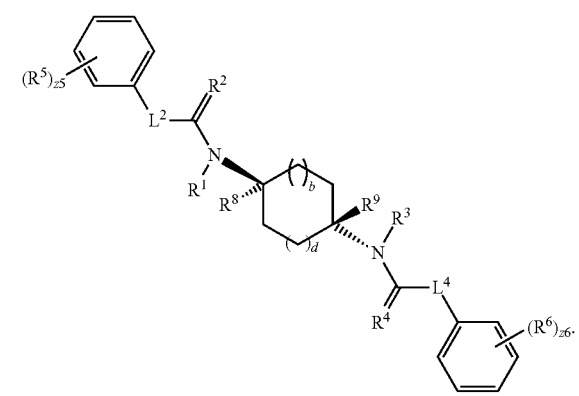

(IIIa)

49. The method of any one of embodiments 47 to 48, wherein b and d are 1.

50. The method of any one of embodiments 47 to 49, wherein R$^8$ and R$^9$ are hydrogen.

51. The method of one of embodiments 26 to 46, wherein the compound has the formula:

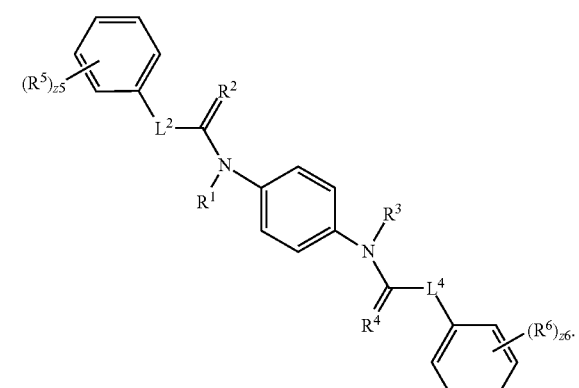

(IV)

52. The method of any one of embodiments 26 to 51, wherein R$^1$ and R$^3$ are hydrogen.

53. The method of any one of embodiments 26 to 51, wherein R$^2$ and R$^4$ are =O.

54. The method of any one of embodiments 26 to 52, wherein L$^2$ is L$^{2A}$-L$^{2B}$-L$^{2C}$, wherein L$^{2A}$ is bonded to the substituted or unsubstituted phenyl; L$^{2A}$ is a bond, —O—, —S—, —NH—, —S(O)—, or —S(O)$_2$—; L$^{2B}$ is a bond or substituted or unsubstituted alkylene; and L$^{2C}$ is a bond, —O—, or —NH—.

55. The method of embodiment 54, wherein L$^{2A}$ is bonded to the substituted or unsubstituted phenyl; L$^{2A}$ is a bond; L$^{2B}$ is unsubstituted methylene; and L$^{2C}$ is —O—.

56. The method of any one of embodiments 26 to 55, wherein L$^4$ is L$^{4A}$-L$^{4B}$-L$^{4C}$, wherein L$^{4A}$ is bonded to the substituted or unsubstituted phenyl; $L^{4A}$ is a bond, —O—, —S—, —NH—, —S(O)—, or —S(O)$_2$—; $L^{4B}$ is a bond or substituted or unsubstituted alkylene; and $L^{4C}$ is a bond, —O—, or —NH—.

57. The method of embodiment 56, wherein $L^{4A}$ is bonded to the substituted or unsubstituted phenyl; $L^{4A}$ is a bond; $L^{4B}$ is unsubstituted methylene; and $L^{4C}$ is —O—.

58. The method of any one of embodiments 26 to 57, wherein $R^5$ and $R^6$ are independently hydrogen, halogen, —OCH$_3$, —OCH$_2$Ph, —C(O)Ph, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH(CH$_3$)$_2$, —CCSi(CH$_3$)$_3$, —CCH, —CH$_2$CCH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCH$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

59. The method of any one of embodiments 26 to 58, wherein z5 and z6 are independently 0 to 2.

60. The method of any one of embodiments 26 to 59, wherein the compound has the formula:

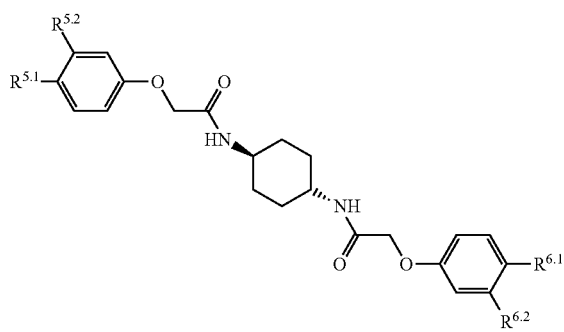

(IIIb)

$R^{5.1}$ and $R^{6.1}$ are independently hydrogen, halogen, —CF$_3$, —CN, —N$_3$, substituted or unsubstituted alkyl, substituted or unsubstituted 2 to 4 membered heteroalkyl, substituted or unsubstituted 5 to 6 membered heteroaryl,

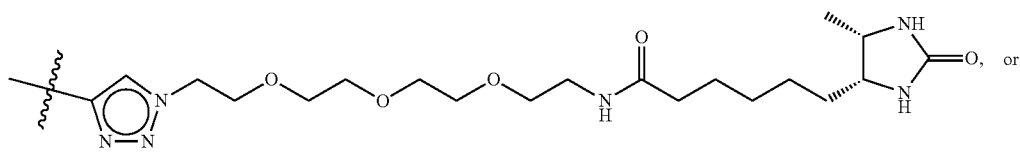

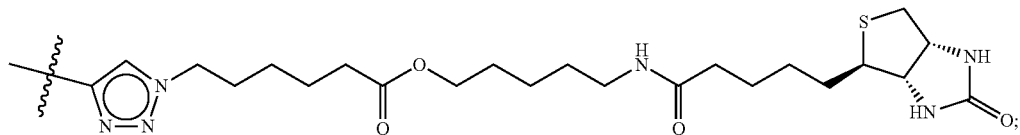

and $R^{5.2}$ and $R^{6.2}$ are independently hydrogen, halogen, —CCSi(CH$_3$)$_3$, —CF$_3$, —NO$_2$, —CN, —N$_3$, substituted or unsubstituted C$_1$-C$_4$ alkyl, substituted or unsubstituted 2 to 4 membered heteroalkyl, substituted or unsubstituted 5 to 6 membered heteroaryl,

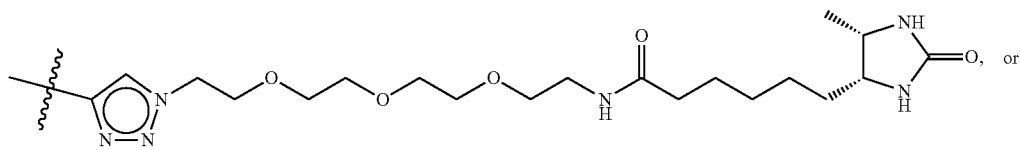

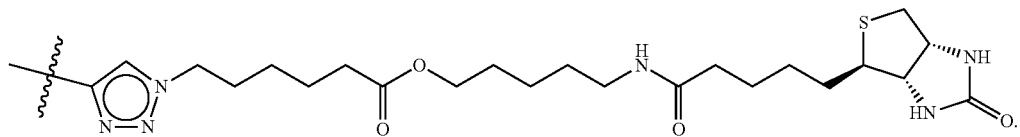

61. The method of embodiment 60, wherein, $R^{5.1}$ and $R^{6.1}$ are independently halogen, unsubstituted $C_1$-$C_3$ alkyl, or unsubstituted $C_1$-$C_3$ haloalkyl; and $R^{5.2}$ and $R^{6.2}$ are independently hydrogen, halogen, —CCSi(CH$_3$)$_3$, —NO$_2$, unsubstituted $C_1$-$C_3$ alkyl, or unsubstituted $C_1$-$C_3$ haloalkyl.

62. The method of embodiment 61, wherein, $R^{5.1}$ and $R^{6.1}$ are independently —Cl, —I, —CF$_3$, —CH$_3$, or —CCH; and $R^{5.2}$ and $R^{6.2}$ are independently hydrogen, —Cl, —F, —I, —CCSi(CH$_3$)$_3$, —CF$_3$, —NO$_2$, —CH$_3$, or —CCH.

63. The method of any one of embodiments 26 to 62, wherein the compound is

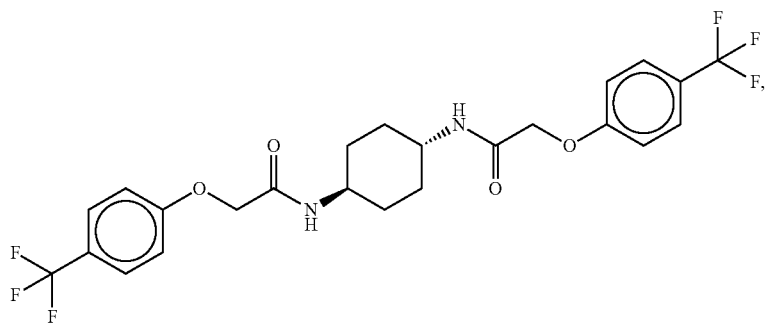

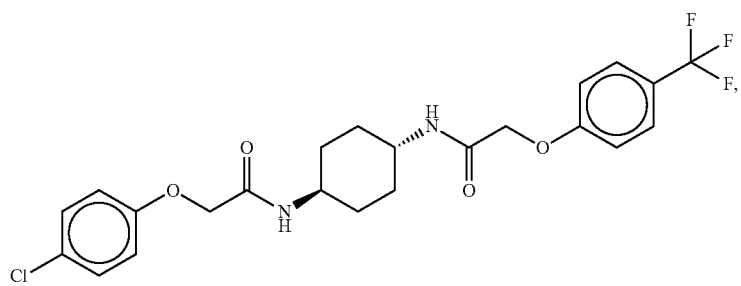

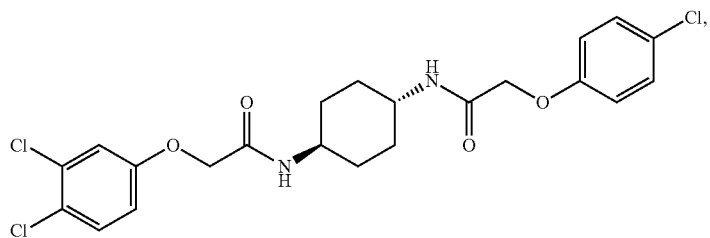

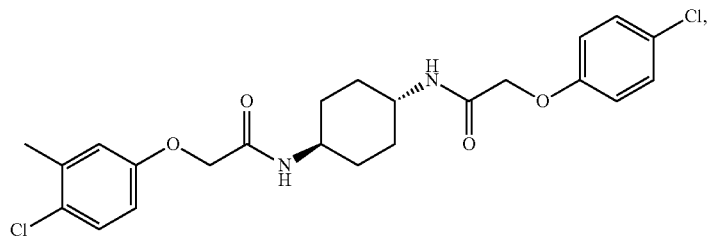

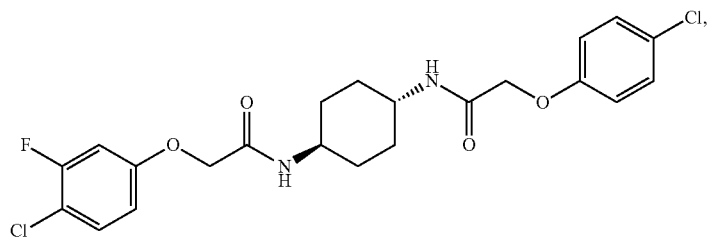

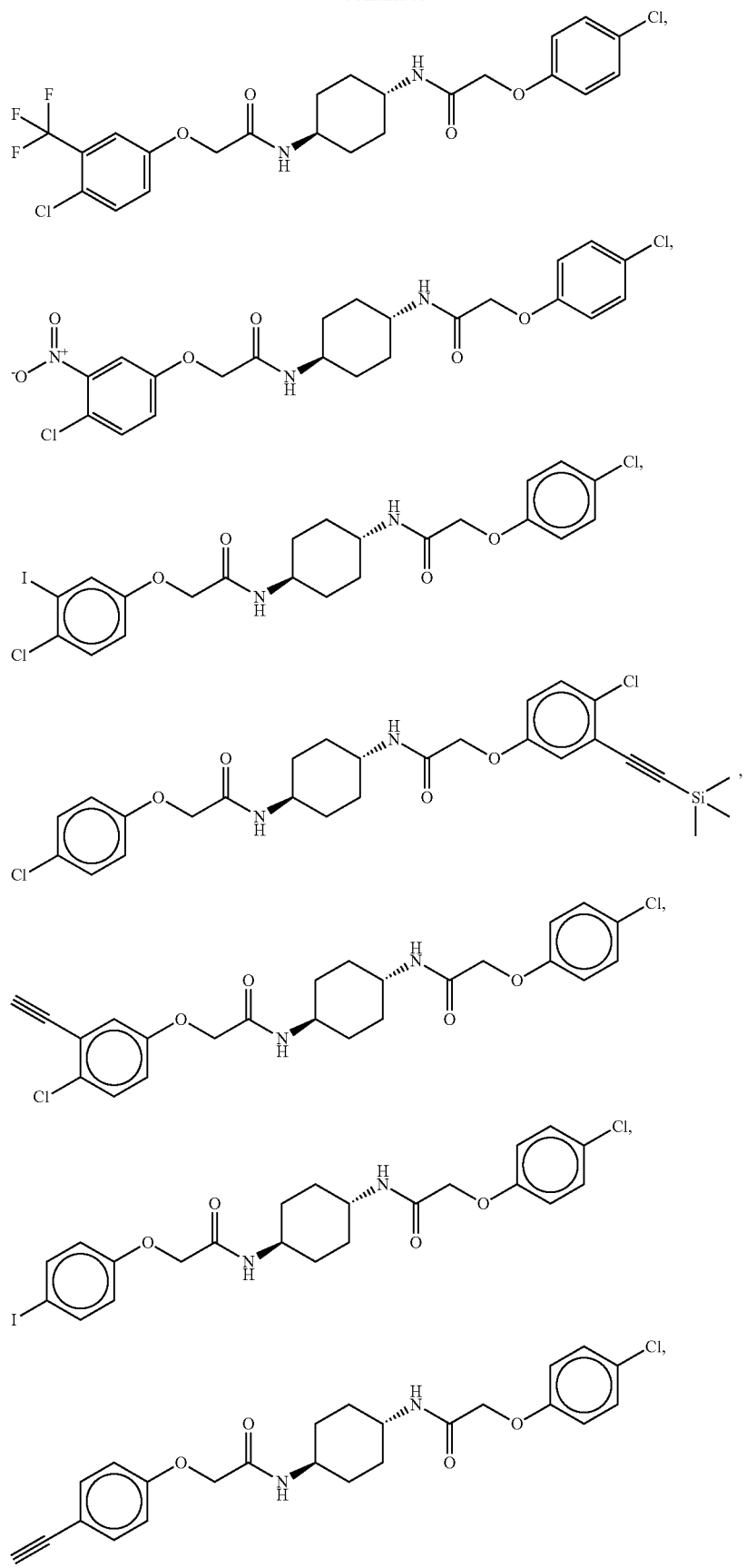

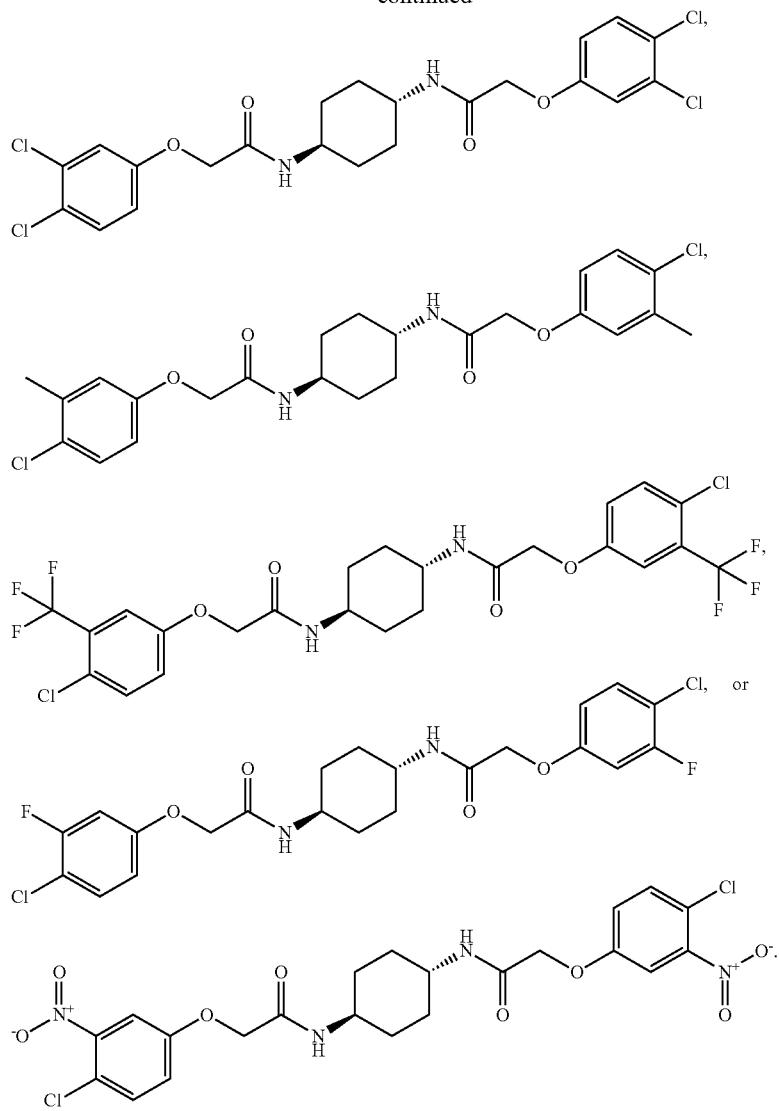
64. The method of any one of embodiments 26 to 62, wherein the compound is
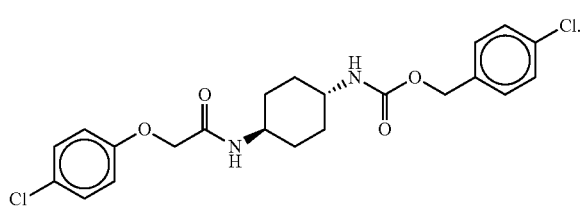
65. The compound of any one of embodiments 1 to 24, wherein the compound is not
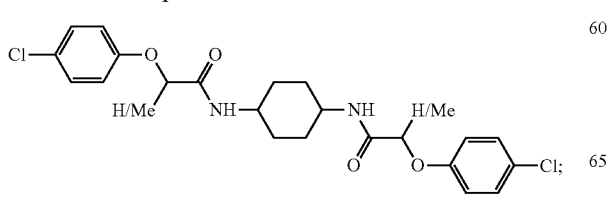
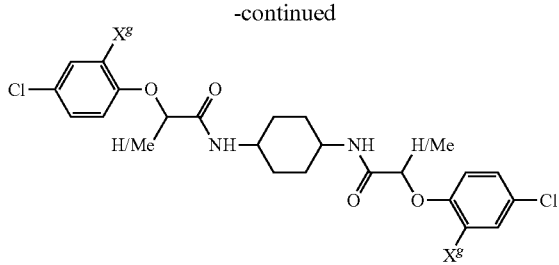
wherein $X^g$ is H, —Cl, —CH$_3$, or —OCH$_3$;
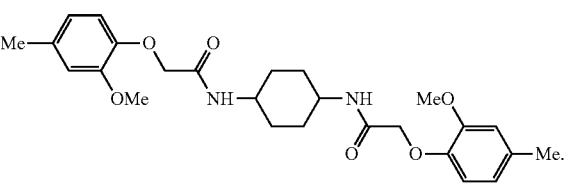 [SMILES: COc1cc(C)ccc1OCC(=O)NC1CCC(NC(=O)COc2ccc(C)cc2OC)CC1]

EXAMPLES

Phosphorylation of the α-subunit of initiation factor 2 (eIF2α) controls protein synthesis by a mechanism that is conserved in eukaryotic cells. In metazoa, four eIF2α kinases (PERK, PKR, GCN2, and HRI) are activated by distinct stress conditions and converge on phosphorylating a unique serine in eIF2α. This collection of signaling pathways is termed "integrated stress response", or ISR. eIF2α phosphorylation globally diminishes protein synthesis but also allows a group of specialized mRNAs to become preferentially translated.

We identified novel small molecules (e.g. ISRIB) that render cells resistant to the effects of eIF2α phosphorylation, restoring the cell's translation capacity. ISRIB is the first reported antagonist of the ISR. It acts as a potent and stereospecific inhibitor with an $IC_{50}$ of 5 nM in cultured cells, suggesting a specific and tight interaction with its cellular target. By blocking signaling through the PERK branch of the UPR, ISRIB prevents cells from re-establishing ER homeostasis. Unmitigated ER stress synergizes with ISRIB to induce apoptosis. ISRIB shows good pharmacokinetic properties and no overt toxicity in mice, making it suitable for in vivo studies. As such, ISRIB emerges as a powerful tool to explore the roles of the UPR and the ISR in disease models and physiological processes. In particular, we utilized ISRIB to show that overriding the consequences of eIF2α phosphorylation enhances memory consolidation in rodents, suggesting an important role of eIF2α phosphorylation in modulating higher-order brain function.

A. Compound Identification and Characterization

Starting with a cell-based, high-throughput screen for small molecule inhibitors of PERK signaling, we identified a compound, named ISRIB, which potently ($IC_{50}$=5 nM) reverses the effects of eIF2α phosphorylation, effectively blunting its functional consequences.

Design of cell-based screen for inhibitors of PERK signaling. By interrogating a large chemical library for small molecules that block PERK signaling, we identified ISRIB as a potent ISR inhibitor, functioning downstream of all eIF2α kinases. ISRIB proves a powerful tool to explore the consequences of acute inhibition of the ISR in cells and animals.

Figure 1B:
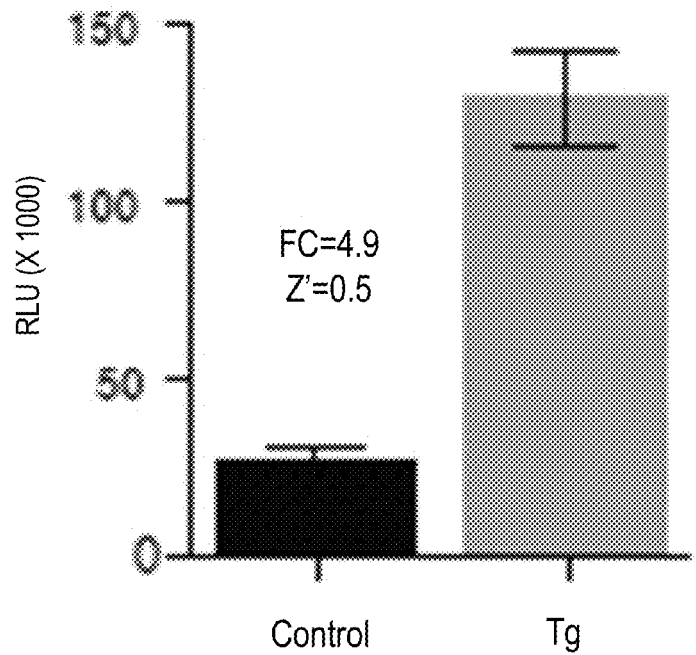
Figure 1C:
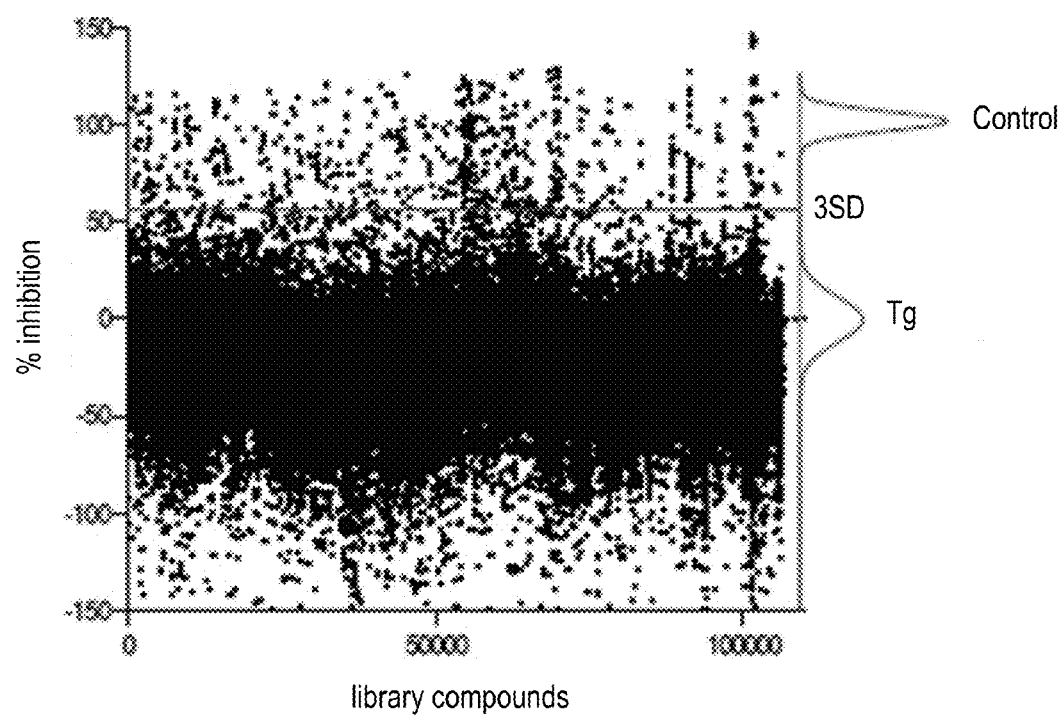

To identify inhibitors of PERK signaling, we engineered a reporter that allows monitoring of PERK activation in living cells. To this end, we constructed a retroviral vector containing the open-reading frame of firefly luciferase fused to the 5'UTR of ATF4 mRNA (FIG. 1A), which contains two short open-reading frames (uORFs) that control ATF4 translation in a stress-dependent manner. After infection, we established a HEK293T cell line harboring the stably integrated reporter. We used thapsigargin, a potent ER stressor that inhibits the ER calcium pump, to activate PERK and induce eIF2α phosphorylation. Thapsigargin treatment resulted in a 4.9-fold induction in luciferase activity in a 384 well format with a Z factor of 0.5 (FIG. 1B). This format was used to screen 106,281 compounds covering a wide chemical space. We identified 460 hits (0.43%) (FIG. 1C), which were further validated in an 8-point dose-response assay using the same reporter. We further triaged the compounds by discarding inhibitors that also affected the IRE1 branch of the UPR using an XBP1-luciferase splicing reporter. Less than half (187 hits) of our initial hits proved unique to the PERK branch. We next used an orthogonal secondary screen that employed a different reporter (bi-cistronic ATF4-dGF-PIRES-mCherry) stably integrated into a different cell line (U2OS cells). The read-out of this latter screen was microscopy-based, which allowed us to simultaneously assess acute toxicity by cell counting, further reducing the number of viable hits to 77. As a tertiary screen, we tested compounds for their ability to inhibit ER stress-elicited induction of endogenous ATF4 by Western blot analysis. Twenty-eight compounds passed this test and were analyzed further.

Figure 2A:
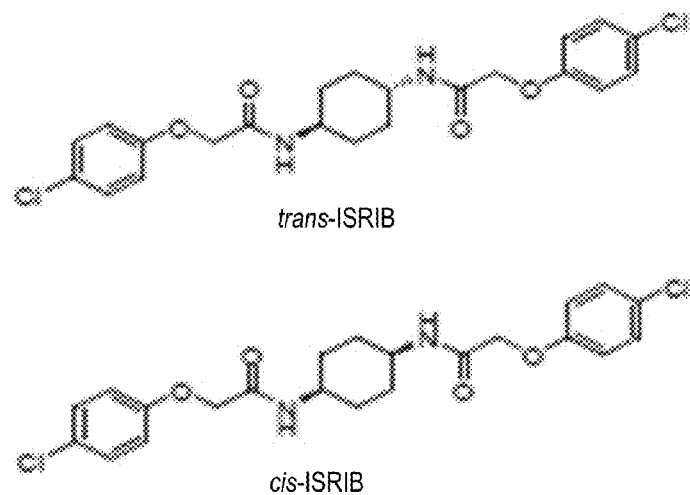
FIGS. 2A-2D. Identification of ISRIB as a potent cell-based inhibitor of PERK signaling.
Figure 2B:
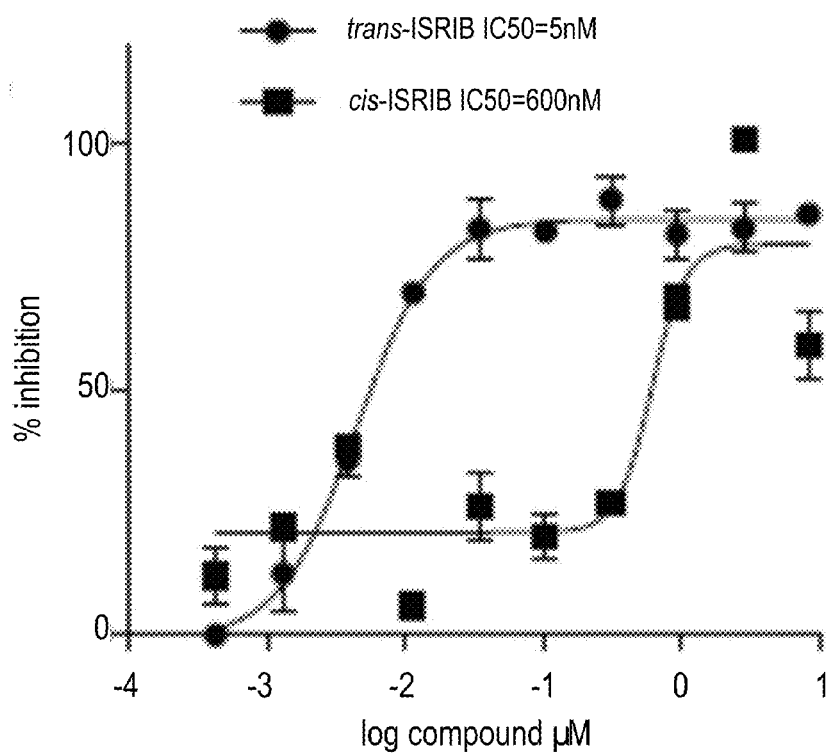

A symmetric bisglycolamide, ISRIB, is a potent inhibitor of PERK signaling. One of the 28 compounds was of particular interest because of its high potency in cells (library compound $IC_{50}$=40 nM). This compound (henceforth referred to as "ISRIB" for Integrated Stress Response inhibitor) is a symmetric bis-glycolamide, containing a central bi-substituted cyclohexane, and can exist as two diastereomers, cis and trans (FIG. 2A). We synthesized both isomers and tested their ability to inhibit the ATF4-luciferase reporter (FIG. 2B). Trans-ISRIB proved 100-fold more potent ($IC_{50}$=5 nM) than cis-ISRIB ($IC_{50}$=600 nM), indicating that the compound's interaction with its cellular target is stereospecific. Given the two-order-of-magnitude difference in activity in this assay, the measured activity of cis-ISRIB may be an over-estimate, as we cannot exclude a small contamination with trans-ISRIB, which is far more potent. The lower $IC_{50}$ of trans-ISRIB relative to the compound in the small molecule library indicates that the library likely contains a mixture of the two stereoisomers. All further experiments in this study were carried out with the synthesized trans-isomer of ISRIB.

Figure 2C:
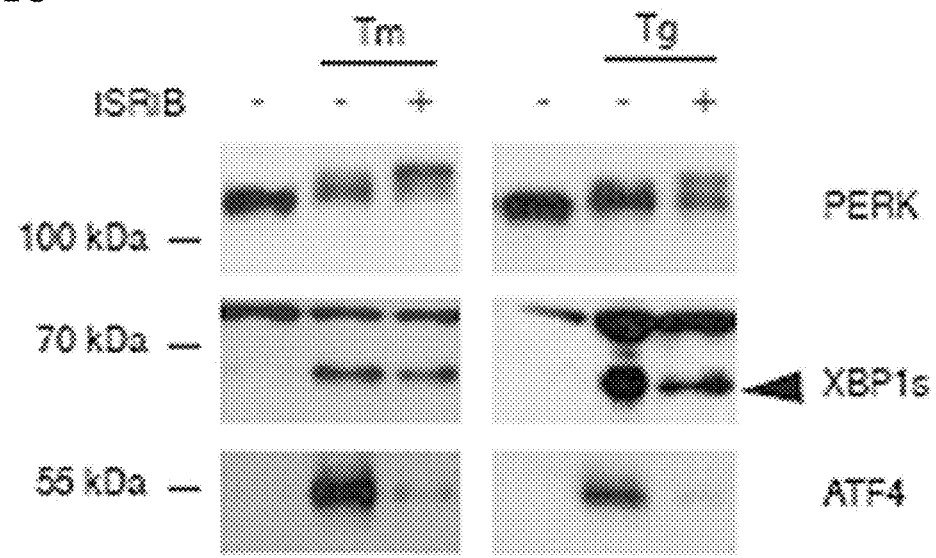
Figure 2D:
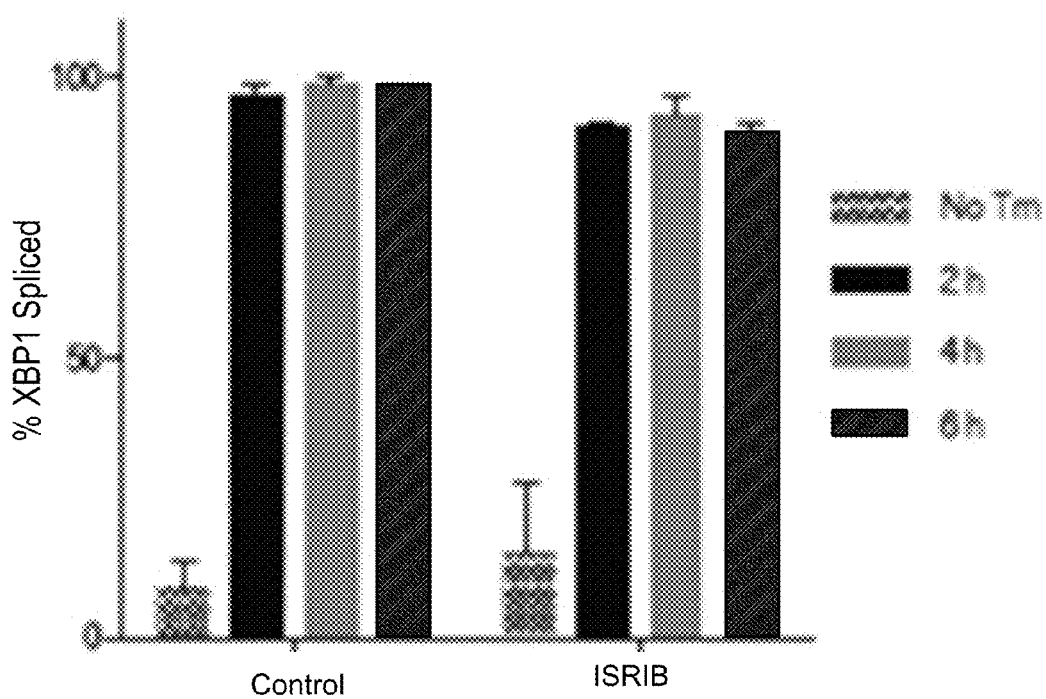

ISRIB is PERK-branch specific but does not impair PERK phosphorylation. We next determined at which step ISRIB blocks ATF4 production. To this end, we first probed the phosphorylation status of PERK by Western blotting. PERK phosphorylation is indicative of its activation by autophosphorylation and can be recognized by reduced mobility on SDS-polyacrylamide gels. Notably, ISRIB did not inhibit the mobility shift of PERK observed in ER-stressed cells (FIG. 2C). Rather, we observed an exaggerated mobility shift, indicative of increased phosphorylation of PERK upon ER stress, induced by either thapsigargin or tunicamycin (an inhibitor of N-linked glycosylation). In each case, ATF4 and XBP1s were produced upon ER stress induction. In agreement with the behavior of the reporters described above, ISRIB blocked production of endogenous ATF4, whereas XBP1 mRNA splicing (FIG. 2D) and XBP1s production persisted (FIG. 2C). As shown below (cf. FIG. 5D), ISRIB also did not affect the ATF6-branch of the UPR. We conclude that ISRIB specifically blocks signaling of the PERK-branch of the UPR.

Figure 3A:
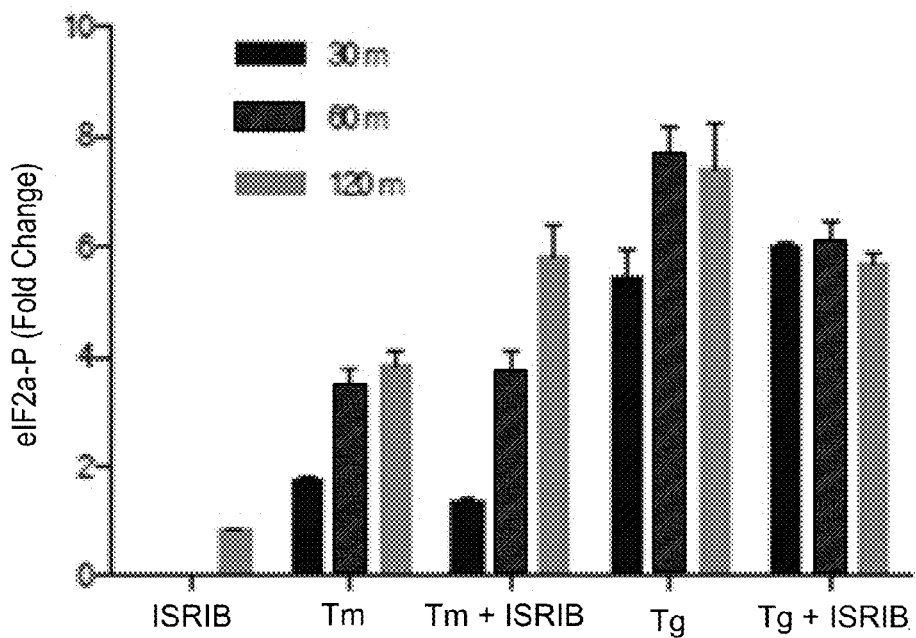
FIGS. 3A-3F. ISRIB makes cells resistant to eIF2α phosphorylation.

ISRIB-treated cells are resistant to eIF2α phosphorylation. Given that PERK phosphorylation was not diminished in ISRIB-treated, ER-stressed cells, we next directly assessed eIF2α phosphorylation. We measured the levels of phosphorylated eIF2α using an antiphospho-eIF2α antibody-based assay to quantify phosphorylation at serine 51 (see Methods). Upon induction of ER stress by tunicamycin or thapsigargin, phosphorylation of eIF2α increased over time, reaching a 4- and 7-fold increase after 120 minutes respectively (FIG. 3A). Unexpectedly, ISRIB did not block eIF2α phosphorylation under either of these ER stress-inducing conditions. On the contrary, 120 min after tunicamycin addition, ISRIB further increased the level of eIF2α phosphorylation, approaching that obtained with thapsigargin. ISRIB alone had no effect on eIF2α phosphorylation. These results indicate that ISRIB blocks effects downstream of PERK and eIF2α phosphorylation.

One way of explaining why ISRIB blocks ATF4 production yet leaves eIF2α phosphorylation intact is by rendering cells insensitive to the effects of this phosphorylation event.

Figure 3B:
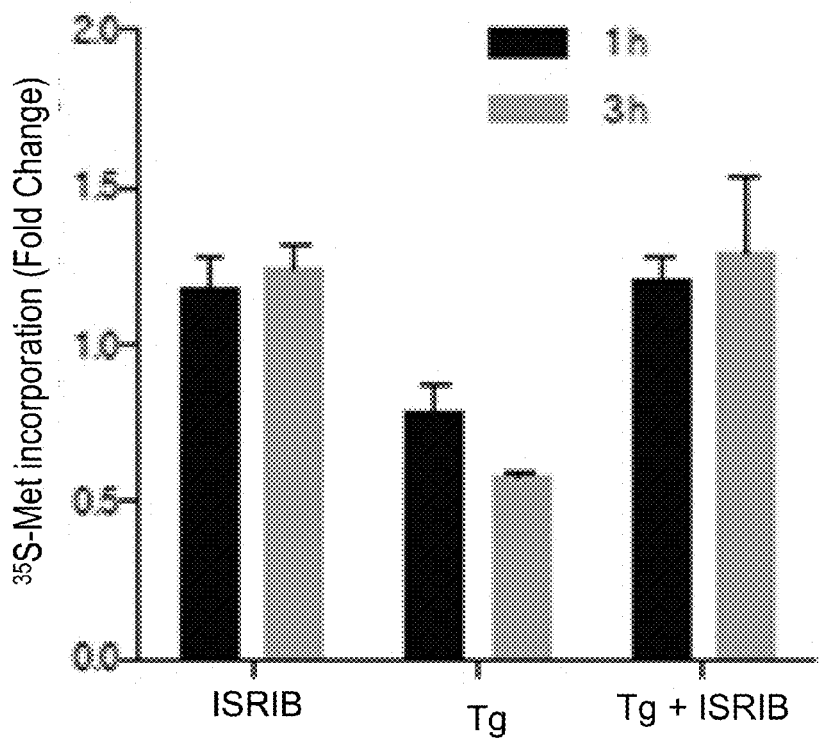

In agreement with this notion, ISRIB sustained global translation (as monitored by $^{35}$S-methionine incorporation into newly synthesized polypeptides) even in the presence of ER stress (FIG. 3B). After thapsigargin treatment, cells experienced a 40% drop in translation, which was abolished by ISRIB. As predicted by this result, extracts prepared from mouse embryonic fibroblasts (MEFs) experiencing ER stress showed a pronounced increase in the 80S monosomes at the expense of polyribosomes (FIG. 3C), which was reversed (at least partially) by addition of ISRIB. We chose MEFs for this analysis because they show stronger translational inhibition in response to ER stress than HEK293T cells. ISRIB was the only molecule in our collection of 28 hits that reversed translational attenuation upon ER-stress.

To further ascertain that cells treated with ISRIB are resistant to the effects of eIF2α phosphorylation, we transduced an inducible phospho-mimetic allele of eIF2α in which serine 51 was changed to an aspartic acid (S51D) into HEK293T cells. Expression of this allele upon doxycycline addition induced translational attenuation (FIG. 3D) as seen by an increase in the 80S peak and a decrease in the polysome population. ISRIB rescued translation returning it to the levels observed in non-induced cells. In conclusion, ISRIB restores translation in cells containing either phospho-eIF2α or eIF2α (S51D), thereby excluding any pleiotropic effects that might have been caused by the reagents used to activate ER stress.

Figure 3C:
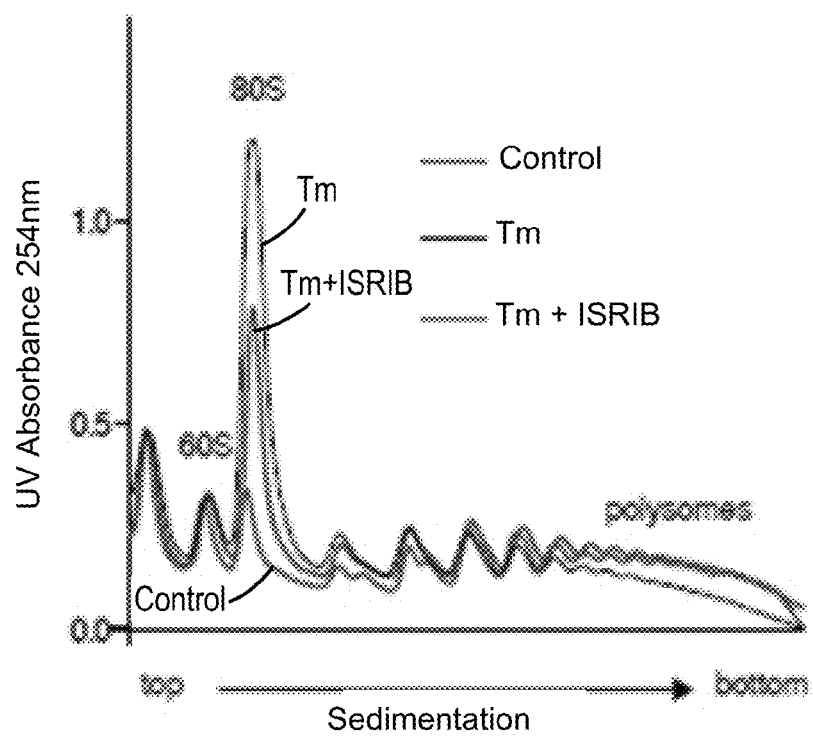
Figure 3D:
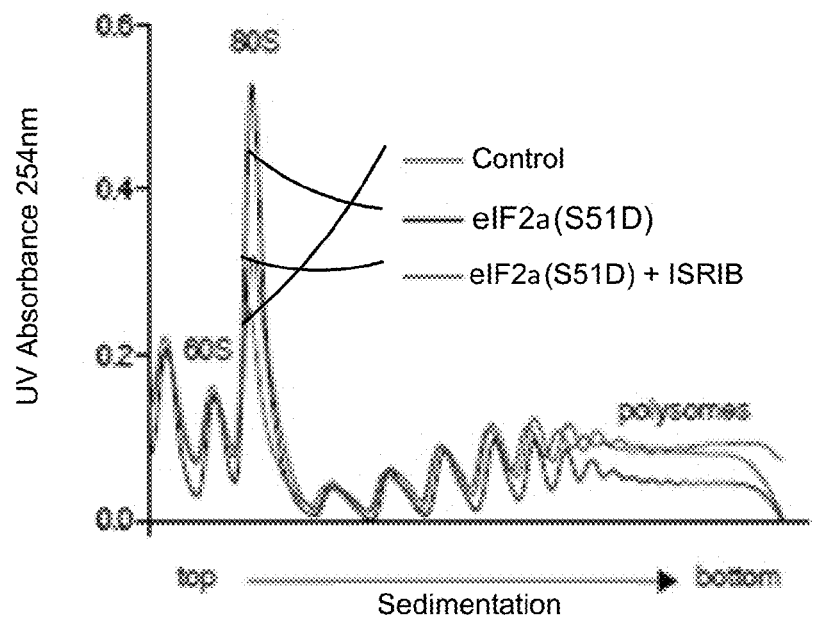
Figure 3E:
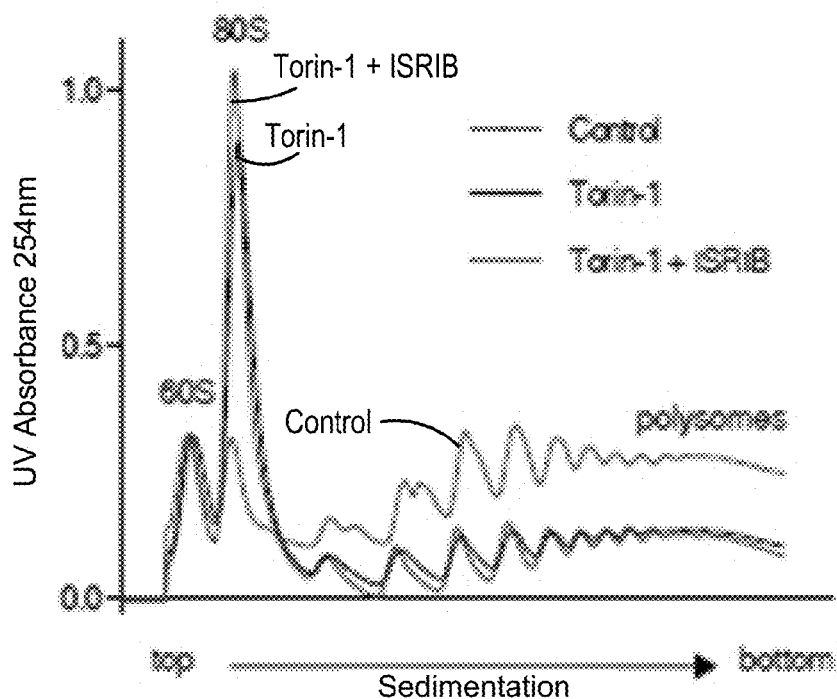

To rule out that ISRIB exerts non-specific effects on translation independent of eIF2α phosphorylation, we tested whether ISRIB reverses a translational block in CAP-mediated initiation. To this end we used Torin-1, an inhibitor of mTOR that blocks phosphorylation of 4E-BP1 and S6K1, and leads to translational attenuation (17). Addition of Torin-1 to MEFs led to an increase in the 80S peak and reduction in the polysome population to a similar degree as shown above in cells treated with ER stressors or expressing eIF2α (S51D) (FIG. 3E, compare with FIGS. 3C and 3D). In contrast to these treatments, addition of ISRIB did not reverse the effect of Torin-1 on translation. Therefore, the ability of ISRIB to block translational attenuation is specific to eIF2α phosphorylation.

Figure 3F:
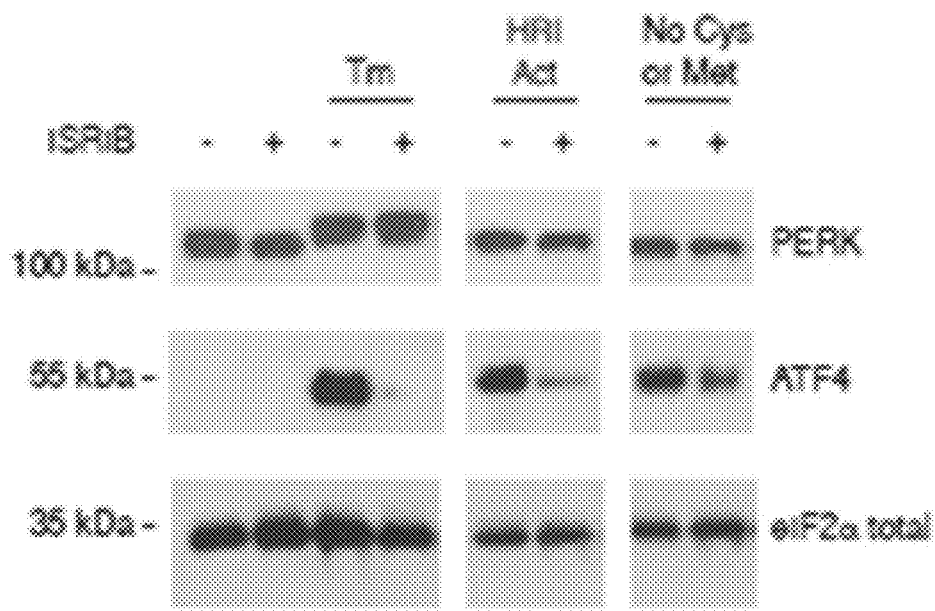

If ISRIB makes cells insensitive to eIF2α phosphorylation, it should not matter which kinase phosphorylates eIF2α. To test this prediction, we subjected cells to amino acid starvation, which activates the eIF2α kinase GCN2 and leads to ATF4 production. In addition, we used a recently identified small molecule activator to induce eIF2α phosphorylation by activating HRI, another eIF2α kinase (18). As expected, ISRIB blocked ATF4 induction after activation of either GCN2 or HRI (FIG. 3F). Under both conditions, PERK was not activated as shown by a lack of mobility shift and presence of eIF2α phosphorylation (data not shown). These data suggest that ISRIB is a bona fide ISR inhibitor that blocks signaling downstream of all eIF2α kinases.

Figure 4A:
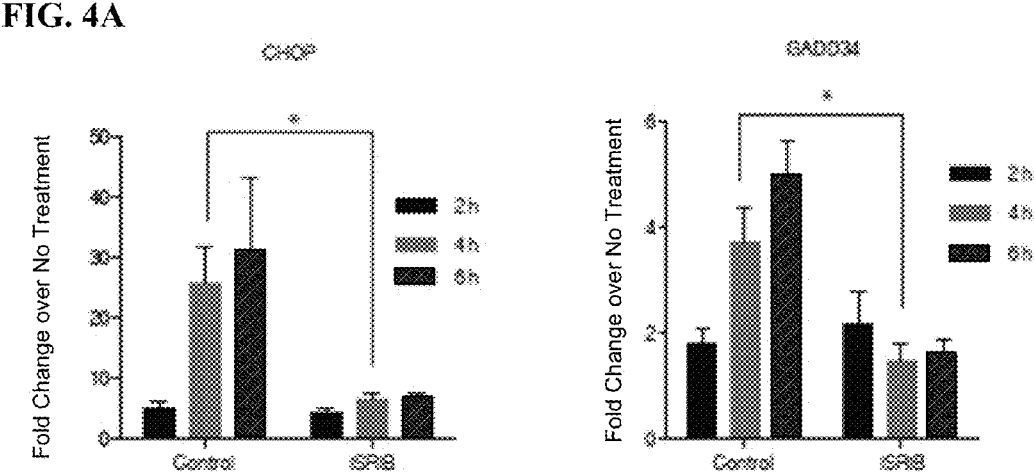
FIGS. 4A-4B. ISRIB impairs induction of the transcriptional network controlled by ATF4.
Figure 4B:
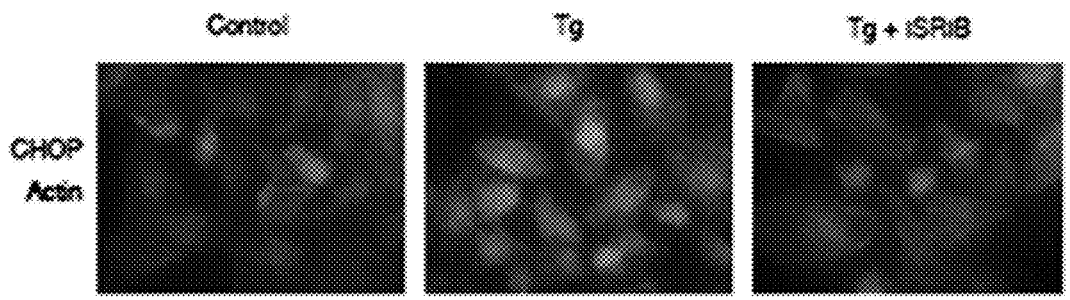

Both CHOP and GADD34 are transcriptional targets of ATF4. Thus, blocking ATF4 accumulation with ISRIB should result in a reduction in the transcriptional induction of the mRNAs encoding these targets. As shown in FIG. 4A, GADD34 and CHOP mRNAs accumulated in ER-stressed U2OS cells, and ISRIB significantly reduced their induction. In agreement, we observed no CHOP accumulation after induction of ER stress in ISRIB-treated cells (FIG. 4B). Thus ISRIB impairs the transcriptional network governed by ATF4 during the ISR.

Cell Culture. HEK293T, TREx293, U2OS, Hela, and mouse embryonic fibroblasts (MEFs) were maintained at 37° C., 5% CO2 in DMEM media supplemented with 10% FBS, L-glutamine and antibiotics (penicillin and streptomycin).

Generation of ATF4 Reporter Constructs and Cell Lines for Small-Molecule Screening ATF4 reporters were constructed by fusing the human full-length ATF4 5'-UTR (NCBI Accession BC022088.2) in front of the firefly luciferase (FLuc) or a destabilized eGFP (dEGFP) coding sequences lacking the initiator methionine.

The ATF4-FLuc reporter was generated by cloning a PCR-product containing the ATF4 full-length 5'-UTR (from +1 position a the transcription start site down to one nucleotide after the terminator codon of the second uORF) flanked by KpnI/XhoI and BglII sites at the 5' and 3' ends, respectively, into the KpnI-BglII sites of pCAX-F-XBP1-Luc. The resulting construct, pCAX-ATF4-FLuc, was then digested with BamHI, blunted with T4 DNA polymerase, and then digested with XhoI. The resulting fragment was then subcloned into the retroviral expression vector pLPCX (Clontech) after digesting it with HindIII, blunting with T4 DNA polymerase and then digesting with XhoI to generate pLPCX-ATF4-FLuc (DAA-312). DAA-312 was used to produce recombinant retroviruses using standard methods and the resulting viral supernatant was used to transduce HEK293T cells, which were then subsequently selected with puromycin to generate a stable cell line employed in the primary screen.

The ATF4-dEGFP reporter was generated using a PCR fusion-based approach. A PCR product containing the ATF4 full-length 5' leader sequence (from +1 position a the transcription start site) fused to the eGFP coding sequence 1 nucleotide downstream of the terminator codon of the second uORF, and flanked by BamHI and EcoRI, was cloned into the cognate sites of pEGFP-N3 (Clontech) to generate pCMV-ATF4-eGFP. To destabilize the eGFP fusion protein and increase the dynamic range of the reporter, residues 422-461 of mouse ornithine decarboxylase (mODC1), corresponding to its PEST sequence (42), were fused to the C-terminus of the ATF-eGFP fusion protein. To such end, the corresponding mODC1 coding sequence was amplified by PCR and cloned into the BstXI and EcoRI sites of pCMV-ATF4-eGFP. The resulting construct was designated pCMV-ATF4-d2EGFP. To further destabilize the ATF4-d1EGFP fusion protein, alanine substitutions E428A, E430A, E431A (42) were introduced in the ODC1 PEST sequence to generate pCMV-ATF4-d1EGFP. The ATF4-d1EGFP coding sequence was then excised from the expression vector using BamHI and EcoRI and subcloned into the BglII-EcoRI sites of the retroviral expression vector pLPCX (Clontech) to generate pLPCX-ATF4-d2EGFP. Lastly, a fusion PCR product containing the encephalomyocarditis virus internal ribosomal entry site (EMCV-IRES) upstream of the monomeric cherry (mCherry) coding sequence and flanked by EcoRI and NotI recognition sites was subcloned into the cognate sites of pLPCX-ATF4-d1EGFP, thereby generating pLPCX-ATF4-d1EGFP-IRES-mCherry (DAA-361). DAA-361 was used to produce recombinant retroviruses using standard methods and the resulting viral supernatant was used to transduce U2OS cells, which were then subsequently selected with puromycin to generate a stable cell line employed in the secondary screen.

Generation of the Inducible eIF2α Phosphomimetic Mutant Construct and Cell Line

The coding sequences of wild type mouse eIF2α, phosphomimetic (S51D) mutant was amplified by PCR from a mammalian expression vector (kind gift of David Ron). BamHI and EcoRI recognition sites were engineered into the primers. In addition a Kozak consensus sequence and a N-terminal FLAG epitope tag were engineered in the forward primer. The resulting PCR products were subcloned into the cognate sites of the tetracycline-inducible retroviral expression vector pRetroX-Tight-Pur-GOI (Clontech). 293T target cells stably expressing the reverse tetracycline transactivator (rtTA) were generated by standard retroviral transduction using VSV-G pseudotyped retroviruses encoding rtTA (pRetroX-Tet-On Advanced, Clontech) and selected with Geneticyn. These cells were subsequently transduced with a VSV-G pseudotyped retrovirus, encoding the eIF2α (S51D) (DAA-A681) mutant allele, resulting in a puromycin-selected, tetracycline inducible, stable cell line.

Generation of the Inducible 6×HIS-3×FLAG-hsATF6-Alpha Cell Line

6×His-3×FLAG-hsATF6-alpha was generated by PCR from p3×FLAGCMV7.1-ATF6 (43) and cloned into pcDNA5/FRT/TO. pcDNA5/FRT/TO-6×His-3×FLAG-hsATF6-alpha was co-transfected with pOG44 into Flp-In TRex cells (44) according to manufacturers instructions (Invitrogen). After selection with 100 μg/ml Hygromycin B (Gold Biotechnology) single colonies were isolated, expanded and tested for expression of tagged ATF6.

High-Throughput Primary Screen

HEK293T cells carrying the ATF4 luciferase reporter were plated on poly-lysine coated 384 well plates (Greiner) at 30,000 cells per well. Cells were treated the next day with 100 nM thapsigargin and 10 μM of the library compounds (diversity library of 106,281 compounds) for 6 h. Luminescence was measured using One Glo (Promega) as specified by the manufacturer. The primary screen had a Z'=0.5 and its hit rate was 0.6% (compounds were considered a hit if their luciferase readouts were beyond three standard deviations of the mean luminescence intensity of thapsigargin treated cells, which corresponded to 54% inhibition). Of these, only 187 compounds did not hit an XBP1-luciferase splicing reporter used as proxy to measure activation of the IRE1 branch of the UPR. Thus, these were considered unique to the PERK branch and were cherry-picked for further analysis.

High-Content Microscopy-Based Secondary Screen

U2OS cells carrying the ATF4-dGFP-IRES-Cherry reporter were plated in 96 well plates and treated with 100 nM Thapsigargin and 10 μM of the cherry-picked compounds for 8 h. Cells were stained with Hoechst 33258 and were visualized using an automated microscope (InCell Analyzer 2000, GE Healthcare). Data acquisition and image analyses were performed with the INCell Developer Toolbox Software, version 1.9 (GE Healthcare). Compounds that blocked induction of the ATF4-dGFP reporter, did not block the accumulation of mCherry downstream of the IRES, and were deemed nontoxic as determined by cell number measured by counting nuclei, were repurchased for further analyses.

Pharmacokinetics of ISRIB

Intra-peritoneal (ip), and intra-venous (iv) routes of administration were performed on 6-7 wk old female CD-1 mice (Harlan Laboratories). Animals received a single, 5 mg/kg dose in groups of three mice/compound/route of administration. For ip and iv dosing ISRIB was dissolved in DMSO then diluted 1:1 in Super-Refined PEG 400 (Croda). Blood (80 ul) was collected from the saphenous vein at intervals post-dosing (20 min, 1 h, 3 h, 8 h, 24 h) in EDTA containing collection tubes (Sarstadt CB300) and plasma was prepared for analysis. Compounds were detected by time-of-flight mass spectroscopy.

TABLE 1

Pharmacokinetic parameters of ISRIB
The data is represented as the mean (n = 3).

| Parameters | mouse |
|---|---|
| ip dose (mg/kg) | 5 |
| AUC (ng * h/ml) | 3318 |
| F % | 13.8 |
| CLt (ml/h) | 8.31826 |
| Vd (ml) | 96.0261 |
| T½ (h) | 8.43 |

Molecular Action of ISRIB. To date, we have synthesized and assayed more than 75 analogs, which demonstrate a tractable structure-activity relationship (to be published elsewhere). The analyses have identified sites on the molecule where affinity tags and/or crosslinking moieties can be added, which promise to aid in target identification. Based on previous insights on how cells can become resistant to eIF2α phosphorylation, we consider two likely scenarios by which ISRIB could act:

First, ISRIB could weaken the effects of the non-productive interaction of phospho-eIF2a with eIF2B, thereby increasing the available eIF2α-GEF activity in the cell, restoring the concentration of ternary complex that can engage in translation initiation. Precedence for this possibility derives from genetic studies in S. cerevisiae, where the molecular mechanism of regulation by eIF2α phosphorylation was first discovered. As in mammalian cells, amino acid starvation in yeast leads to GCN2 activation and eIF2α phosphorylation, resulting in overall translational down-regulation and translational induction of a transcriptional activator, GCN4, mediated by uORFs in the 5'UTR of its mRNA (4). eIF2B is a conserved protein complex comprised of five different subunits, two of which form the catalytic core, and the remaining three have regulatory roles. Mutations in different eIF2B subunits can elicit a phospho-eIF2α resistant phenotype (23-25). These mutations have been proposed to act either by weakening the interaction of phospho-eIF2α with eIF2B, reducing its ability to outcompete non-phosphorylated eIF2 for binding, or by allowing binding of phospho-eIF2α to the mutant eIF2B in a manner that is conducive to nucleotide exchange. ISRIB could be altering the affinity of phospho-eIF2α for eIF2B or overcoming the nonproductive interaction that blocks GTP loading, mimicking the effect of these mutations.

Second, ISRIB could increase the activity of eIF2B, so that the residual amount not engaged with phospho-eIF2α is sufficient to sustain normal levels of ternary complex. Precedence for this possibility derives from studies in macrophages, where engagement of toll-like receptor (TLR) 4 results in activation of the catalytic activity of eIF2B (26). This activation results from engagement of the TLR-signaling pathway that induces a phosphatase removing a constitutively present inhibitory phosphate from the eIF2B ε-subunit. Pathogens utilize this mechanism to circumvent translational attenuation and CHOP production under prolonged stress-inducing conditions (27). Similarly, ISRIB could activate or inhibit a signaling pathway that modulates eIF2B activity.

B. Impairment of Adaptation to ER Stress

Figure 5A:
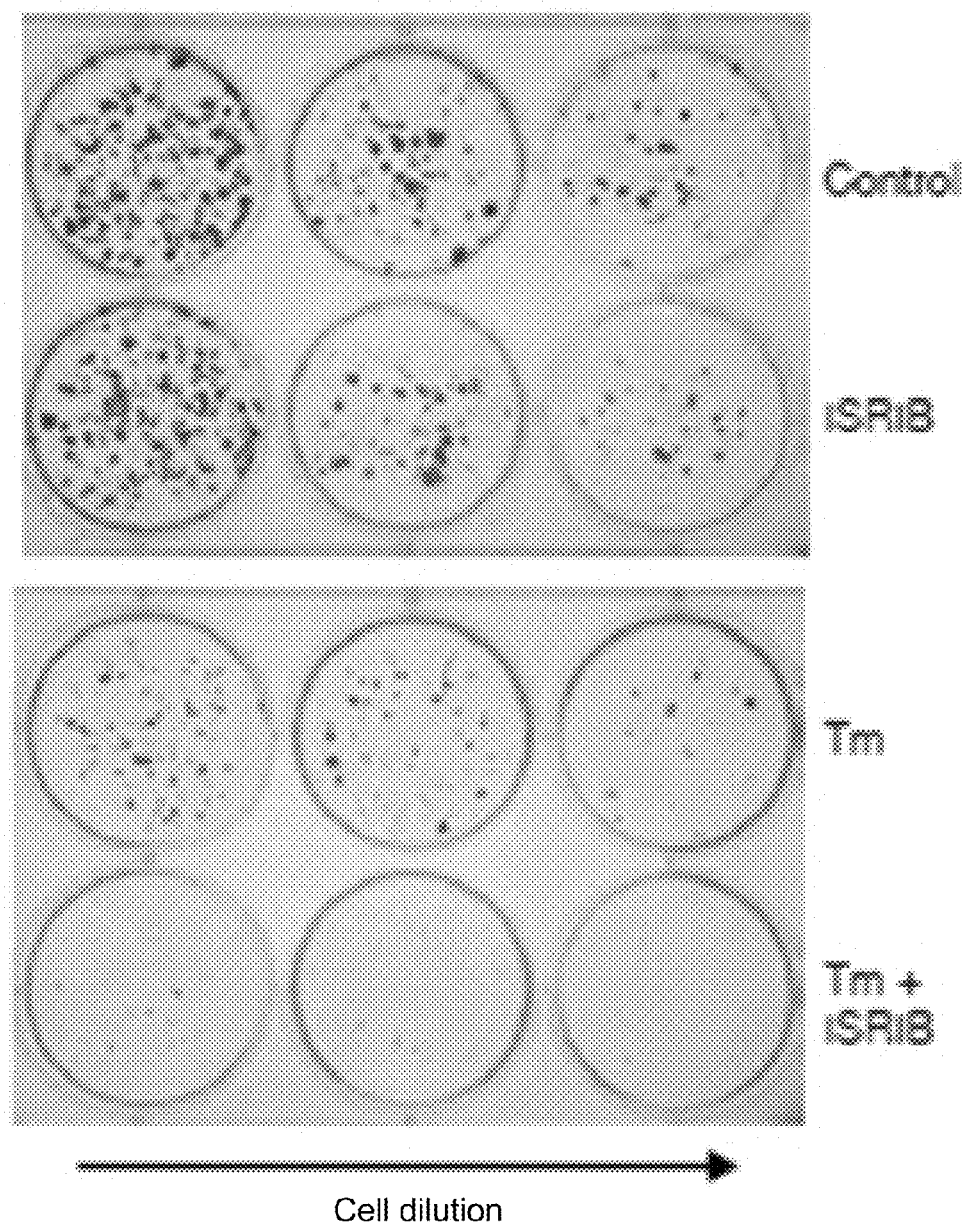
FIGS. 5A-5D. ISRIB impairs adaptation to ER-stress prolonging activation of the UPR sensors.
Figure 5B:
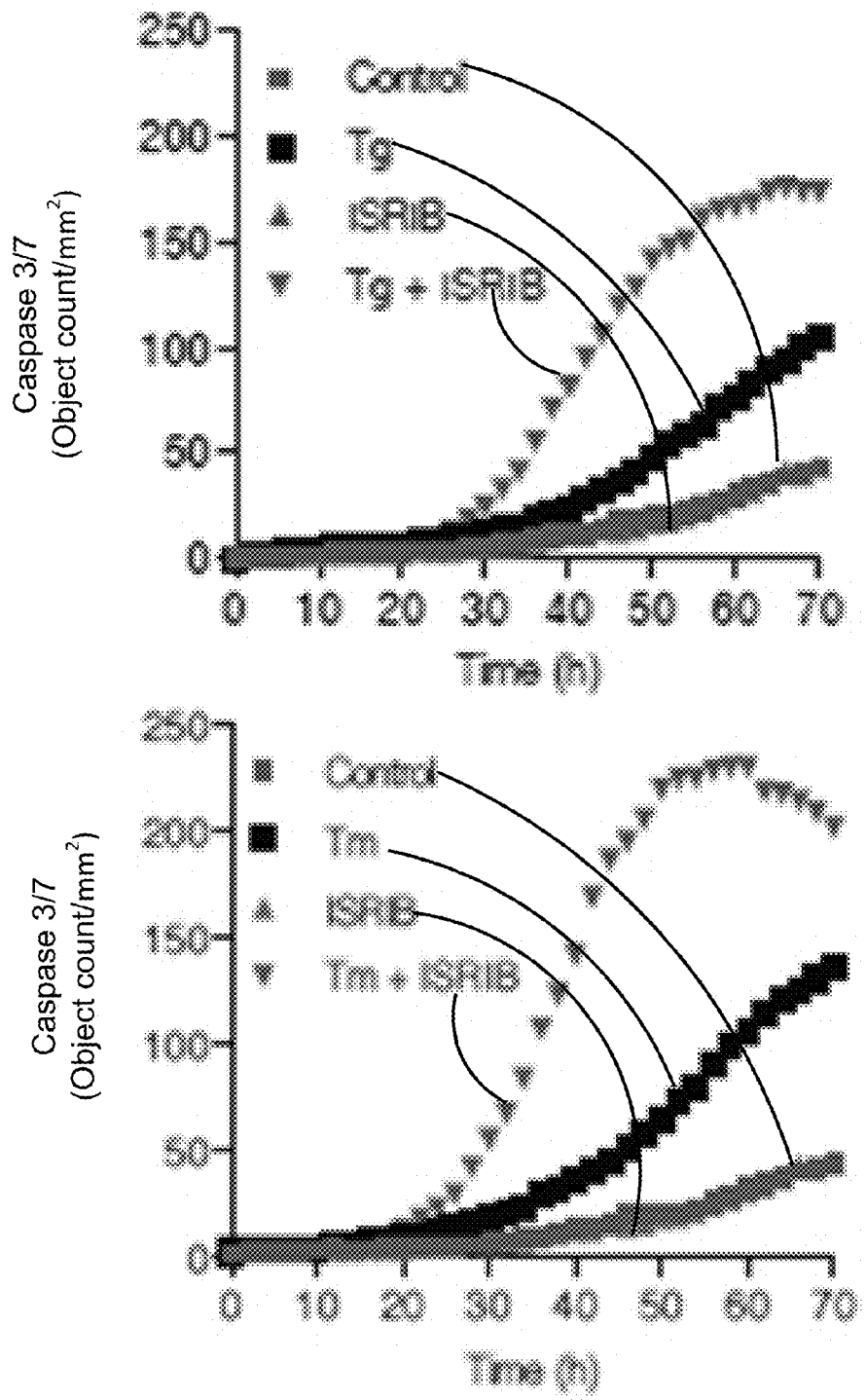

As previously shown, cells homozygous for non-phosphorylatable eIF2α, eIF2α(S51A), are unable to cope with ER stress properly, leading to reduced viability (19). This indicates that events downstream of eIF2α phosphorylation are required to resolve the stress. As shown in FIG. 5A, ISRIB treatment of wild-type cells had similar consequences. Importantly, addition of ISRIB alone did not affect cell viability, as judged by the number of colonies that form after acute treatment. By contrast, ISRIB addition caused a strong synergistic effect on ER-stressed cells, reducing colony number and size significantly more than ER-stress alone. This reduction in cell survival resulted from activation of apoptosis as the activity of the executioner caspases 3 and/or 7 was significantly induced under these conditions (FIG. 5B) (20).

Figure 5C:
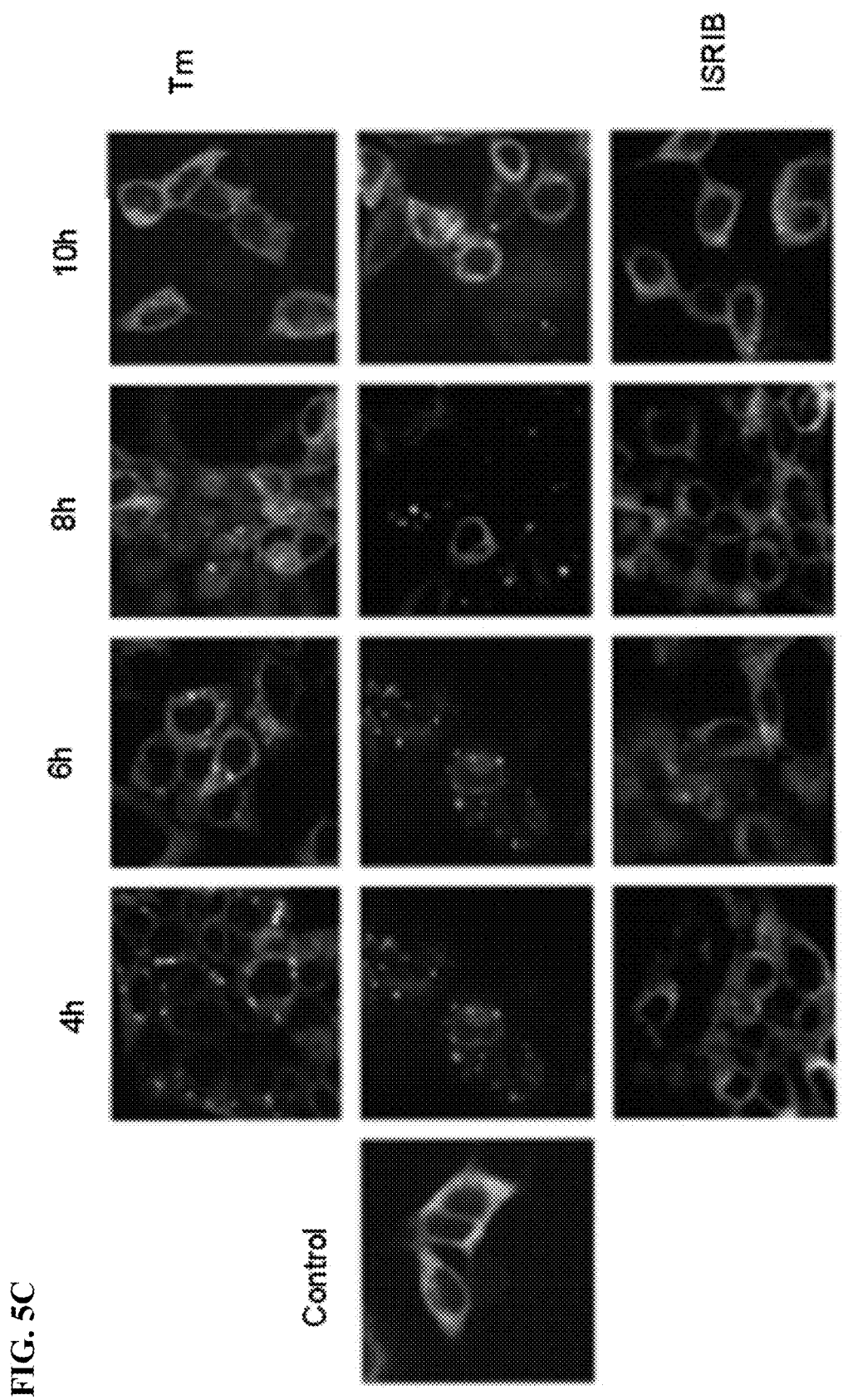
Figure 5D:
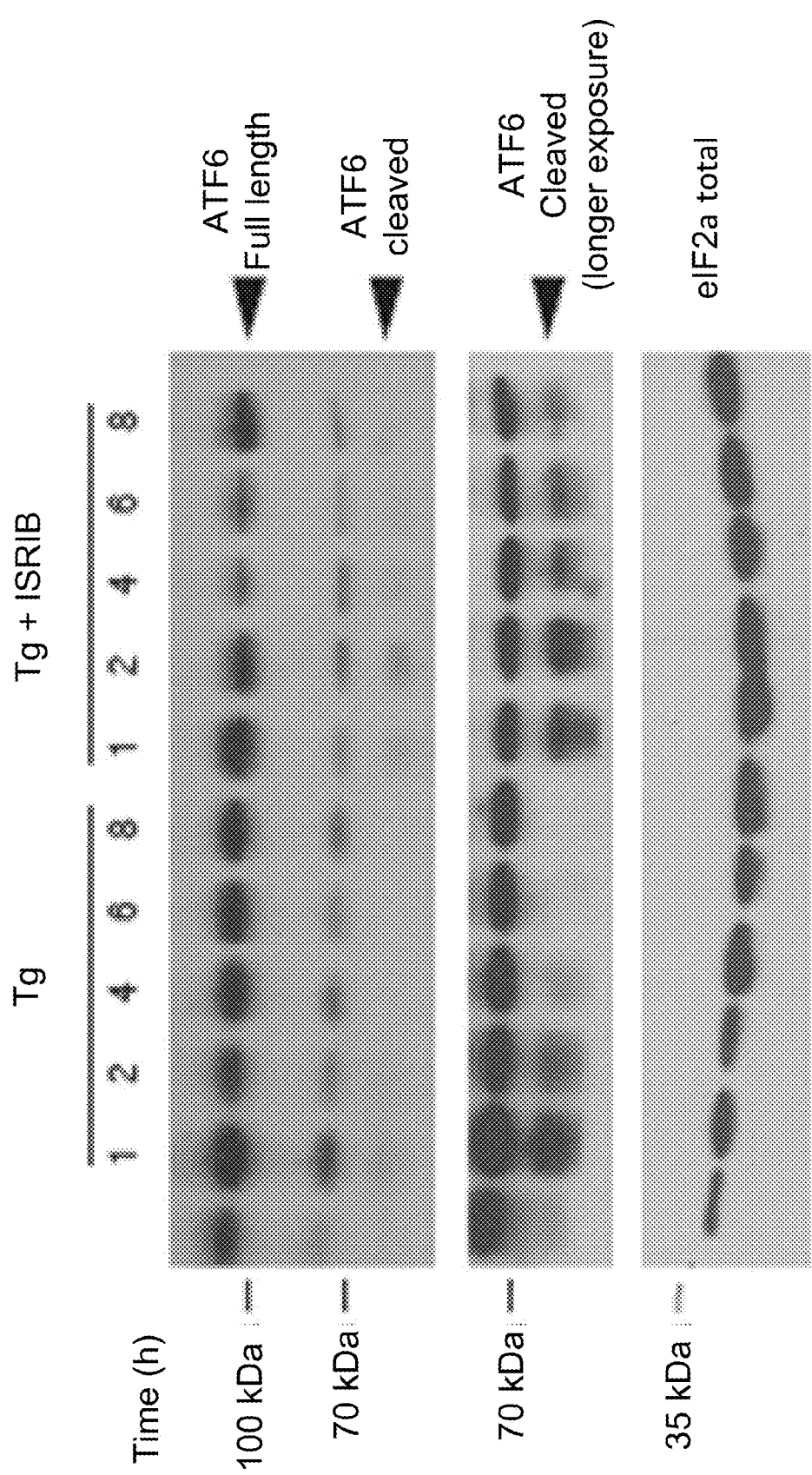

The notion that ER stress remains unmitigated in ISRIB-treated cells is supported by sustained activation of all three UPR sensors. First, as shown in FIG. 2C, PERK was hyper-phosphorylated. Second, cells expressing an IRE1-GFP fusion protein showed prolonged foci formation (FIG. 5C), indicative of IRE1 oligomerization. Third, we observed prolonged ER stress-induced proteolytic processing of ATF6 (FIG. 5D). Importantly, in the absence of ER stress ISRIB treatment alone did not induce any of these sensors (FIGS. 3F and 5C).

Alpha Screen for Phospho-S51 eIF2α

U2OS cells were plated on 96 well plates and left to recover overnight. Cells were treated with either with 2 µg/ml tunicamycin or 100 nM thapsigargin in the presence or absence of 100 nM ISRIB or with ISRIB alone for the indicated and the level of eIF2α phosphorylation was determined using the AlphaScreen SureFire eIF2α(p-Ser51) Assay kit (Perkin Elmer) following the manufacturer's recommendations. Plates were read in an Envision Xcite Multilabel Reader using the standard Alpha Screen settings.

Metabolic Labeling

HEK293T cells were seeded on 12 well plates, allowed to recover overnight and treated for the indicated times with the indicated compounds. The cells were subsequently switched to media lacking methionine and cysteine supplemented with the indicated compounds and 50 µCi of $^{35}$S-methionine (Perkin Elmer) for 20 min. Cells were lysed by addition of SDS-PAGE loading buffer. Lysates were sonicated and equal amounts were loaded on SDS-PAGE gels (BioRad). The gel was dried and radioactive methionine incorporation was detected by exposure to a phosphor-screen and visualized with a Typhoon 9400 Variable Mode Imager (GE Healthcare).

Live Cell Imaging

T-REx293 cells carrying GFP-IRE1 were imaged as described in Li et al, PNAS (45).

Caspase3/7 Activation

Hela cells were plated in 96 well Corning plates at $0.4 \times 10^4$ cells/well 24 hours prior to imaging. On the day of experiment, DMEM media was replaced with F12 media with appropriate concentration of inhibitors and ER stress inducers and caspase 3/7 reagent at 1:1000 dilution (Essen Bioscience #4440). Cells were imaged in the IncuCyte FLR live cell imaging system at 2 hour intervals for 70 hours. In order to quantify the total number of cells, Vybrant Dye-Cycle Green staining solution (1 µM) was added directly to the well immediately after the final Caspase-3/7 scan and incubated for 1 h prior to acquiring final images. Data was analyzed using IncuCyte analysis software.

qRT-PCR

U2OS cells were plated on 96 well plates and allowed to recover overnight. Cells were treated for the indicated times with the indicated compounds, lysed and cDNA was synthesized using the PowerSYBR Green Cells-to-CT kit (Ambion) following the manufacturer's recommendations. The reactions were ran in an Opticon 2 thermal cycler (BioRad) and analyzed with the Opticon Monitor v3 software (BioRad). The following oligonucleotides were used for the amplification reaction: Human GADD34: 5'-GTAGCCT-GATGGGGTGCTT-3' (SEQ ID NO:1) and 5'-TGAGGCA-GCCGGAGATAC-3'(SEQ ID NO:2); Human CHOP: 5'-AGCCAAAATCAGAGCTGGAA-3' (SEQ ID NO:3) and 5'-TGGATCAGTCTGGAAAAGCA-3'(SEQ ID NO:4); Human GAPDH: 5'-TGGAAGATGGTGATGGGATT-3' (SEQ ID NO:5) and 5'-AGCCACATCGCTCAGACAC-3' (SEQ ID NO:6).

TAQMAN® Assay to Measure XBP1 mRNA Splicing cDNA obtained with the POWERSYBR® GREEN CELLS-TO-CT™ kit (Ambion) as described above was used for the TAQMAN® Assay. TAQMAN® assays were set up using IQ™ Supermix (BioRad), 250 nM of each outer primer, 200 nM FAM-XBP1U probe, or 100 nM HEX-XBP1S probe. The reactions were then run on a real-time DNA Engine OPTICON® 2 PCR thermal cycler (BioRad) and analyzed with the OPTICON MONITOR® v3 software (BioRad). The outer primers employed for the human XBP1 unspliced/spliced (u/s) TAQMAN® assay were: 5'-GAAGCCAAGGGGAATGAAGT-3' (SEQ ID NO:7), and 5'-GAGATGTTCTGGAGGGGTGA-3' (SEQ ID NO:8). TAQMAN® probes specific for human XBP1s or XBP1u were: 5'-FAM-CAGCACTCAGACTACGTGCAC-CTCTG-BHQ1-3' (SEQ ID NO:9), and 5'-HEX-TCTGCT-GAGTCCGCAGCAGGTGCA-BHQ1-3' (SEQ ID NO:10). A person of ordinary skill in the art will understand the meaning of the terms "HEX", "FAM", and "BHQ-1" as they are used for TAQMAN® probes.

RNA Isolation and Semi-Quantitative RT-PCR

Total RNA from treated or untreated HEK293T cells was extracted using TRIzol (Invitrogen) following the manufacturer's recommendations. 500 ng of total RNA were reverse transcribed using the SuperScriptVilo cDNA Synthesis kit (Invitrogen). The cDNA was diluted 1 in 10 in TE (pH=8) and 1% of the total reaction was used as a template for the PCR amplification reactions. The XBP1 primers flank the 26-nucleotide intron and produce both spliced (222 bp) and unspliced (248 bp) amplicons. The PCR products were resolved in 2.5% agarose. The following oligonucleotides were used for the amplification reaction: for human XBP1, 5'-ACTGGGTCCAAGTTGTCCAG-3' (SEQ ID NO:11) and 5'-GGAGTTAAGACAGCGCTTGG-3'(SEQ ID NO:12); for human GAPDH 5'-TGGAAGATGGT-GATGGGATT-3' (SEQ ID NO:13) and 5'-AGCCA-CATCGCTCAGACAC-3'(SEQ ID NO:14).

Protein Analysis

Cells were lysed in SDS-PAGE loading buffer (1% SDS, 62.5 mM Tris-HCl pH 6.8, 10% glycerol). Lysates were sonicated and equal amounts were loaded on SDS-PAGE gels (BioRad). Proteins were transferred onto nitrocellulose and probed with primary antibodies diluted in Tris-buffered saline supplemented with 0.1% Tween 20 and 5% bovine serum albumin. The following antibodies were used: CREB-2 (C-20) (1:800) (Santa Cruz Biotechnologies); PERK (D11A8) (1:1000), PERK (C33E10) (1:1000), eIF2α (9722) (1:1000), phospho-eIF2α (Ser51) (D9G8) XP (3398) (1:1000) (Cell Signaling Technology); XBP1s (C-terminus) (1:500) (BioLegend); M2 Flag (1:1000) (Sigma). An HRP-conjugated secondary antibody (Amersham) was employed to detect immune-reactive bands using enhanced chemiluminescence (SuperSignal, Thermo Scientific).

Immunofluorescence

U2OS cells were seeded on Slide Flasks (Thermo Scientific) 18 h prior to processing for immunofluorescence. Cells (60% confluent) were fixed with 4% paraformaldehyde in PBS for 15 min. The cells were then rinsed 3 times with PBS and permeabilized with 0.3% Triton X-100. The fixed cells were rinsed 3 times with PBS and blocked for 1 h at room temperature in PBS supplemented with 0.1% Triton X-100 and 5% normal goat serum. The cells were then incubated overnight at 4° C. with an anti-CHOP mouse monoclonal antibody (Cell Signaling Technology L63F7) at a 1:1000 dilution in blocking buffer. The next morning the slides were washed 3 times (5 min each time) with PBST (PBS-0.1% Triton X-100). The slides were then incubated for 1 h at room temperature in a 1:500 dilution (in blocking buffer) of secondary anti-mouse antibody labeled with Alexa Dye 488 (Molecular Probes). The slides were then washed 3 additional times with PBST. The cells were then counterstained with rhodaminephalloidin (1:1,000 in PBS) for 10 min at room temperature to reveal the actin cytoskeleton. Lastly, the slides were mounted using Vectashield (Vector) mounting medium and imaged using a Zeiss Axiovert 200M epifluorescence microscope.

Polysome Gradients

Mouse Embryonic Fibroblasts (MEFs) or TREx-293 cells expressing eIF2α(S51D) were seeded on 150 mm plates and allowed to grow to 80% confluence. Cells were then induced with 25 nM doxycycline for 14 h and subsequently treated with the appropriate compounds for the indicated times. 100 µg/ml of cycloheximide was added to the cells for 1 min before lysis. Cells were washed twice with PBS supplemented with 100 µg/ml cycloheximide and subsequently lysed in 20 mM Tris pH 7.4, 200 mM NaCl, 15 mM MgCl, 1 mM DTT, 8% Glycerol, 100 µg/ml cycloheximide, 1% Triton X-100 and EDTA-free protease inhibitor tablets (Roche). Cells were scraped, collected, triturated with a $25^{7/8}$ gauge needle, and the homogenate was centrifuged for 10 min at 10,000×g. The supernatant was loaded on a 10-50% sucrose gradient and sedimented in a SW40 rotor at 150,000×g for 2.4 h. The gradients were fractionated using a piston gradient fractionator (BioComp) and UV absorbance at 254 nm was monitored using a UV-Monitor (Bio-Rad).

ISRIB can influence cell fate. As a signaling network with interconnected signaling branches, the UPR exhibits both cytoprotective and pro-apoptotic functions. When faced with ER stress, PERK-mediated translational attenuation contributes to adaptation by reducing the load of newly synthesized proteins that are translocated into the ER (13). In addition, induction of the transcription regulator ATF4 upregulates many genes that increase the protein folding capacity in the ER. Both of these activities serve to reestablish homeostasis, balancing the protein folding load and protein folding capacity in the ER lumen. This reasoning is supported by the increased sensitivity to ER stress exhibited by MEFs that lack PERK or ATF4, as well as MEFs that carry a non-phosphorylatable knock-in allele of eIF2α (S51A) (13,19,28). In agreement, we show that ISRIB decreases the viability of cells that are subjected to ER-stress. In these cells, ISRIB sustains IRE1 and ATF6 activation, indicating that ER stress remains unmitigated in the absence of PERK signaling. As some cancer cells sustain an activated UPR to aid in their survival, ISRIB could provide a new therapeutic approach to cancer chemotherapy. In agreement, a PERK-specific inhibitor demonstrates antitumor activity in a human pancreatic tumor xenograft model (29). The deleterious synergistic effect between ER-stress and ISRIB may be generally advantageous to kill cancer cells, especially those derived from secretory lineages that have increased secretory load and increased basal levels of ER stress (including myelomas, and pancreatic and breast cancers).

Importantly, by acting downstream of eIF2α phosphorylation, ISRIB blocks multiple stress effectors (i.e., all eIF2α kinases). During tumor growth, hypoxic conditions and a lack of nutrients can activate both PERK and GCN2, and PERK$^{-/-}$ or GCN2$^{-/-}$ MEFs give rise to significantly smaller tumors in mouse xenograft models than their wild-type counterparts (30,31). Hence both kinases have pro-survival roles in tumor development. By blocking signaling by both kinases, ISRIB displays unique properties that may be beneficial in reducing cellular fitness of tumor cells.\

Figure 22:
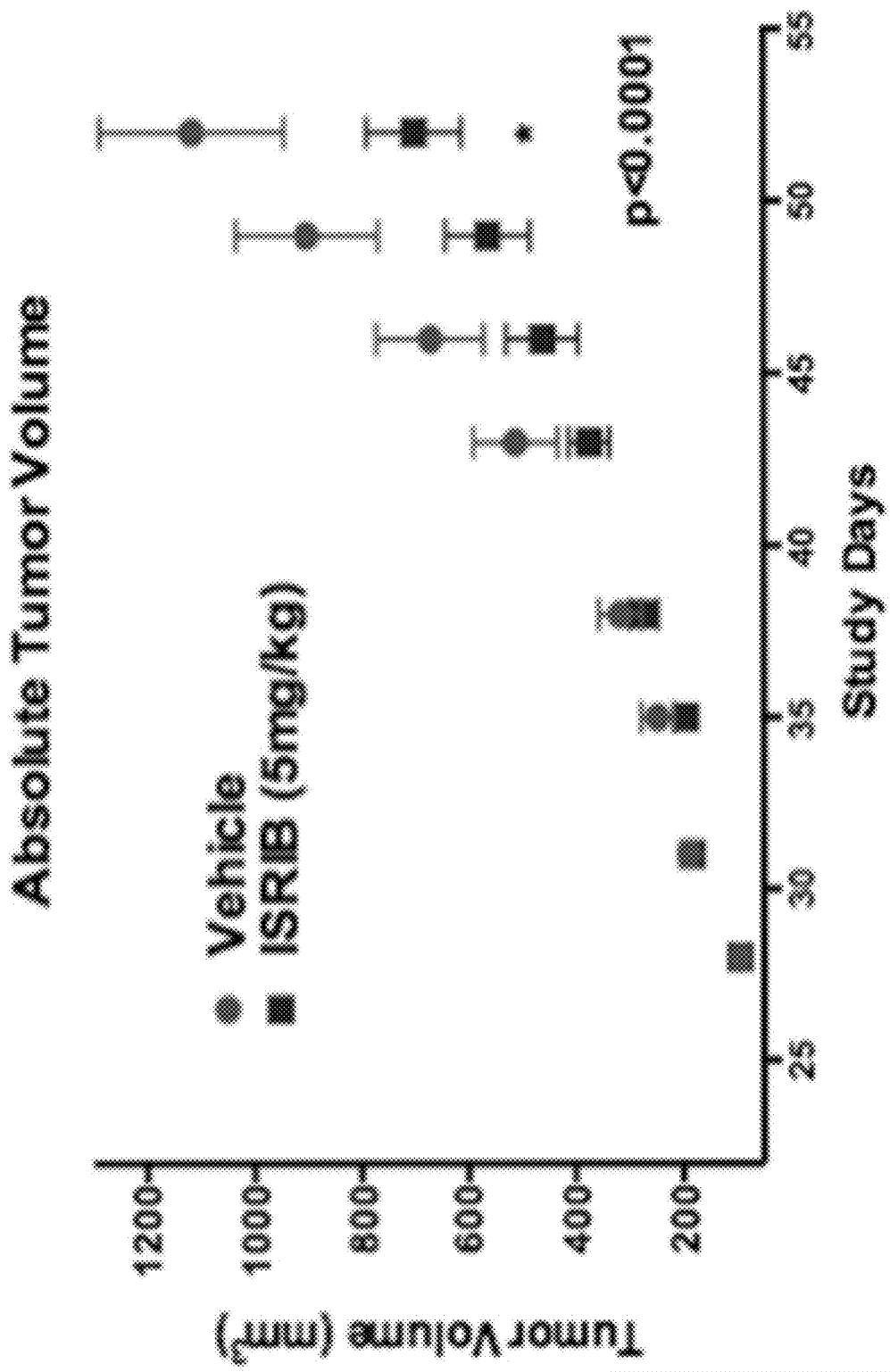
FIG. 22. RMPI 8226 cells were implanted subcutaneously in BALB/c scid mice; at day 26, when tumors had an average size of 95 mm3, mice were orally dosed (daily) with vehicle or 5 mg/kg of ISRIB; tumor size was measured twice weekly and the mean tumor volume was plotted as a function of study days (error bars show standard error of the mean); after 26 days of dosing, a significant difference in tumor size is observed between ISRIB-treated and the vehicle-treated control group (non-parametric t-test Mann-Whitney p<0.0001)

Results in a multiple myeloma xenograft model suggest that ISRIB has antitumor activity in subcutaneous plasmacytomas arising from RPMI 8226 cells (FIG. 22). In this experiment, ISRIB, given orally to tumor bearing mice, resulted in a significant reduction in the rate of tumor growth. At the endpoint of the study, there was a 50% reduction in tumor size in animals dosed with ISRIB.

C. Memory Studies

Reversing translational attenuation with ISRIB synergistically reduces the viability of cells subjected to PERK-activation by chronic endoplasmic reticulum (ER) stress. eIF2α phosphorylation has been implicated in memory consolidation by modulating new protein synthesis in the brain. Remarkably, wild-type mice injected with ISRIB display significant enhancement in both spatial and fear-associated learning. These results show that memory consolidation in normal animals is inherently limited by the ISR and that ISRIB can release this break. As such, ISRIB promises to contribute to our understanding and treatment of cognitive disorders.

Eight to ten-week-old male C57BL/6J mice were used for behavioral experiments. Food and water were provided ad libitum, and mice were kept on a 12:12 h light/dark cycle (lights on at 08:00 h). All procedures complied with Canadian Council on Animal Care guidelines Morris Water Maze Mice were trained in a water pool of 100 cm diameter with a hidden platform of 10 cm diameter. Mice were handled daily for 3 days before the experiment, and the training protocol consisted of 1 swimming trial per day. Each mouse swam until it found the hidden platform or 120 s, when it was gently guided to the platform and stayed there for 10 s before being returned to the cage. Immediately after the swimming trial the mice were injected intraperitoneally with ISRIB (0.25 mg/kg in saline, 1% DMSO). For the probe test, the platform was removed and each mouse was allowed to swim for 60 s, while its swimming trajectory was monitored with a video tracking system (HVS Image, Buckingham).

Contextual Fear Conditioning

Mice were handled for 3 days and thereafter injected daily intraperitoneally with ISRIB (0.25 mg/kg in saline, 1% DMSO) for 4 consecutive days. One hour after the last injection the mice were trained with the protocol, which consisted of a 2-min period of context exploration, followed by a single foot shock of 0.35 mA for 1 s. The mice were returned to their home cage 1 min after the shock. One and 24 h after training, the mice were tested for contextual fear memory by placing the animals in the conditioning context for a 4-min period. The incidence of freezing was scored in 5-s intervals as either "freezing" or "not freezing". Percent of freezing indicates the number of intervals in which freezing was observed divided by total number of 5-s intervals. Statistical analyses were done by Student's t tests and one-way ANOVA followed by between-group comparisons using Tukey's posthoc test.

Cannulation and Auditory Fear Conditioning

Male Sprague Dawley rats (275-350 g) were used for cannulation as described in Migues et al, 2010 (46). ISRIB (0.05 mg/ml, 5 µl) was infused bilaterally into the amygdala immediately after auditory fear conditioning training. The infusion was performed with a microinjector (28 gauge) connected to a Hamilton syringe with plastic tubing at a rate of 0.4 µl/min. To allow for the solution containing ISRIB to diffuse from the tip of the cannula into the tissue, the microinjector stayed in the cannula for one additional minute. Training protocol for auditory fear conditioning consisted of a 2-min period of context A exploration, followed by one pairing of a tone (2800 Hz, 85 dB, 30 s) with a co-terminating foot shock (0.75 mA, 1 s). Rats were returned to their home cage 1 min after the shock. Test for auditory fear memory consisted of a 2 min acclimatizing period to the context B (pre-CS), followed by tone presentation (CS) (2800 Hz, 85 dB, 30 s). Freezing time was measured and percent of freezing was calculated. At the end of the experiment, cannula placement was checked by examining 50 µm brain sections stained with formal-thionin under a light microscope.

Figure 6A:
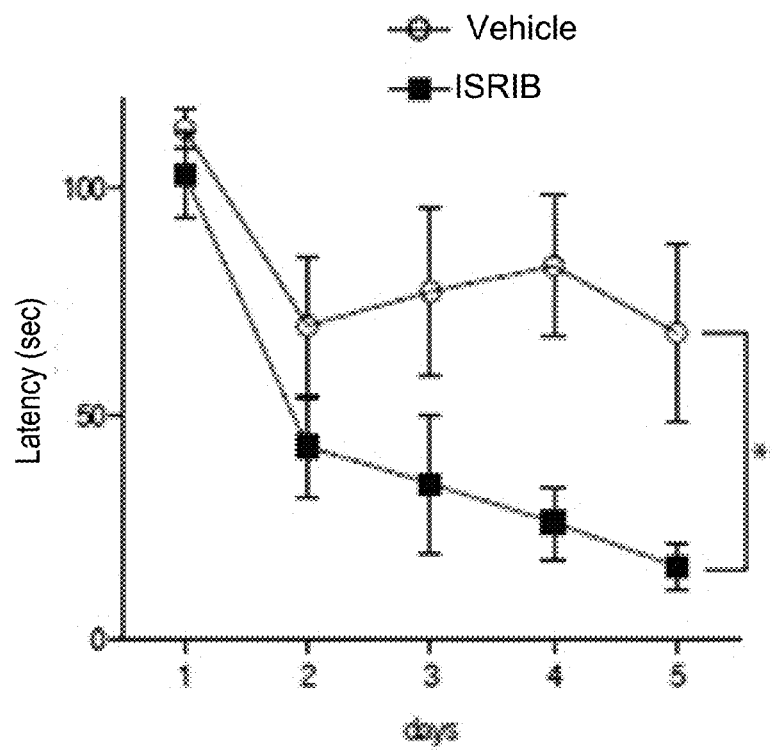
FIG. 6A-6E. ISRIB enhances spatial and fear-associated learning in rodents.
Figure 6B:
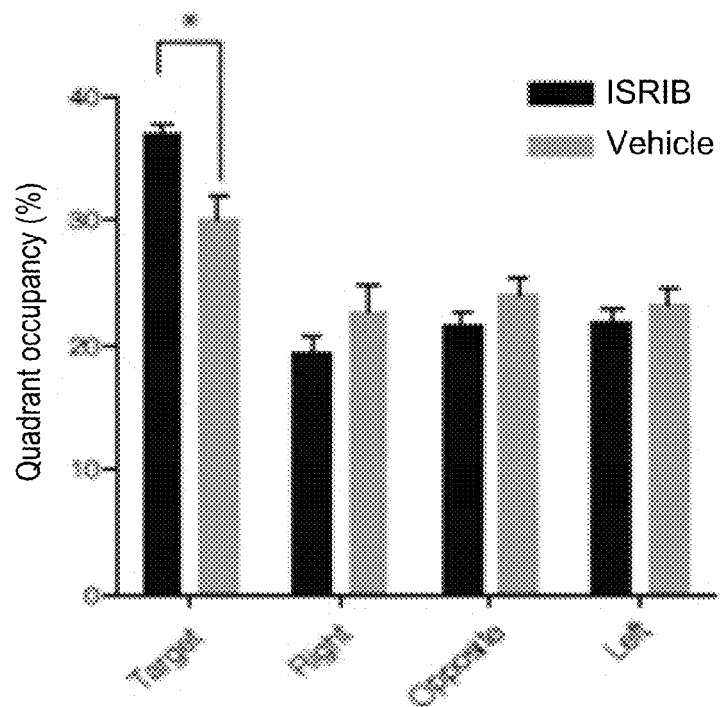
Figure 6C:
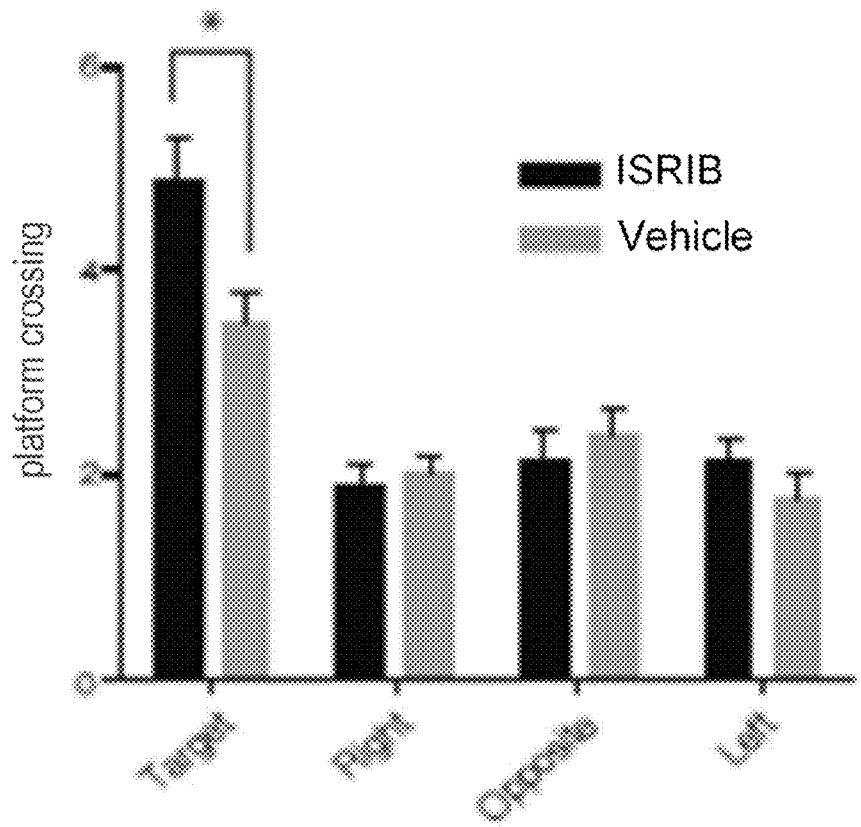

ISRIB increases long-term memory in rodents. eIF2α(+/S51A) heterozygote mice display enhanced memory, while induction of the eIF2α kinase PKR in brain pyramidal cells impairs memory (21,22). Based on these observations, we wondered whether treatment of mice with ISRIB would affect memory. ISRIB showed favorable properties in pharmacokinetic profiling experiments indicating sufficient bioavailability for in vivo studies (Table 1). To explore ISRIB's effects on memory, we injected mice intraperitoneally with ISRIB and tested hippocampus-dependent spatial learning. To this end, we trained mice in a Morris water maze, in which animals learn to associate visual cues with the location of a submerged hidden platform. Because we were looking for memory enhancement, we used a weak training protocol. As shown in FIG. 6A, ISRIB-treated mice reached the hidden platform significantly faster (escape latency after 5 days of training=16.4+/−4.8 s) compared to vehicle treated controls (68.1+/−20 s, $p<0.05$). The difference was already pronounced by days 3 and 4. In agreement with these results, ISRIB-treated mice significantly preferred the target quadrant in a "probe test" conducted at the end of the training sessions, in which the platform was removed from the pool ($p<0.05$; FIG. 6B) and showed increased crossing of the platform location ($p<0.05$; FIG. 6C).

Figure 6D:
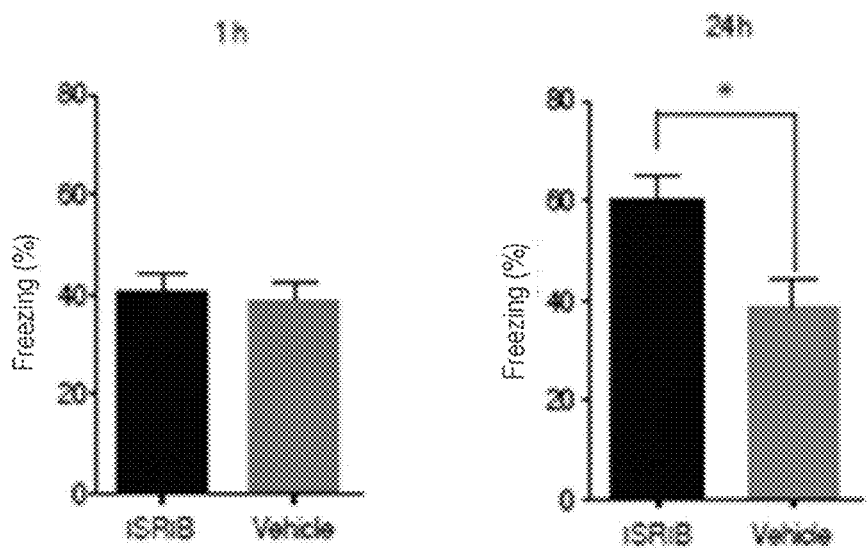

We next tested contextual fear conditioning, which represents a different kind of hippocampus-dependent learning in which eIF2α phosphorylation has also been implicated to play a role (22). In these experiments, we paired a particular environmental context (a different cage) with a foot shock. In this case the context acts as the "conditioned stimulus, CS" and is associated with the foot shock, the "unconditioned stimulus, US". ISRIB-treated mice showed increased freezing upon presentation of the conditioned environment 24 h after training as compared to vehicle treated mice ($p<0.05$; FIG. 6D). No differences were observed in short-term memory (1 h) between these two treatments. Taken together, we conclude that treatment with ISRIB enhances both hippocampus-dependent spatial learning and hippocampus-dependent contextual fear conditioning.

Figure 6E:
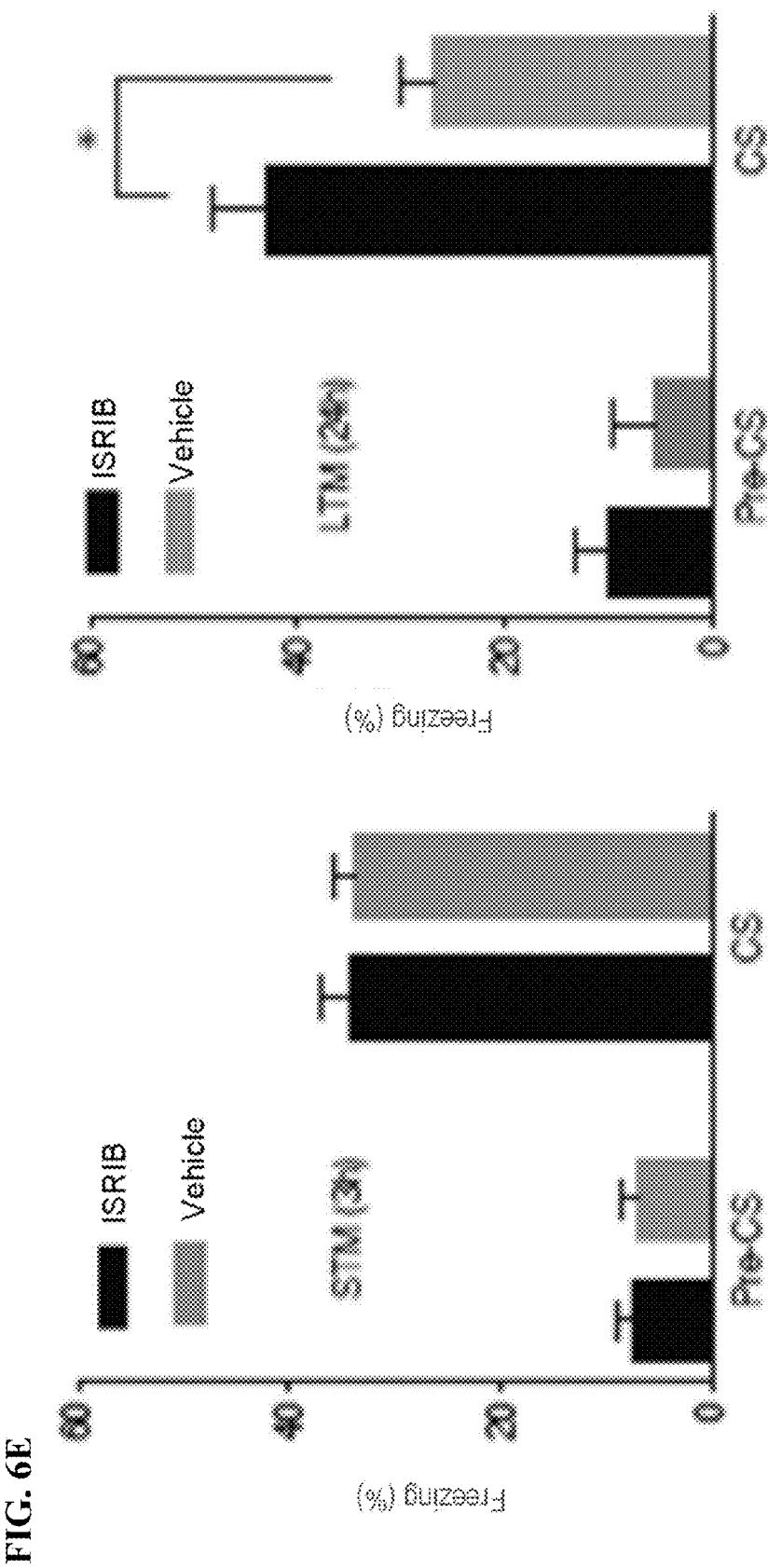
Figure 7A:
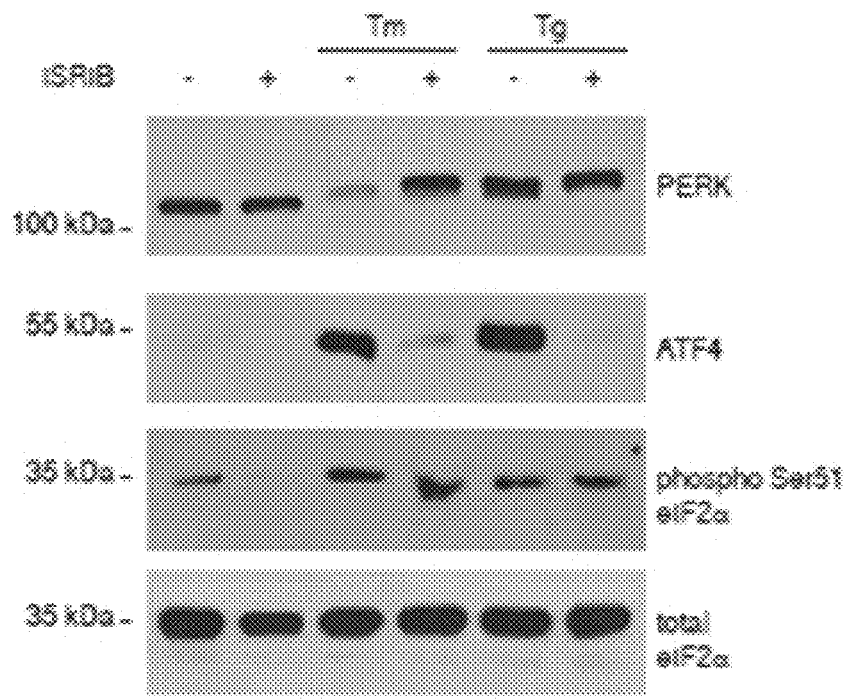
FIG. 7A-7E. ISRIB makes cells resistant to eIF2α phosphorylation.
Figure 7B:
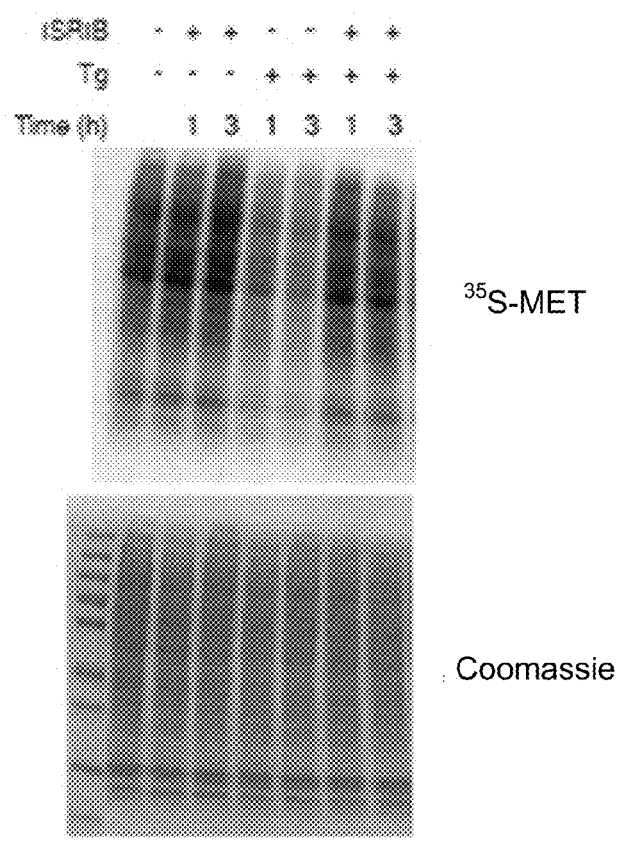
Figure 7C:
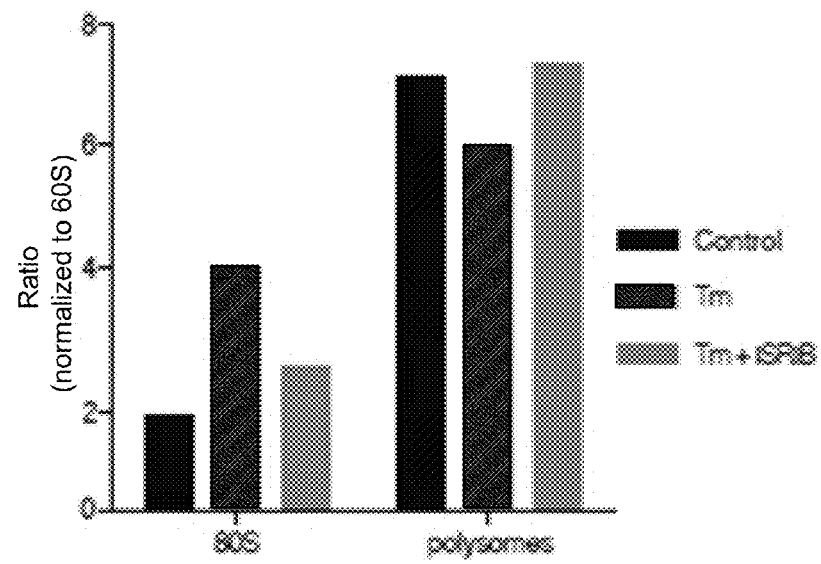
Figure 7D:
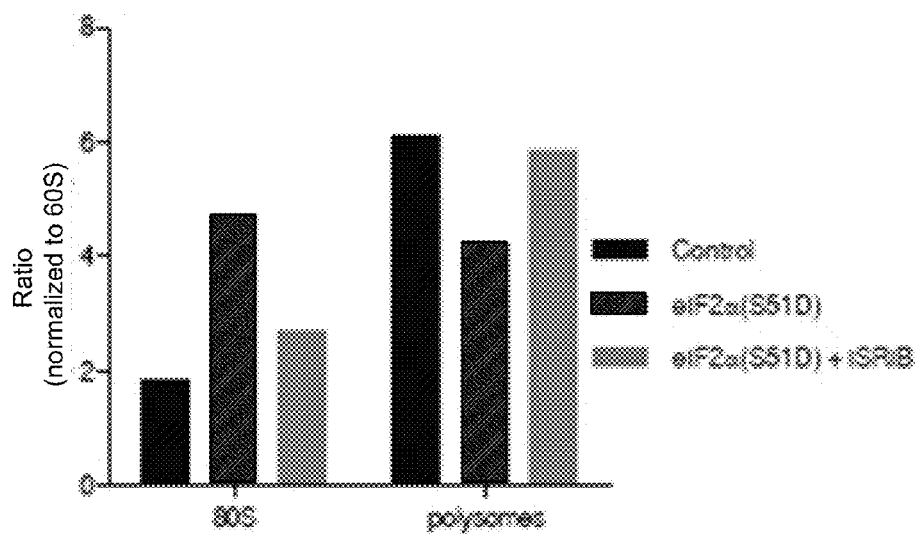
Figure 7E:
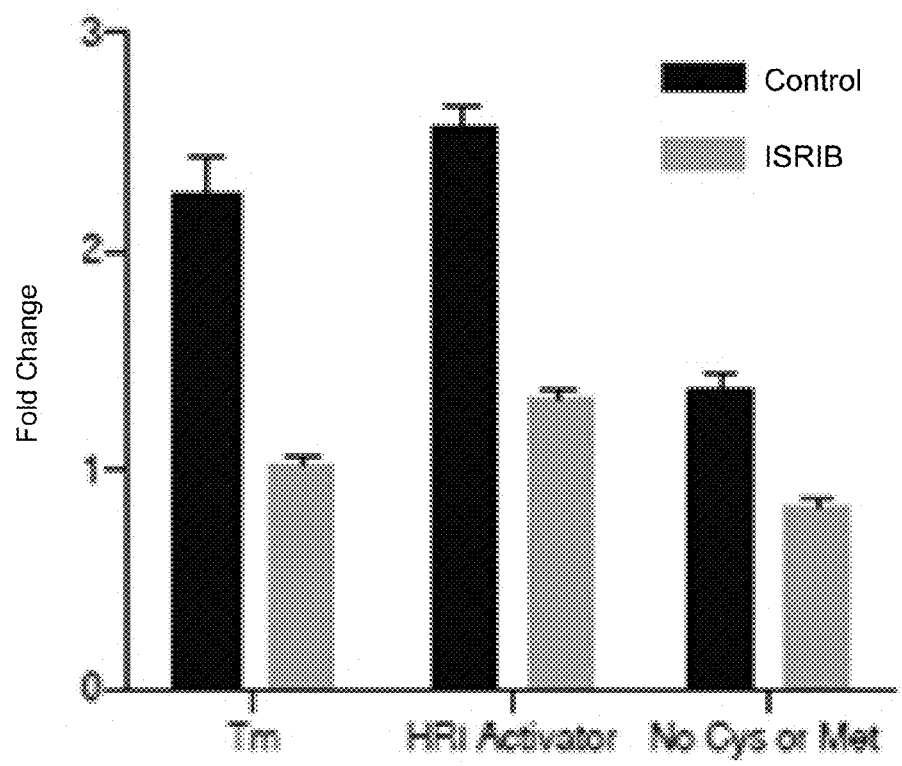
Figure 8A:
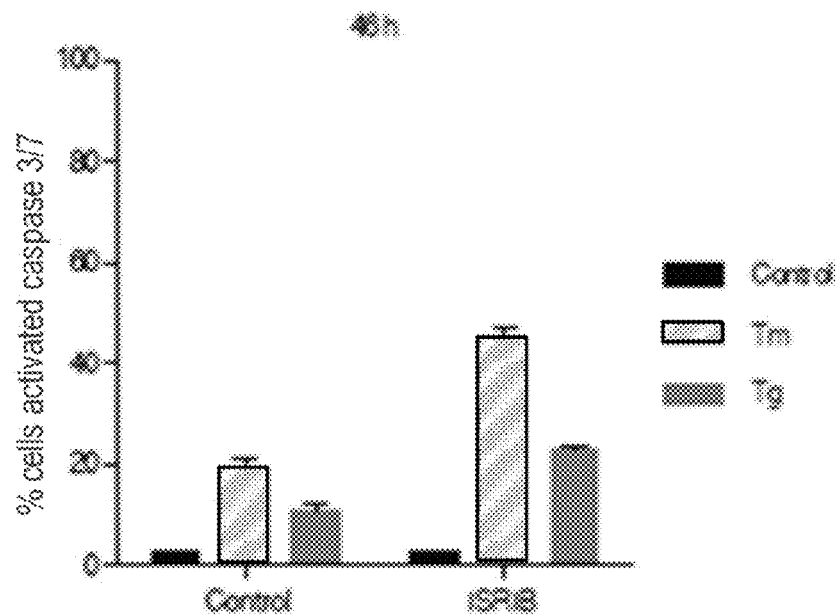
FIGS. 8A-8C. ISRIB impairs adaptation to ER-stress prolonging activation of the UPR sensors.
Figure 8B:
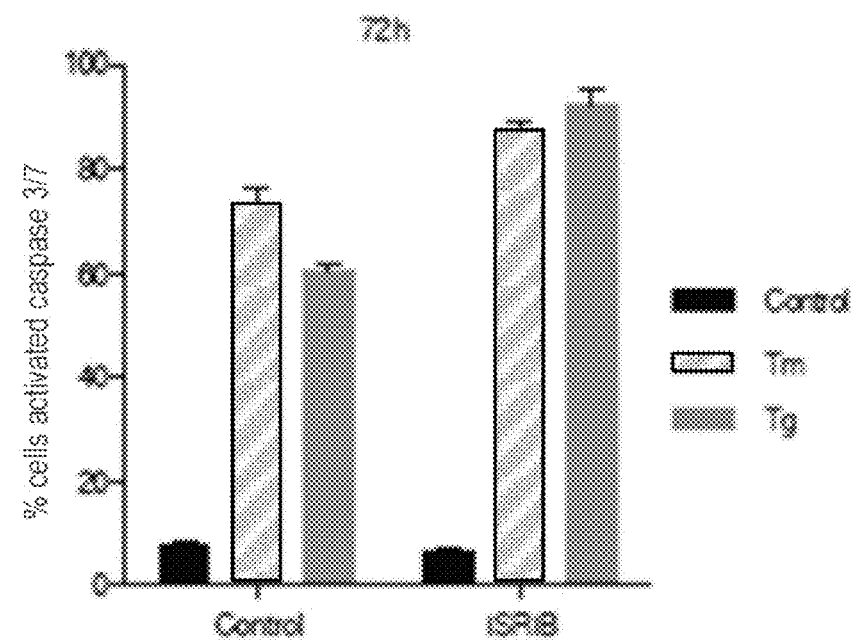
Figure 8C:
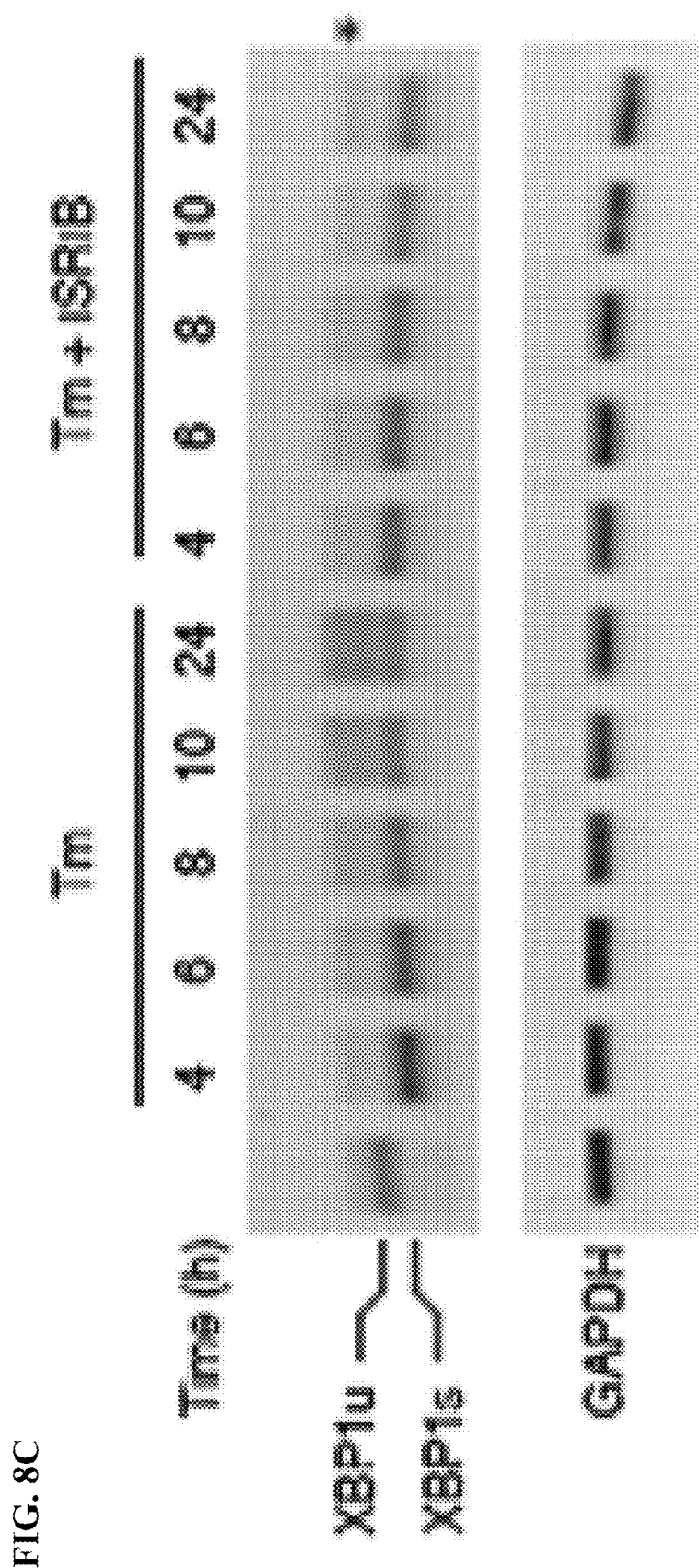
Figure 9:
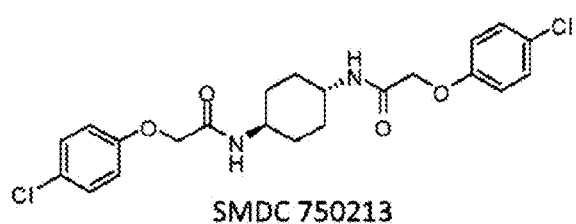
FIG. 9. Overview of SMDC 750213/ISRIB analogs.
Figure 10:
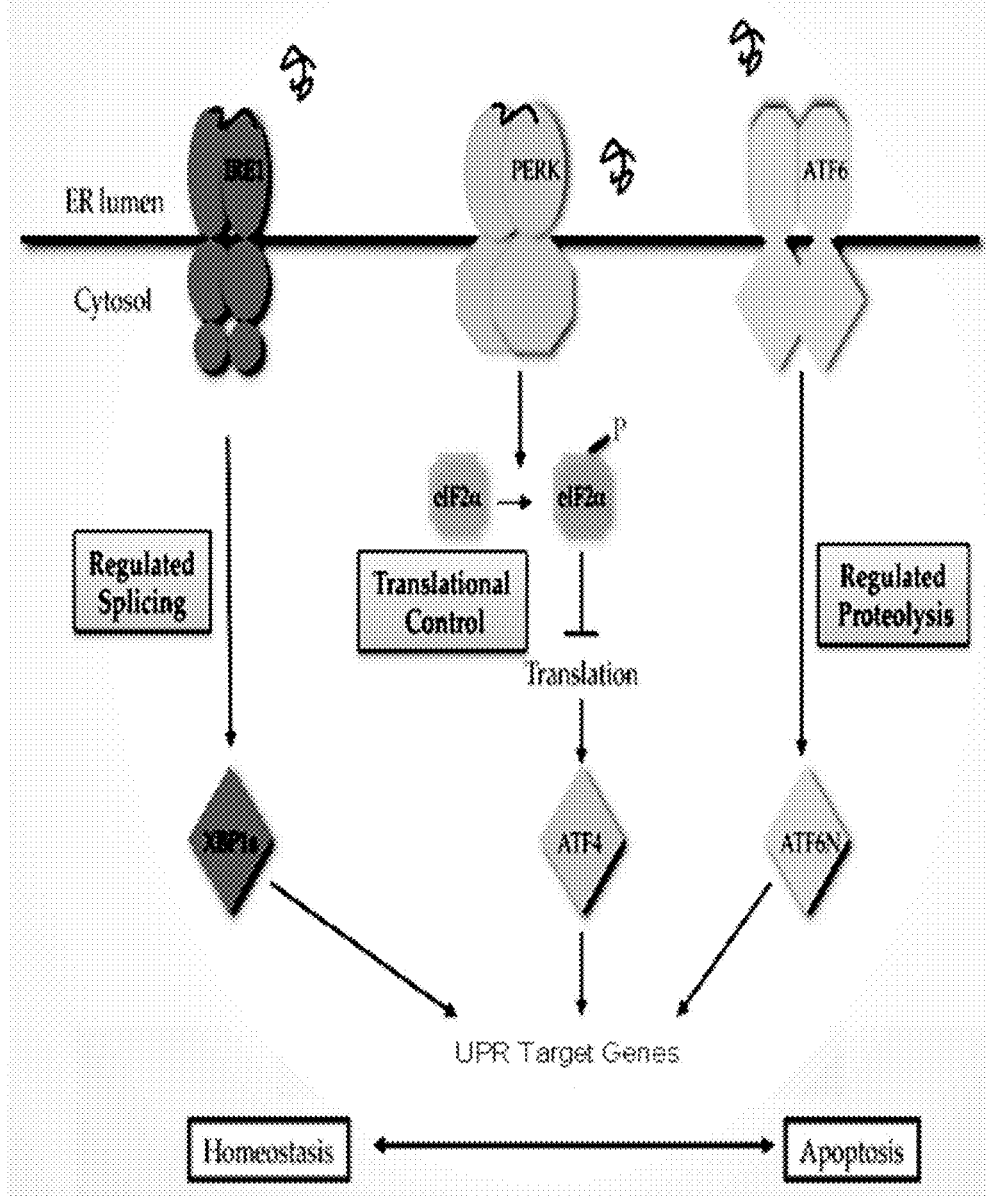
FIG. 10. Overview of unfolded protein response.
Figure 11:
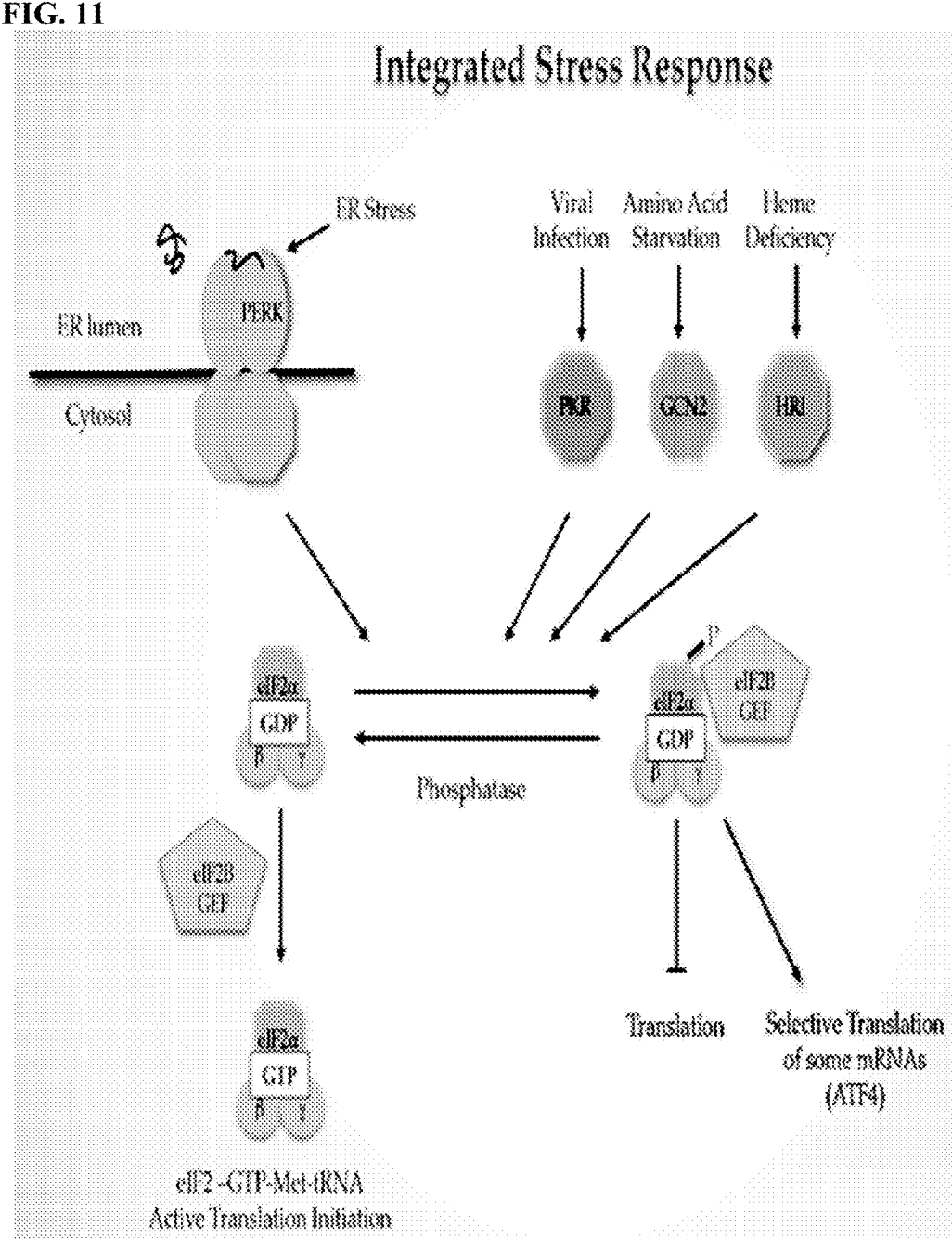
FIG. 11. Overview of integrated stress response.
Figure 12:
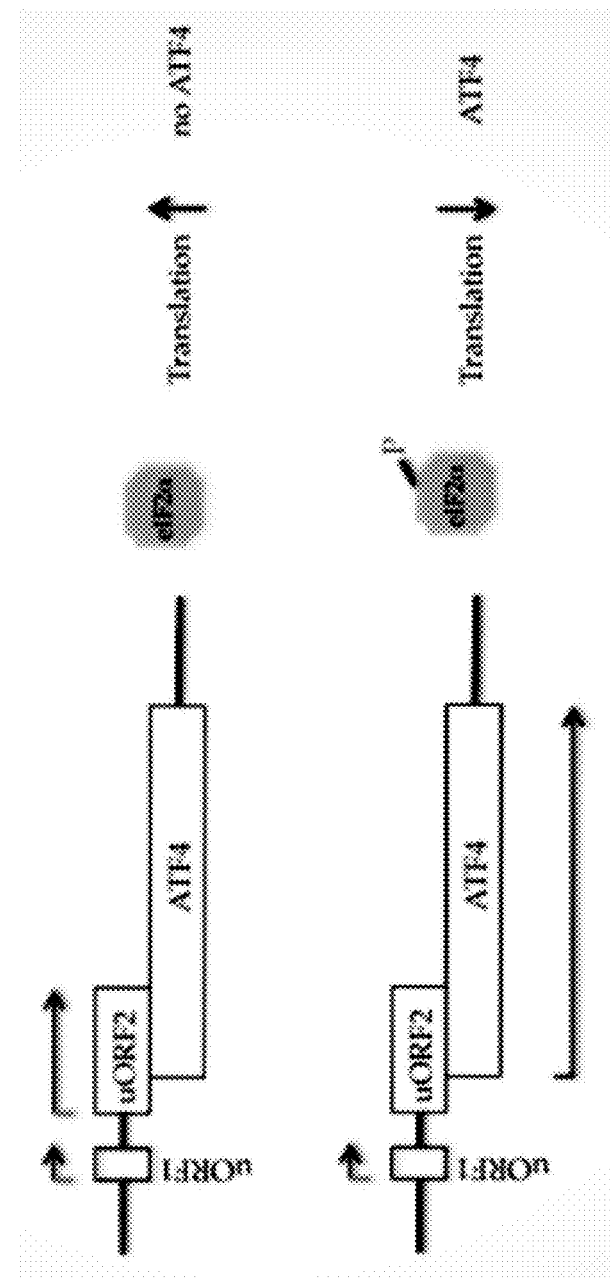
FIG. 12. Overview of regulation of ATF4 translation.
Figure 13:
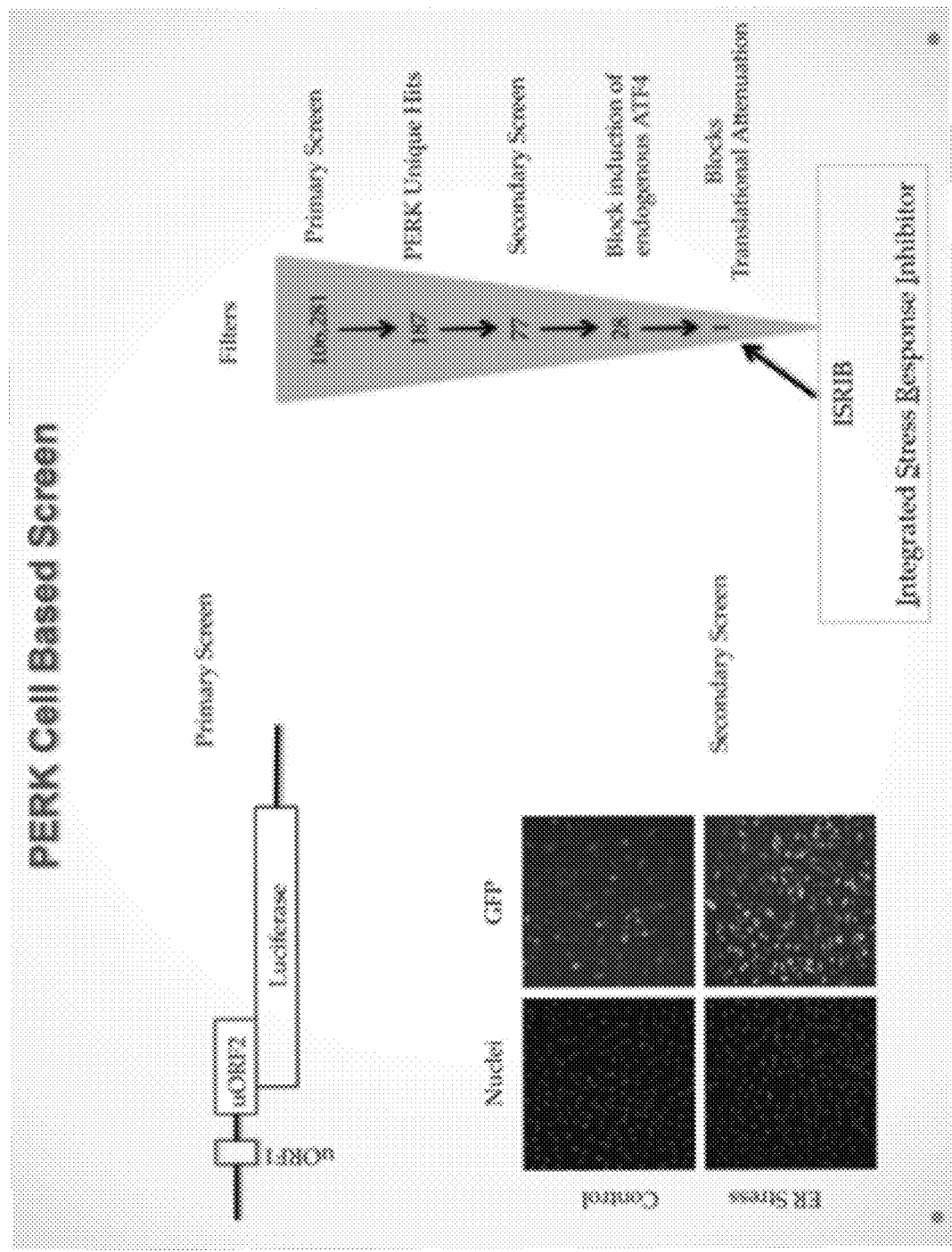
FIG. 13. Overview of PERK cell based screen.
Figure 14:
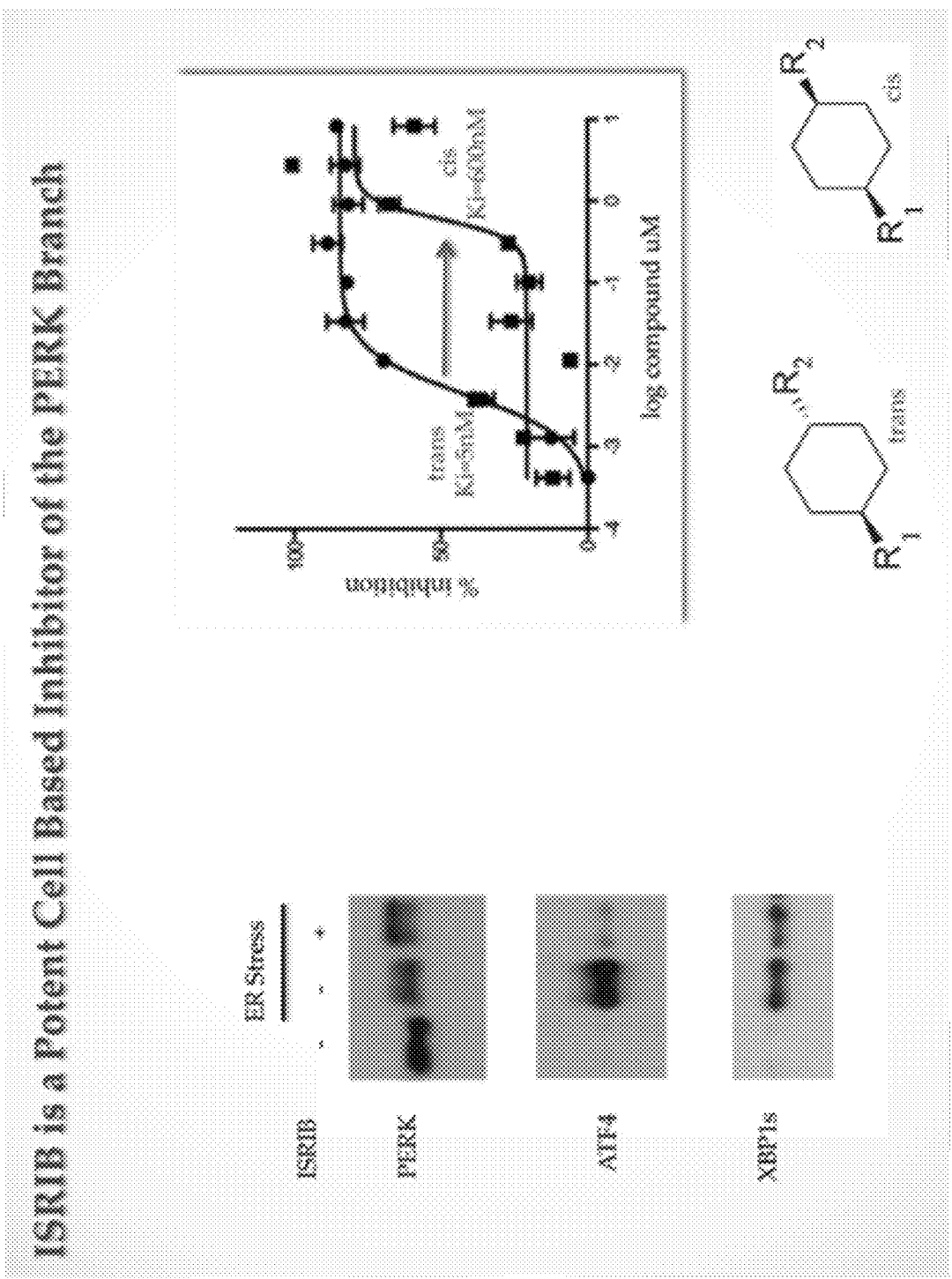
FIG. 14. ISRIB as a potent cell based inhibitor of the PERK branch.
Figure 15:
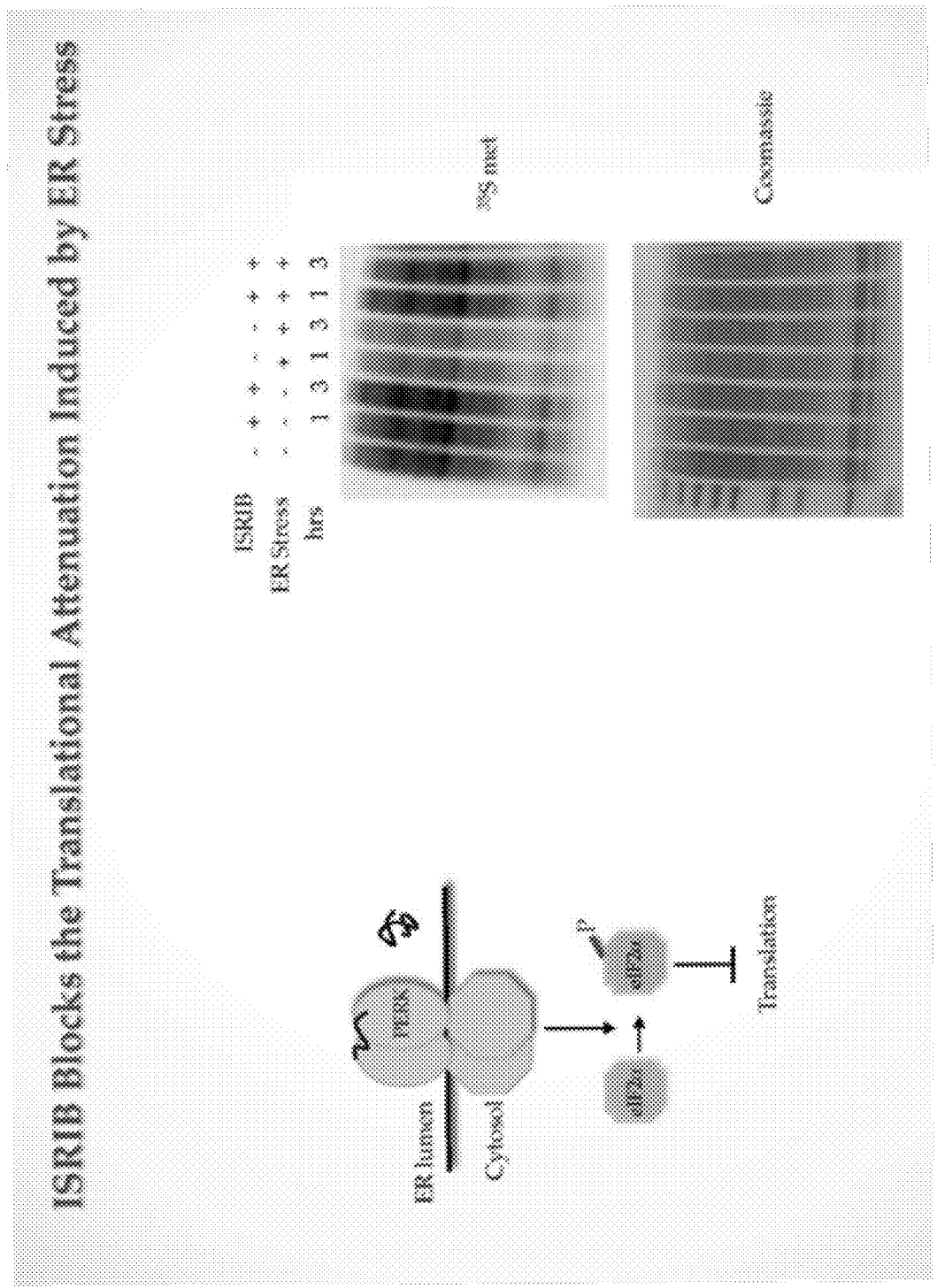
FIG. 15. ISRIB blocks the translational attenuation induced by ER stress.
Figure 16:
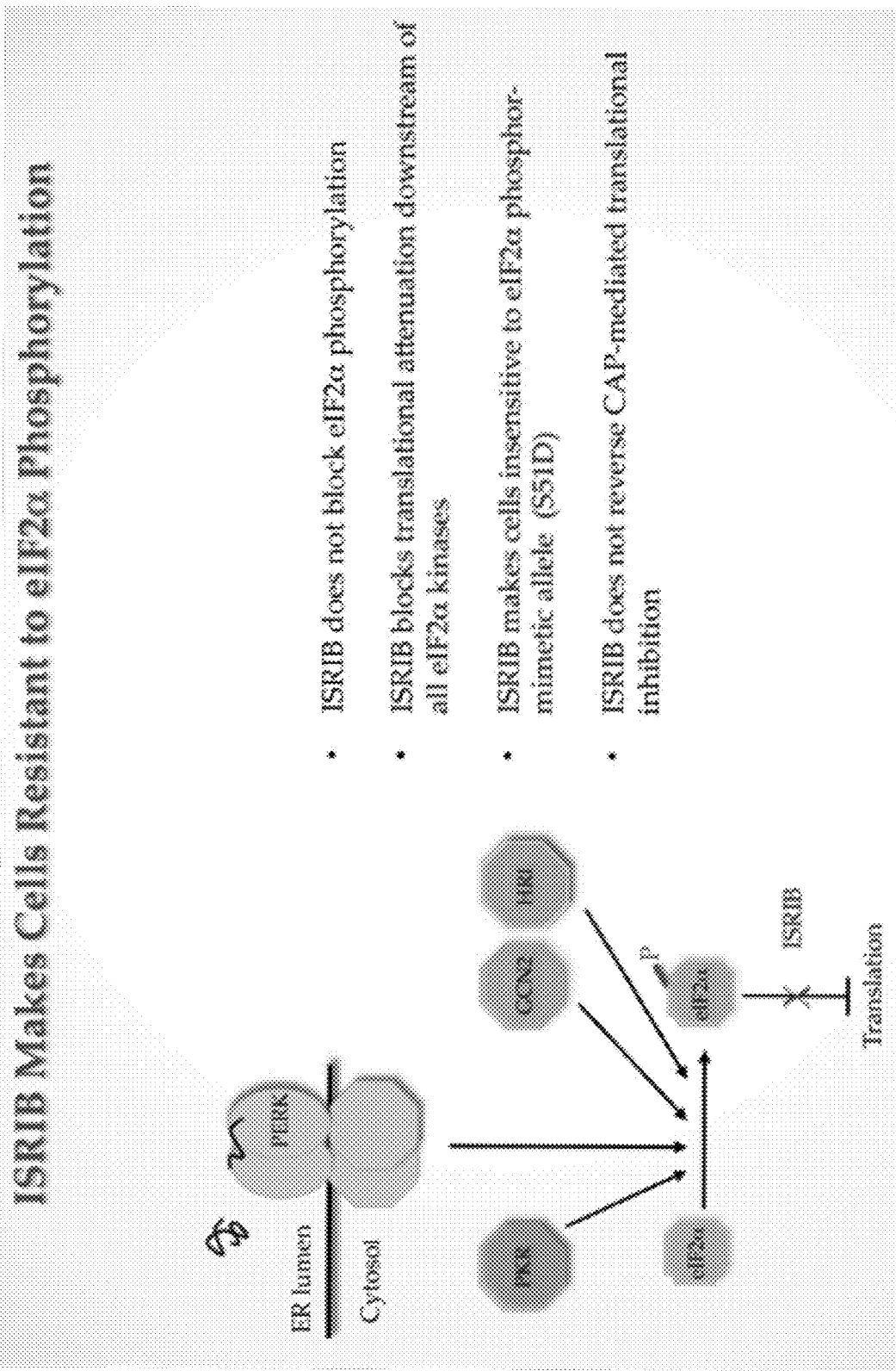
FIG. 16. ISRIB makes cells resistant to eIF2α phosphorylation.
Figure 17:
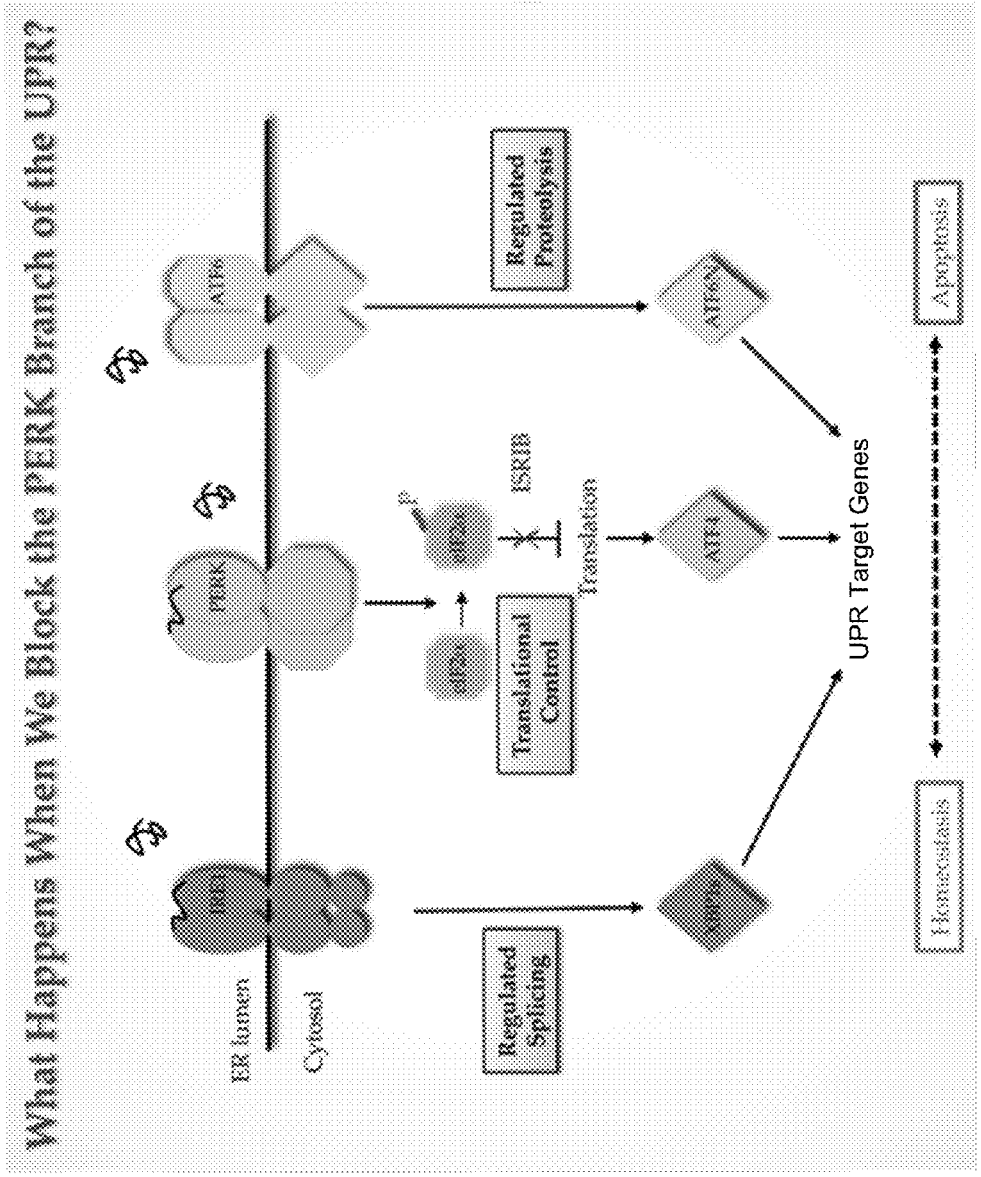
FIG. 17. ISRIB blocks the PERK branch of the UPR.
Figure 18:
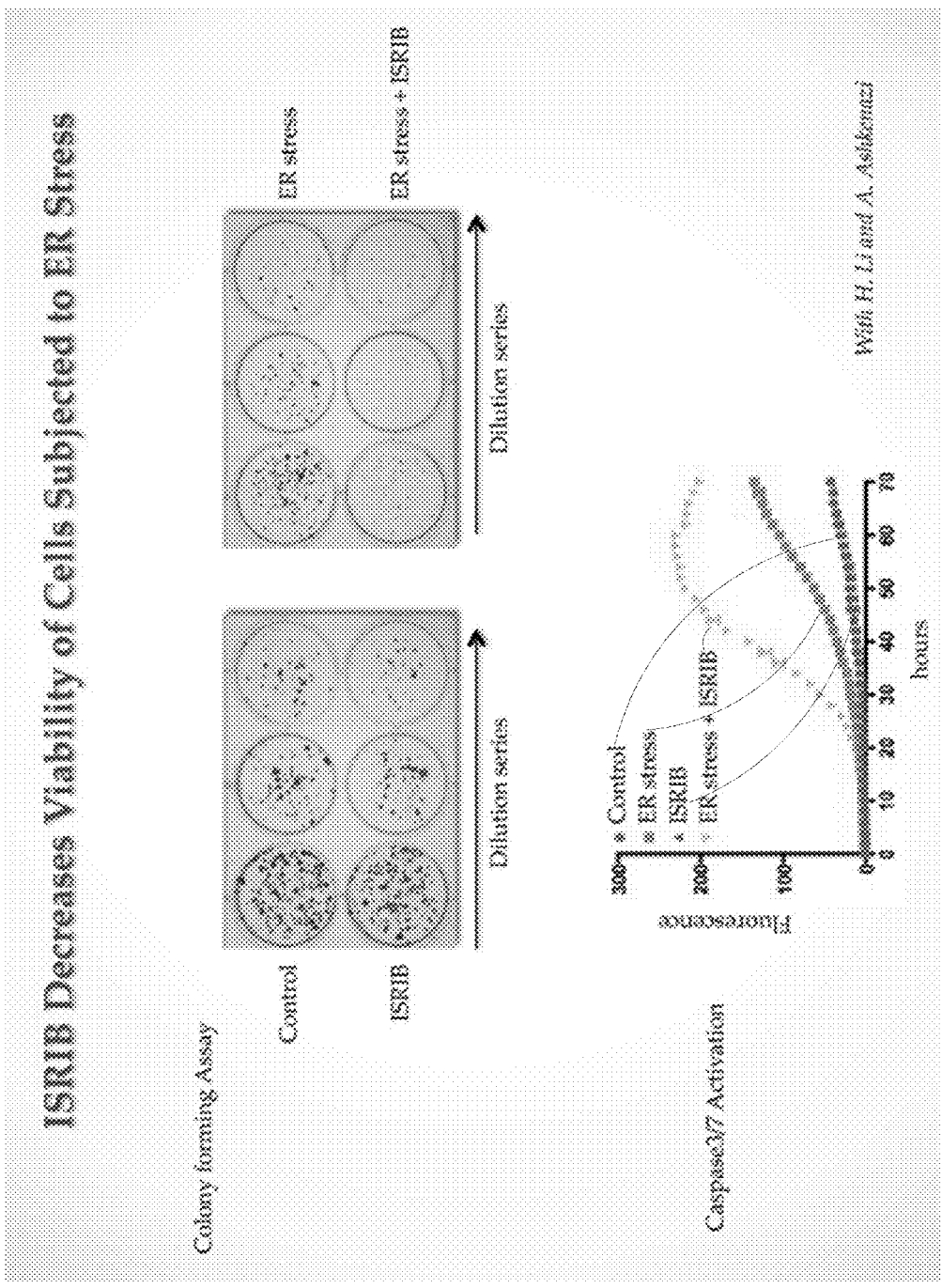
FIG. 18. ISRIB decreases viability of cells subjected to ER stress.
Figure 19:
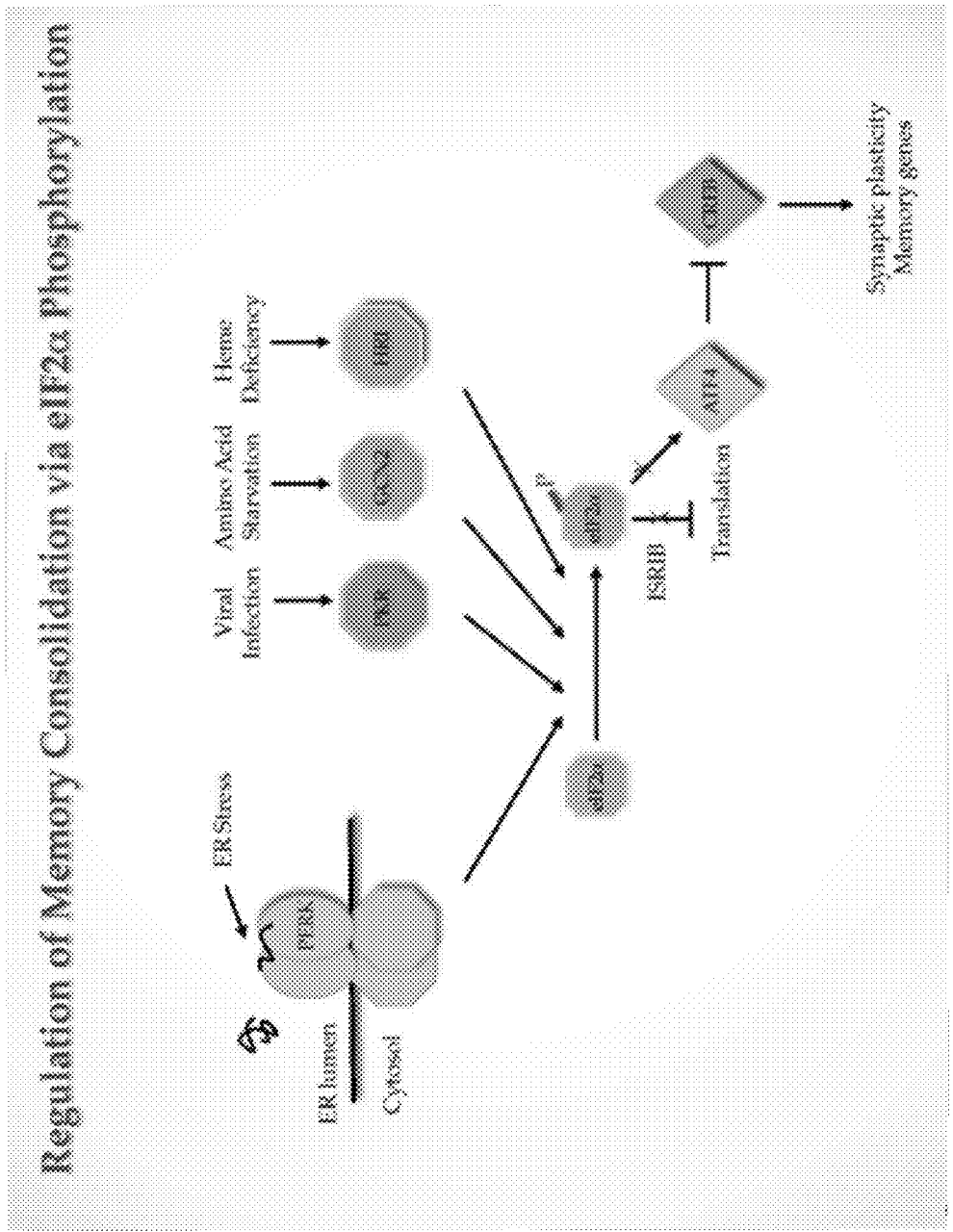
FIG. 19. Regulation of memory consolidation via eIF2α phosphorylation.
Figure 20:
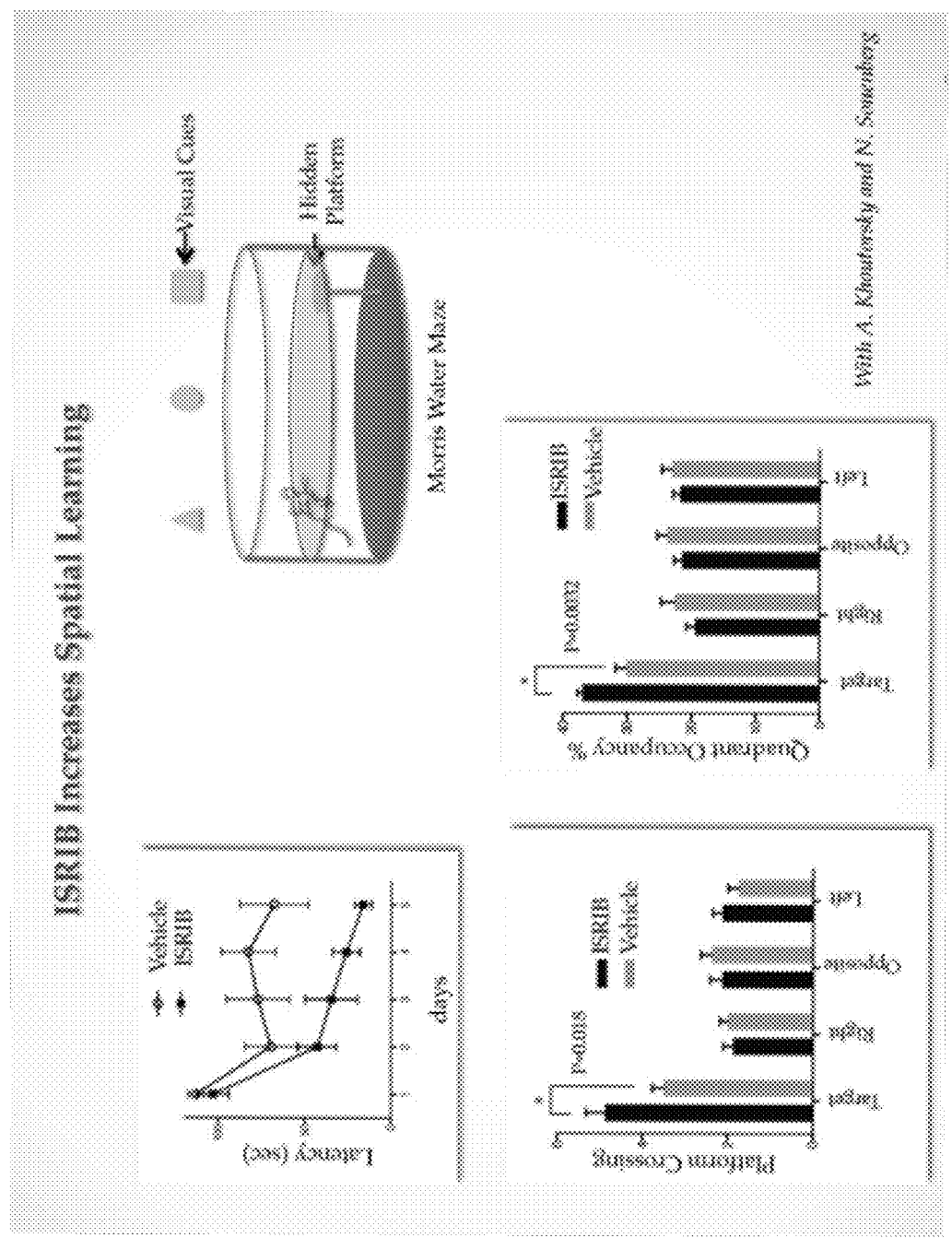
FIG. 20. ISRIB increases spatial learning.
Figure 21:
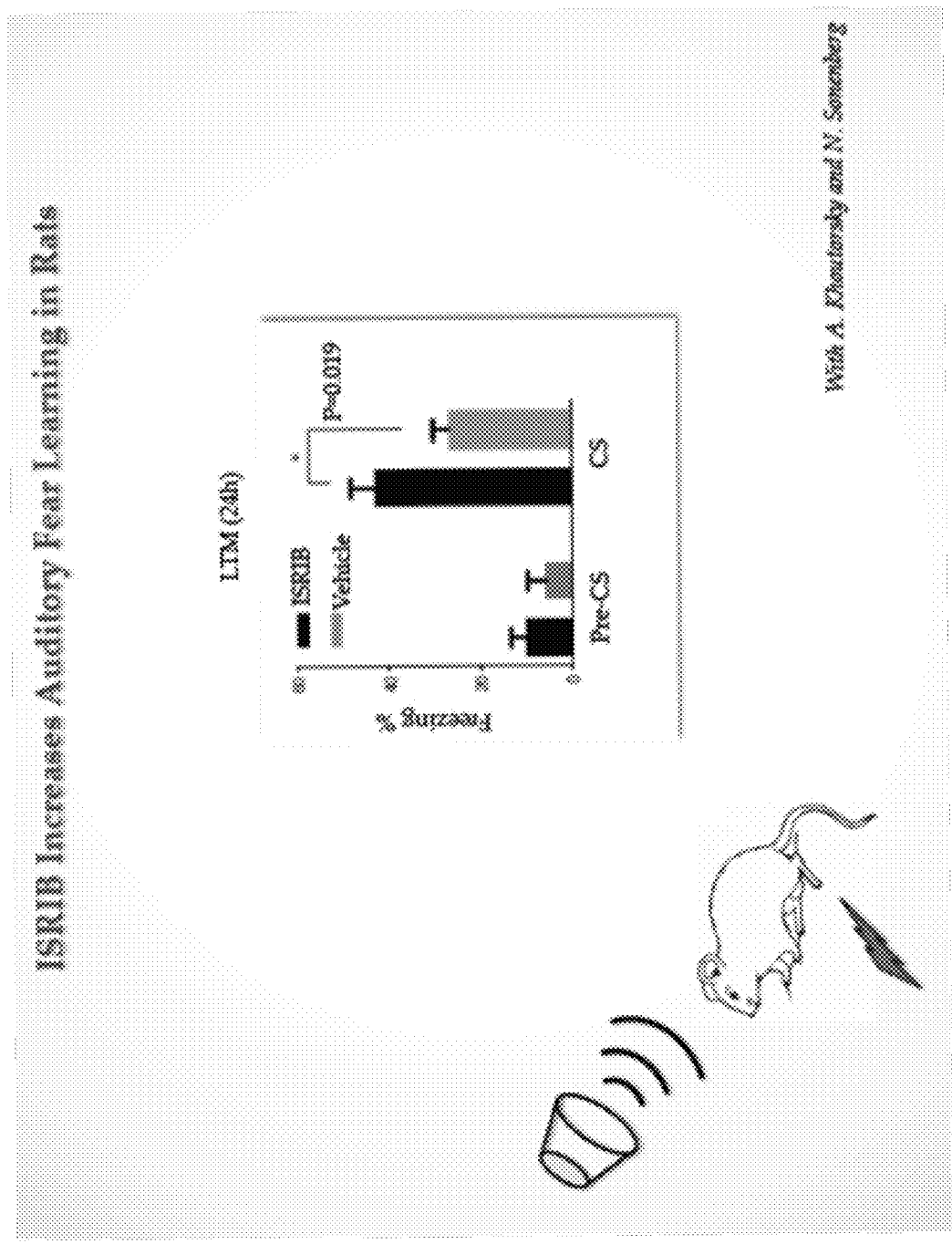
FIG. 21. ISRIB increases auditory fear learning in rats.

To test learning associated with a different region of the brain, we explored the effects of ISRIB on auditory fear conditioning, which depends on the amygdala. In this type of learning a tone (CS) is paired with a foot shock (US). In these experiments, we injected ISRIB or vehicle directly into the amygdala of rats via cannulation. ISRIB-treated rats showed a significant increase over vehicle-injected rats in the level of freezing when presented with the tone (CS) at 24 h (long-term memory, $p<0.05$; FIG. 6E). By contrast, we observed no difference between ISRIB- and vehicle-treated rats at 3 h (short-term memory). As expected, both ISRIB- and vehicle-treated rats showed similar freezing responses prior to training (pre-CS). Taken together, these data suggest that long-term memory is selectively enhanced in ISRIB-treated animals.

ISRIB and brain function. The importance of eIF2/eIF2B function in the human brain is underscored by familial diseases caused by mutations in these factors. One example is Childhood Ataxia with CNS Hypomyelination (CACH), also known as Vanishing White Matter disease (VWM), which has been mapped to mutations in different subunits of eIF2B (32). A second example links a familial intellectual disability syndrome to a mutation in the γ-subunit of eIF2 complex (33).

Several lines of genetic evidence in mice suggest that phosphorylation-dependent regulation of eIF2α phosphorylation is a critical hub for the control of synaptic plasticity (as assessed by late long-term potentiation (L-LTP) in brain slices) and memory consolidation (as assessed in behavioral tasks in animals). In particular, the threshold for induction of L-LTP is reduced and memory consolidation is enhanced in mice lacking GCN2 or PKR and in mice heterozygous for non-phosphorylatable eIF2α(S51A), which have reduced levels of eIF2α phosphorylation (22,34,35). As we show here, ISRIB pharmacologically phenocopies these genetic manipulations in behavioral tasks by rendering cells insensitive to eIF2α phosphorylation. In agreement, treatment of mice with a PKR inhibitor was reported to enhance memory consolidation, and, conversely, treatment with salubrinal, an inhibitor that prolongs eIF2α phosphorylation, to block L-LTP and memory consolidation (22,35).

eIF2α phosphorylation results in a dual effect on gene expression: a global translational diminution and translational upregulation of select mRNA, including ATF4 mRNA. Both may be important to explain the observed effects on L-LTP and memory. It has long been appreciated that new protein synthesis is required for memory consolidation and that ATF4 represses CREB-mediated transcription of "memory genes" (36,37). Indeed, this latter function of ATF4 in memory consolidation is evolutionarily conserved from Aplysia to rodents (38-40). Because a small physiological increase in the level of eIF2α phosphorylation that does not significantly alter overall translation is sufficient to induce ATF4, production of this transcription factor can be finely tuned in neuronal cells by perhaps selective activation of different eIF2α kinases. The observed effects of ISRIB may therefore result from overcoming effects caused by a relatively small level of regulatory phosphorylation that is distinct from the high level resulting from ER stress-inducing agents. In light of this reasoning, a therapeutic window may exist in which ISRIB's effects as memory enhancer can be exploited without encountering long-term toxic consequences.

ISRIB increases memory consolidation, allowing pharmacological enhancement of the brain's ability to learn. Evolution therefore did not arrive at a maximally optimized process, imposing a break (via eIF2α phosphorylation) on memory consolidation. This mechanism may underscore the importance of filtering memories before committing them to long-term storage. Indeed, eIF2α phosphorylation also plays a role in dynamic restructuring of memory, as indicated by studies showing that ablation of PERK in the brain impairs behavioral flexibility (41). Our findings raise the possibility that ISRIB or compounds with related activities could serve as invaluable tools in deciphering these higher order brain functions and perhaps be beneficial as a therapeutic agent effecting memory improvement in diseases associated with memory impairment.

D. Synthesis of ISRIB

General Methods

Commercially-available reagents and solvents were used as received. Silica gel chromatography was performed using a Biotage Isolera Four flash purification system with Silicycle SiliaSep™ cartridges. $^1$H NMR spectra were recorded on a Varian INOVA-400 400 MHz spectrometer. Chemical shifts are reported in δ units (ppm) relative to residual solvent peak. Coupling constants (J) are reported in hertz (Hz). LCMS analyses were carried out using a Waters 2795 separations module equipped with a Waters 2996 photodiode array detector, a Waters 2424 ELS detector, a Waters micromass ZQ single quadropole mass detector, and an XBridge C18 column (5 μm, 4.6×50 mm).

Synthesis of Bisglycolamides

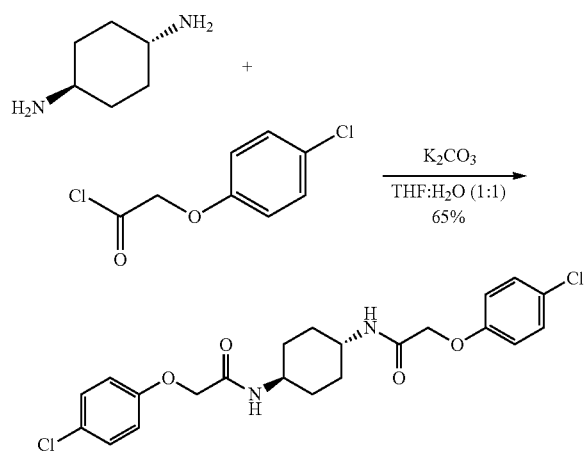

trans-ISRIB: 2-(4-Chlorophenoxy)-N-[(1r, 4r)-4-[2-(4-chlorophenoxy)acetamido]cyclohexyl]acetamide To a mixture of (1r,4r)-cyclohexane-1,4-diamine (20 mg, 0.18 mmol) in tetrahydrofuran:water (1:1, 1 ml) were sequentially added potassium carbonate (73 mg, 0.53 mmol) and 4-chlorophenoxyacetyl chloride (56 μl, 0.36 mmol). Upon addition of the acid chloride, a white solid immediately formed. The reaction mixture was vigorously stirred at ambient temperature for 30 min. Water (2.5 ml) was added. The mixture was vigorously vortexed then centrifuged, and the water was decanted. This washing protocol was repeated with potassium bisulfate (1% aq, 2.5 ml), water (2.5 ml), and diethyl ether (2×2.5 ml). The resulting wet white solid was dried by partially dissolving in dichloromethane/methanol (10/1, 10 ml) and gravity filtering through an Autochem 4.5 mL reaction tube. The residual undissolved product was extracted from the wet filter cake by adding dichloromethane (4×4.5 ml) and gravity filtering. The combined filtrate was concentrated using rotary evaporation to afford 51 mg (65%) of the title compound as a white solid. $^1$H NMR (400 MHz, DMSO-d$_6$) δ 7.91 (d, J=8.1 Hz, 2H), 7.31 (d, J=9.0 Hz, 4H), 6.94 (d, J=9.0 Hz, 4H), 4.42 (s, 4H), 3.55 (br. s., 2H), 1.73 (br. d, J=5.9 Hz, 4H), 1.30 (quin, J=10.5 Hz, 4H); LC-MS: m/z=451 [M+H, $^{35}$Cl×2]+, 453 [M+H, $^{35}$Cl, $^{37}$Cl]$^+$.

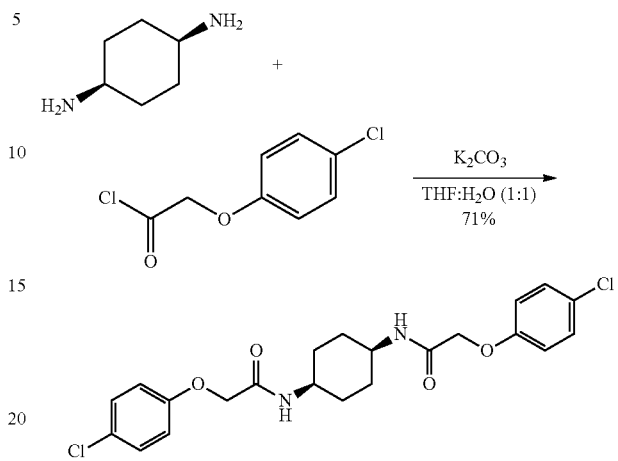

cis-ISRIB: 2-(4-chlorophenoxy)-N-[(1s, 4s)-4-[2-(4-chlorophenoxy)acetamido]cyclohexyl]acetamide To a mixture of (1s,4s)-cyclohexane-1,4-diamine (21 μl, 20 mg, 0.18 mmol) in tetrahydrofuran:water (1:1, 1 ml) were sequentially added potassium carbonate (73 mg, 0.53 mmol) and 4-chlorophenoxyacetyl chloride (56 μL, 0.36 mmol). The reaction mixture was vigorously stirred at ambient temperature for 1.5 h then partitioned between 30 mL of 1:1 dichloromethane:KHSO$_4$ (10% aq.). After separating the organic layer, it was sequentially washed with water (1×10 ml) and brine (1×10 ml) then dried by gravity filtration using an Autochem 4.5 mL reaction tube. The filtrate was concentrated and loaded onto a Silicycle 4 g SiO$_2$ column using a minimal amount of dichloromethane (~2 ml). The product was eluted with acetone in dichloromethane (0%-50%). Product-containing fractions were combined and concentrated to afford 56 mg (71%) of the title compound as a white solid. $^1$H NMR (400 MHz, DMSO-d$_6$) δ 7.76 (d, J=7.0 Hz, 2H), 7.32 (d, J=9.0 Hz, 4H), 6.94 (d, J=9.0 Hz, 4H), 4.47 (s, 4H), 3.70 (br. s., 2H), 1.44-1.67 (m, 8H); LC-MS: m/z=451 [M+H, $_{35}$Cl×2]$_+$, 453 [M+H, $^{35}$Cl, $^{37}$Cl]$^+$.

E. Increasing Protein Expression

Figure 23A:
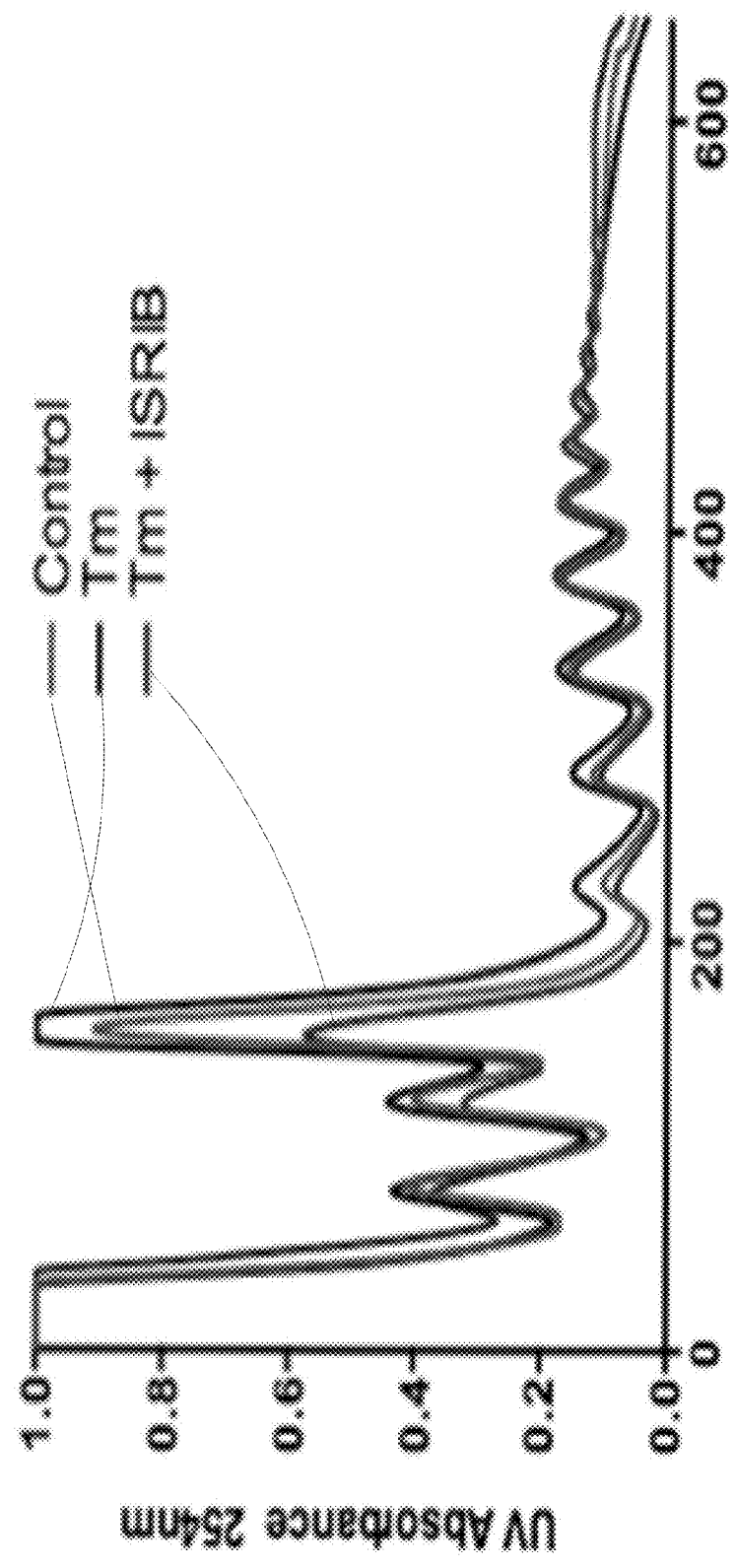
FIGS. 23A-23B. ISRIB enhances translation in both ER-stressed (FIG. 23A) and unstressed (FIG. 23B) RPMI8226 cells; polysome gradient analysis of RPMI cells in the presence or absence of 5 µg/ml of tunicamycin with or without 1 µM ISRIB; cell lysates were fractionated on a sucrose gradient; addition of ISRIB leads to a decrease in the 80S peak and increase in the polysome population.
Figure 23B:
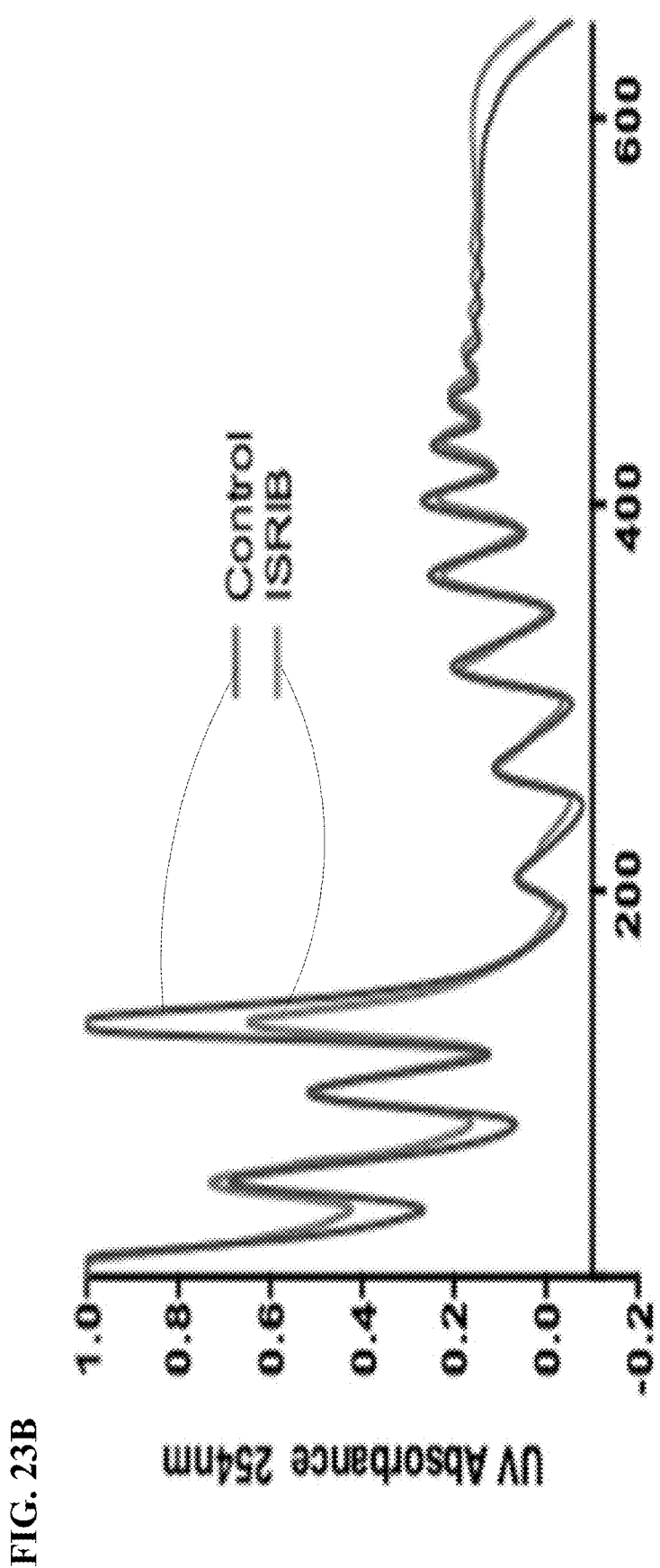
Figure 24:
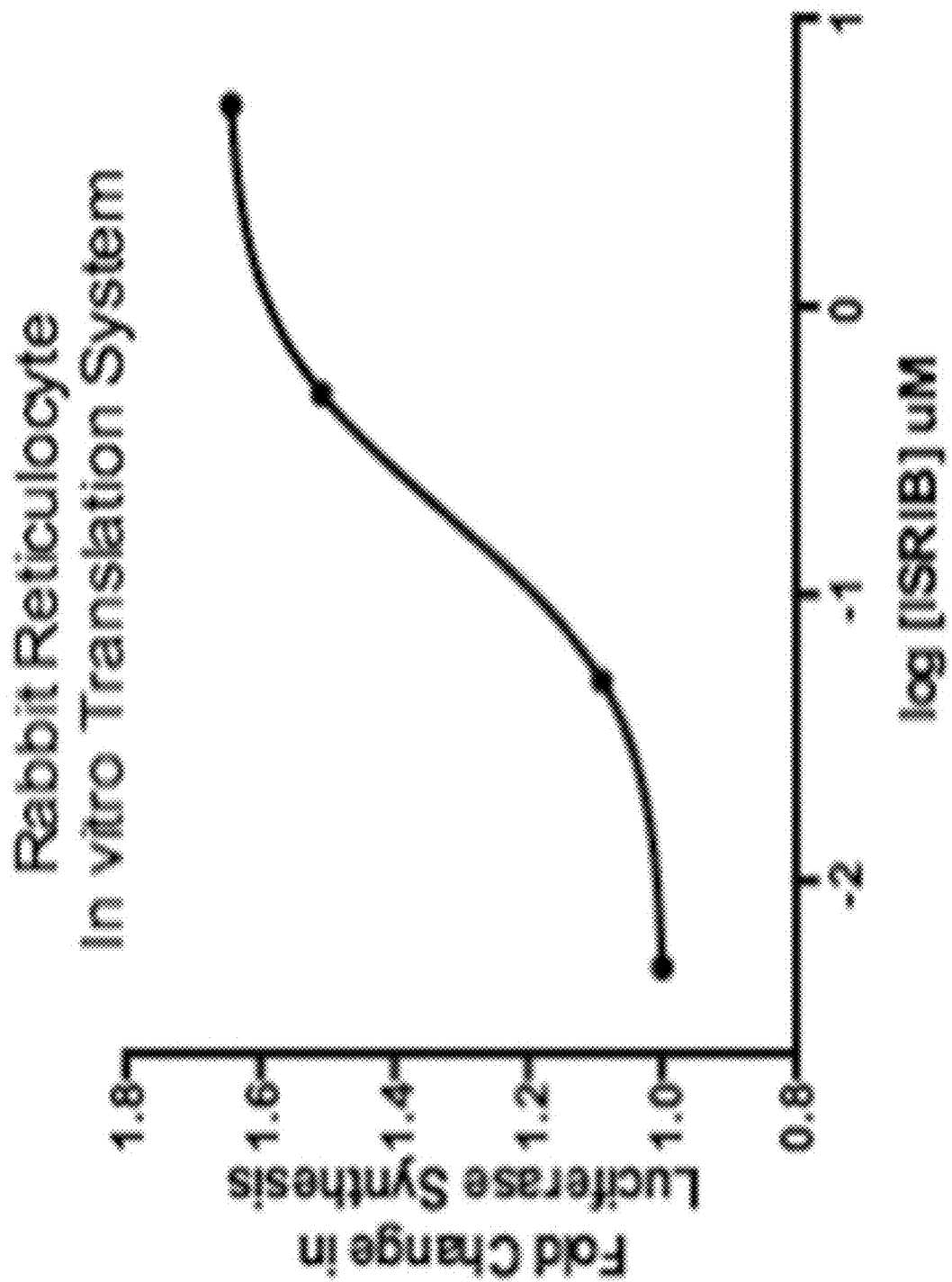
FIG. 24. ISRIB enhances production of luciferase in a rabbit reticulocyte in vitro translation assay; luciferase mRNA was added to the lysates in the presence or absence of different concentrations of ISRIB; the amount of luciferase protein produced was quantitated by addition of One-Glo and the Relative luminescent units were normalized to no-addition control.
Figure 25:
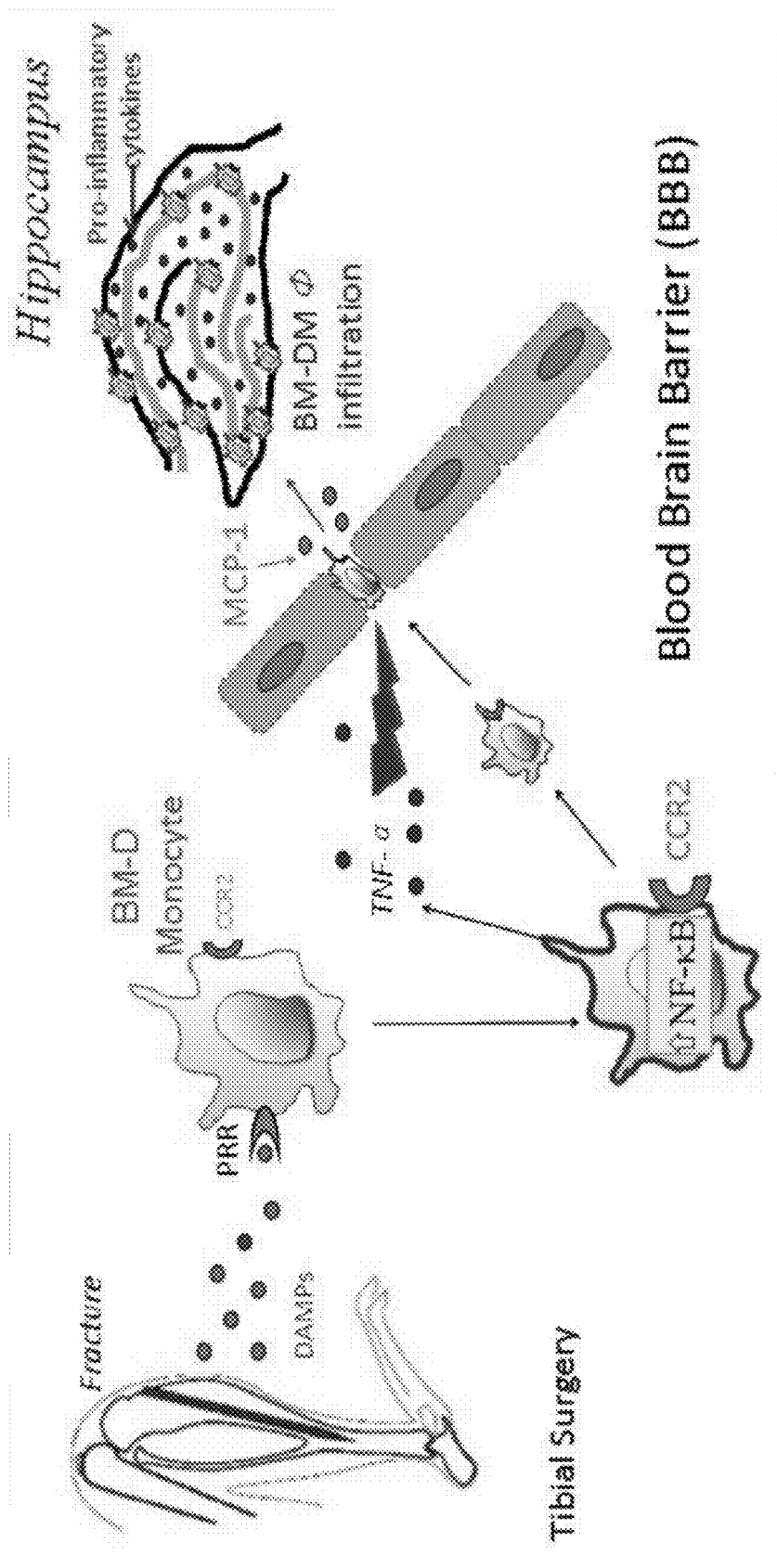
FIG. 25. Inflammation and proposed mechanism for postsurgical cognitive dysfunction.
Figure 26:
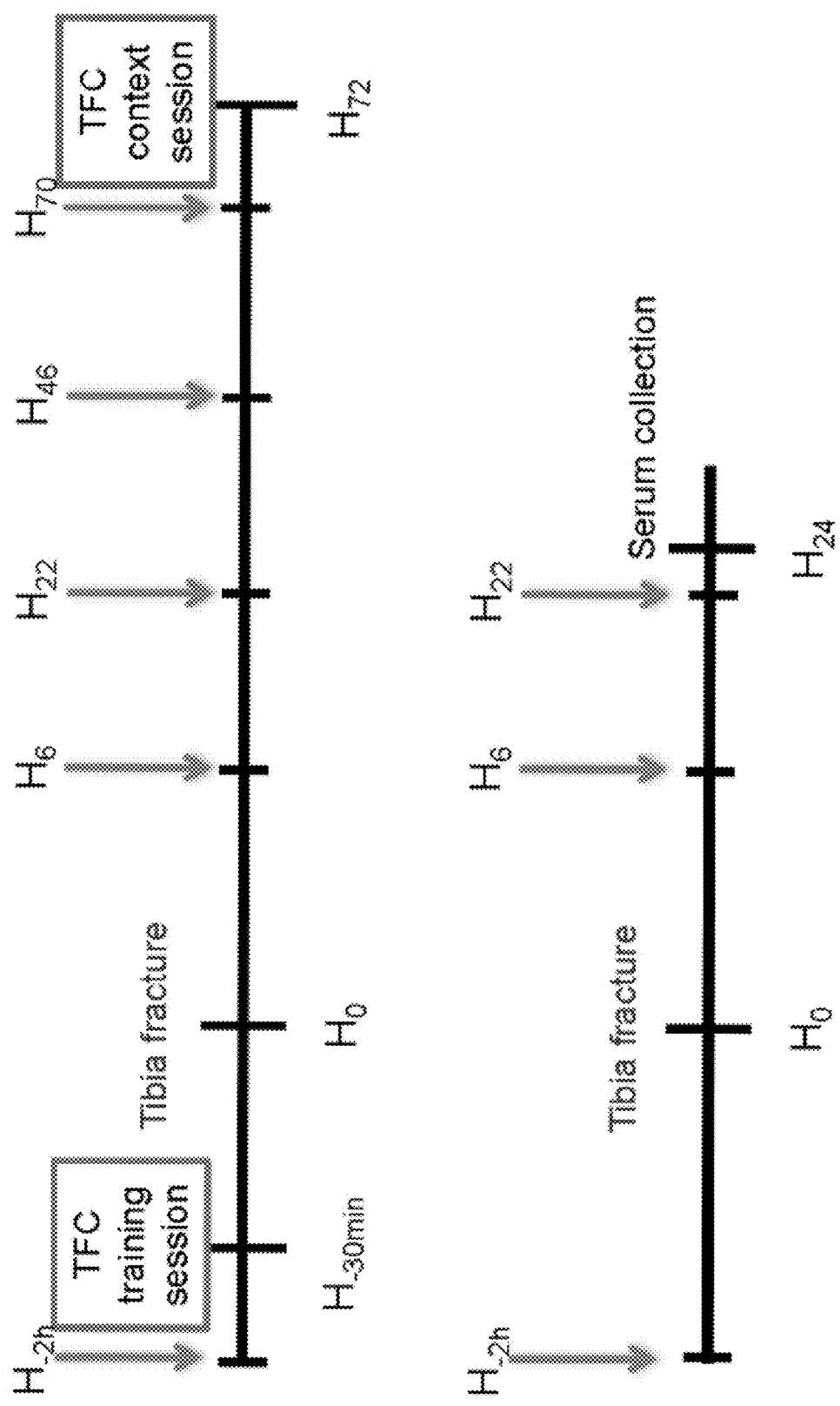
FIG. 26. Experimental design for measuring postsurgical cognitive dysfunction and effects of ISRIB on cognitive function; measurement of memory is a behavioral test using trace fear conditioning (TFC), which aims to establish a permanent memory in animals by using sensorial information; associative learning is presented with a neutral conditioning stimulus, paired with an aversive unconditioning stimulus (e.g. shock); freezing by the animal corresponds to the ability of the animal to retain memory from the context in which it has been trained. Separate cohorts of animals were used to assess inflammatory status 24 h after surgery. Downwards arrows represent injection points.
Figure 27:
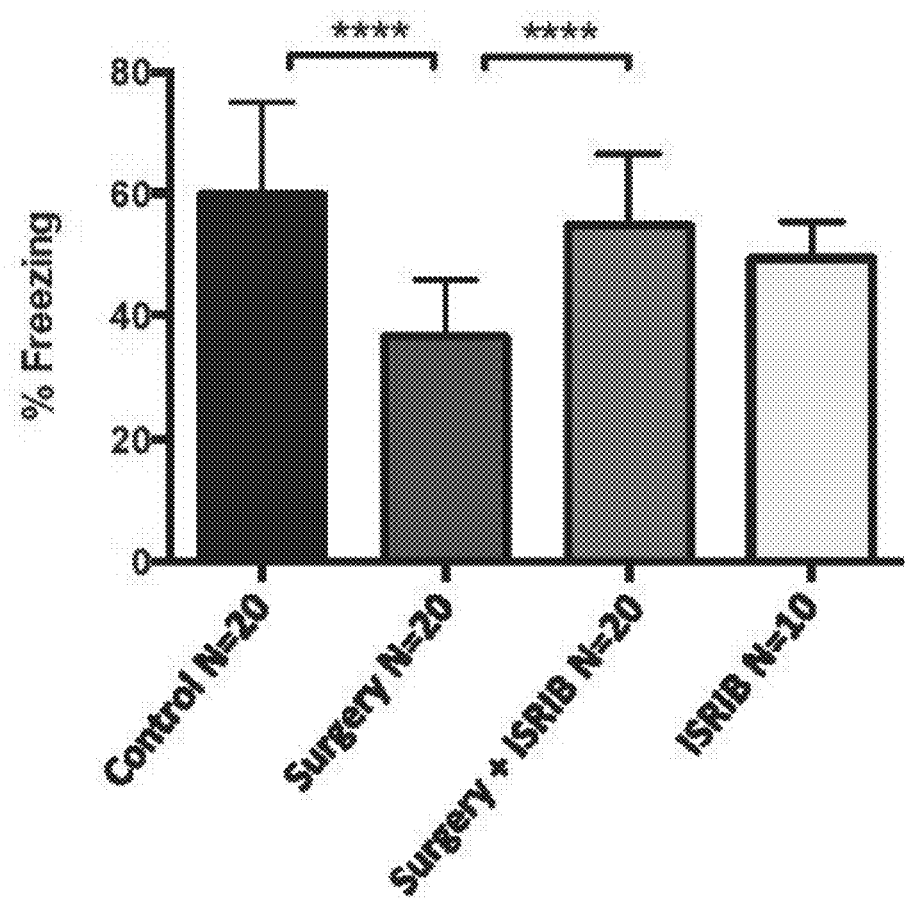
FIG. 27. Trace fear conditioning: hippocampal-dependent memory test; postsurgical cognitive dysfunction measured in animal model and measurement of effects of ISRIB on cognitive function; mice subjected to surgery exhibited reduced freezing when compared to control mice at postoperative day three; perioperative administration of ISRIB mitigated memory impairment after surgery. Control animals were given vehicle solution.
Figure 28:
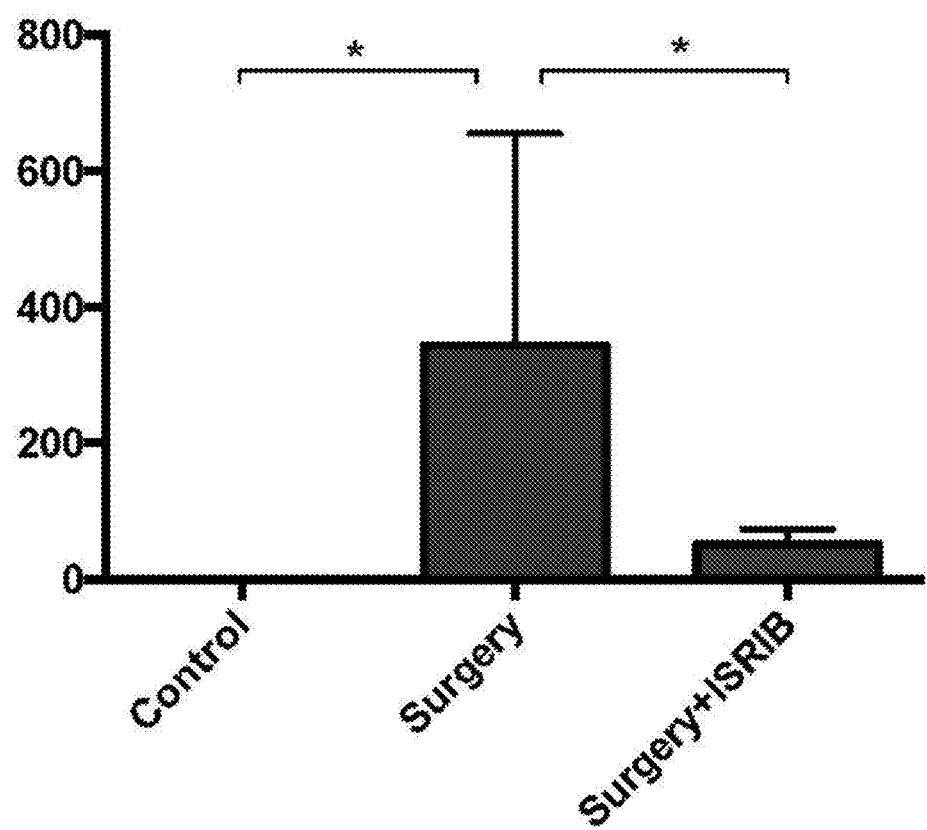
FIG. 28. Inflammation measurements based on IL-6 serum levels as an inflammation marker; measuring the effects of ISRIB on systemic inflammation; mice subjected to surgery exhibited an increase in serum IL-6 24 h after surgery when compared to control mice; perioperative administration of ISRIB abrogated the increase in IL6. Levels were measured using an enzyme-linked immunosorbent kit.

Compounds described herein (e.g. ISRIB) can be used to increase protein production (e.g. antibodies) in cell systems such as antibody-producing cells or hybridomas by increasing overall protein translation. ISRIB can also be used to increase recombinant protein production in cell-free systems (rabbit reticulocyte or Hela in vitro translation system). ISRIB blocks the effects of eIF2α phosphorylation on translation initiation and thus enhances overall translation in cells where this phosphorylation event normally imposes a brake. We showed that in multiple myeloma cells, which produce and secrete antibodies, addition of ISRIB leads to increased translation both in ER-stressed and un-stressed cells (FIGS. 23A and 23B, respectively). By increasing overall translation, addition of ISRIB may allow for increased antibody production. ISRIB enhances translation of an exogenously added mRNA in a rabbit-reticulocyte in vitro translation system (FIG. 24).

TABLE 2

| SMDC ID | IC50 (nM) Cell-luc | Smiles |
|---|---|---|
| 751591 | 250 | O=C(N[C@@H]1CC[C@@H](NC(COC2=CC=C(OC)C=C2)=O)CC1)COC3=CC=C(Cl)C=C3 |
| 751592 | >10000 | O=C(N[C@@H]1CC[C@@H](NC(COC2=CC=C(OCC3=CC=CC=C3)C=C2)=O)CC1)COC4=CC=C(Cl)C=C4 |
| 751593 | 384 | O=C(COC1=CC=C(C=C1)Cl)N[C@@H]2CC[C@H](CC2)NC(COC3=CC=CC=C3)=O |
| 751594 | 69 | O=C(N[C@@H]1CC[C@@H](NC(COC2=CC=C(Cl)C=C(Cl)C=C2)=O)CC1)COC3=CC=C(Cl)C=C3 |
| 751595 | >10000 | O=C(N[C@@H]1CC[C@@H](NC(CC2=CC=C(C)C=C2)=O)CC1)COC3=CC=C(Cl)C=C3 |
| 751596 | >10000 | O=C(N[C@@H]1CC[C@@H](NC(C2=CC=C(Cl)C=C2)=O)CC1)COC3=CC=C(Cl)C=C3 |
| 751597 | >10000 | O=C(N[C@@H]1CC[C@@H](NC(COC2=CC=C(O)C=C2)=O)CC1)COC3=CC=C(Cl)C=C3 |
| 754123 | >10000 | COc1ccc(OCC(=O)N[C@@H]2CC[C@H](CC2)NC(=O)COc3ccc(Cl)cc3)cc1 |
| 754124 | >10000 | Clc1ccc(OCC(=O)N[C@@H]2CC[C@H](CC2)NC(=O)COc3ccc(Cl)cc3Cl)cc1 |
| 754128 | 95 | Cc1ccc(OCC(=O)N[C@@H]2CC[C@H](CC2)NC(=O)COc3ccc(Cl)cc3)cc1 |
| 754125 | >10000 | Clc1ccc(CCC(=O)N[C@@H]2CC[C@H](CC2)NC(=O)CCc3ccc(Cl)cc3)cc1 |
| 754127 | 13 | FC(F)(F)c1ccc(OCC(=O)N[C@@H]2CC[C@H](CC2)NC(=O)COc3ccc(cc3)C(F)(F)F)cc1 |
| 754126 | 327 | Cc1ccc(OCC(=O)N[C@@H]2CC[C@H](CC2)NC(=O)COc3ccc(C)cc3)cc1 |
| 755854.1 | 2700 | Clc1ccc(OCC(=O)N[C@@H]2CC[C@H](CC2)N(CC#C)C(=O)COc3ccc(Cl)cc3)cc1 |
| 755854.4 | 64 | Clc1ccc(OCC(=O)N[C@@H]2CC[C@H](CC2)N(CC#C)C(=O)COc3ccc(Cl)cc3)cc1 |
| 755854.2 | 440 | Clc1ccc(OCC(=O)N[C@@H]2CC[C@H](CC2)N(CC#C)C(=O)COc3ccc(Cl)cc3)cc1 |
| 755855 | 142 | Clc1ccc(OCC(=O)N[C@@H]2CC[C@@H](C2)NC(=O)COc3ccc(Cl)cc3)cc1 |
| 755856 | 1000 | Clc1ccc(OCC(=O)N[C@@H]2CC[C@@H](C2)NC(=O)COc3ccc(Cl)cc3)cc1 |
| 757095 | >10000 | O=C(COc1ccc(cc1)C#N)N[C@@H]2CC[C@H](CC2)NC(=O)COc3ccc(cc3)C#N |
| 757096 | >10000 | CS(=O)c1ccc(OCC(=O)N[C@@H]2CC[C@H](CC2)NC(=O)COc3ccc(cc3)S(=O)C)cc1 |
| 757131 | 270 | Fc1ccc(OCC(=O)N[C@@H]2CC[C@H](CC2)NC(=O)COc3ccc(F)cc3)cc1 |
| 757130 | >10000 | [O-][N+](=O)c1ccc(OCC(=O)N[C@@H]2CC[C@H](CC2)NC(=O)COc3ccc(cc3)[N+](=O)[O-])cc1 |
| 757132 | 3000 | Clc1ccc(OCC(N[C@H]2CC[C@](NC(COc3ccc(Cl)cc3)=O)(C#C)CC2)=O)cc1 |
| 755854.3 | 100 | Clc1ccc(OCC(=O)N[C@@H]2CC[C@H](CC2)N(CC#C)C(=O)COc3ccc(Cl)cc3)cc1 |
| 750213.2 | 3 | Clc1ccc(OCC(=O)N[C@@H]2CC[C@H](CC2)NC(=O)COc3ccc(Cl)cc3)cc1 |
| 835195 | 170 | Clc1ccc(OCCN[C@@H]2CC[C@H](CC2)NC(=O)COc3ccc(Cl)cc3)cc1 |
| 835196 | 1400 | Clc1ccc(OCCN(CCOc2ccc(Cl)cc2)[C@@H]3CC[C@H](CC3)NC(=O)COc4ccc(Cl)cc4)cc1 |
| 835197 | >10000 | Clc1ccc(OCC(=N)N[C@@H]2CC[C@H](CC2)N(Cc3cn(CCOCCOCCOCCNC(=O)CCCC[C@@H]4SCC5NC(=O)NC45)nn3)C(=O)COc6ccc(Cl)cc6)cc1 |
| 757257 | 48 | Fc1ccc(OCC(=O)N[C@@H]2CC[C@H](CC2)NC(=O)COc3ccc(Cl)cc3)cc1 |
| 757258 | 10 | FC(F)(F)c1ccc(OCC(=O)N[C@@H]2CC[C@H](CC2)NC(=O)COc3ccc(Cl)cc3)cc1 |
| 757259 | 263 | Clc1ccc(OCC(=O)N[C@@H]2CC[C@H](CC2)NC(=O)COc3ccc(cc3)C#N)cc1 |
| 757260 | >10000 | CS(=O)c1ccc(OCC(=O)N[C@@H]2CC[C@H](CC2)NC(=O)COc3ccc(Cl)cc3)cc1 |
| 757261 | >10000 | Clc1ccc(OCC(=O)N[C@@H]2CC[C@H](CC2)NC(=O)CSc3ccc(Cl)cc3)cc1 |
| 757262 | >10000 | Clc1ccc(OCC(=O)N[C@@H]2CC[C@H](CC2)NC(=O)CS(=O)c3ccc(Cl)cc3)cc1 |
| 757263 | >10000 | Clc1ccc(OCC(=O)N[C@@H]2CC[C@H](CC2)NC(=O)CS(=O)(=O)c3ccc(Cl)cc3)cc1 |
| 757264.1 | 100 | Clc1ccc(OCC(=N)N[C@@H]2CC[C@H](CC2)NC(=O)COc3ccc(Cl)cc3)cc1 |
| 757264.2 | 34 | Clc1ccc(OCC(=N)N[C@@H]2CC[C@H](CC2)NC(=O)COc3ccc(Cl)cc3)cc1 |
| 835087 | 2700 | Clc1ccc(OCC(=O)N[C@@H]2CC[C@](CC2)(NC(=O)COc3ccc(Cl)cc3)c4cn(CCOCCOCCOCCNH(=O)CCCC[C@H]5SCC6NC(=O)NC56)nn4)cc1 |
| 835089 | 700 | Clc1ccc(NCC(=O)N[C@@H]2CC[C@H](CC2)NC(=O)COc3ccc(Cl)cc3)cc1 |
| 757149 | 37 | Clc1ccc(OCC(=O)N[C@@H]2CC[C@H](C2)(CC2)NC(=O)COc3ccc(Cl)cc3)C#C)cc1 |
| 843983 | >10000 | CC(=O)c1ccc(OCC(=O)N[C@@H]2CC[C@H](CC2)NC(=O)COc3ccc(Cl)cc3)cc1 |
| 843984 | 1000 | CC(=O)c1cccc(OCC(=O)N[C@@H]2CC[C@H](CC2)NC(=O)COc3ccc(Cl)cc3)c1 |
| 843987 | 75 | [O-][N+](c1c(OCC(N[C@H]2CC[C@H](NC(COc3ccc(Cl)cc3)=O)CC2)=O)ccc(Cl)c1)=O |
| 811769 | >10000 | Clc1ccc(OCC(=O)N[C@@H]2CC[C@H](CC2)NC(=O)CSc3ccccc3)cc1 |
| 811770 | 900 | Fc1ccc(SCC(=O)N[C@@H]2CC[C@H](CC2)NC(=O)COc3ccc(Cl)cc3)cc1 |
| 811771 | >10000 | Clc1ccc(OCC(=O)N[C@@H]2CC[C@H](C2)(CC2)NC(=O)CSc3ccc(Cl)cc3)cc1 |
| 811772 | >10000 | Fc1ccc(SCC(=O)N[C@@H]2C[C@H](C2)NC(=O)COc3ccc(Cl)cc3)cc1 |
| 811773 | >10000 | Clc1ccc(OCC(=O)N[C@@H]2CC[C@H](C2)NC(=O)CSc3ccccc3)cc1 |
| 873882 | >10000 | Clc1ccc(OCC(=O)NCc2cccc(NC(=O)COc3ccc(Cl)cc3)c2)cc1 |
| 873883 | 2600 | C[C@@H]1NC(=O)N[C@@H]1CCCCCC(=O)NCCOCCOCCOCCn2cc(nn2)[C@@]3(CC[C@@H](CC3)NC(=O)COc4ccc(Cl)cc4)NC(=O)COc5ccc(Cl)cc5 |
| 873972 | >10000 | O=C(COC1=CC=C(Cl)C=C1)N[C@@H]2CC[C@@H](NC(COC3=C(C(C)=O)C=C(Cl)C=C3)=O)CC2 |
| 873973 | >10000 | O=C(COC1=CC=C(Cl)C=C1)N[C@@H]2CC[C@@H](NC(COC3=C(C(C4=CC=CC=C4)=O)C=C(Cl)C=C3)=O)CC2 |
| 757264-L3 | 60 | O=C(COC1=CC=C(Cl)C=C1)N[C@@H]2CC[C@@H](NC(COC3=CC=C(Cl)C=C3)=N)CC2 |
| 874796 | >10000 | O=C(COC1=CC=C(Cl)C=C1)NCC2=CC=C(CNC(COC3=CC=C(Cl)C=C3)=O)C=C2 |
| 874797 | 122 | O=C(COC1=CC=C(Cl)C=C1)N[C@@H]2CC=C(NC(OCC3=CC=C(Cl)C=C3)=O)CC2 |
| 874798 | 200 | O=C(COC1=CC=C(Cl)C=C1)N[C@@H]2CC[C@@H](NC(COC3=CC=C(C(C)C)C=C3)=O)CC2 |
| 874799 | 210 | O=C(COC1=CC=C(Cl)C=C1)N[C@@H]2CC[C@@H](NC(C(C)OC3=CC=C(Cl)C=C3)=O)CC2 |
| 874800 | 2 | O=C(COC1=CC=C(Cl)C=C1)N[C@@H]2CC[C@@H](NC(COC3=CC=C(Cl)C(C)=C3)=O)CC2 |
| 874801 | 2.4 | O=C(COC1=CC=C(Cl)C=C1)N[C@@H]2CC[C@@H](NC(COC3=CC=C(Cl)C(C)=C3)=O)CC2 |
| 874802 | 2 | O=C(COC1=CC=C(Cl)C=C1)N[C@@H]2CC[C@@H](NC(COC3=CC=C(Cl)C(F)=C3)=O)CC2 |
| 874803 | 4 | O=C(COC1=CC=C(Cl)C=C1)N[C@@H]2CC[C@@H](NC(COC3=CC=C(Cl)C(C(F)(F)F)=C3)=O)CC2 |
| 874804 | 3 | O=C(COC1=CC=C(Cl)C=C1)N[C@@H]2CC[C@@H](NC(COC3=CC=C(Cl)C([N+]([O-])=O)=C3)=O)CC2 |
| 874805 | >10000 | ClC(C=CC=C1)=C1CNC[C@H]2CC[C@H](CNCC3=CC=CC=C3Cl)CC2 |
| 885253 | >10000 | O=C(CC1=CC=C(Cl)C=C1)NCC2=CC=C(CNC(CC3=CC=C(Cl)C=C3)=O)C=C2 |
| 885254 | >10000 | O=C(OC1=CC=C(Cl)C=C1)NCC2=CC=C(CNC(OC3=CC=C(Cl)C=C3)=O)C=C2 |
| 885255 | 30 | O=C(OC1=CC=C(Cl)C=C1)N[C@@H]2CC[C@H](NC(COC3=CC=C(Cl)C=C3)=O)CC2 |
| 885256 | 152 | O=C(OC1=CC=C(Cl)C=C1)N[C@@H]2CC[C@H](NC(COC3=CC=C(Cl)C=C3)=O)CC2 |
| 885257 | >10000 | O=C(OCC1=CC=C(Cl)C=C1)N[C@@H](CC2)CC[C@H]2NC(OCC3=CC=C(Cl)C=C3)=O |
| 102509 | 53 | ClC(C=C1)=CC=C1OCC(NC2=CC=C(NC(COC3=CC=C(Cl)C=C3)=O)C=C2)=O |
| 912562 | 125 | Fc1ccccc(OCC(=O)N[C@@H]2CC[C@H](CC2)NC(=O)COc3ccc(Cl)cc3)c1 |
| 912563 | 334 | Fc1cccc(OCC(=O)N[C@@H]2CC[C@H](CC2)NC(=O)COc3ccc(Cl)cc3)c1F |
| 912564 | 220 | Fc1cc(F)cc(OCC(=O)N[C@@H]2CC[C@H](CC2)NC(=O)COc3ccc(Cl)cc3)c1 |

TABLE 2-continued

| | | |
|---|---|---|
| 912565 | >10000 | Clc1ccc(OCC(=O)N[C@@H]2CC[C@H](CC2)NC(=O)COc3cc(Cl)cc(Cl)c3)cc1 |
| 912566 | 149 | CC(=O)c1cc(OCC(=O)N[C@@H]2CC[C@H](CC2)NC(=O)COc3ccc(Cl)cc3)ccc1Cl |
| 913815 | >10000 | Clc1ccc(OC(=O)NC[C@@H]2CC[C@@H](CNC(=O)Oc3ccc(Cl)cc3)CC2)cc1 |
| 914582 | 5.2 | Clc1ccc(OCC(=O)N[C@@H]2CC[C@H](CC2)NC(=O)COc3ccc(Cl)c(I)c3)cc1 |
| 914583 | 12 | C[Si](C)(C)C#Cc1cc(OCC(=O)N[C@@H]2CC[C@H](CC2)NC(=O)COc3ccc(Cl)cc3)ccc1Cl |
| 914584 | 12 | Clc1ccc(OCC(=O)N[C@@H]2CC[C@H](CC2)NC(=O)COc3ccc(Cl)c(c3)C#C)cc1 |
| 914989 | 5.6 | Clc1ccc(OCC(=O)N[C@@H]2CC[C@H](CC2)NC(=O)COc3ccc(I)cc3)cc1 |
| | | Clc1ccc(OCC(N[C@H]2CC[C@@H](NC(COc3ccc(Cl)cc3)=O)CC2)=O)cc1 |
| | | Clc1ccc(OCC(NC2CCC(NC(COc3ccc(Cl)cc3)=O)CC2)=O)cc1 |
| 916348 | 160 | C[Si](C)(C)C#Cc1ccc(OCC(=O)N[C@@H]2CC[C@H](CC2)NC(=O)COc3ccc(Cl)cc3)cc1 |
| 916353 | 14 | Clc1ccc(OCC(=O)N[C@@H]2CC[C@H](CC2)NC(=O)COc3ccc(cc3)C#C)cc1 |
| 916727 | 520 | C[C@@H]1NC(=O)N[C@@H]1CCCCCC(=O)NCCOCCOCCOCCn2cc(nn2)c3ccc(OCC(=O)N[C@@H]4CC[C@H](CC4)NC(=O)COc5ccc(Cl)cc5)cc3 |
| 916728 | 1,270 | C[C@@H]1NC(=O)N[C@@H]1CCCCCC(=O)NCCOCCOCCOCCn2cc(nn2)c3ccc(OCC(=O)N[C@@H]4CC[C@H](CC4)NC(=O)COc5ccc(Cl)cc5)ccc3Cl |
| 916744 | >10000 | FC(F)(F)C1(NN1)c2ccc(OCC(=O)N[C@@H]3CC[C@H](CC3)NC(=O)COc4ccc(I)cc4)cc2 |
| 916751 | >10000 | O=C(COC1=CC=C(C#C)C=C1)N[C@@H]2CC[C@@H](NC(COC3=CC=C(C4(N=N4)C(F)(F)F)C=C3)=O)CC2 |
| 916784 | 51 | Ic1ccc(OCC(=O)N[C@@H]2CC[C@H](CC2)NC(=O)COc3ccc(I)cc3)cc1 |
| 916785 | >10000 | C[Si](C)(C)C#Cc1ccc(OCC(=O)N[C@@H]2CC[C@H](CC2)NC(=O)COc3ccc(cc3)C#C[Si](C)(C)C)cc1 |
| 916786 | 158 | O=C(COc1ccc(cc1)C#C)N[C@@H]2CC[C@H](CC2)NC(=O)COc3ccc(cc3)C#C |
| 955278 | >10000 | O=C(COC1=CC=C(C#C)C=C1)N[C@@H]2CC[C@@H](NC(COC3=CC=C(Cl)C(C4(N=N4)C(F)(F)F)=C3)=O)CC2 |
| 916846 | 200 | Clc1ccc(OCC(=O)N[C@@H]2CC[C@H](CC2)NC(=O)COc3ccc(cc3)c4cn(CCCCCC(=O)OCCCCCNC(=O)CCCC[C@H]5SC[C@@H]6NC(=O)N[C@H]56)nn4)cc1 |
| 916847 | 900 | Clc1ccc(OCC(=O)N[C@@H]2CC[C@H](CC2)NC(=O)COc3ccc(Cl)c(c3)c4cn(CCCCCC(=O)OCCCCCNC(=O)CCCC[C@H]5SC[C@@H]6NC(=O)N[C@H]56)nn4)cc1 |
| 957866 | 232 | O=C(COC1=CC=C(N=[N+]=[N-])C=C1)N[C@@H]2CC[C@@H](NC(COC3=CC=C(C#C)C=C3)=O)CC2 |
| 957885 | 0.8 | O=C(COC1=CC=C(Cl)C(Cl)=C1)N[C@@H]2CC[C@@H](NC(COC3=CC=C(Cl)C(Cl)=C3)=O)CC2 |
| 957886 | 3 | O=C(COC1=CC=C(Cl)C(C)=C1)N[C@@H]2CC[C@@H](NC(COC3=CC=C(Cl)C(C)=C3)=O)CC2 |
| 957887 | 11 | O=C(COC1=CC=C(Cl)C(C(F)(F)F)=C1)N[C@@H]2CC[C@@H](NC(COC3=CC=C(Cl)C(C(F)(F)F)=C3)=O)CC2 |
| 957888 | 0.6 | O=C(COC1=CC=C(Cl)C(F)=C1)N[C@@H]2CC[C@@H](NC(COC3=CC=C(Cl)C(F)=C3)=O)CC2 |
| 957889 | 11 | O=C(COC1=CC=C(Cl)C([N+]([O-])=O)=C1)N[C@@H]2CC[C@@H](NC(COC3=CC=C(Cl)C([N+]([O-])=O)=C3)=O)CC2 |
| 957914 | 40 | O=C(COC1=CC(Cl)=C(Cl)C=C1)N[C@H]2CC[C@H](NC(COC3=CC=C(Cl)C(Cl)=C3)=[NH2+])CC2•[Cl-] |
| 957915 | 344 | O=C(COC1=CC(F)=C(Cl)C=C1)N[C@H]2CC[C@H](NC(COC3=CC=C(Cl)C(F)=C3)=[NH2+])CC2 |
| 957916 | 122 | O=C(COC1=CC(F)=C(Cl)C=C1)N[C@H]2CC[C@H](NC(COC3=CC=C(Cl)C(F)=C3)=[NH2+])CC2 |

| SMDC ID | Structure |
|---|---|
| 751591 | 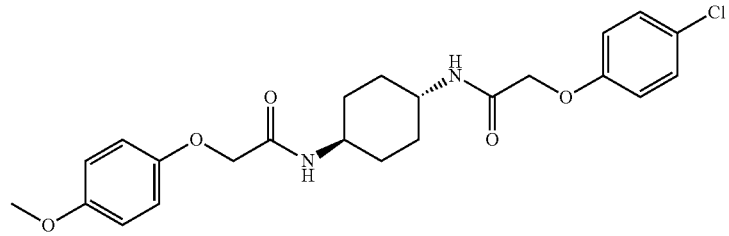 [SMILES: COc1ccc(OCC(=O)N[C@H]2CC[C@H](NC(=O)COc3ccc(Cl)cc3)CC2)cc1] |
| 751592 | 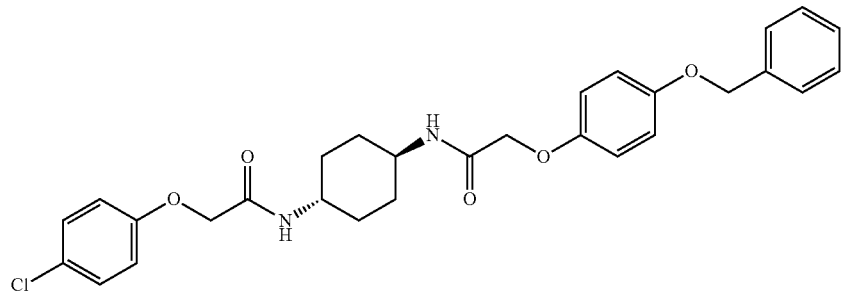 [SMILES: O=C(COc1ccc(Cl)cc1)N[C@H]1CC[C@H](NC(=O)COc2ccc(OCc3ccccc3)cc2)CC1] |
| 751593 | 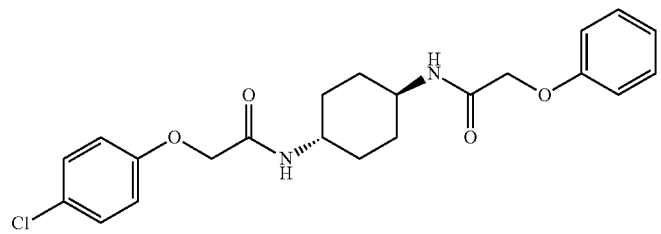 [SMILES: O=C(COc1ccccc1)N[C@H]1CC[C@H](NC(=O)COc2ccc(Cl)cc2)CC1] |

TABLE 2-continued
751594
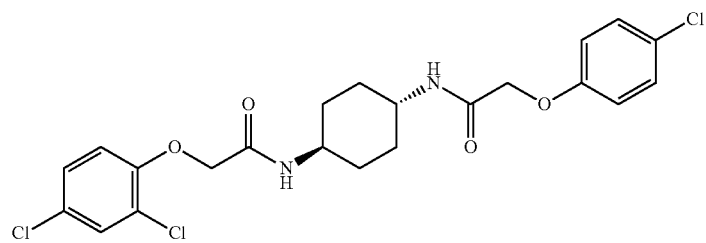 [SMILES: O=C(COc1ccc(Cl)cc1)N[C@H]1CC[C@H](NC(=O)COc2ccc(Cl)cc2Cl)CC1]
751595
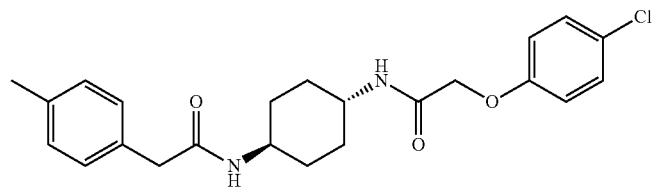 [SMILES: Cc1ccc(CC(=O)N[C@H]2CC[C@H](NC(=O)COc3ccc(Cl)cc3)CC2)cc1]
751596
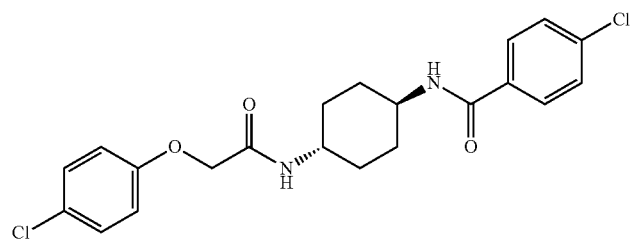 [SMILES: O=C(COc1ccc(Cl)cc1)N[C@H]1CC[C@H](NC(=O)c2ccc(Cl)cc2)CC1]
751597
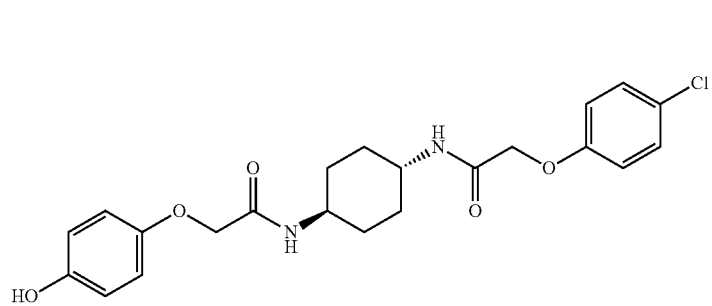 [SMILES: O=C(COc1ccc(O)cc1)N[C@H]1CC[C@H](NC(=O)COc2ccc(Cl)cc2)CC1]
754123
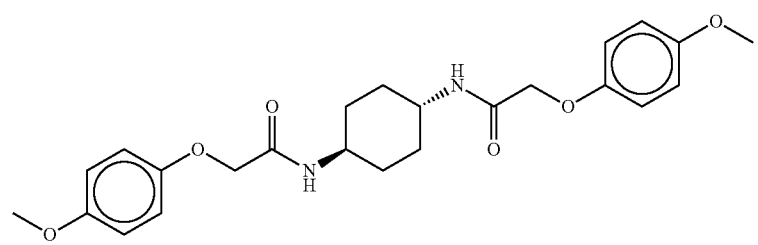
754124
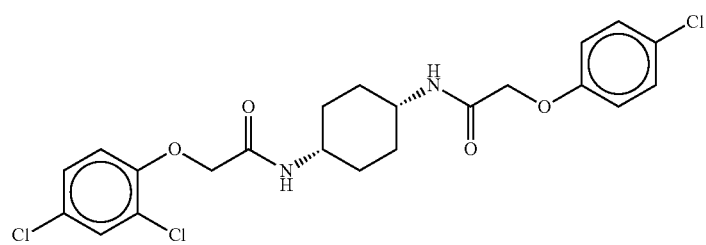

TABLE 2-continued
754128
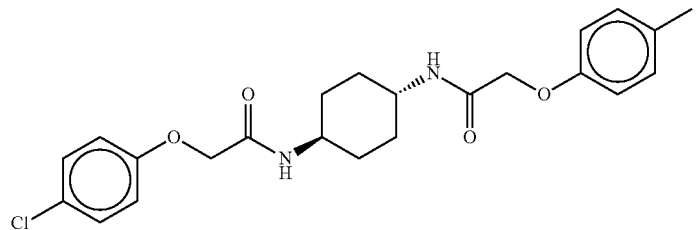
754125
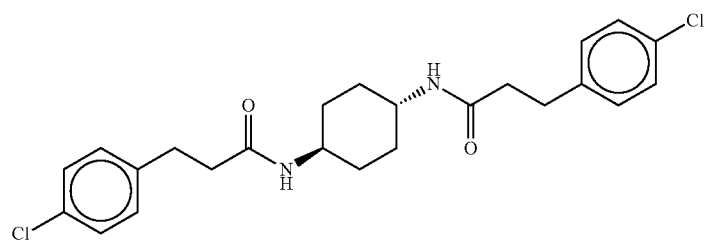
754127
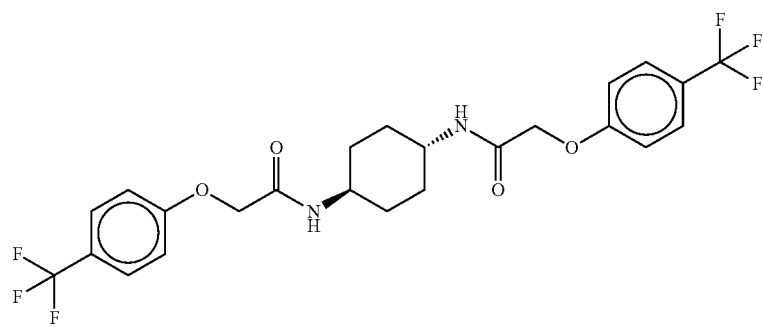
754126
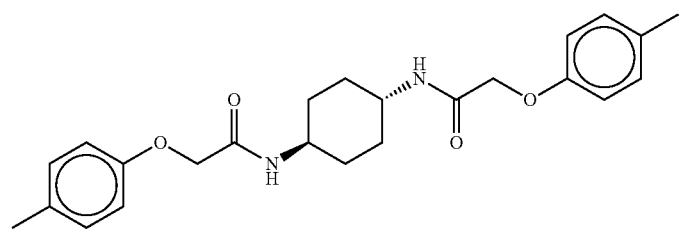
755854.1
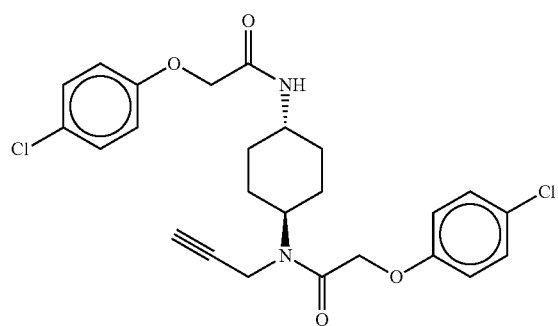

TABLE 2-continued
755854.4
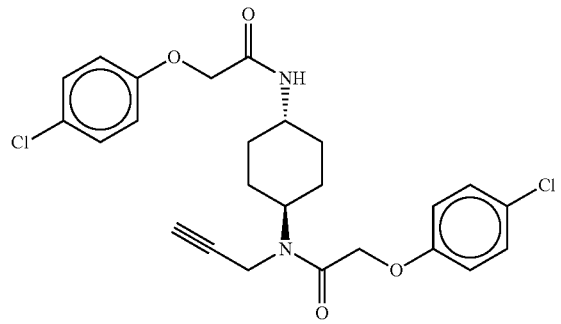
755854.2
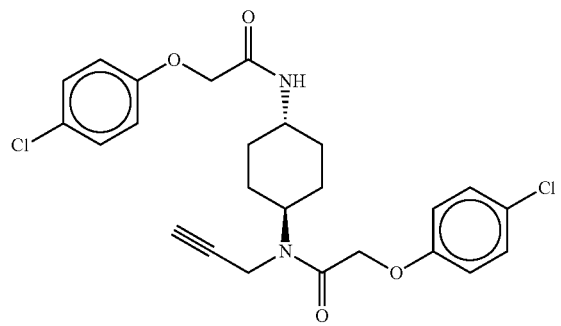
755855
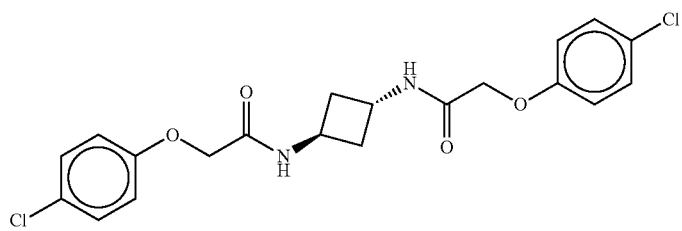
755856
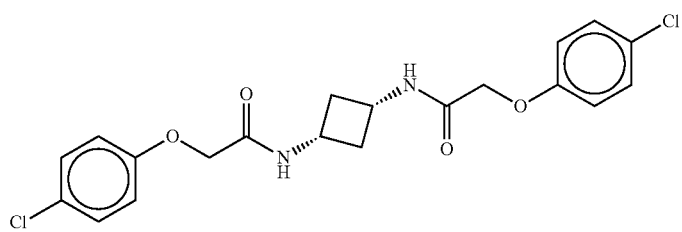
757095
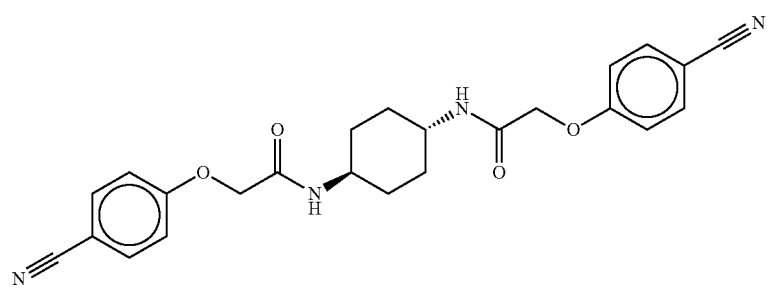

TABLE 2-continued
757096
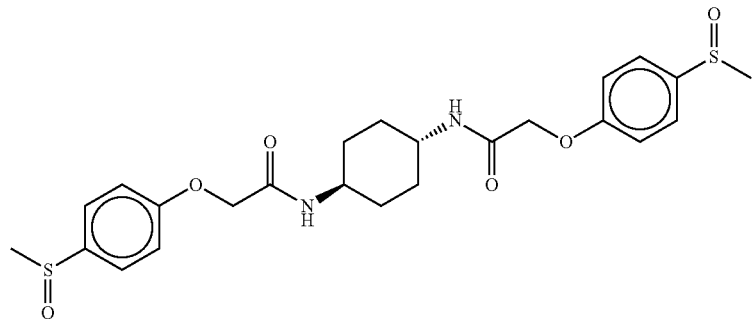
757131
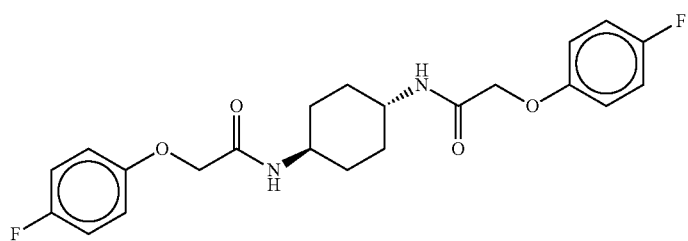
757130
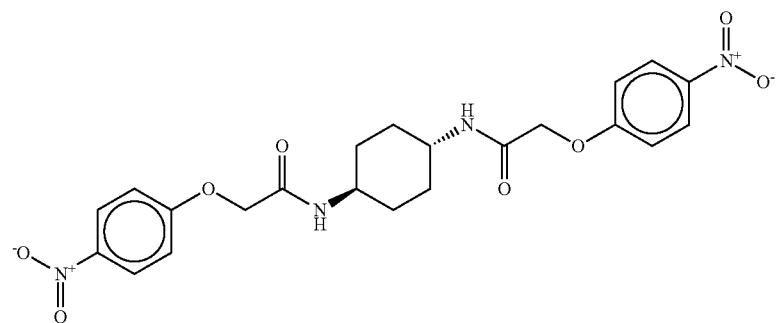
757132
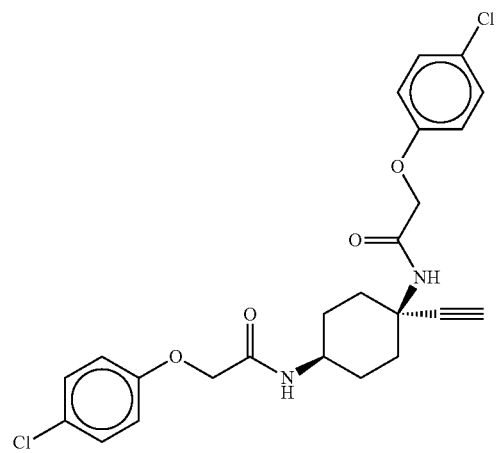

TABLE 2-continued
755854.3
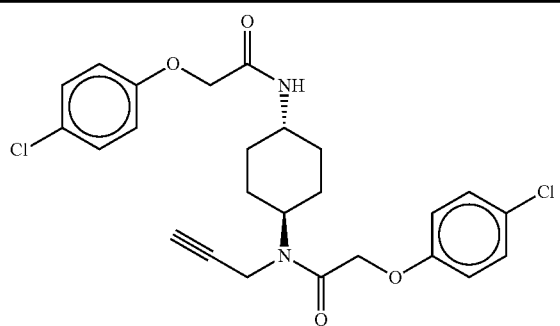
750213.2
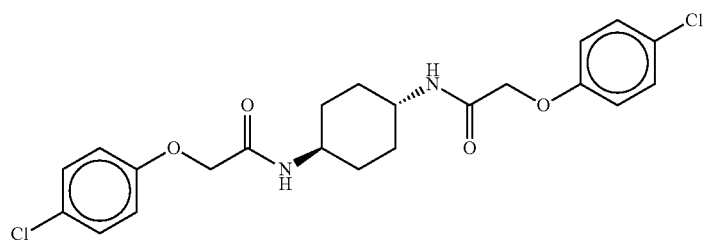
835195
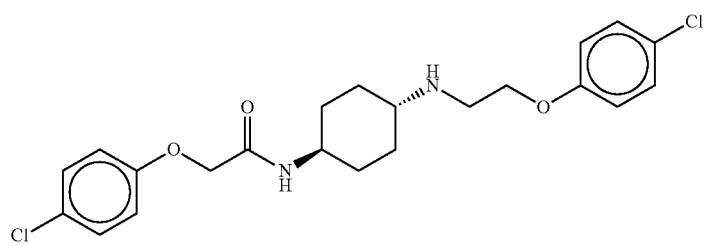
835196
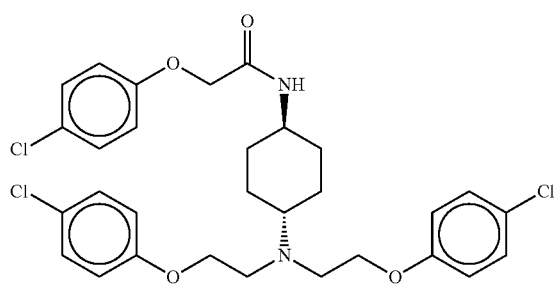
835197
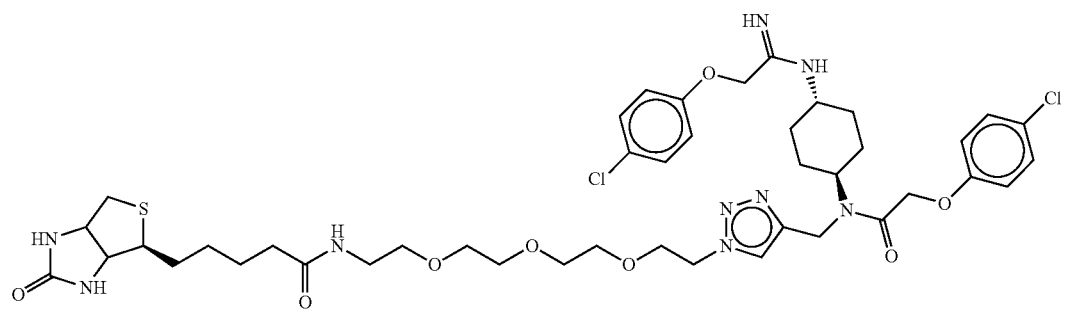
757257
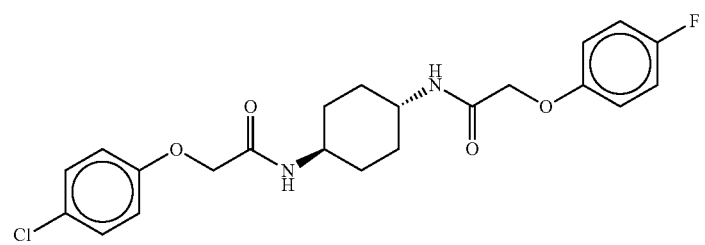

TABLE 2-continued
757258
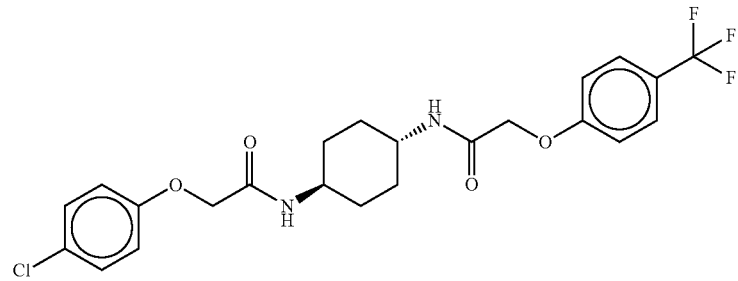
757259
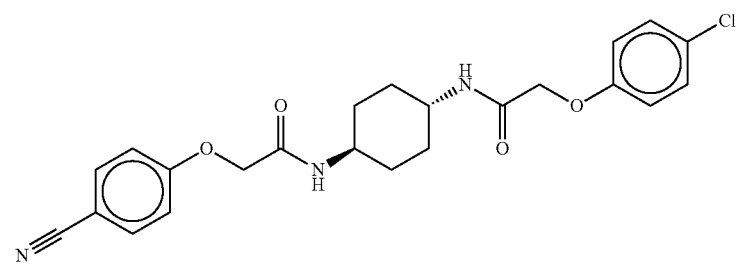
757260
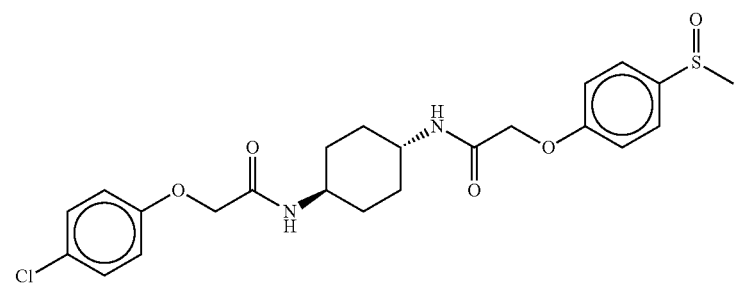
757261
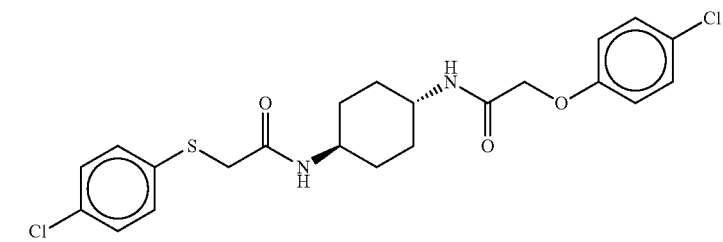
757262
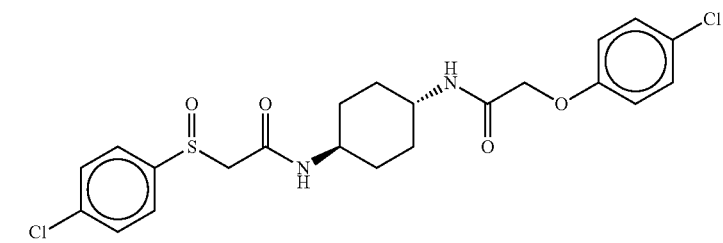
757263
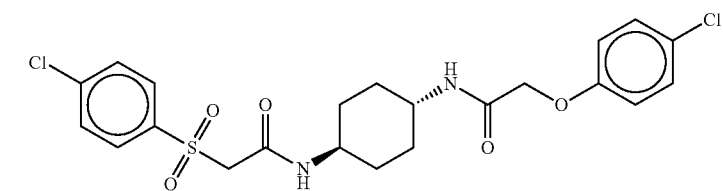

TABLE 2-continued
757264.1
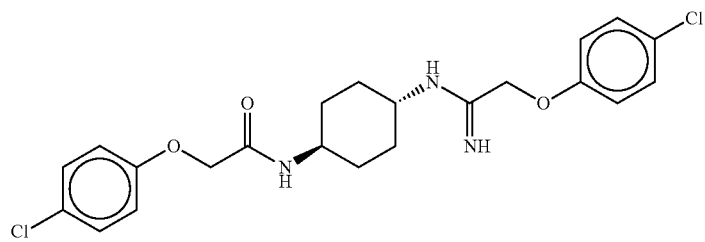
757264.2
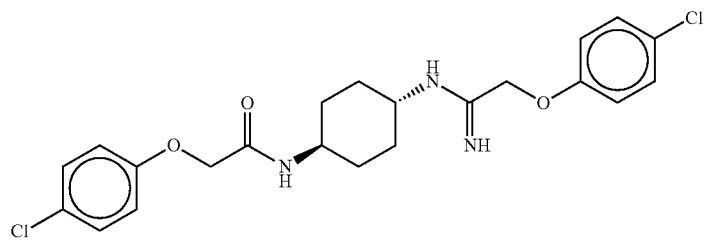
835087
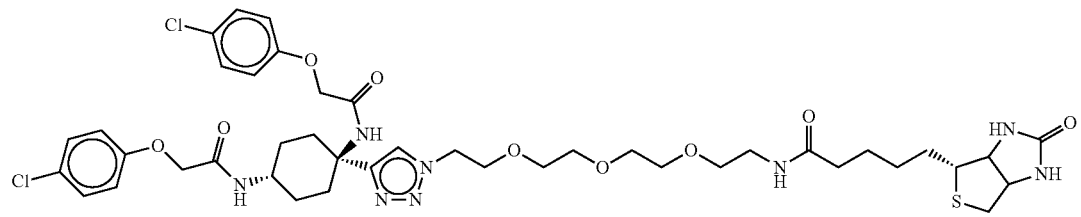
835089
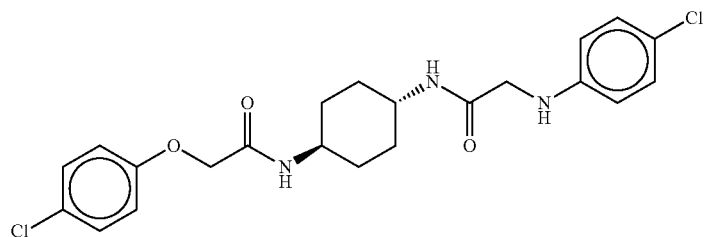
757149
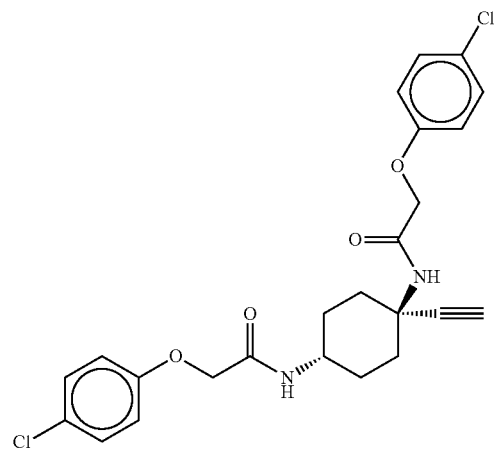

TABLE 2-continued
843983
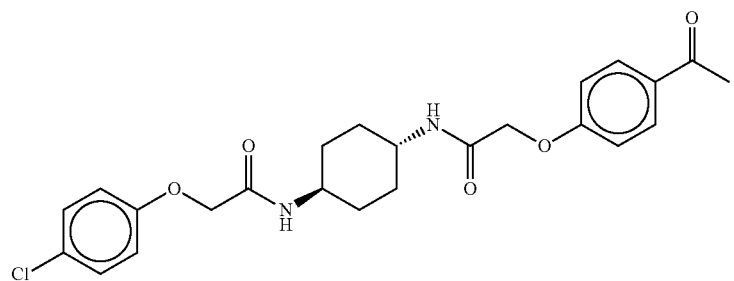
843984
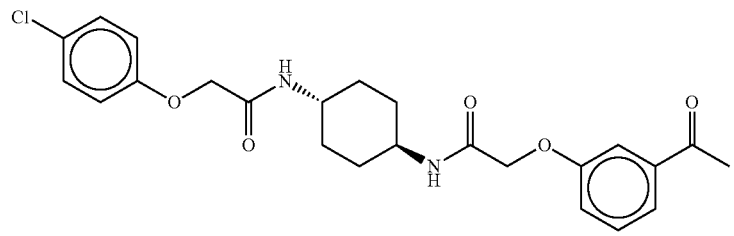
843987
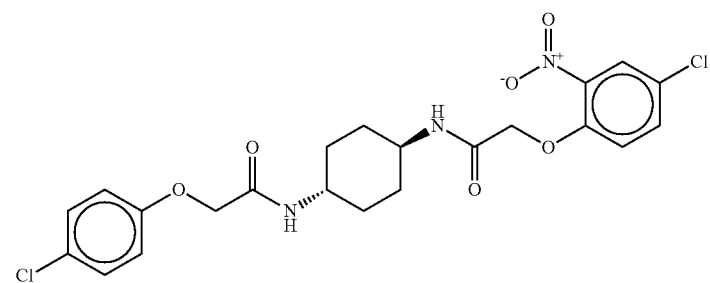
811769
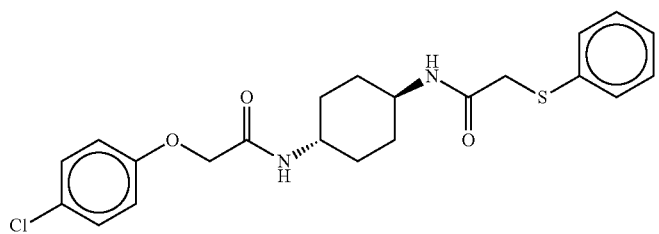
811770
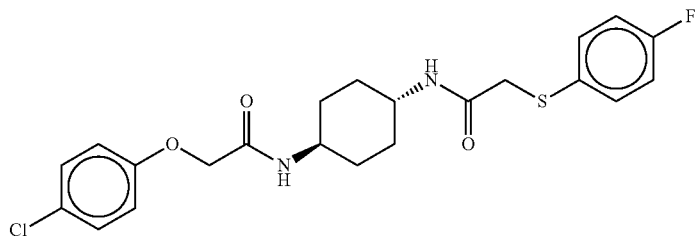
811771
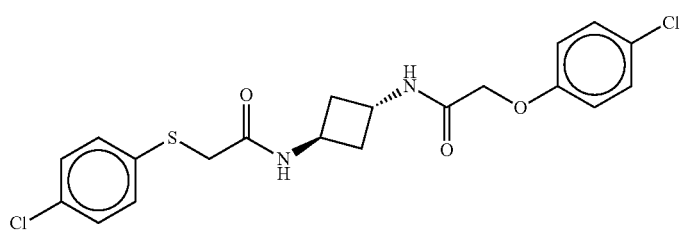

TABLE 2-continued
811772
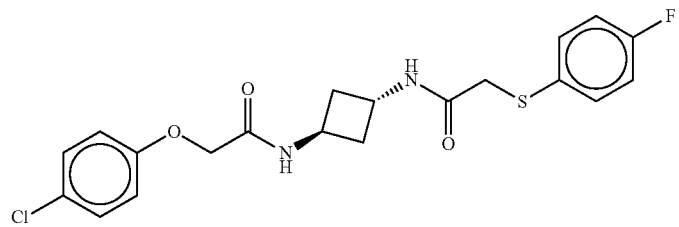
811773
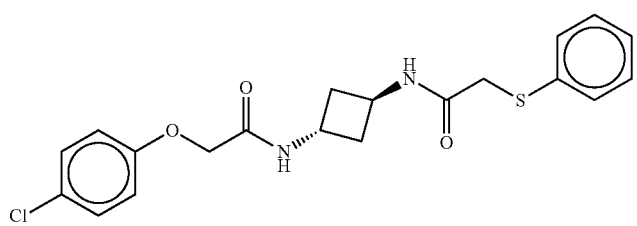
873882
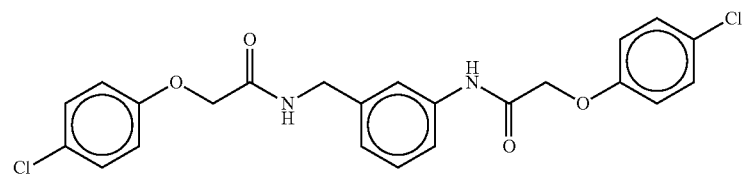
873883
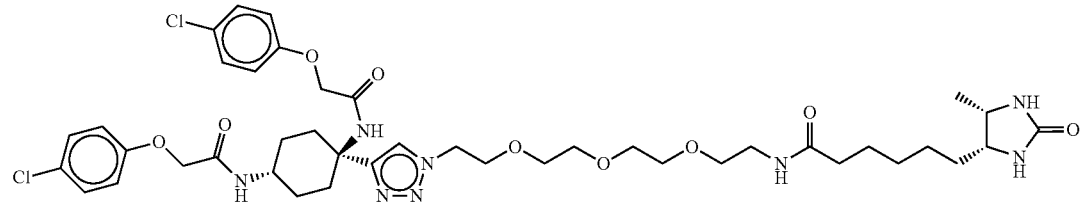
873972
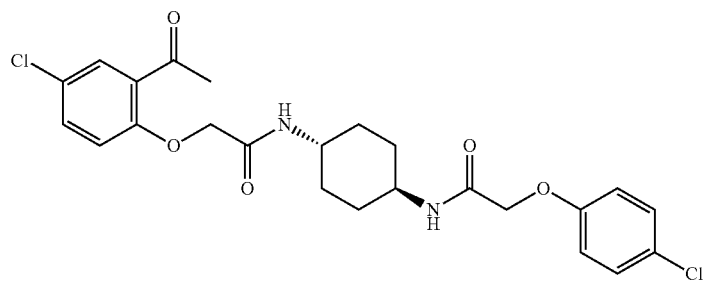 [SMILES: CC(=O)c1cc(Cl)ccc1OCC(=O)N[C@H]1CC[C@H](NC(=O)COc2ccc(Cl)cc2)CC1]
873973
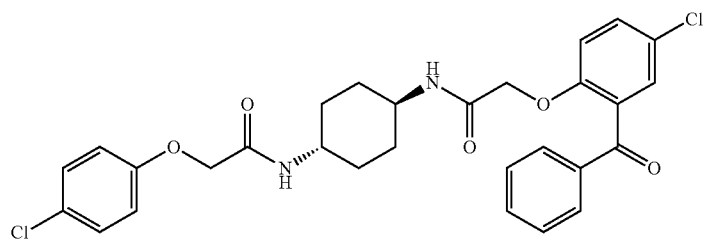 [SMILES: O=C(COc1ccc(Cl)cc1)N[C@H]1CC[C@H](NC(=O)COc2ccc(Cl)cc2C(=O)c2ccccc2)CC1]
757264-L3
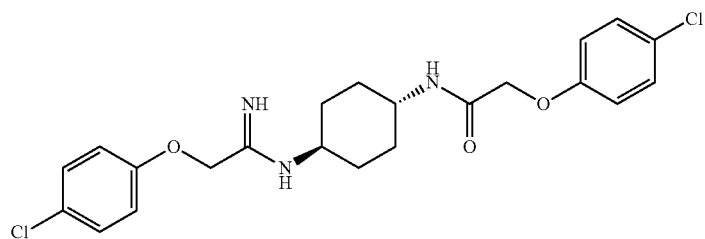 [SMILES: N=C(COc1ccc(Cl)cc1)N[C@H]1CC[C@H](NC(=O)COc2ccc(Cl)cc2)CC1]

874796 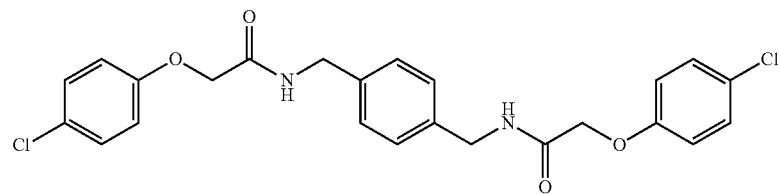 [SMILES: O=C(COc1ccc(Cl)cc1)NCc1ccc(CNC(=O)COc2ccc(Cl)cc2)cc1]
874797 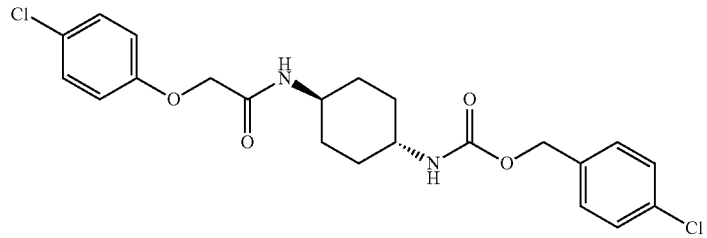 [SMILES: O=C(COc1ccc(Cl)cc1)N[C@H]1CC[C@H](NC(=O)OCc2ccc(Cl)cc2)CC1]
874798 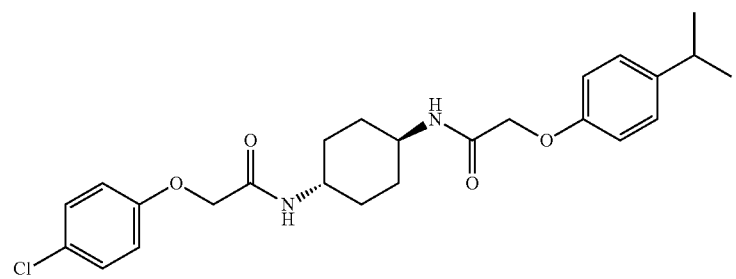 [SMILES: CC(C)c1ccc(OCC(=O)N[C@H]2CC[C@H](NC(=O)COc3ccc(Cl)cc3)CC2)cc1]
874799 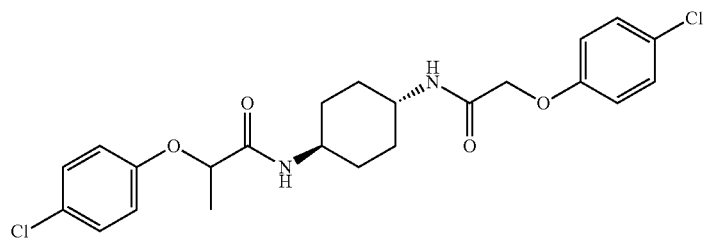 [SMILES: CC(Oc1ccc(Cl)cc1)C(=O)N[C@H]1CC[C@H](NC(=O)COc2ccc(Cl)cc2)CC1]
874800 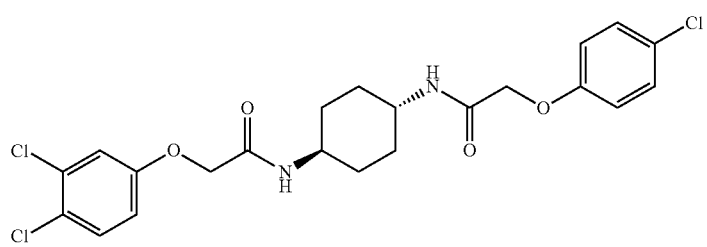 [SMILES: O=C(COc1ccc(Cl)cc1)N[C@H]1CC[C@H](NC(=O)COc2ccc(Cl)c(Cl)c2)CC1]
874801 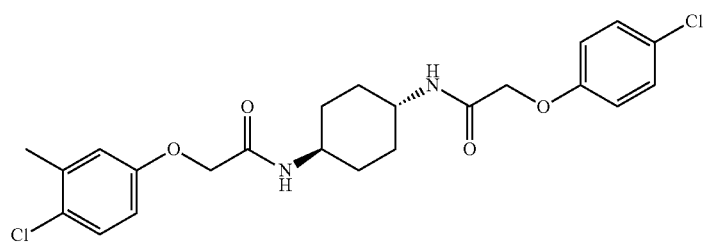 [SMILES: Cc1cc(OCC(=O)N[C@H]2CC[C@H](NC(=O)COc3ccc(Cl)cc3)CC2)ccc1Cl]

TABLE 2-continued
874802 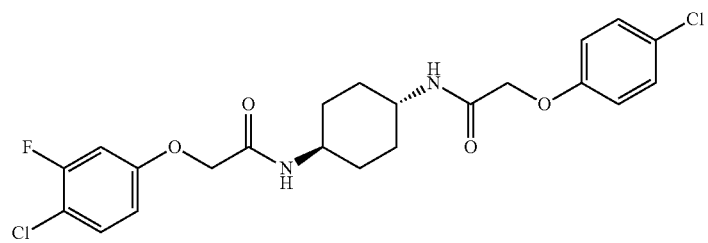 [SMILES: O=C(COc1ccc(Cl)cc1)N[C@H]1CC[C@H](NC(=O)COc2ccc(Cl)c(F)c2)CC1]
876803 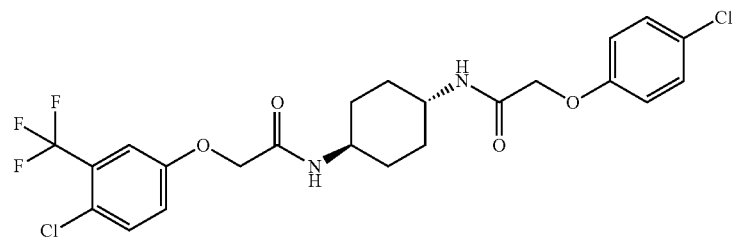 [SMILES: O=C(COc1ccc(Cl)cc1)N[C@H]1CC[C@H](NC(=O)COc2ccc(Cl)c(C(F)(F)F)c2)CC1]
874804 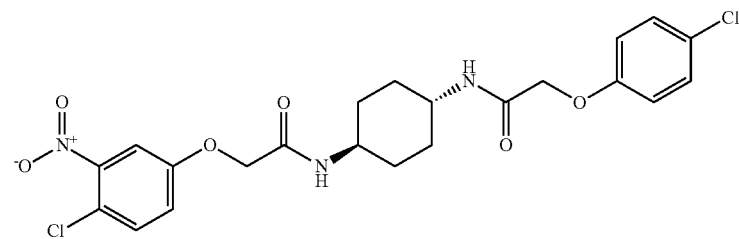
874805 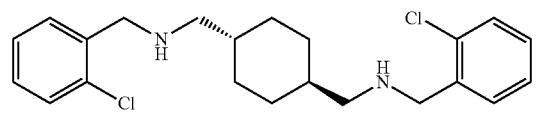 [SMILES: Clc1ccccc1CNC[C@H]1CC[C@H](CNCc2ccccc2Cl)CC1]
885253 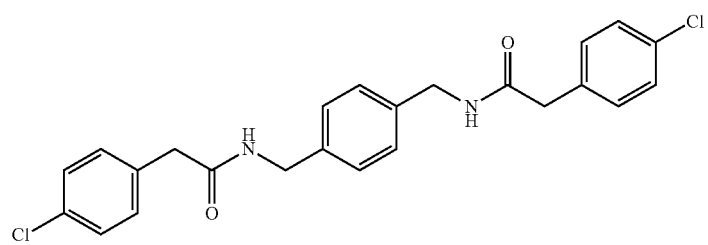 [SMILES: O=C(Cc1ccc(Cl)cc1)NCc1ccc(CNC(=O)Cc2ccc(Cl)cc2)cc1]
885254 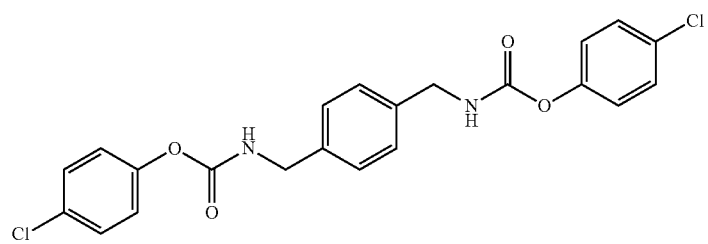
885255 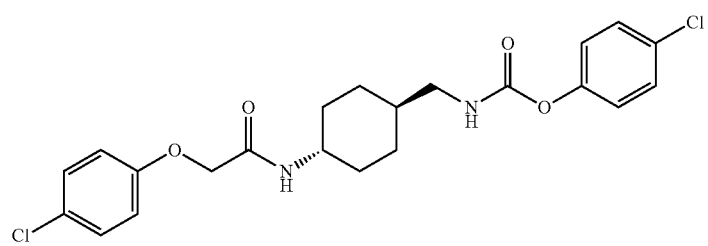

TABLE 2-continued
885256
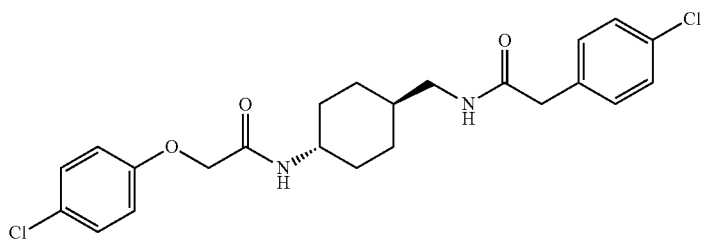 [SMILES: O=C(Cc1ccc(Cl)cc1)NC[C@H]1CC[C@H](NC(=O)COc2ccc(Cl)cc2)CC1]
885257
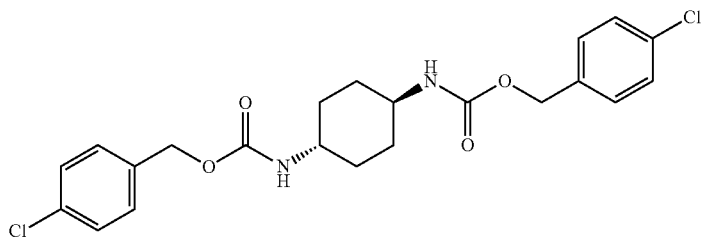 [SMILES: O=C(N[C@H]1CC[C@H](NC(=O)OCc2ccc(Cl)cc2)CC1)OCc1ccc(Cl)cc1]
102509
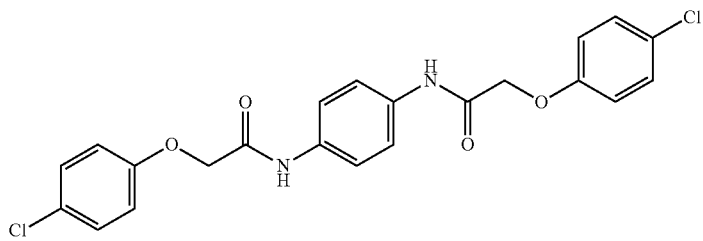 [SMILES: O=C(COc1ccc(Cl)cc1)Nc1ccc(NC(=O)COc2ccc(Cl)cc2)cc1]
912562
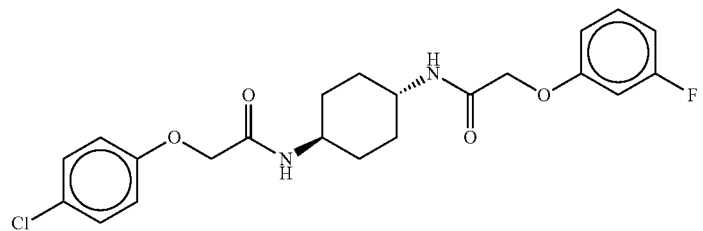
912563
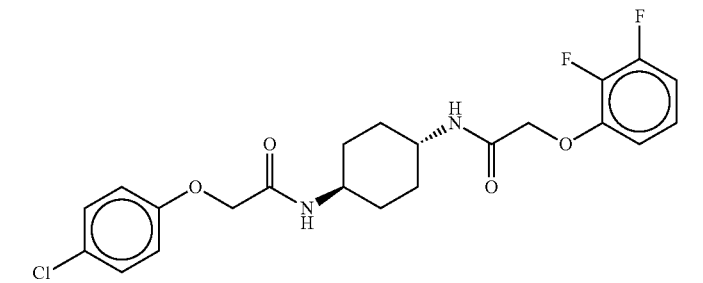
912564
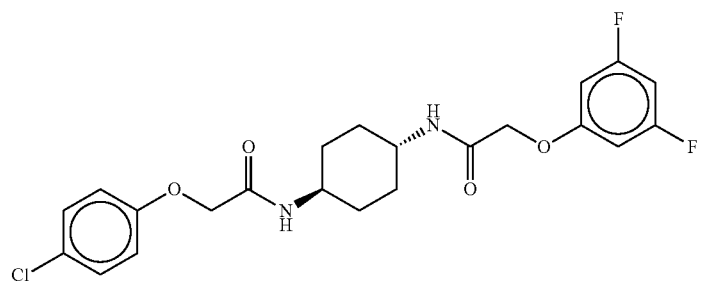

TABLE 2-continued
912565 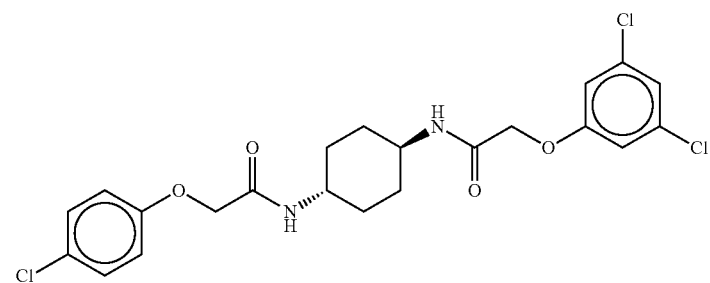
912566 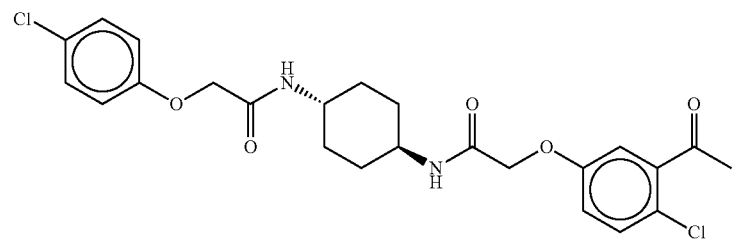
913815 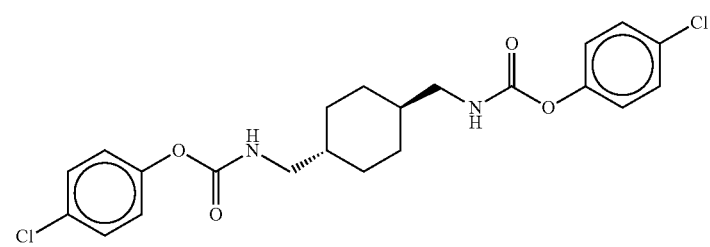
914582 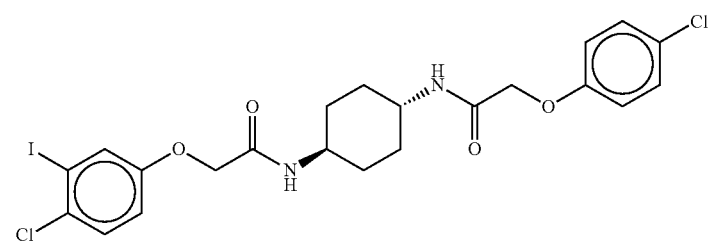
914583 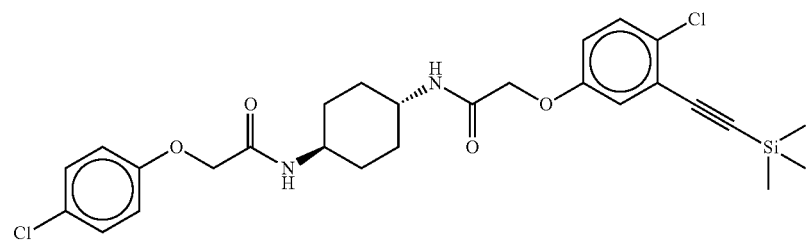
914584 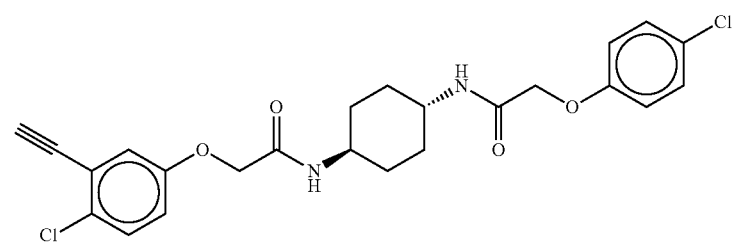

TABLE 2-continued
914989
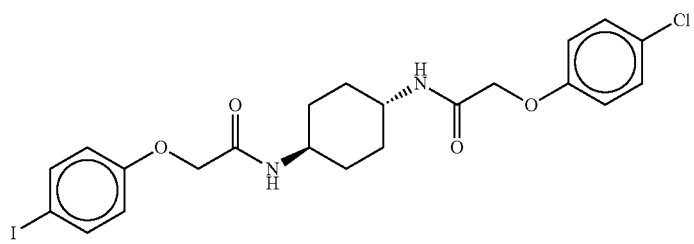
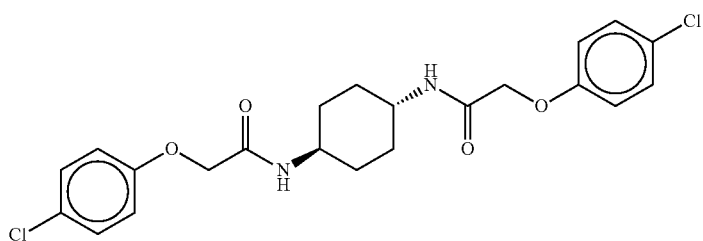
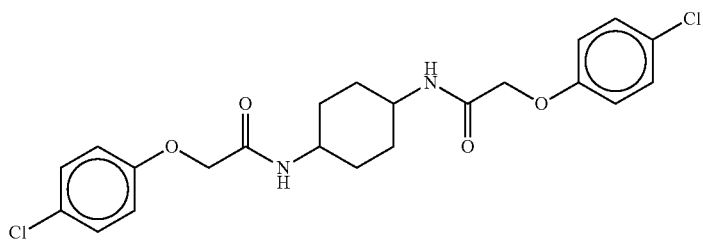
916348
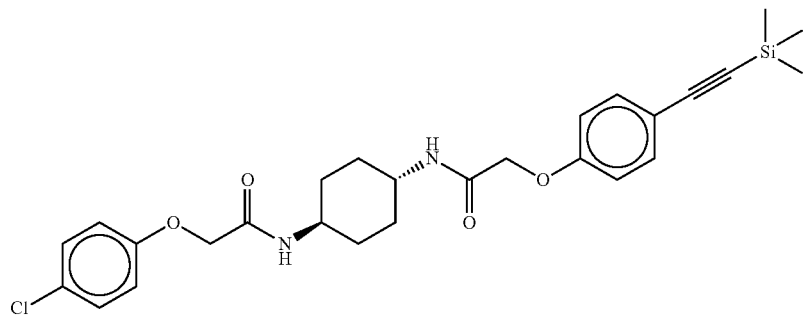
916353
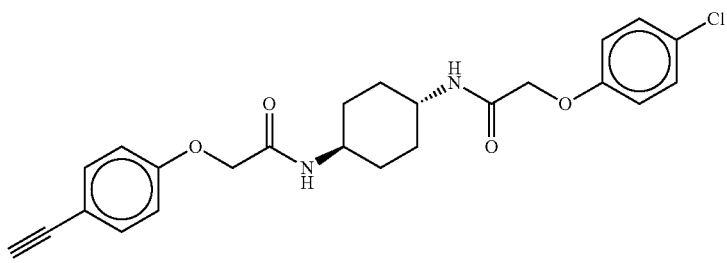
916727
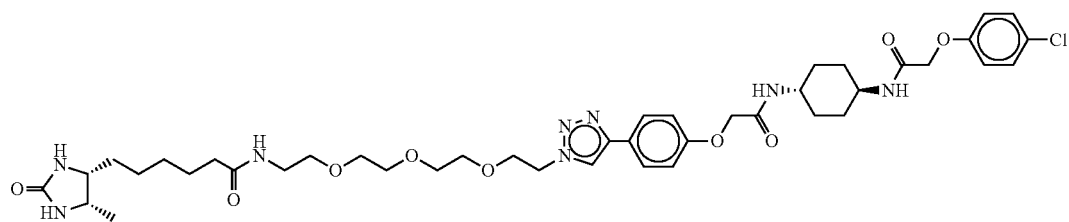

TABLE 2-continued
916728
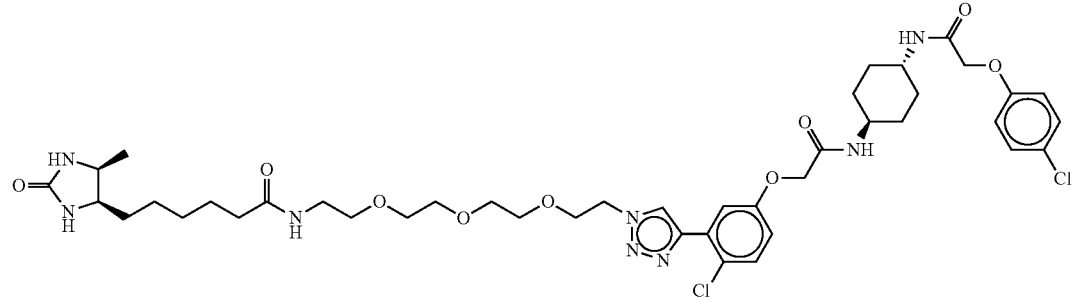
916744
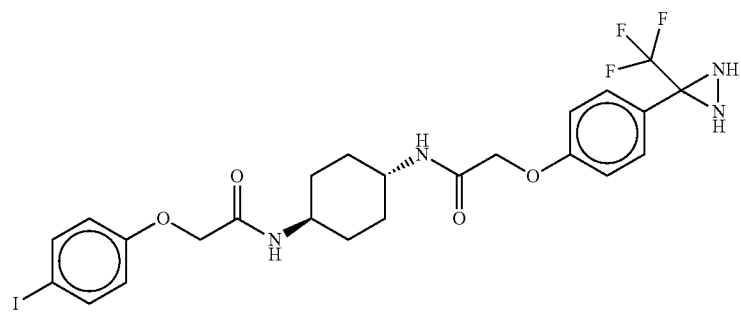
916751
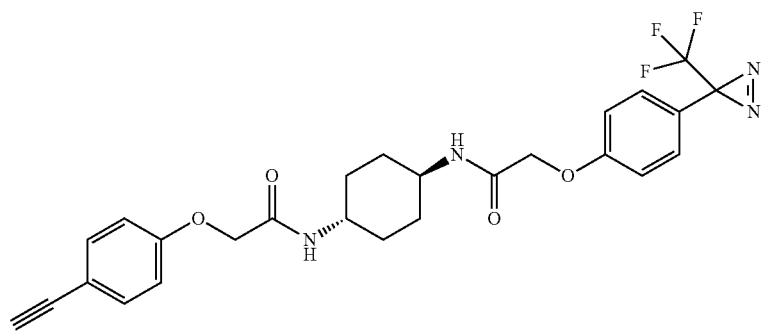 [SMILES: C#Cc1ccc(OCC(=O)N[C@H]2CC[C@H](NC(=O)COc3ccc(C4(C(F)(F)F)N=N4)cc3)CC2)cc1]
916784
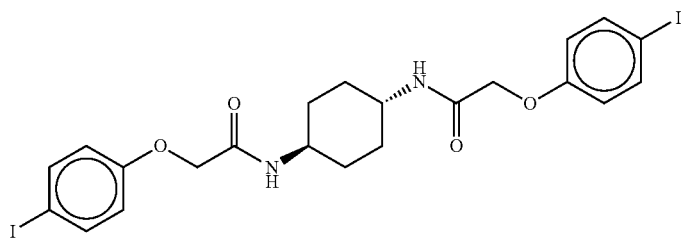
916785
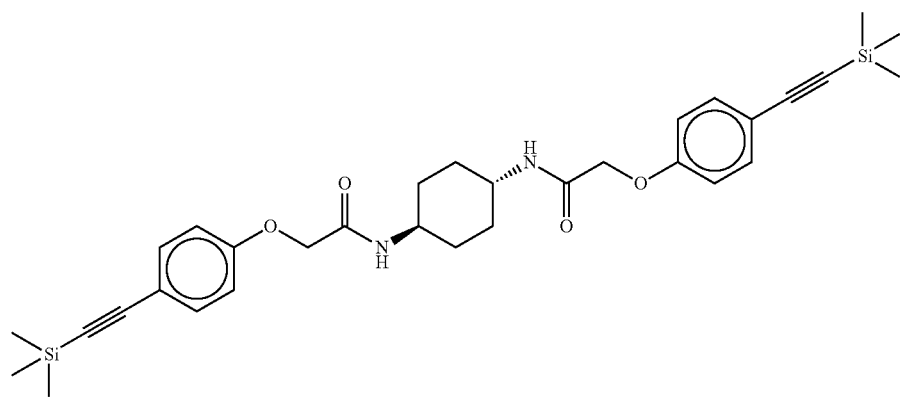

TABLE 2-continued
916786
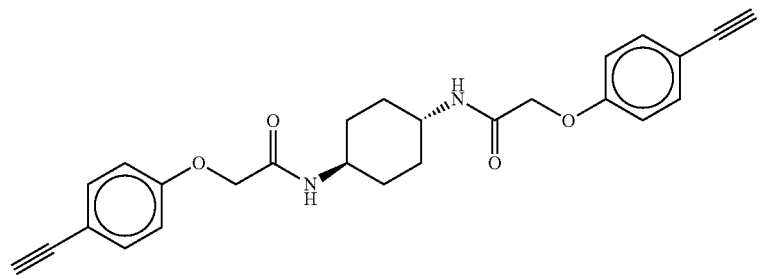
955278
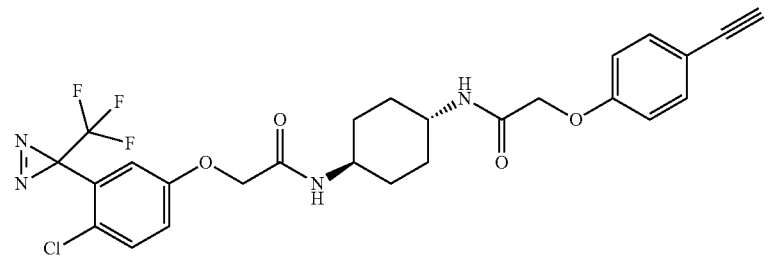 [SMILES: C#Cc1ccc(OCC(=O)N[C@H]2CC[C@H](NC(=O)COc3ccc(Cl)c(C4(C(F)(F)F)N=N4)c3)CC2)cc1]
916846
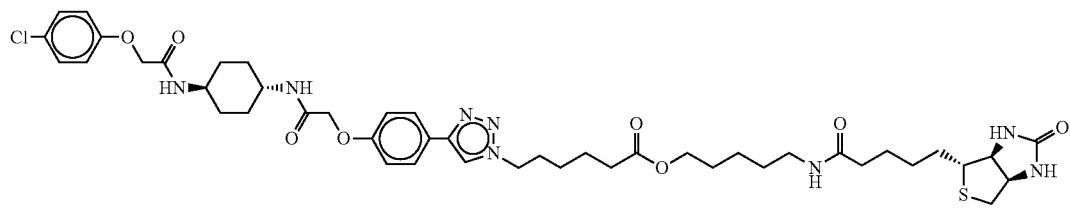
916847
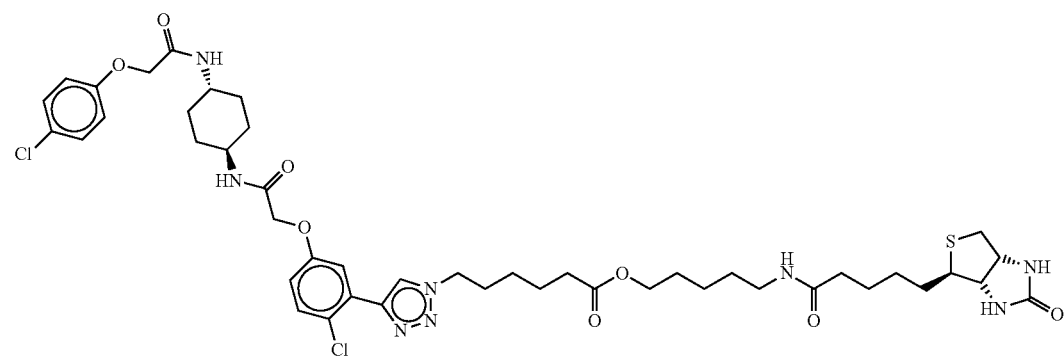
957866
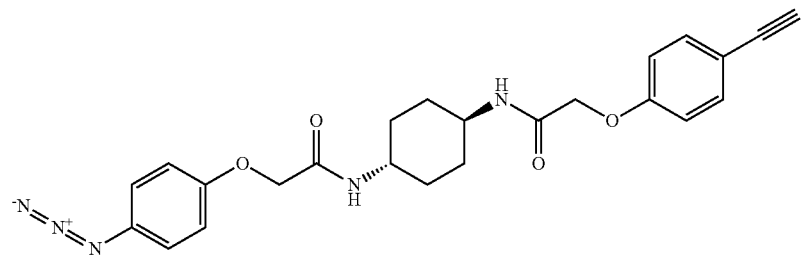
957885
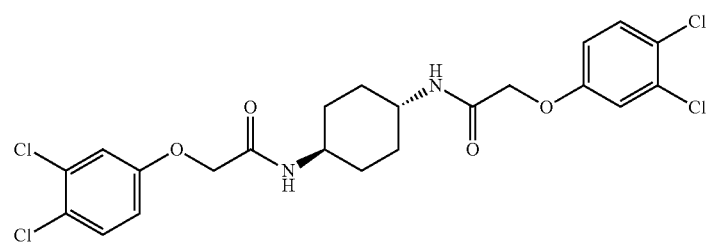 [SMILES: O=C(COc1ccc(Cl)c(Cl)c1)N[C@H]1CC[C@H](NC(=O)COc2ccc(Cl)c(Cl)c2)CC1]

TABLE 2-continued
957886
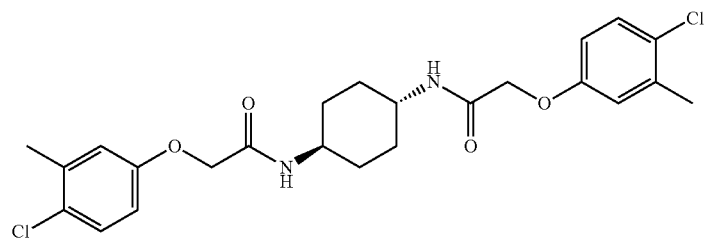 [SMILES: Cc1cc(OCC(=O)N[C@H]2CC[C@H](NC(=O)COc3ccc(Cl)c(C)c3)CC2)ccc1Cl]
957887
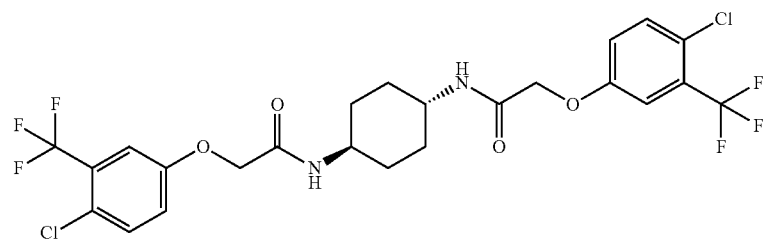 [SMILES: O=C(COc1ccc(Cl)c(C(F)(F)F)c1)N[C@H]1CC[C@H](NC(=O)COc2ccc(Cl)c(C(F)(F)F)c2)CC1]
957888
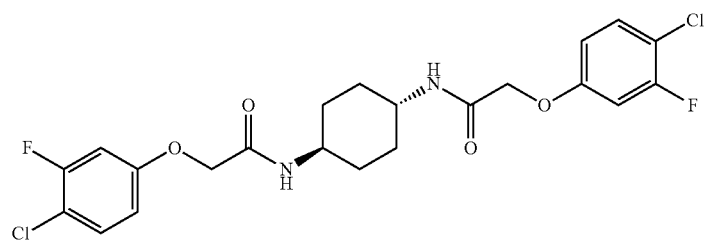
957889
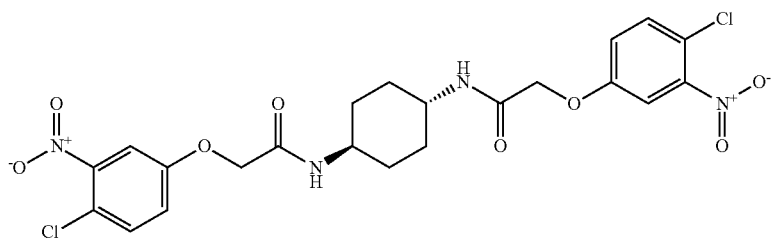
957914
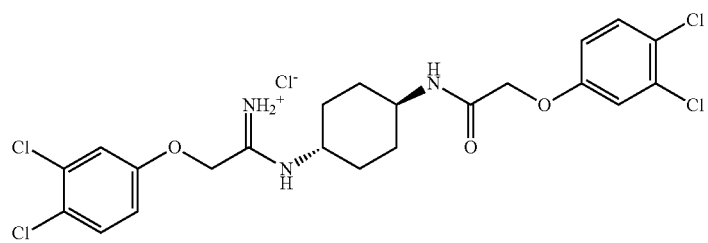 [SMILES: [NH2+]=C(COc1ccc(Cl)c(Cl)c1)N[C@H]1CC[C@H](NC(=O)COc2ccc(Cl)c(Cl)c2)CC1 ; [Cl-]]
957915
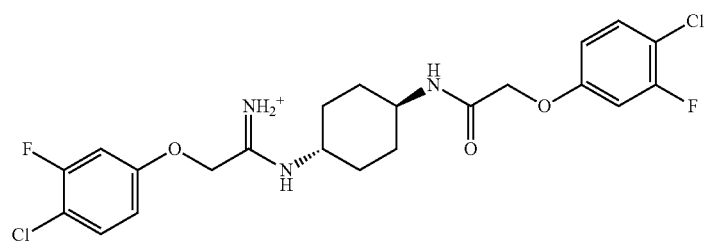 [SMILES: [NH2+]=C(COc1ccc(Cl)c(F)c1)N[C@H]1CC[C@H](NC(=O)COc2ccc(Cl)c(F)c2)CC1]

957916

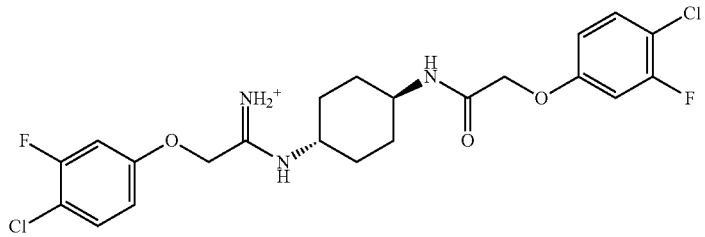 [SMILES: [NH2+]=C(COc1ccc(Cl)c(F)c1)N[C@H]1CC[C@H](NC(=O)COc2ccc(Cl)c(F)c2)CC1]

REFERENCES

1. Wek R C, Jiang H-Y, Anthony T G. Coping with stress: eIF2 kinases and translational control. Biochem. Soc. Trans. 2006 February; 34(Pt 1):7-11. 2. Hinnebusch A G, Lorsch J R. The mechanism of eukaryotic translation initiation: new insights and challenges. Cold Spring Harb Perspect Biol. 2012; 4(10). 3. Krishnamoorthy T, Pavitt G D, Zhang F, Dever T E, Hinnebusch A G. Tight binding of the phosphorylated alpha subunit of initiation factor 2 (eIF2alpha) to the regulatory subunits of guanine nucleotide exchange factor eIF2B is required for inhibition of translation initiation. Mol Cell Biol. 2001 August; 21(15):5018-30. 4. Hinnebusch A G. Translational regulation of GCN4 and the general amino acid control of yeast. Annu Rev. Microbiol. 2005; 59:407-50. 5. Jackson R J, Hellen C U T, Pestova T V. The mechanism of eukaryotic translation initiation and principles of its regulation. Nat Rev Mol Cell Biol. 2010 Feb. 1; 11(2):113-27. 6. Harding H P, Novoa I, Zhang Y, Zeng H, Wek R, Schapira M, et al. Regulated translation initiation controls stress-induced gene expression in mammalian cells. Mol Cell. 2000 November; 6(5):1099-108. 7. Palam L R, Baird T D, Wek R C. Phosphorylation of eIF2 facilitates ribosomal bypass of an inhibitory upstream ORF to enhance CHOP translation. Journal of Biological Chemistry. 2011 Apr. 1; 286(13):10939-49. 8. Vattem K M, Wek R C. Reinitiation involving upstream ORFs regulates ATF4 mRNA translation in mammalian cells. Proc Natl Acad Sci USA. 2004 Aug. 3; 101(31):11269-74. 9. Ma Y, Brewer J W, Diehl J A, Hendershot L M. Two distinct stress signaling pathways converge upon the CHOP promoter during the mammalian unfolded protein response. J. Mol. Biol. 2002 May 17; 318(5):1351-65. 10. Pavitt G D, Ron D. New insights into translational regulation in the endoplasmic reticulum unfolded protein response. Cold Spring Harb Perspect Biol. 2012 June; 4(6). 11. Ron D, Walter P. Signal integration in the endoplasmic reticulum unfolded protein response. Nat Rev Mol Cell Biol. 2007 July; 8(7):519-29. 12. Gardner B M, Walter P. Unfolded proteins are Ire1-activating ligands that directly induce the unfolded protein response. Science. 2011 Sep. 30; 333(6051):1891-4. 13. Harding H P, Zhang Y, Bertolotti A, Zeng H, Ron D. Perk is essential for translational regulation and cell survival during the unfolded protein response. Mol Cell. 2000 May; 5(5): 897-904. 14. Walter P, Ron D. The unfolded protein response: from stress pathway to homeostatic regulation. Science. 2011 Nov. 25; 334(6059):1081-6. 15. Tabas I, Ron D. Integrating the mechanisms of apoptosis induced by endoplasmic reticulum stress. Nat Cell Biol. 2011 Mar. 1; 13(3):184-90. 16. Shore G C G, Papa F R F, Oakes S A S. Signaling cell death from the endoplasmic reticulum stress response. Current Opinion in Cell Biology. 2011 Apr. 1; 23(2):143-9. 17. Thoreen C C, Chantranupong L, Keys H R, Wang T, Gray N S, Sabatini D M. A unifying model for mTORC1-mediated regulation of mRNA translation. Nature. 2012 May 3; 485(7396):109-13. 18. Chen T, Ozel D, Qiao Y, Harbinski F, Chen L, Denoyelle S, et al. Chemical genetics identify eIF2α kinase heme-regulated inhibitor as an anticancer target. Nature Chemical Biology. 2011 Sep. 1; 7(9):610-6. 19. Lu P D, Jousse C, Marciniak S J, Zhang Y, Novoa I, Scheuner D, et al. Cytoprotection by pre-emptive conditional phosphorylation of translation initiation factor 2. EMBO J. 2004 Jan. 14; 23(1):169-79. 20. Salvesen G S, Ashkenazi A. Snapshot: caspases. Cell. 2011 Oct. 14; 147 (2):476-476.e1. 21. Jiang Z, Belforte J E, Lu Y, Yabe Y, Pickel J, Smith C B, et al. eIF2alpha Phosphorylation-dependent translation in CA1 pyramidal cells impairs hippocampal memory consolidation without affecting general translation. Journal of Neuroscience. 2010 Feb. 17; 30(7): 2582-94. 22. Costa-Mattioli M, Gobert D, Stern E, Gamache K, Colina R, Cuello C, et al. eIF2alpha phosphorylation bidirectionally regulates the switch from short- to long-term synaptic plasticity and memory. Cell. 2007 Apr. 6; 129(1): 195-206. 23. Vazquez de Aldana C R, Hinnebusch A G. Mutations in the GCD7 subunit of yeast guanine nucleotide exchange factor eIF-2B overcome the inhibitory effects of phosphorylated eIF-2 on translation initiation. Mol Cell Biol. 1994 May; 14(5):3208-22. 24. Pavitt G D, Ramaiah K V, Kimball S R, Hinnebusch A G. eIF2 independently binds two distinct eIF2B subcomplexes that catalyze and regulate guanine-nucleotide exchange. Genes Dev. 1998 Feb. 15; 12(4):514-26. 25. Pavitt G D, Yang W, Hinnebusch A G. Homologous segments in three subunits of the guanine nucleotide exchange factor eIF2B mediate translational regulation by phosphorylation of eIF2. Mol Cell Biol. 1997 March; 17(3):1298-313. 26. Woo C W, Kutzler L, Kimball S R, Tabas I. Toll-like receptor activation suppresses ER stress factor CHOP and translation inhibition through activation of eIF2B. Nat Cell Biol. 2012 Feb. 1; 14(2):192-200. 27. Woo C W, Cui D, Arellano J, Dorweiler B, Harding H, Fitzgerald K A, et al. Adaptive suppression of the ATF4-CHOP branch of the unfolded protein response by toll-like receptor signalling. Nat Cell Biol. 2009 December; 11(12): 1473-80. 28. Harding H P, Zhang Y, Zeng H, Novoa I, Lu P D, Calfon M, et al. An integrated stress response regulates amino acid metabolism and resistance to oxidative stress. Mol Cell. 2003 March; 11(3):619-33. 29. Axten J M, Medina J R, Feng Y, Shu A, Romeril S P, Grant S W, et al. Discovery of 7-methyl-5-(1-{[3-(trifluoromethyl)phenyl]acetyl}-2,3-dihydro-1H-indol-5-yl)-7H-pyrrolo[2,3-d]pyrimidin-4-amine (GSK2606414), a potent and selective first-in-class inhibitor of protein kinase R (PKR)-like endoplasmic reticulum kinase (PERK). J Med Chem. 2012 Aug. 23; 55(16): 7193-207. 30. Bi M, Naczki C, Koritzinsky M, Fels D, Blais J, Hu N, et al. ER stress-regulated translation increases tolerance to extreme hypoxia and promotes tumor growth. EMBO J. 2005 Oct. 5; 24(19):3470-81. 31. Ye J, Kumanova M, Hart L S, Sloane K, Zhang H, De Panis D N, et al. The GCN2-ATF4 pathway is critical for tumour cell survival and proliferation in response to nutrient deprivation. EMBO J. 2010 Jun. 16; 29(12):2082-96. 32. Li W, Wang X, Van Der Knaap M S, Proud C G. Mutations Linked to Leukoencephalopathy with Vanishing White Matter Impair the Function of the Eukaryotic Initiation Factor 2B Complex in Diverse Ways. Mol Cell Biol. 2004 Apr. 15; 24(8):3295-306. 33. Borck G, Shin B-S, Stiller B, Mimouni-Bloch A, Thiele H, Kim J-R, et al. eIF2γ Mutation that Disrupts eIF2 Complex Integrity Links Intellectual Disability to Impaired Translation Initiation. Mol Cell. 2012 October 34. Costa-Mattioli M, Gobert D, Harding H, Herdy B, Azzi M, Bruno M, et al. Translational control of hippocampal synaptic plasticity and memory by the elF2alpha kinase GCN2. Nature. 2005 Aug. 25; 436(7054):1166-73. 35. Zhu P J, Huang W, Kalikulov D, Yoo J W, Placzek A N, Stoica L, et al. Suppression of PKR Promotes Network Excitability and Enhanced Cognition by Interferon-γ-Mediated Disinhibition. Cell. 2011 Dec. 9; 147(6):13-3. 36. Sutton M A, Schuman E M. Dendritic protein synthesis, synaptic plasticity, and memory. Cell. 2006 Oct. 6; 127(1):49-58. 37. Klann E, Dever T E. Biochemical mechanisms for translational regulation in synaptic plasticity. Nat. Rev. Neurosci. 2004 December; 5(12):931-42. 38. Bartsch D, Ghirardi M, Skehel P A, Karl K A, Herder S P, Chen M, et al. Aplysia CREB2 represses long-term facilitation: relief of repression converts transient facilitation into long-term functional and structural change. Cell. 1995 Dec. 15; 83(6):979-92. 39. Yin J C, Wallach J S, Del Vecchio M, Wilder E L, Zhou H, Quinn W G, et al. Induction of a dominant negative CREB transgene specifically blocks long-term memory in Drosophila. Cell. 1994 Oct. 7; 79(1): 49-58. 40. Chen A, Muzzio I A, Malleret G, Bartsch D, Verbitsky M, Pavlidis P, et al. Inducible enhancement of memory storage and synaptic plasticity in transgenic mice expressing an inhibitor of ATF4 (CREB-2) and C/EBP proteins. Neuron. 2003 Aug. 14; 39(4):655-69. 41. Trinh M A M, Kaphzan H H, Wek R C R, Pierre P P, Cavener D R D, Klann E E. Brain-specific disruption of the eIF2α kinase PERK decreases ATF4 expression and impairs behavioral flexibility. Cell Rep. 2012 Jun. 28; 1(6):676-88. 42. Li X, Zhao X, Fang Y, Jiang X, Duong T, Fan C, et al. Generation of destabilized green fluorescent protein as a transcription reporter. J Biol Chem. 1998 Dec. 25; 273(52):34970-5. 43. Shen J, Chen X, Hendershot L, Prywes R. ER stress regulation of ATF6 localization by dissociation of BiP/GRP78 binding and unmasking of Golgi localization signals. Developmental Cell. 2002 July; 3(1):99-111. 44. Cohen H R, Panning B. XIST RNA exhibits nuclear retention and exhibits reduced association with the export factor TAP/NXF1. Chromosoma. 2007 August; 116(4):373-83. 45. Li H, Korennykh A V, Behrman S L, Walter P. Mammalian endoplasmic reticulum stress sensor IRE1 signals by dynamic clustering. Proceedings of the National Academy of Sciences. 2010 Sep. 14; 107(37):16113-8. 46. Migues P V, Hardt O, Wu D C, Gamache K, Sacktor T C, Wang Y T, et al. PKMzeta maintains memories by regulating GluR2-dependent AMPA receptor trafficking. Nat. Neurosci. 2010 May; 13(5):630-4. 47. Bi M, Naczki C, Koritzinsky M, Fels D, Blais J, Hu N, Harking H, Novoa I, Varia M, Raleigh J, Scheuner D, Kaufman R J, Bell J, Ron D, Wouters B G, Koumenis C. 2005. ER stress-regulated translation increases tolerance to extreme hypoxia and promotes tumor growth. EMBO J. 24:3470-3481. 48. Bobrovnikova-Marjon E, Pytel D, Vaites L P, Singh N, Koretzky G A, Diehl J A. 2010. PERK promotes cancer cell proliferation and tumor growth by limiting oxidative DNA damage. Oncogene 29: 3881-3895. 49. Avivar-Valderas A, Bobrovnikova-Marjon E, Diehl A, Nagi C, Debnath J, Aguirre-Guiso J A 2011. PERK integrates autophagy and oxidative stress responses to promote survival during extracellular matrix detachment. Mol Cel Biol 31: 3616-3629. 50. Axten J M., Medina J. R., Feng Y., Shu A., Romeril S. P. et al. 2012. Discovery of 7-methy-5(1-{[3-(trifluoromethyl)phenyl]acetyl}-2,3-dihydro-1H-indol-5yl)-7H-pyrrolo[2,3-d]pyrimidin-4 amine (GSK2606414), a potent and selective first-in class inhibitor of protein kinase R (PKR)-like endplasmic reticulum kinase (PERK). J. Med. Chem. 55(16): 7193-7207 51. Ye J. Kumanova M., Hart L. S., Sloane K., Zhang H. et al. 2010. The GCN2-ATF4 pathway is critical for tumour cell survival and proliferation in response to nutrient deprivation. EMBO J. 29: 2082-2096. 52. Moreno J A, Radford H, Peretti D, Steinert J R, Verity N, Martin M G, Halliday M, Morgan J, Dinsdale D, Ortori C A, Barrett D A, Tsaytler P, Bertolotti A, Willis A E, Bushell M, Mallucci G R. 2012. Sustained translational repression by eIF2α-P mediates prion neurodegeneration. Nature 485:507-511. 53. Pavitt G D and Proud C G. 2009. Protein synthesis and its control in neuronal cells with a focus on vanishing white matter disease. Biochem Soc Trans 37:1298-1310. 54. Costa-Mattioli M. Gobert D., Harding H., Herdy B. Azzi M., Bruno M. et al, 2005. Translational control of hippocampal synaptic plasticity and memory by the eIF2α kinase GCN2. Nature 436:1166-1173. 55. Costa-Mattioli M., Gobert D., Stern E., Garnache K., Colina Rl, Cuello C., Sossin W., Kaufman R., Pelletier J., Rosenblum et al. 2007. eIF2α phosphorylation bidirectionally regulates the switch from short to long term synaptic plasticity and memory. Cell 129: 195-206. 56. Zhu P. J, Huan W., Kalikulov D., Yoo J. W., Placzek A. N., Stoica L, Zhou H., Bell J. C., Frielander M. J., Krnjevic K., Noebels J. L., Costa-Mattioli M. 2011. Suppression of PKR promotes network excitability and enhanced cognition by interferon-γ-mediated disinhibition. Cell 147: 1384-1396. 57. Borck G., Shin B. S., Stiller B., et al 2012. eIF2γ mutation that disrupts eIF2 complex integrity links intellectual disability to impaired translation initiation. Mol Cell 48:1-6. 58. Zeenko V. V., Wang C, Majumder M, Komar A. A., Snider M. D., Merrick W. C., Kaufman R. J. and Hatzoglou M. (2008). An efficient in vitro translation system from mammalian cell lacking translational inhibition caused by eIF2 phosphorylation. RNA 14: 593-602. 59. Mikami S., Masutani M., Sonenber N., Yokoyama S. and Imataka H. 2006. An efficient mammalian cell-free translation system supplemented with translation factors. Protein Expr. Purif 46: 348-357.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating traumatic brain injury in a patient in need of such treatment, said method comprising administering a therapeutically effective amount of a compound or a pharmaceutically acceptable salt thereof, to said patient, wherein said compound has the formula:

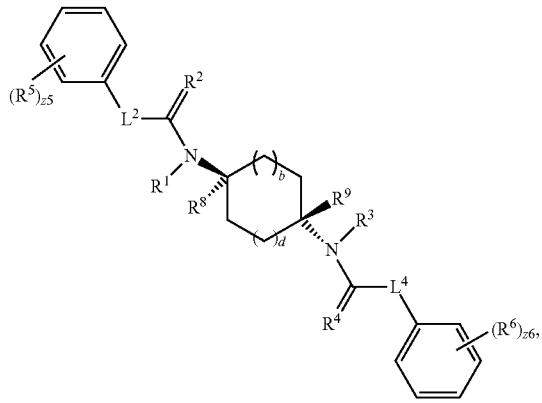

(IIIa)

wherein
L² is —OCH₂ or —SCH₂;
L⁴ is a bond, (CH₂)₁₋₂O, ethylene, —CH₂NH—, or —SCH₂—;
R¹, R³, R⁵, R⁶, and R⁷ are independently hydrogen, halogen, —OCH₃, —OCH₂Ph, —C(O)Ph, —CH₃, —CF₃, —CCl₃, —CN, —S(O)CH₃, —OH, —NH₂, —COOH, —CONH₂, —NO₂, —C(O)CH₃, —CH(CH₃)₂, —CCSi(CH3)₃, —CCH, —CH2CCH, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCH₃, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R² and R⁴ are independently ═NR⁷ or ═O;
z5 and z6 are independently an integer from 0 to 5;
R⁸ and R⁹ are independently hydrogen, halogen, —OCH₃, —OCH₃, —OCH₂Ph, —C(O)Ph, —CH₃, —CF₃, —CCl₃, —CN, —S(O)CH₃, —OH, —NH₂, —COOH, —CONH₂, —NO₂, —C(O)CH₃, —CH(CH₃)₂, —CCSi(CH₃)₃, —CCH, —CH₂CCH, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
and b and d are independently 0 or 1.

2. The method of claim 1, wherein the compound has the formula:

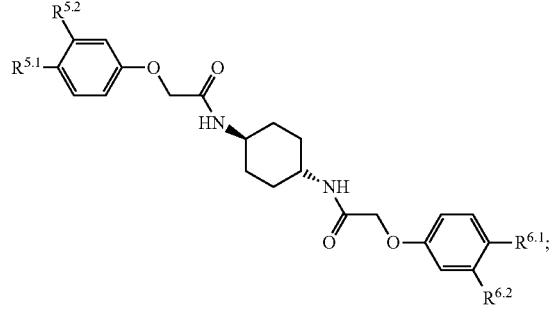

(IIIb)

wherein
R⁵·¹ and R⁶·¹ are independently hydrogen, halogen, —CF₃, —CN, —N₃, substituted or unsubstituted C₁-C₄ alkyl, substituted or unsubstituted 2 to 4 membered heteroalkyl, substituted or unsubstituted 5 to 6 membered heteroaryl,

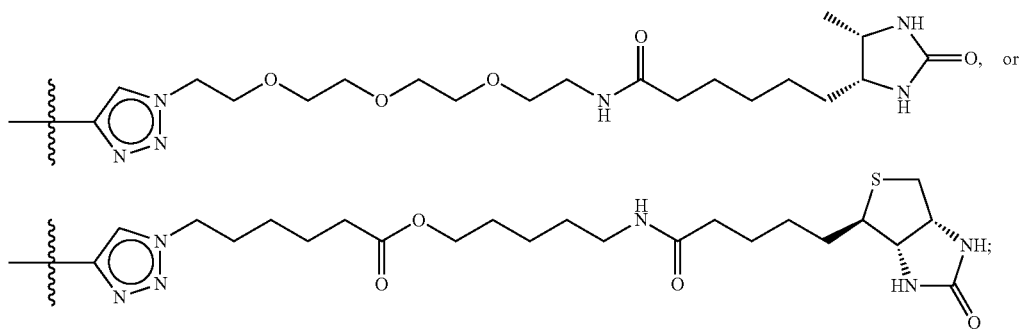

$R^{5.2}$ and $R^{6.2}$ are independently hydrogen, halogen, —CCSi(CH$_3$)$_3$, —CF$_3$, —NO$_2$, —CN, —N$_3$, substituted or unsubstituted C$_1$-C$_4$ alkyl, substituted or unsubstituted 2 to 4 membered heteroalkyl, substituted or unsubstituted 5 to 6 membered heteroaryl,

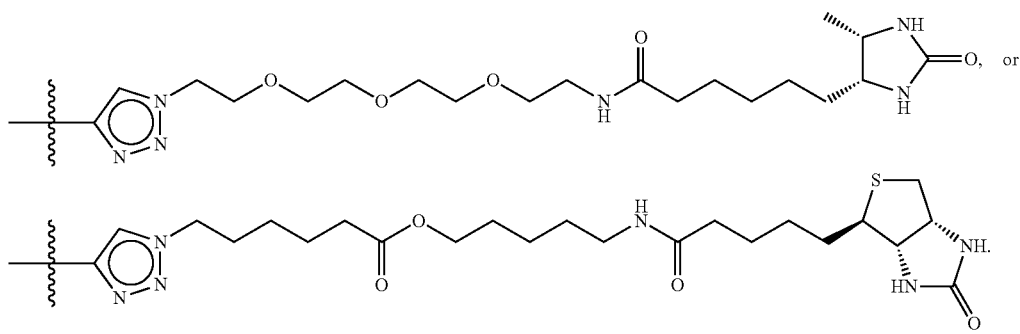

3. The method of claim 2, wherein
$R^{5.1}$ and $R^{6.1}$ are independently —Cl, —I, —CF$_3$, —CH$_3$, or —CCH; and $R^{5.2}$ and $R^{6.2}$ are independently hydrogen, —Cl, —F, —I, —CCSi(CH$_3$)$_3$, —CF$_3$, —NO$_2$, —CH$_3$, or CCH.

4. The method of claim 1, wherein the compound is

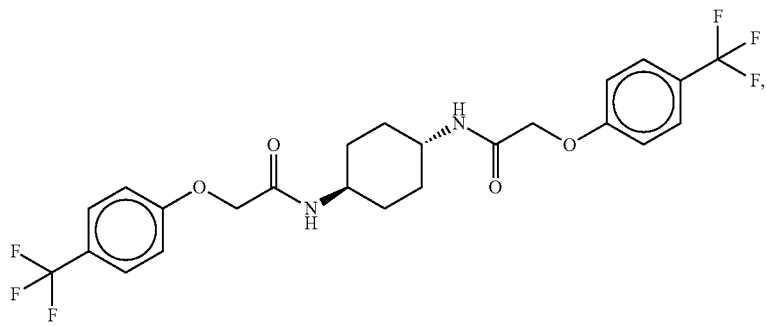

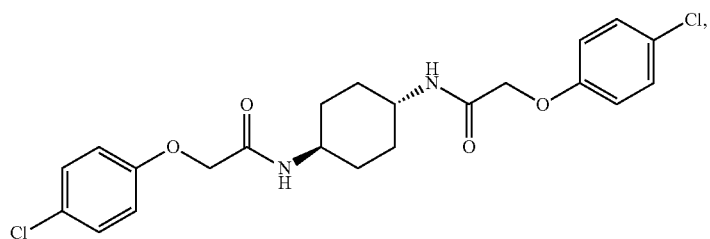

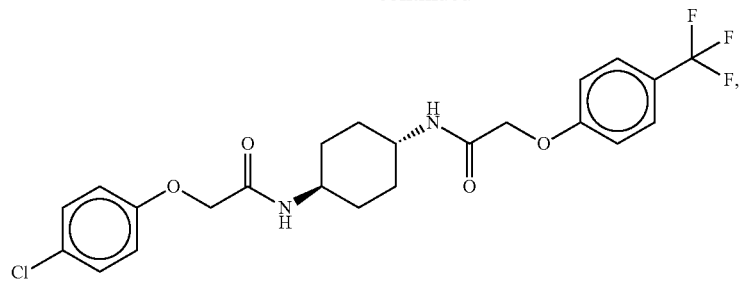
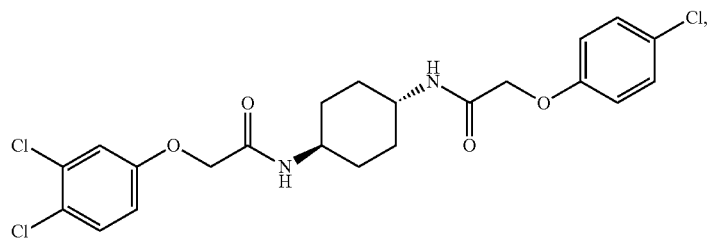
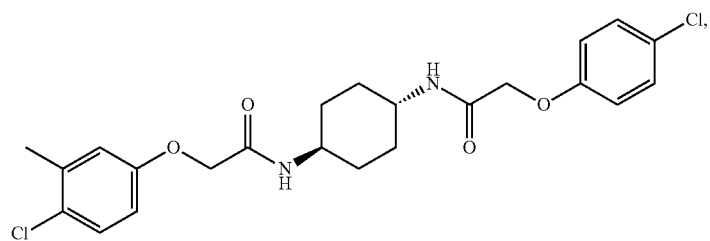
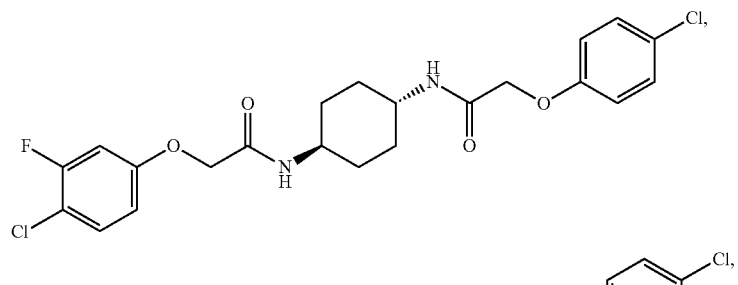
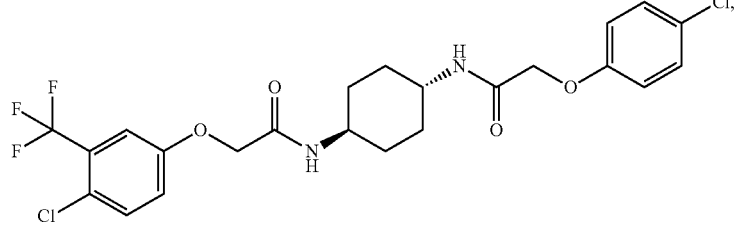
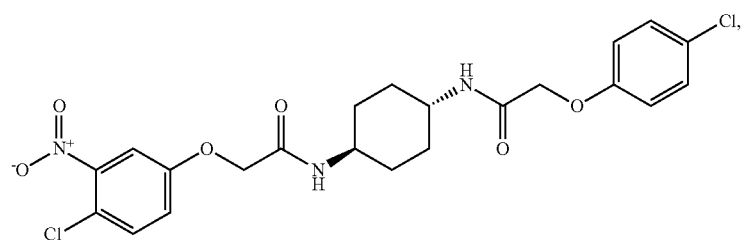
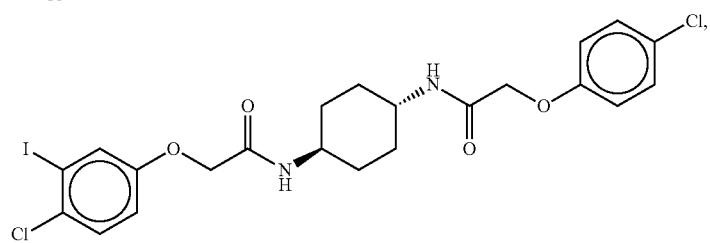

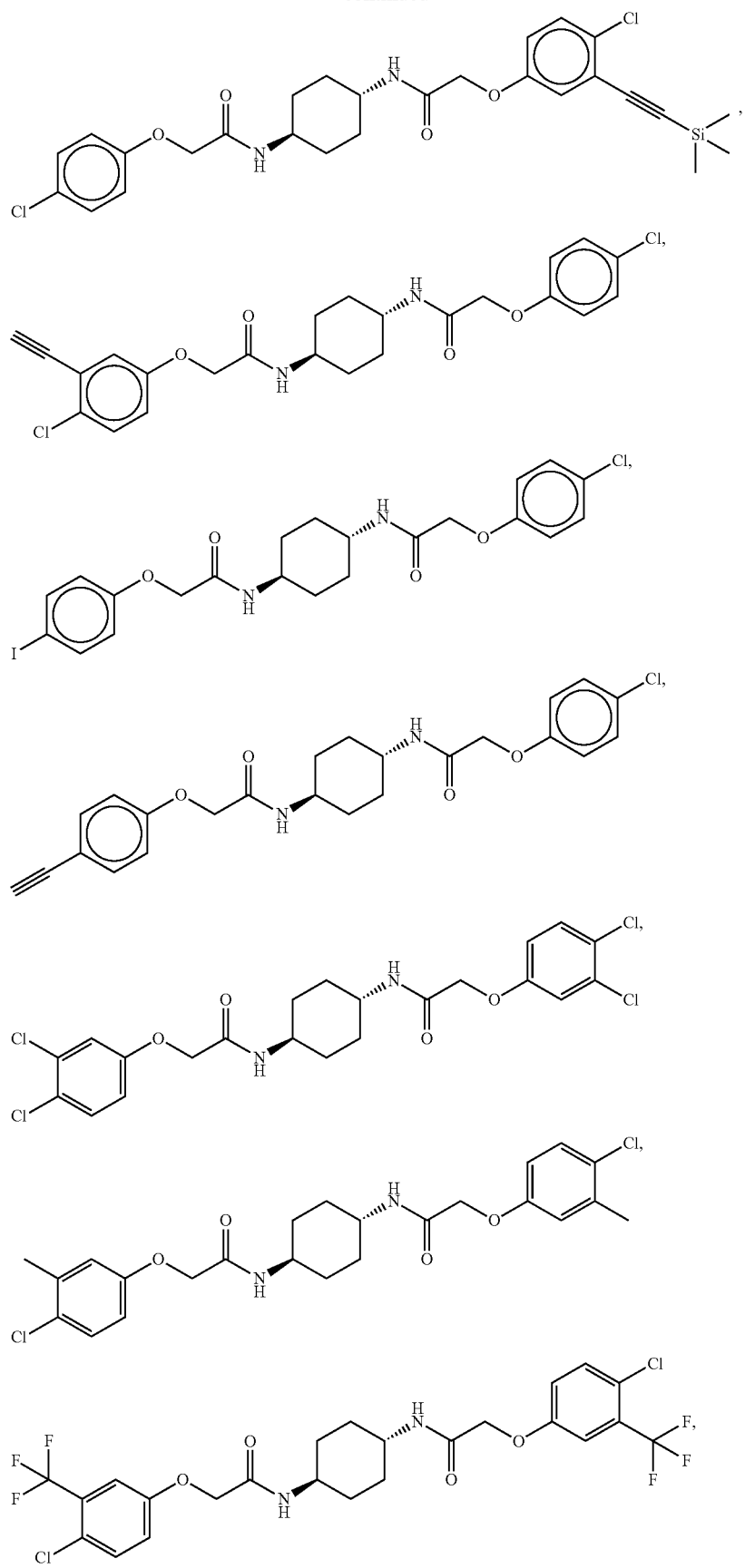

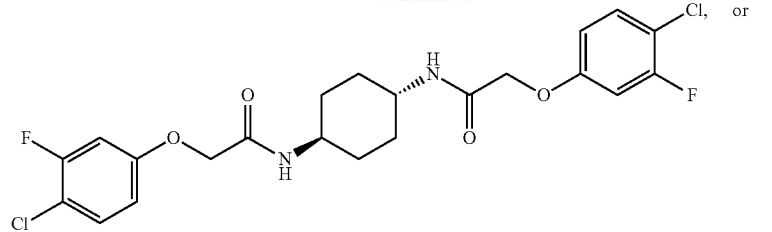
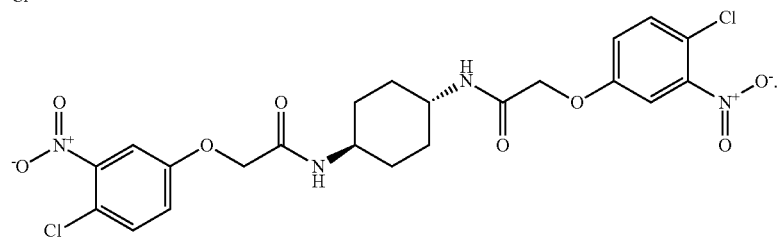
5. The method of claim 1, wherein the compound is
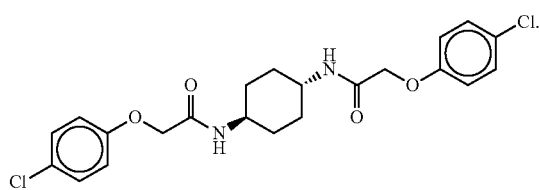
6. The method of claim 1, wherein the method comprises improving long term memory, increasing spatial learning, improving cognitive function after surgery, or improving cognitive function after a traumatic brain injury.
* * * * *

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1
gtagcctgat ggggtgctt                                               19

<210> SEQ ID NO 2
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 2
tgaggcagcc ggagatac                                                18

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
agccaaaatc agagctggaa                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
tggatcagtc tggaaaagca                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
tggaagatgg tgatgggatt                                              20

<210> SEQ ID NO 6
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 6
agccacatcg ctcagacac                                               19

<210> SEQ ID NO 7
<211> LENGTH: 20
<212> TYPE: DNA
<213> ORGANISM: Artificial Sequence

```
<220> FEATURE:
<223> OTHER INFORMATION: Synthetic polynucleotide

<400> SEQUENCE: 7
gaagccaagg ggaatgaagt                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
gagatgttct ggagggtga                                                20

<210> SEQ ID NO 9
<211> LENGTH: 26
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with FAM
<220> FEATURE:
<221> NAME/KEY: misc_feature
<222> LOCATION: (26)..(26)
<223> OTHER INFORMATION: 3'-terminal modified with BHQ1

<400> SEQUENCE: 9
cagcactcag actacgtgca cctctg                                        26

<210> SEQ ID NO 10
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'-terminal modified with HEX
<220> FEATURE:
<221> NAME/KEY: misc_feature
<222> LOCATION: (24)..(24)
<223> OTHER INFORMATION: 3'-terminal modified with BHQ1

<400> SEQUENCE: 10
tctgctgagt ccgcagcagg tgca                                          24

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
actgggtcca agttgtccag                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide
```

```
<400> SEQUENCE: 12
ggagttaaga cagcgcttgg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
tggaagatgg tgatgggatt                                              20

<210> SEQ ID NO 14
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 14
agccacatcg ctcagacac                                               19
```